(12) United States Patent
Boulikas

(10) Patent No.: US 9,278,067 B2
(45) Date of Patent: Mar. 8, 2016

(54) ENCAPSULATION OF PLASMID DNA (LIPOGENES™) AND THERAPEUTIC AGENTS WITH NUCLEAR LOCALIZATION SIGNAL/FUSOGENIC PEPTIDE CONJUGATES INTO TARGETED LIPOSOME COMPLEXES

(71) Applicant: Regulon, Inc., Athens (GR)

(72) Inventor: Teni Boulikas, Athens (GR)

(73) Assignee: REGULON, INC., Athens (GR)

( * ) Notice: Subject to any disclaimer, the term of this patent is extended or adjusted under 35 U.S.C. 154(b) by 0 days.

(21) Appl. No.: 13/900,433

(22) Filed: May 22, 2013

(65) Prior Publication Data

US 2014/0134232 A1 May 15, 2014

Related U.S. Application Data

(63) Continuation of application No. 12/830,118, filed on Jul. 2, 2010, now abandoned, which is a continuation of application No. 09/876,904, filed on Jun. 8, 2001, now abandoned.

(60) Provisional application No. 60/210,925, filed on Jun. 9, 2000.

(51) Int. Cl.
*A61K 9/127* (2006.01)
*C12N 15/88* (2006.01)
*A61K 9/107* (2006.01)

(52) U.S. Cl.
CPC .............. *A61K 9/127* (2013.01); *A61K 9/1271* (2013.01); *C12N 15/88* (2013.01); *A61K 9/1075* (2013.01); *A61K 9/1277* (2013.01); *A61K 9/1278* (2013.01)

(58) Field of Classification Search
None
See application file for complete search history.

*Primary Examiner* — Robert M Kelly
(74) *Attorney, Agent, or Firm* — Foley & Lardner LLP; Antoinette F. Konski

(57) ABSTRACT

A method is disclosed for encapsulating plasmids, oligonucleotides or negatively-charged drugs into liposomes having a different lipid composition between their inner and outer membrane bilayers and able to reach primary tumors and their metastases after intravenous injection to animals and humans. The formulation method includes complex formation between DNA with cationic lipid molecules and fusogenic/NLS peptide conjugates composed of a hydrophobic chain of about 10-20 amino acids and also containing four or more histidine residues or NLS at their one end. The encapsulated molecules display therapeutic efficacy in eradicating a variety of solid human tumors including but not limited to breast carcinoma and prostate carcinoma. Combination of the plasmids, oligonucleotides or negatively-charged drugs with other anti-neoplastic drugs (the positively-charged cis-platin, doxorubicin) encapsulated into liposomes are of therapeutic value. Also of therapeutic value in cancer eradication are combinations of encapsulated the plasmids, oligonucleotides or negatively-charged drugs with HSV-tk plus encapsulated ganciclovir.

11 Claims, 8 Drawing Sheets

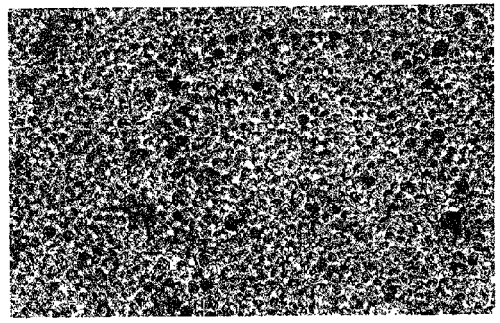
L2+polyR
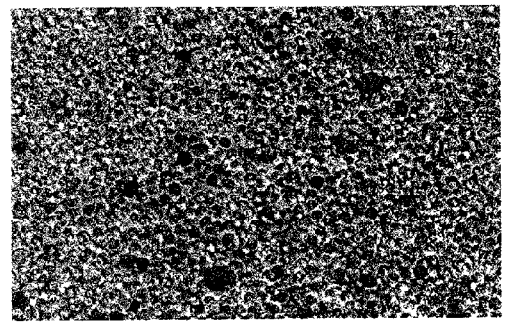
L5
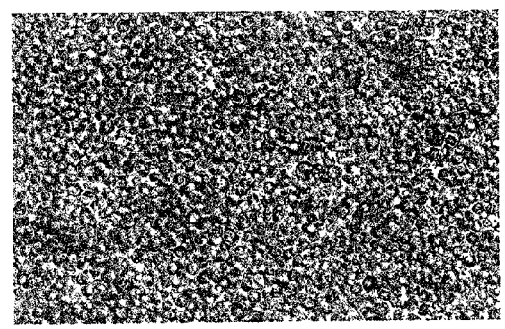
L3
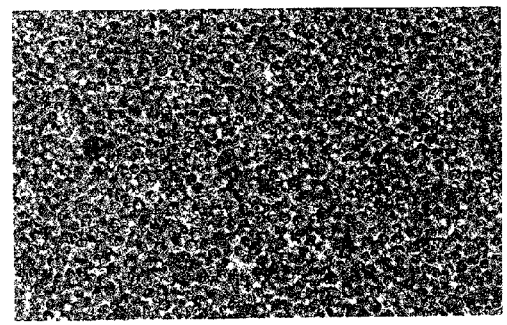
L6
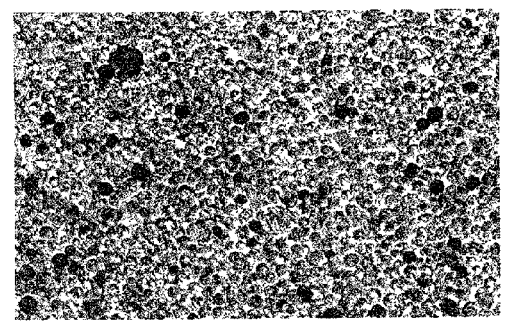
L4
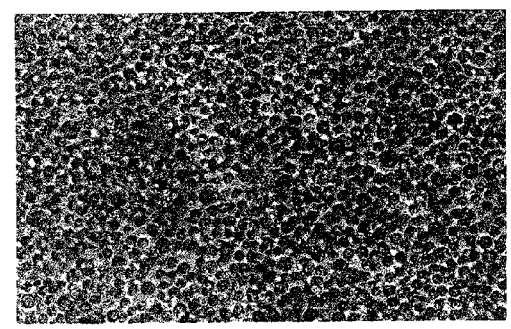
SFV
FIGURE 2 (CON'T)

SEQUENCE LISTING

<160> NUMBER OF SEQ ID NOS: 631

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Trp Leu Lys Ala Phe Lys Ala Trp Leu Lys Ala Phe Lys Ala
1               5                   10                  15

Trp Leu Lys Ala Phe
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Phe Lys Ala Ala Ala Lys Leu Leu Lys Ser Leu Trp Lys Leu
1               5                   10                  15

Leu Leu Lys Ala
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Leu Leu Lys Ala Phe Ala Lys Leu Leu Lys Ser Leu Trp Lys Leu
1               5                   10                  15

Leu Leu Lys Ala
            20

<210> SEQ ID NO 4
<211> LENGTH: 24
<212> TYPE: PRT
<213> ORGANISM: Influenza A virus

<400> SEQUENCE: 4

Gly Leu Phe Lys Ala Ile Ala Gly Phe Ile Lys Asn Gly Trp Lys Gly
1               5                   10                  15

Met Ile Asp Gly Gly Gly Tyr Cys
            20

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
1               5                   10

-continued

```
<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(22)
<223> OTHER INFORMATION: Lys, Arg, or His and this region may
      encompass 1 to 6 residues

<400> SEQUENCE: 6

Met Ser Gly Thr Phe Gly Gly Ile Leu Ala Gly Leu Ile Gly Leu Leu
1               5                   10                  15

Xaa Xaa Xaa Xaa Xaa Xaa
            20

<210> SEQ ID NO 7
<211> LENGTH: 16
<212> TYPE: PRT
<213> ORGANISM: Ebola virus

<400> SEQUENCE: 7

Gly Ala Ala Ile Gly Leu Ala Trp Ile Pro Tyr Phe Gly Pro Ala Ala
1               5                   10                  15

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(29)
<223> OTHER INFORMATION: Ala, Leu, Ile, Tyr, Trp or Phe and this
      region may encompass 12 to 20 residues

<400> SEQUENCE: 8

Pro Lys Lys Arg Arg Gly Pro Ser Pro Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 9
<211> LENGTH: 24
<212> TYPE: PRT
<213> ORGANISM: Influenza A virus

<400> SEQUENCE: 9

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 10
<211> LENGTH: 11
<212> TYPE: PRT
<213> ORGANISM: Human immunodeficiency virus

<400> SEQUENCE: 10

Tyr Gly Arg Lys Lys Arg Arg Gln Arg Arg
1               5                   10
```

```
<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 11

His Glu Xaa Xaa His
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Lys Ala Lys Asn Trp Lys
1               5

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Phe Glu Ala Leu Leu Glu Leu Leu Glu Ser Leu Trp Glu Leu
1               5                   10                  15

Leu Leu Glu Ala
            20

<210> SEQ ID NO 14
<211> LENGTH: 16
<212> TYPE: PRT
<213> ORGANISM: Hepatitis B virus

<400> SEQUENCE: 14

Met Ser Pro Ser Ser Leu Leu Gly Leu Leu Ala Gly Leu Gln Val Val
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Lys Lys Leu Leu Lys Lys Leu Leu Lys Lys Leu Leu Lys Lys Leu
1               5                   10                  15

<210> SEQ ID NO 16
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Leu Ala Arg Leu Leu Ala Arg Leu Leu Ala Arg Leu
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Ala Leu Ala Gly Ala Leu Ala Gly Ala Leu Ala Gly Ala Leu
1               5                   10                  15

Ala Gly Ala Leu Ala Gly Ala Leu Ala Gly Ala Leu Ala Gly Ala
            20                  25                  30

Leu Ala

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-aminoisobutyric acid
<220> FEATURE:
<221> NAME/KEY: MOD_RES
<222> LOCATION: (4)..(4)
<223> OTHER INFORMATION: 2-aminoisobutyric acid

<400> SEQUENCE: 18

Glu Xaa Leu Xaa
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Pro Val
1

<210> SEQ ID NO 20
<211> LENGTH: 7
<212> TYPE: PRT
<213> ORGANISM: Simian virus 40

<400> SEQUENCE: 20

Pro Lys Lys Lys Arg Lys Val
1               5

<210> SEQ ID NO 21
<211> LENGTH: 7
<212> TYPE: PRT
```

```
<213> ORGANISM: Simian virus 40

<400> SEQUENCE: 21

Pro Lys Lys Lys Arg Met Val
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Lys Lys Lys Arg Lys Val Glu Asp Pro
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gly Tyr Gly Pro Lys Lys Lys Arg Lys Val Gly Gly
1               5                   10

<210> SEQ ID NO 24
<211> LENGTH: 34
<212> TYPE: PRT
<213> ORGANISM: Simian virus 40

<400> SEQUENCE: 24

Cys Tyr Asp Asp Glu Ala Thr Ala Asp Ser Gln His Ser Thr Pro Pro
1               5                   10                  15

Lys Lys Lys Arg Lys Val Glu Asp Pro Lys Asp Phe Glu Ser Glu Leu
            20                  25                  30

Leu Ser

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Gly Gly Pro Lys Lys Lys Arg Lys Val Gly
1               5                   10

<210> SEQ ID NO 26
<211> LENGTH: 7
<212> TYPE: PRT
<213> ORGANISM: Simian virus 40

<400> SEQUENCE: 26

Pro Lys Lys Lys Ile Lys Val
1               5

<210> SEQ ID NO 27
<211> LENGTH: 46
```

```
<212> TYPE: PRT
<213> ORGANISM: Saccharomyces cerevisiae
<220> FEATURE:
<221> NAME/KEY: MOD_RES
<222> LOCATION: (3)..(13)
<223> OTHER INFORMATION: Any amino acid
<220> FEATURE:
<221> NAME/KEY: MOD_RES
<222> LOCATION: (34)..(38)
<223> OTHER INFORMATION: Any amino acid
<220> FEATURE:
<221> NAME/KEY: MOD_RES
<222> LOCATION: (40)..(42)
<223> OTHER INFORMATION: Any amino acid

<400> SEQUENCE: 27

Met Lys Xaa Xaa Xaa Xaa Xaa Xaa Xaa Xaa Xaa Xaa Cys Arg Leu
1               5                   10                  15

Lys Lys Leu Lys Cys Ser Lys Glu Lys Pro Lys Cys Ala Lys Cys Leu
            20                  25                  30

Lys Xaa Xaa Xaa Xaa Xaa Arg Xaa Xaa Xaa Lys Thr Lys Arg
        35                  40                  45

<210> SEQ ID NO 28
<211> LENGTH: 29
<212> TYPE: PRT
<213> ORGANISM: Saccharomyces cerevisiae
<220> FEATURE:
<221> NAME/KEY: MOD_RES
<222> LOCATION: (3)..(13)
<223> OTHER INFORMATION: Any amino acid

<400> SEQUENCE: 28

Met Lys Xaa Xaa Xaa Xaa Xaa Xaa Xaa Xaa Xaa Xaa Cys Arg Leu
1               5                   10                  15

Lys Lys Leu Lys Cys Ser Lys Glu Lys Pro Lys Cys Ala
            20                  25

<210> SEQ ID NO 29
<211> LENGTH: 7
<212> TYPE: PRT
<213> ORGANISM: Polyoma virus

<400> SEQUENCE: 29

Pro Lys Lys Ala Arg Glu Asp
1               5

<210> SEQ ID NO 30
<211> LENGTH: 7
<212> TYPE: PRT
<213> ORGANISM: Polyoma virus

<400> SEQUENCE: 30

Val Ser Arg Lys Arg Pro Arg
1               5

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Gly Tyr Gly Val Ser Arg Lys Arg Pro Arg Pro Gly
1               5                   10
```

```
<210> SEQ ID NO 32
<211> LENGTH: 8
<212> TYPE: PRT
<213> ORGANISM: Simian virus 40

<400> SEQUENCE: 32

Ala Pro Thr Lys Arg Lys Gly Ser
1               5

<210> SEQ ID NO 33
<211> LENGTH: 11
<212> TYPE: PRT
<213> ORGANISM: Polyoma virus

<400> SEQUENCE: 33

Ala Pro Lys Arg Lys Ser Gly Val Ser Lys Cys
1               5                   10

<210> SEQ ID NO 34
<211> LENGTH: 7
<212> TYPE: PRT
<213> ORGANISM: Simian virus 40

<400> SEQUENCE: 34

Pro Asn Lys Lys Lys Arg Lys
1               5

<210> SEQ ID NO 35
<211> LENGTH: 12
<212> TYPE: PRT
<213> ORGANISM: Polyoma virus

<400> SEQUENCE: 35

Glu Glu Asp Gly Pro Gln Lys Lys Lys Arg Arg Leu
1               5                   10

<210> SEQ ID NO 36
<211> LENGTH: 7
<212> TYPE: PRT
<213> ORGANISM: Saccharomyces cerevisiae

<400> SEQUENCE: 36

Gly Lys Lys Arg Ser Lys Ala
1               5

<210> SEQ ID NO 37
<211> LENGTH: 5
<212> TYPE: PRT
<213> ORGANISM: Adenovirus

<400> SEQUENCE: 37

Lys Arg Pro Arg Pro
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Gly Gly Leu Ser Ser Lys Arg Pro Arg Pro
1               5                   10
```

<210> SEQ ID NO 39
<211> LENGTH: 13
<212> TYPE: PRT
<213> ORGANISM: Xenopus laevis

<400> SEQUENCE: 39

Leu Val Arg Lys Lys Arg Lys Thr Glu Glu Glu Ser Pro
1               5                   10

<210> SEQ ID NO 40
<211> LENGTH: 12
<212> TYPE: PRT
<213> ORGANISM: Xenopus laevis

<400> SEQUENCE: 40

Leu Lys Asp Lys Asp Ala Lys Lys Ser Lys Gln Glu
1               5                   10

<210> SEQ ID NO 41
<211> LENGTH: 10
<212> TYPE: PRT
<213> ORGANISM: Unknown
<220> FEATURE:
<223> OTHER INFORMATION: Description of Unknown: V-Rel
      transforming peptide

<400> SEQUENCE: 41

Gly Asn Lys Ala Lys Arg Gln Arg Ser Thr
1               5                   10

<210> SEQ ID NO 42
<211> LENGTH: 11
<212> TYPE: PRT
<213> ORGANISM: Influenza A virus

<400> SEQUENCE: 42

Pro Phe Leu Asp Arg Leu Arg Arg Asp Gln Lys
1               5                   10

<210> SEQ ID NO 43
<211> LENGTH: 9
<212> TYPE: PRT
<213> ORGANISM: Influenza A virus

<400> SEQUENCE: 43

Pro Lys Gln Lys Arg Lys Met Ala Arg
1               5

<210> SEQ ID NO 44
<211> LENGTH: 9
<212> TYPE: PRT
<213> ORGANISM: Homo sapiens

<400> SEQUENCE: 44

Ser Val Thr Lys Lys Arg Lys Leu Glu
1               5

<210> SEQ ID NO 45
<211> LENGTH: 9
<212> TYPE: PRT
<213> ORGANISM: Xenopus laevis

<400> SEQUENCE: 45

Ser Ala Ser Lys Arg Arg Arg Leu Glu

```
<210> SEQ ID NO 46
<211> LENGTH: 9
<212> TYPE: PRT
<213> ORGANISM: Xenopus laevis

<400> SEQUENCE: 46

Thr Lys Gly Lys Arg Lys Arg Ile Asp
1               5

<210> SEQ ID NO 47
<211> LENGTH: 14
<212> TYPE: PRT
<213> ORGANISM: Xenopus laevis

<400> SEQUENCE: 47

Cys Val Arg Thr Thr Lys Gly Lys Arg Lys Arg Ile Asp Val
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Ala Lys Arg Val Lys Leu Asp
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Lys Arg Val Lys Leu Asp
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Gln Arg Arg Asn Glu Leu Lys Arg Ser Pro
1               5                   10

<210> SEQ ID NO 51
<211> LENGTH: 12
<212> TYPE: PRT
<213> ORGANISM: Mus sp.

<400> SEQUENCE: 51

Ser Ala Leu Ile Lys Lys Lys Lys Lys Met Ala Pro
1               5                   10

<210> SEQ ID NO 52
```

-continued

```
<211> LENGTH: 11
<212> TYPE: PRT
<213> ORGANISM: Adenovirus

<400> SEQUENCE: 52

Pro Pro Lys Lys Arg Met Arg Arg Ile Glu
1               5                   10

<210> SEQ ID NO 53
<211> LENGTH: 8
<212> TYPE: PRT
<213> ORGANISM: Adenovirus

<400> SEQUENCE: 53

Pro Lys Lys Lys Lys Lys Arg Pro
1               5

<210> SEQ ID NO 54
<211> LENGTH: 28
<212> TYPE: PRT
<213> ORGANISM: Rattus sp.

<400> SEQUENCE: 54

Tyr Arg Lys Cys Leu Gln Ala Gly Met Asn Leu Glu Ala Arg Lys Thr
1               5                   10                  15

Lys Lys Lys Ile Lys Gly Ile Gln Gln Ala Thr Ala
            20                  25

<210> SEQ ID NO 55
<211> LENGTH: 48
<212> TYPE: PRT
<213> ORGANISM: Homo sapiens

<400> SEQUENCE: 55

Arg Lys Asp Arg Arg Gly Gly Arg Met Leu Lys His Lys Arg Gln Arg
1               5                   10                  15

Asp Asp Gly Glu Gly Arg Gly Glu Val Gly Ser Ala Gly Asp Met Arg
            20                  25                  30

Ala Ala Asn Leu Trp Pro Ser Pro Leu Met Ile Lys Arg Ser Lys Lys
        35                  40                  45

<210> SEQ ID NO 56
<211> LENGTH: 8
<212> TYPE: PRT
<213> ORGANISM: Unknown
<220> FEATURE:
<223> OTHER INFORMATION: Description of Unknown: Rabbit PG
      peptide

<400> SEQUENCE: 56

Arg Lys Phe Lys Lys Phe Asn Lys
1               5

<210> SEQ ID NO 57
<211> LENGTH: 8
<212> TYPE: PRT
<213> ORGANISM: Gallus sp.

<400> SEQUENCE: 57

Gly Lys Arg Lys Asn Lys Pro Lys
1               5

<210> SEQ ID NO 58
<211> LENGTH: 8
```

```
<212> TYPE: PRT
<213> ORGANISM: Unknown
<220> FEATURE:
<223> OTHER INFORMATION: Description of Unknown: C-myb gene
      product peptide

<400> SEQUENCE: 58

Pro Leu Leu Lys Lys Ile Lys Gln
1               5

<210> SEQ ID NO 59
<211> LENGTH: 8
<212> TYPE: PRT
<213> ORGANISM: Unknown
<220> FEATURE:
<223> OTHER INFORMATION: Description of Unknown: N-myc gene
      product peptide

<400> SEQUENCE: 59

Pro Pro Gln Lys Lys Ile Lys Ser
1               5

<210> SEQ ID NO 60
<211> LENGTH: 7
<212> TYPE: PRT
<213> ORGANISM: Unknown
<220> FEATURE:
<223> OTHER INFORMATION: Description of Unknown: P53
      peptide

<400> SEQUENCE: 60

Pro Gln Pro Lys Lys Lys Pro
1               5

<210> SEQ ID NO 61
<211> LENGTH: 9
<212> TYPE: PRT
<213> ORGANISM: Unknown
<220> FEATURE:
<223> OTHER INFORMATION: Description of Unknown: C-erb-A gene
      product peptide

<400> SEQUENCE: 61

Ser Lys Arg Val Ala Lys Arg Lys Leu
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Gly Gly Leu Ser Ser Lys Arg Pro Arg Pro
1               5                   10

<210> SEQ ID NO 63
<211> LENGTH: 14
<212> TYPE: PRT
<213> ORGANISM: Saccharomyces cerevisiae

<400> SEQUENCE: 63

Met Thr Gly Ser Lys Thr Arg Lys His Arg Gly Ser Gly Ala
1               5                   10
```

```
<210> SEQ ID NO 64
<211> LENGTH: 14
<212> TYPE: PRT
<213> ORGANISM: Saccharomyces cerevisiae

<400> SEQUENCE: 64

Met Thr Gly Ser Lys His Arg Lys His Pro Gly Ser Gly Ala
1               5                   10

<210> SEQ ID NO 65
<211> LENGTH: 6
<212> TYPE: PRT
<213> ORGANISM: Saccharomyces cerevisiae

<400> SEQUENCE: 65

Arg His Arg Lys His Pro
1               5

<210> SEQ ID NO 66
<211> LENGTH: 6
<212> TYPE: PRT
<213> ORGANISM: Saccharomyces cerevisiae

<400> SEQUENCE: 66

Lys Arg Arg Lys His Pro
1               5

<210> SEQ ID NO 67
<211> LENGTH: 6
<212> TYPE: PRT
<213> ORGANISM: Saccharomyces cerevisiae

<400> SEQUENCE: 67

Lys Tyr Arg Lys His Pro
1               5

<210> SEQ ID NO 68
<211> LENGTH: 6
<212> TYPE: PRT
<213> ORGANISM: Saccharomyces cerevisiae

<400> SEQUENCE: 68

Lys His Arg Arg His Pro
1               5

<210> SEQ ID NO 69
<211> LENGTH: 6
<212> TYPE: PRT
<213> ORGANISM: Saccharomyces cerevisiae

<400> SEQUENCE: 69

Lys His Lys Lys His Pro
1               5

<210> SEQ ID NO 70
<211> LENGTH: 6
<212> TYPE: PRT
<213> ORGANISM: Saccharomyces cerevisiae

<400> SEQUENCE: 70

Arg His Leu Lys His Pro
1               5

<210> SEQ ID NO 71
<211> LENGTH: 6
```

```
<212> TYPE: PRT
<213> ORGANISM: Saccharomyces cerevisiae

<400> SEQUENCE: 71

Lys His Arg Lys Tyr Pro
1               5

<210> SEQ ID NO 72
<211> LENGTH: 6
<212> TYPE: PRT
<213> ORGANISM: Saccharomyces cerevisiae

<400> SEQUENCE: 72

Lys His Arg Gln His Pro
1               5

<210> SEQ ID NO 73
<211> LENGTH: 33
<212> TYPE: PRT
<213> ORGANISM: Hepatitis B virus

<400> SEQUENCE: 73

Pro Glu Thr Thr Val Val Arg Arg Arg Gly Arg Ser Pro Arg Arg
1               5                   10                  15

Thr Pro Ser Pro Arg Arg Arg Arg Ser Pro Arg Arg Arg Ser Gln
                20                  25                  30

Ser

<210> SEQ ID NO 74
<211> LENGTH: 9
<212> TYPE: PRT
<213> ORGANISM: Unknown
<220> FEATURE:
<223> OTHER INFORMATION: Description of Unknown: Viral Jun
      peptide

<400> SEQUENCE: 74

Ala Ser Lys Ser Arg Lys Arg Lys Leu
1               5

<210> SEQ ID NO 75
<211> LENGTH: 16
<212> TYPE: PRT
<213> ORGANISM: Leukemia virus

<400> SEQUENCE: 75

Gly Gly Leu Cys Ser Ala Arg Leu His Arg His Ala Leu Leu Ala Thr
1               5                   10                  15

<210> SEQ ID NO 76
<211> LENGTH: 18
<212> TYPE: PRT
<213> ORGANISM: Mus sp.

<400> SEQUENCE: 76

Asp Thr Arg Glu Lys Lys Lys Phe Leu Lys Arg Arg Leu Leu Arg Leu
1               5                   10                  15

Asp Glu

<210> SEQ ID NO 77
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 77

Cys Gly Tyr Gly Pro Lys Lys Arg Lys Val
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Gly Tyr Gly Asp Arg Asn Lys Lys Lys Lys Glu
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Gly Tyr Gly Ala Arg Lys Thr Lys Lys Lys Ile Lys
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Gly Tyr Gly Ile Arg Lys Asp Arg Arg Gly Gly Arg
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Gly Tyr Gly Ala Arg Lys Leu Lys Lys Leu Gly Asn
1               5                   10

<210> SEQ ID NO 82
<211> LENGTH: 13
<212> TYPE: PRT
<213> ORGANISM: Homo sapiens

<400> SEQUENCE: 82

Arg Lys Arg Gln Arg Ala Leu Met Leu Arg Gln Ala Arg
1               5                   10

<210> SEQ ID NO 83
<211> LENGTH: 11
<212> TYPE: PRT

```
<213> ORGANISM: Agrobacterium tumefaciens

<400> SEQUENCE: 83

Glu Tyr Leu Ser Arg Lys Gly Lys Leu Glu Leu
1               5                   10

<210> SEQ ID NO 84
<211> LENGTH: 8
<212> TYPE: PRT
<213> ORGANISM: Saccharomyces cerevisiae

<400> SEQUENCE: 84

Lys Lys Ser Lys Lys Lys Arg Cys
1               5

<210> SEQ ID NO 85
<211> LENGTH: 8
<212> TYPE: PRT
<213> ORGANISM: Unknown
<220> FEATURE:
<223> OTHER INFORMATION: Description of Unknown: Max
      peptide

<400> SEQUENCE: 85

Pro Gln Ser Arg Lys Lys Leu Arg
1               5

<210> SEQ ID NO 86
<211> LENGTH: 13
<212> TYPE: PRT
<213> ORGANISM: Human foamy virus

<400> SEQUENCE: 86

Gln Pro Gln Arg Tyr Gly Gly Arg Gly Arg Arg Trp
1               5                   10

<210> SEQ ID NO 87
<211> LENGTH: 10
<212> TYPE: PRT
<213> ORGANISM: Xenopus laevis

<400> SEQUENCE: 87

Thr Lys Lys Ala Gly Gln Ala Lys Lys Lys
1               5                   10

<210> SEQ ID NO 88
<211> LENGTH: 13
<212> TYPE: PRT
<213> ORGANISM: Xenopus laevis

<400> SEQUENCE: 88

Thr Lys Lys Ala Gly Gln Ala Lys Lys Lys Lys Leu Asp
1               5                   10

<210> SEQ ID NO 89
<211> LENGTH: 13
<212> TYPE: PRT
<213> ORGANISM: Xenopus laevis

<400> SEQUENCE: 89

Thr Lys Lys Ala Gly Gln Ala Lys Lys Lys Lys Leu Asp
1               5                   10

<210> SEQ ID NO 90
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Gly Gln Ala Lys Lys Lys Leu Asp
1               5

<210> SEQ ID NO 91
<211> LENGTH: 16
<212> TYPE: PRT
<213> ORGANISM: Xenopus laevis

<400> SEQUENCE: 91

Lys Arg Pro Ala Ala Thr Lys Lys Ala Gly Gln Ala Lys Lys Lys Lys
1               5                   10                  15

<210> SEQ ID NO 92
<211> LENGTH: 19
<212> TYPE: PRT
<213> ORGANISM: Saccharomyces cerevisiae
<220> FEATURE:
<221> NAME/KEY: MOD_RES
<222> LOCATION: (10)..(15)
<223> OTHER INFORMATION: Any amino acid

<400> SEQUENCE: 92

His Arg Lys Tyr Glu Ala Pro Arg His Xaa Xaa Xaa Xaa Xaa Xaa Pro
1               5                   10                  15

Arg Lys Arg

<210> SEQ ID NO 93
<211> LENGTH: 35
<212> TYPE: PRT
<213> ORGANISM: Simian virus 40

<400> SEQUENCE: 93

Asn Lys Lys Lys Arg Lys Leu Ser Arg Gly Ser Ser Gln Lys Thr Lys
1               5                   10                  15

Gly Thr Ser Ala Ser Ala Lys Ala Arg His Lys Arg Arg Asn Arg Ser
            20                  25                  30

Ser Arg Ser
        35

<210> SEQ ID NO 94
<211> LENGTH: 19
<212> TYPE: PRT
<213> ORGANISM: Simian sarcoma virus

<400> SEQUENCE: 94

Arg Val Thr Ile Arg Thr Val Arg Val Arg Arg Pro Pro Lys Gly Lys
1               5                   10                  15

His Arg Lys

<210> SEQ ID NO 95
<211> LENGTH: 15
<212> TYPE: PRT
<213> ORGANISM: Xenopus laevis

<400> SEQUENCE: 95

Lys Arg Lys Ile Glu Glu Pro Glu Pro Glu Pro Lys Lys Ala Lys
1               5                   10                  15
```

```
<210> SEQ ID NO 96
<211> LENGTH: 21
<212> TYPE: PRT
<213> ORGANISM: Saccharomyces cerevisiae

<400> SEQUENCE: 96

Lys Lys Tyr Glu Asn Val Val Ile Lys Arg Ser Pro Arg Lys Arg Gly
1               5                   10                  15

Arg Pro Arg Lys Asp
            20

<210> SEQ ID NO 97
<211> LENGTH: 7
<212> TYPE: PRT
<213> ORGANISM: Influenza A virus

<400> SEQUENCE: 97

Met Lys Arg Lys Arg Asn Ser
1               5

<210> SEQ ID NO 98
<211> LENGTH: 46
<212> TYPE: PRT
<213> ORGANISM: Influenza A virus

<400> SEQUENCE: 98

Gly Ile Glu Ser Ile Asp Asn Val Met Gly Met Ile Gly Ile Leu Pro
1               5                   10                  15

Asp Met Thr Pro Ser Thr Glu Met Ser Met Arg Gly Val Arg Ile Ser
            20                  25                  30

Lys Met Gly Val Asp Glu Thr Ser Ser Ala Glu Lys Ile Val
        35                  40                  45

<210> SEQ ID NO 99
<211> LENGTH: 8
<212> TYPE: PRT
<213> ORGANISM: Adenovirus

<400> SEQUENCE: 99

Ala His Arg Ala Arg Arg Leu His
1               5

<210> SEQ ID NO 100
<211> LENGTH: 11
<212> TYPE: PRT
<213> ORGANISM: Adenovirus

<400> SEQUENCE: 100

Pro Pro Arg Arg Arg Val Arg Gln Gln Pro Pro
1               5                   10

<210> SEQ ID NO 101
<211> LENGTH: 10
<212> TYPE: PRT
<213> ORGANISM: Adenovirus

<400> SEQUENCE: 101

Pro Ala Arg Ala Arg Arg Arg Arg Ala Pro
1               5                   10

<210> SEQ ID NO 102
<211> LENGTH: 20
```

```
<212> TYPE: PRT
<213> ORGANISM: Homo sapiens
<220> FEATURE:
<221> NAME/KEY: MOD_RES
<222> LOCATION: (4)..(14)
<223> OTHER INFORMATION: Any amino acid

<400> SEQUENCE: 102

Lys Arg Lys Xaa Xaa Xaa Xaa Xaa Xaa Xaa Xaa Xaa Xaa Lys Lys
1               5                   10                  15

Lys Ser Lys Lys
            20

<210> SEQ ID NO 103
<211> LENGTH: 22
<212> TYPE: PRT
<213> ORGANISM: Herpes simplex virus

<400> SEQUENCE: 103

Gly Arg Lys Arg Ala Phe His Gly Asp Asp Pro Phe Gly Glu Gly Pro
1               5                   10                  15

Pro Asp Lys Lys Gly Asp
            20

<210> SEQ ID NO 104
<211> LENGTH: 21
<212> TYPE: PRT
<213> ORGANISM: Agrobacterium tumefaciens

<400> SEQUENCE: 104

Lys Arg Pro Arg Glu Asp Asp Asp Gly Glu Pro Ser Glu Arg Lys Arg
1               5                   10                  15

Ala Arg Asp Asp Arg
            20

<210> SEQ ID NO 105
<211> LENGTH: 30
<212> TYPE: PRT
<213> ORGANISM: Influenza A virus

<400> SEQUENCE: 105

Gln Leu Val Trp Met Ala Cys Asn Ser Ala Ala Phe Glu Asp Leu Arg
1               5                   10                  15

Val Leu Ser Phe Ile Arg Gly Thr Lys Val Ser Pro Arg Gly
            20                  25                  30

<210> SEQ ID NO 106
<211> LENGTH: 13
<212> TYPE: PRT
<213> ORGANISM: Saccharomyces cerevisiae

<400> SEQUENCE: 106

Met Asn Lys Ile Pro Ile Lys Asp Leu Leu Asn Pro Gln
1               5                   10

<210> SEQ ID NO 107
<211> LENGTH: 19
<212> TYPE: PRT
<213> ORGANISM: Saccharomyces cerevisiae

<400> SEQUENCE: 107

Val Arg Ile Leu Glu Ser Trp Phe Ala Lys Asn Ile Glu Asn Pro Tyr
1               5                   10                  15
```

Leu Asp Thr

```
<210> SEQ ID NO 108
<211> LENGTH: 46
<212> TYPE: PRT
<213> ORGANISM: Drosophila melanogaster
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(24)
<223> OTHER INFORMATION: Any amino acid
<220> FEATURE:
<221> NAME/KEY: MOD_RES
<222> LOCATION: (29)..(31)
<223> OTHER INFORMATION: Any amino acid

<400> SEQUENCE: 108
```

Arg Xaa Xaa Xaa Xaa Xaa Xaa Lys Xaa Xaa Xaa Xaa Xaa Xaa Xaa
1               5                   10                  15

Xaa Xaa Xaa Xaa Xaa Xaa Xaa Xaa Lys Ile Pro Arg Xaa Xaa Xaa His
            20                  25                  30

Phe Tyr Glu Glu Arg Leu Ser Trp Tyr Ser Asp Asn Glu Asp
        35                  40                  45

```
<210> SEQ ID NO 109
<211> LENGTH: 19
<212> TYPE: PRT
<213> ORGANISM: Leukemia virus

<400> SEQUENCE: 109
```

Met Pro Lys Thr Arg Arg Arg Pro Arg Arg Ser Gln Arg Lys Arg Pro
1               5                   10                  15

Pro Thr Pro

```
<210> SEQ ID NO 110
<211> LENGTH: 12
<212> TYPE: PRT
<213> ORGANISM: Adenovirus

<400> SEQUENCE: 110
```

Arg Leu Pro Val Arg Arg Arg Arg Arg Arg Val Pro
1               5                   10

```
<210> SEQ ID NO 111
<211> LENGTH: 11
<212> TYPE: PRT
<213> ORGANISM: Human immunodeficiency virus

<400> SEQUENCE: 111
```

Gly Arg Lys Lys Arg Arg Gln Arg Arg Arg Pro
1               5                   10

```
<210> SEQ ID NO 112
<211> LENGTH: 12
<212> TYPE: PRT
<213> ORGANISM: Human immunodeficiency virus

<400> SEQUENCE: 112
```

Arg Lys Lys Arg Arg Gln Arg Arg Arg Ala His Gln
1               5                   10

```
<210> SEQ ID NO 113
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Arg Val Lys Leu Asp Gln Arg Arg Arg Pro
1               5                   10

<210> SEQ ID NO 114
<211> LENGTH: 18
<212> TYPE: PRT
<213> ORGANISM: Homo sapiens

<400> SEQUENCE: 114

Phe Lys Arg Lys His Lys Lys Asp Ile Ser Gln Asn Lys Arg Ala Val
1               5                   10                  15

Arg Arg

<210> SEQ ID NO 115
<211> LENGTH: 16
<212> TYPE: PRT
<213> ORGANISM: Human immunodeficiency virus

<400> SEQUENCE: 115

Arg Gln Ala Arg Arg Asn Arg Arg Arg Trp Arg Glu Arg Gln Arg
1               5                   10                  15

<210> SEQ ID NO 116
<211> LENGTH: 17
<212> TYPE: PRT
<213> ORGANISM: Human immunodeficiency virus

<400> SEQUENCE: 116

Arg Gln Ala Arg Arg Asn Arg Arg Arg Trp Arg Glu Arg Gln Arg
1               5                   10                  15

Gln

<210> SEQ ID NO 117
<211> LENGTH: 9
<212> TYPE: PRT
<213> ORGANISM: Unknown
<220> FEATURE:
<223> OTHER INFORMATION: Description of Unknown: Bovine, human
      beta type peptide

<400> SEQUENCE: 117

Phe Val Val His Lys Arg Cys His Glu
1               5

<210> SEQ ID NO 118
<211> LENGTH: 12
<212> TYPE: PRT
<213> ORGANISM: Unknown
<220> FEATURE:
<223> OTHER INFORMATION: Description of Unknown: Bovine, human
      beta type peptide

<400> SEQUENCE: 118

Asp Asp Pro Arg Ser Lys His Lys Phe Lys Ile His
1               5                   10

<210> SEQ ID NO 119
```

```
<211> LENGTH: 9
<212> TYPE: PRT
<213> ORGANISM: Unknown
<220> FEATURE:
<223> OTHER INFORMATION: Description of Unknown: Bovine, human
      beta type peptide

<400> SEQUENCE: 119

Thr Lys His Pro Gly Lys Arg Leu Gly
1               5

<210> SEQ ID NO 120
<211> LENGTH: 10
<212> TYPE: PRT
<213> ORGANISM: Unknown
<220> FEATURE:
<223> OTHER INFORMATION: Description of Unknown: Bovine, human
      gamma type peptide

<400> SEQUENCE: 120

Phe Val Val His Arg Arg Cys His Glu Phe
1               5                   10

<210> SEQ ID NO 121
<211> LENGTH: 12
<212> TYPE: PRT
<213> ORGANISM: Unknown
<220> FEATURE:
<223> OTHER INFORMATION: Description of Unknown: Bovine, human
      gamma type peptide

<400> SEQUENCE: 121

Asp Asp Pro Arg Asn Lys His Lys Phe Arg Leu His
1               5                   10

<210> SEQ ID NO 122
<211> LENGTH: 9
<212> TYPE: PRT
<213> ORGANISM: Unknown
<220> FEATURE:
<223> OTHER INFORMATION: Description of Unknown: Bovine, human
      gamma type peptide

<400> SEQUENCE: 122

Thr Lys His Pro Ala Lys Arg Leu Gly
1               5

<210> SEQ ID NO 123
<211> LENGTH: 9
<212> TYPE: PRT
<213> ORGANISM: Unknown
<220> FEATURE:
<223> OTHER INFORMATION: Description of Unknown: Rabbit type
      alpha and beta peptide

<400> SEQUENCE: 123

Phe Val Val His Lys Arg Cys His Glu
1               5

<210> SEQ ID NO 124
<211> LENGTH: 12
<212> TYPE: PRT
<213> ORGANISM: Unknown
<220> FEATURE:
<223> OTHER INFORMATION: Description of Unknown: Rabbit type
      alpha and beta peptide

<400> SEQUENCE: 124
```

```
Asp Asp Pro Arg Ser Lys His Lys Phe Lys Ile His
1               5                   10
```

<210> SEQ ID NO 125
<211> LENGTH: 9
<212> TYPE: PRT
<213> ORGANISM: Unknown
<220> FEATURE:
<223> OTHER INFORMATION: Description of Unknown: Rabbit type
      alpha and beta peptide

<400> SEQUENCE: 125

```
Thr Lys His Pro Gly Lys Arg Leu Gly
1               5
```

<210> SEQ ID NO 126
<211> LENGTH: 9
<212> TYPE: PRT
<213> ORGANISM: Rattus sp.

<400> SEQUENCE: 126

```
Phe Val Val His Arg Arg Cys His Glu
1               5
```

<210> SEQ ID NO 127
<211> LENGTH: 12
<212> TYPE: PRT
<213> ORGANISM: Rattus sp.

<400> SEQUENCE: 127

```
Asp Asp Pro Arg Asn Lys His Lys Phe Arg Leu His
1               5                   10
```

<210> SEQ ID NO 128
<211> LENGTH: 9
<212> TYPE: PRT
<213> ORGANISM: Rattus sp.

<400> SEQUENCE: 128

```
Thr Lys His Pro Gly Lys Arg Leu Gly
1               5
```

<210> SEQ ID NO 129
<211> LENGTH: 12
<212> TYPE: PRT
<213> ORGANISM: Drosophila melanogaster

<400> SEQUENCE: 129

```
Gly Glu Asn Lys Met Lys Ser Arg Leu Arg Lys Gly
1               5                   10
```

<210> SEQ ID NO 130
<211> LENGTH: 13
<212> TYPE: PRT
<213> ORGANISM: Drosophila melanogaster

<400> SEQUENCE: 130

```
Ser Tyr Val Val His Lys Arg Cys His Glu Tyr Val Thr
1               5                   10
```

<210> SEQ ID NO 131
<211> LENGTH: 15
<212> TYPE: PRT
<213> ORGANISM: Drosophila melanogaster

<400> SEQUENCE: 131

Pro Asp Asp Lys Asp Gln Ser Lys Lys Thr Arg Thr Ile Lys
1               5                   10                  15

<210> SEQ ID NO 132
<211> LENGTH: 14
<212> TYPE: PRT
<213> ORGANISM: Drosophila melanogaster

<400> SEQUENCE: 132

Pro Pro Phe Lys Pro Lys Ile Lys His Arg Lys Met Cys Pro
1               5                   10

<210> SEQ ID NO 133
<211> LENGTH: 8
<212> TYPE: PRT
<213> ORGANISM: Drosophila melanogaster

<400> SEQUENCE: 133

Val Val His Lys Arg Cys His Glu
1               5

<210> SEQ ID NO 134
<211> LENGTH: 8
<212> TYPE: PRT
<213> ORGANISM: Drosophila melanogaster

<400> SEQUENCE: 134

Val Val His Arg Arg Cys His Glu
1               5

<210> SEQ ID NO 135
<211> LENGTH: 21
<212> TYPE: PRT
<213> ORGANISM: Rattus sp.

<400> SEQUENCE: 135

Lys Lys Val Leu Gln Asp Lys Arg Phe Lys Asn Arg Glu Leu Gln Ile
1               5                   10                  15

Met Arg Lys Leu Asp
            20

<210> SEQ ID NO 136
<211> LENGTH: 12
<212> TYPE: PRT
<213> ORGANISM: Drosophila melanogaster

<400> SEQUENCE: 136

Leu Gln Asp Arg Arg Phe Lys Asn Arg Glu Leu Gln
1               5                   10

<210> SEQ ID NO 137
<211> LENGTH: 17
<212> TYPE: PRT
<213> ORGANISM: Rattus sp.

<400> SEQUENCE: 137

Glu Cys Leu Lys Lys Phe Asn Ala Arg Arg Lys Leu Lys Gly Ala Ile
1               5                   10                  15

Leu

<210> SEQ ID NO 138
<211> LENGTH: 18
<212> TYPE: PRT

<213> ORGANISM: Rattus sp.

<400> SEQUENCE: 138

Leu Lys Lys Phe Asn Ala Arg Arg Lys Leu Lys Gly Ala Ile Leu Thr
1               5                   10                  15
Thr Met

<210> SEQ ID NO 139
<211> LENGTH: 12
<212> TYPE: PRT
<213> ORGANISM: Rattus sp.

<400> SEQUENCE: 139

Glu Glu Thr Arg Val Trp His Arg Arg Asp Gly Lys
1               5                   10

<210> SEQ ID NO 140
<211> LENGTH: 15
<212> TYPE: PRT
<213> ORGANISM: Bos sp.

<400> SEQUENCE: 140

Gly Phe Ala Lys Arg Val Lys Gly Arg Thr Trp Thr Leu Cys Gly
1               5                   10                  15

<210> SEQ ID NO 141
<211> LENGTH: 15
<212> TYPE: PRT
<213> ORGANISM: Bos sp.

<400> SEQUENCE: 141

Gly Phe Ala Lys Arg Val Lys Gly Arg Thr Trp Thr Leu Cys Gly
1               5                   10                  15

<210> SEQ ID NO 142
<211> LENGTH: 19
<212> TYPE: PRT
<213> ORGANISM: Bos sp.

<400> SEQUENCE: 142

Glu Glu Glu Ile Gln Glu Leu Lys Arg Lys Leu His Lys Cys Gln Ser
1               5                   10                  15
Val Leu Pro

<210> SEQ ID NO 143
<211> LENGTH: 12
<212> TYPE: PRT
<213> ORGANISM: Bos sp.

<400> SEQUENCE: 143

Lys Ile Leu Lys Lys Arg His Ile Val Asp Thr Arg
1               5                   10

<210> SEQ ID NO 144
<211> LENGTH: 5
<212> TYPE: PRT
<213> ORGANISM: Bos sp.

<400> SEQUENCE: 144

Cys Gly Asp Pro Lys
1               5

<210> SEQ ID NO 145

```
<211> LENGTH: 10
<212> TYPE: PRT
<213> ORGANISM: Saccharomyces cerevisiae

<400> SEQUENCE: 145

Lys Thr Leu Lys Lys His Thr Ile Val Lys
1               5                   10

<210> SEQ ID NO 146
<211> LENGTH: 15
<212> TYPE: PRT
<213> ORGANISM: Saccharomyces cerevisiae

<400> SEQUENCE: 146

Glu Tyr Cys His Arg His Lys Ile Val His Arg Asp Leu Lys Pro
1               5                   10                  15

<210> SEQ ID NO 147
<211> LENGTH: 14
<212> TYPE: PRT
<213> ORGANISM: Saccharomyces cerevisiae

<400> SEQUENCE: 147

Pro Leu Val Thr Lys Lys Ser Lys Thr Arg Trp His Phe Gly
1               5                   10

<210> SEQ ID NO 148
<211> LENGTH: 12
<212> TYPE: PRT
<213> ORGANISM: Drosophila melanogaster

<400> SEQUENCE: 148

Pro Val Lys Lys Lys Lys Ile Lys Arg Glu Ile Lys
1               5                   10

<210> SEQ ID NO 149
<211> LENGTH: 14
<212> TYPE: PRT
<213> ORGANISM: Drosophila melanogaster

<400> SEQUENCE: 149

Asp Ile Leu Gln Arg His Ser Arg Lys Arg Trp Glu Arg Phe
1               5                   10

<210> SEQ ID NO 150
<211> LENGTH: 11
<212> TYPE: PRT
<213> ORGANISM: Drosophila melanogaster

<400> SEQUENCE: 150

Pro Lys Ser Ser Arg His His His Thr Asp Gly
1               5                   10

<210> SEQ ID NO 151
<211> LENGTH: 11
<212> TYPE: PRT
<213> ORGANISM: Bos sp.

<400> SEQUENCE: 151

Pro Lys Ser Ser Arg His His His Thr Asp Gly
1               5                   10

<210> SEQ ID NO 152
<211> LENGTH: 10
<212> TYPE: PRT
```

<213> ORGANISM: Saccharomyces cerevisiae

<400> SEQUENCE: 152

Pro Lys Gln Arg His Arg Lys Ser Leu Gly
1               5                   10

<210> SEQ ID NO 153
<211> LENGTH: 16
<212> TYPE: PRT
<213> ORGANISM: Saccharomyces cerevisiae

<400> SEQUENCE: 153

Gly Ser Met Cys Lys Val Lys Leu Ala Lys His Arg Tyr Thr Asn Glu
1               5                   10                  15

<210> SEQ ID NO 154
<211> LENGTH: 10
<212> TYPE: PRT
<213> ORGANISM: Saccharomyces cerevisiae

<400> SEQUENCE: 154

Asp Arg Lys His Ala Lys Ile Arg Asn Gln
1               5                   10

<210> SEQ ID NO 155
<211> LENGTH: 17
<212> TYPE: PRT
<213> ORGANISM: Saccharomyces cerevisiae

<400> SEQUENCE: 155

Gly Asn Ile Phe Arg Lys Leu Ser Gln Arg Arg Lys Lys Thr Ile Glu
1               5                   10                  15

Gln

<210> SEQ ID NO 156
<211> LENGTH: 13
<212> TYPE: PRT
<213> ORGANISM: Saccharomyces cerevisiae

<400> SEQUENCE: 156

Pro Pro Leu Asn Val Ala Lys Gly Arg Lys Leu His Pro
1               5                   10

<210> SEQ ID NO 157
<211> LENGTH: 11
<212> TYPE: PRT
<213> ORGANISM: Saccharomyces cerevisiae

<400> SEQUENCE: 157

Glu Leu Arg Gln Phe His Arg Arg Ser Leu Gly
1               5                   10

<210> SEQ ID NO 158
<211> LENGTH: 13
<212> TYPE: PRT
<213> ORGANISM: Saccharomyces cerevisiae

<400> SEQUENCE: 158

Gly Lys Val Lys Leu Val Lys His Arg Gln Thr Lys Glu
1               5                   10

<210> SEQ ID NO 159
<211> LENGTH: 14
<212> TYPE: PRT

<213> ORGANISM: Saccharomyces cerevisiae

<400> SEQUENCE: 159

Gly Ser Leu Lys Glu His His Ala Arg Lys Phe Ala Arg Gly
1               5                   10

<210> SEQ ID NO 160
<211> LENGTH: 11
<212> TYPE: PRT
<213> ORGANISM: Saccharomyces cerevisiae

<400> SEQUENCE: 160

Leu Ser Val Pro Lys Gly Arg Lys Leu His Pro
1               5                   10

<210> SEQ ID NO 161
<211> LENGTH: 13
<212> TYPE: PRT
<213> ORGANISM: Saccharomyces cerevisiae

<400> SEQUENCE: 161

Phe Leu Arg Arg Gly Ile Lys Lys Lys Leu Thr Leu Asp
1               5                   10

<210> SEQ ID NO 162
<211> LENGTH: 27
<212> TYPE: PRT
<213> ORGANISM: Saccharomyces cerevisiae

<400> SEQUENCE: 162

Pro Ser Lys Asp Asp Lys Phe Arg His Trp Cys Arg Lys Ile Lys Ser
1               5                   10                  15

Lys Ile Lys Glu Asp Lys Arg Ile Lys Arg Glu
            20                  25

<210> SEQ ID NO 163
<211> LENGTH: 12
<212> TYPE: PRT
<213> ORGANISM: Xenopus laevis

<400> SEQUENCE: 163

Gln Arg Arg Val Lys Lys Leu Pro Ser Thr Thr Leu
1               5                   10

<210> SEQ ID NO 164
<211> LENGTH: 12
<212> TYPE: PRT
<213> ORGANISM: Xenopus laevis

<400> SEQUENCE: 164

Gln Arg Arg Val Lys Lys Leu Pro Ser Ile Thr Leu
1               5                   10

<210> SEQ ID NO 165
<211> LENGTH: 12
<212> TYPE: PRT
<213> ORGANISM: Gallus sp.

<400> SEQUENCE: 165

Gln Arg Arg Val Lys Lys Leu Pro Ser Thr Thr Leu
1               5                   10

<210> SEQ ID NO 166
<211> LENGTH: 12

```
<212> TYPE: PRT
<213> ORGANISM: Mus sp.

<400> SEQUENCE: 166

Gln Arg Arg Val Arg Lys Leu Pro Ser Thr Thr Leu
1               5                   10

<210> SEQ ID NO 167
<211> LENGTH: 12
<212> TYPE: PRT
<213> ORGANISM: Homo sapiens

<400> SEQUENCE: 167

Gly Val Val Tyr Lys Gly Arg His Lys Thr Thr Gly
1               5                   10

<210> SEQ ID NO 168
<211> LENGTH: 14
<212> TYPE: PRT
<213> ORGANISM: Homo sapiens

<400> SEQUENCE: 168

Phe Cys His Ser Arg Arg Val Leu His Arg Asp Leu Lys Pro
1               5                   10

<210> SEQ ID NO 169
<211> LENGTH: 13
<212> TYPE: PRT
<213> ORGANISM: Schizosaccharomyces pombe

<400> SEQUENCE: 169

Gly Val Val Tyr Lys Ala Arg His Lys Leu Ser Gly Arg
1               5                   10

<210> SEQ ID NO 170
<211> LENGTH: 12
<212> TYPE: PRT
<213> ORGANISM: Homo sapiens

<400> SEQUENCE: 170

His Ser His Arg Val Leu His Arg Asp Leu Lys Pro
1               5                   10

<210> SEQ ID NO 171
<211> LENGTH: 14
<212> TYPE: PRT
<213> ORGANISM: Xenopus laevis

<400> SEQUENCE: 171

Phe Cys His Ser His Arg Val Leu His Arg Asp Leu Lys Pro
1               5                   10

<210> SEQ ID NO 172
<211> LENGTH: 17
<212> TYPE: PRT
<213> ORGANISM: Saccharomyces cerevisiae

<400> SEQUENCE: 172

Gly Ile Ala Tyr Cys His Ser His Arg Ile Leu His Arg Asp Leu Lys
1               5                   10                  15

Pro

<210> SEQ ID NO 173
<211> LENGTH: 12
```

```
<212> TYPE: PRT
<213> ORGANISM: Homo sapiens

<400> SEQUENCE: 173

His Ser His Arg Val Ile His Arg Asp Leu Lys Pro
1               5                   10

<210> SEQ ID NO 174
<211> LENGTH: 10
<212> TYPE: PRT
<213> ORGANISM: Homo sapiens

<400> SEQUENCE: 174

Lys Glu Leu Lys His Lys Asn Ile Val Arg
1               5                   10

<210> SEQ ID NO 175
<211> LENGTH: 7
<212> TYPE: PRT
<213> ORGANISM: Homo sapiens

<400> SEQUENCE: 175

Pro Ser Ser Ala Leu Arg Glu
1               5

<210> SEQ ID NO 176
<211> LENGTH: 10
<212> TYPE: PRT
<213> ORGANISM: Homo sapiens

<400> SEQUENCE: 176

Met Asp Arg Met Lys Lys Ile Lys Arg Gln
1               5                   10

<210> SEQ ID NO 177
<211> LENGTH: 11
<212> TYPE: PRT
<213> ORGANISM: Homo sapiens

<400> SEQUENCE: 177

Asp Lys Pro Leu Ser Arg Arg Leu Arg Arg Val
1               5                   10

<210> SEQ ID NO 178
<211> LENGTH: 7
<212> TYPE: PRT
<213> ORGANISM: Homo sapiens

<400> SEQUENCE: 178

Met Lys Lys Phe Lys Arg Arg
1               5

<210> SEQ ID NO 179
<211> LENGTH: 9
<212> TYPE: PRT
<213> ORGANISM: Homo sapiens

<400> SEQUENCE: 179

Arg Asn Arg Ile His Arg Arg Ile Ser
1               5

<210> SEQ ID NO 180
<211> LENGTH: 8
<212> TYPE: PRT
<213> ORGANISM: Homo sapiens
```

```
<400> SEQUENCE: 180

Ser Arg Arg Ser Arg Arg Ala Ser
1               5

<210> SEQ ID NO 181
<211> LENGTH: 8
<212> TYPE: PRT
<213> ORGANISM: Homo sapiens

<400> SEQUENCE: 181

His Arg Arg Lys Val Leu His Arg
1               5

<210> SEQ ID NO 182
<211> LENGTH: 12
<212> TYPE: PRT
<213> ORGANISM: Homo sapiens

<400> SEQUENCE: 182

Gly His Gly Lys Asn Arg Arg Gln Ser Met Leu Phe
1               5                   10

<210> SEQ ID NO 183
<211> LENGTH: 8
<212> TYPE: PRT
<213> ORGANISM: Homo sapiens

<400> SEQUENCE: 183

His Thr Arg Lys Ile Leu His Arg
1               5

<210> SEQ ID NO 184
<211> LENGTH: 12
<212> TYPE: PRT
<213> ORGANISM: Homo sapiens

<400> SEQUENCE: 184

Pro Gly Arg Gly Lys Asn Arg Arg Gln Ser Ile Phe
1               5                   10

<210> SEQ ID NO 185
<211> LENGTH: 10
<212> TYPE: PRT
<213> ORGANISM: Homo sapiens

<400> SEQUENCE: 185

Glu Val Phe Arg Arg Lys Arg Arg Leu His
1               5                   10

<210> SEQ ID NO 186
<211> LENGTH: 15
<212> TYPE: PRT
<213> ORGANISM: Homo sapiens

<400> SEQUENCE: 186

Asp Lys Pro Thr Arg Lys Thr Leu Arg Lys Ser Arg Lys His His
1               5                   10                  15

<210> SEQ ID NO 187
<211> LENGTH: 7
<212> TYPE: PRT
<213> ORGANISM: Homo sapiens

<400> SEQUENCE: 187
```

Lys Lys Ile Ala Leu Arg Glu
1               5

<210> SEQ ID NO 188
<211> LENGTH: 8
<212> TYPE: PRT
<213> ORGANISM: Schizosaccharomyces pombe

<400> SEQUENCE: 188

Met Val Lys Arg His Lys Asn Thr
1               5

<210> SEQ ID NO 189
<211> LENGTH: 13
<212> TYPE: PRT
<213> ORGANISM: Schizosaccharomyces pombe

<400> SEQUENCE: 189

Asp Gly Glu Leu Phe His Tyr Ile Arg Lys His Gly Pro
1               5                   10

<210> SEQ ID NO 190
<211> LENGTH: 15
<212> TYPE: PRT
<213> ORGANISM: Schizosaccharomyces pombe

<400> SEQUENCE: 190

Asp Ala Val Ala His Cys His Arg Phe Arg Phe Arg His Arg Asp
1               5                   10                  15

<210> SEQ ID NO 191
<211> LENGTH: 17
<212> TYPE: PRT
<213> ORGANISM: Schizosaccharomyces pombe

<400> SEQUENCE: 191

Lys Lys Ser Ser Ser Lys Lys Val Val Arg Arg Leu Gln Gln Arg Asp
1               5                   10                  15
Asp

<210> SEQ ID NO 192
<211> LENGTH: 12
<212> TYPE: PRT
<213> ORGANISM: Schizosaccharomyces pombe

<400> SEQUENCE: 192

Pro Ala Gln Lys Leu Arg Lys Lys Asn Asn Phe Asp
1               5                   10

<210> SEQ ID NO 193
<211> LENGTH: 16
<212> TYPE: PRT
<213> ORGANISM: Schizosaccharomyces pombe

<400> SEQUENCE: 193

Lys Gln His Arg Pro Arg Lys Asn Thr Asn Phe Thr Pro Leu Pro Pro
1               5                   10                  15

<210> SEQ ID NO 194
<211> LENGTH: 14
<212> TYPE: PRT
<213> ORGANISM: Schizosaccharomyces pombe

<400> SEQUENCE: 194

```
Lys Tyr Ala Val Lys Lys Leu Lys Val Lys Phe Ser Gly Pro
1               5                   10

<210> SEQ ID NO 195
<211> LENGTH: 14
<212> TYPE: PRT
<213> ORGANISM: Saccharomyces cerevisiae

<400> SEQUENCE: 195

Pro Asn Glu Thr Arg Arg Ile Lys Arg Ala Asn Arg Ala Gly
1               5                   10

<210> SEQ ID NO 196
<211> LENGTH: 13
<212> TYPE: PRT
<213> ORGANISM: Rattus sp.

<400> SEQUENCE: 196

Tyr Asp His Val Arg Lys Thr Arg Val Ala Ile Lys Lys
1               5                   10

<210> SEQ ID NO 197
<211> LENGTH: 8
<212> TYPE: PRT
<213> ORGANISM: Saccharomyces cerevisiae

<400> SEQUENCE: 197

Ile Leu Lys His Phe Lys His Glu
1               5

<210> SEQ ID NO 198
<211> LENGTH: 10
<212> TYPE: PRT
<213> ORGANISM: Saccharomyces cerevisiae

<400> SEQUENCE: 198

Gln Ile Lys Ser Lys Arg Ala Lys Glu Tyr
1               5                   10

<210> SEQ ID NO 199
<211> LENGTH: 12
<212> TYPE: PRT
<213> ORGANISM: Saccharomyces cerevisiae

<400> SEQUENCE: 199

Glu Leu Val Lys His Leu Val Lys His Gly Ser Asn
1               5                   10

<210> SEQ ID NO 200
<211> LENGTH: 11
<212> TYPE: PRT
<213> ORGANISM: Saccharomyces cerevisiae

<400> SEQUENCE: 200

Gly Lys Ala Lys Lys Ile Arg Ser Gln Leu Leu
1               5                   10

<210> SEQ ID NO 201
<211> LENGTH: 15
<212> TYPE: PRT
<213> ORGANISM: Schizosaccharomyces pombe

<400> SEQUENCE: 201

Glu Gln Arg Leu Lys Arg His Arg Ile Asp Val Ser Asp Glu Asp
```

```
1               5                   10                  15

<210> SEQ ID NO 202
<211> LENGTH: 11
<212> TYPE: PRT
<213> ORGANISM: Schizosaccharomyces pombe

<400> SEQUENCE: 202

Ser Asn Ile Lys Ser Lys Cys Arg Arg Val Val
1               5                   10

<210> SEQ ID NO 203
<211> LENGTH: 8
<212> TYPE: PRT
<213> ORGANISM: Saccharomyces cerevisiae

<400> SEQUENCE: 203

Pro Pro Lys Arg Ile Arg Thr Asp
1               5

<210> SEQ ID NO 204
<211> LENGTH: 9
<212> TYPE: PRT
<213> ORGANISM: Saccharomyces cerevisiae

<400> SEQUENCE: 204

Lys Leu Ala Arg Lys Gln Lys Arg Pro
1               5

<210> SEQ ID NO 205
<211> LENGTH: 13
<212> TYPE: PRT
<213> ORGANISM: Unknown
<220> FEATURE:
<223> OTHER INFORMATION: Description of Unknown: Rabbit
      peptide

<400> SEQUENCE: 205

Gly Val Ser Ser Val Val Arg Arg Cys Ile His Lys Pro
1               5                   10

<210> SEQ ID NO 206
<211> LENGTH: 16
<212> TYPE: PRT
<213> ORGANISM: Gallus sp.

<400> SEQUENCE: 206

Lys Lys Tyr Met Ala Arg Arg Lys Trp Gln Lys Thr Gly His Ala Val
1               5                   10                  15

<210> SEQ ID NO 207
<211> LENGTH: 20
<212> TYPE: PRT
<213> ORGANISM: Unknown
<220> FEATURE:
<223> OTHER INFORMATION: Description of Unknown: Rabbit
      peptide

<400> SEQUENCE: 207

Pro Trp Leu Asn Asn Leu Ala Glu Lys Ala Lys Arg Cys Asn Arg Arg
1               5                   10                  15

Leu Lys Ser Gln
            20

<210> SEQ ID NO 208
```

```
<211> LENGTH: 20
<212> TYPE: PRT
<213> ORGANISM: Unknown
<220> FEATURE:
<223> OTHER INFORMATION: Description of Unknown: Rabbit
      peptide

<400> SEQUENCE: 208

Ile Leu Leu Lys Lys Tyr Leu Met Lys Arg Arg Trp Lys Lys Asn Phe
1               5                   10                  15

Ile Ala Val Ser
            20

<210> SEQ ID NO 209
<211> LENGTH: 13
<212> TYPE: PRT
<213> ORGANISM: Mus sp.

<400> SEQUENCE: 209

Gly Val Ser Ser Val Val Arg Arg Cys Ile His Lys Pro
1               5                   10

<210> SEQ ID NO 210
<211> LENGTH: 22
<212> TYPE: PRT
<213> ORGANISM: Unknown
<220> FEATURE:
<223> OTHER INFORMATION: Description of Unknown: DBD peptide

<400> SEQUENCE: 210

Met Asp Pro Gly Lys Asp Lys Glu Gly Val Pro Gln Pro Ser Gly Pro
1               5                   10                  15

Pro Ala Arg Lys Lys Phe
            20

<210> SEQ ID NO 211
<211> LENGTH: 15
<212> TYPE: PRT
<213> ORGANISM: Unknown
<220> FEATURE:
<223> OTHER INFORMATION: Description of Unknown: DNA helicase
      component of TFIIH, essential for
      cell viability peptide

<400> SEQUENCE: 211

Asp Lys Arg Phe Ala Arg Gly Asp Lys Arg Gly Lys Leu Pro Arg
1               5                   10                  15

<210> SEQ ID NO 212
<211> LENGTH: 16
<212> TYPE: PRT
<213> ORGANISM: Unknown
<220> FEATURE:
<223> OTHER INFORMATION: Description of Unknown: Helicase,
      component of TFIIH essential for
      cell viability peptide

<400> SEQUENCE: 212

Asp Arg Asp Lys Lys Lys Ser Arg Lys Arg His Tyr Glu Asp Glu Glu
1               5                   10                  15

<210> SEQ ID NO 213
<211> LENGTH: 15
<212> TYPE: PRT
<213> ORGANISM: Unknown
<220> FEATURE:
<223> OTHER INFORMATION: Description of Unknown: Helicase,
``` component of TFIIH essential for
cell viability peptide

<400> SEQUENCE: 213

Tyr Val Ala Ile Lys Thr Lys Arg Ile Leu Leu Tyr Thr Met
1               5                   10                  15

<210> SEQ ID NO 214
<211> LENGTH: 14
<212> TYPE: PRT
<213> ORGANISM: Unknown
<220> FEATURE:
<223> OTHER INFORMATION: Description of Unknown: Helicase,
      component of TFIIH essential for
      cell viability peptide

<400> SEQUENCE: 214

Pro Ser Lys His Val His Pro Leu Phe Lys Arg Phe Arg Lys
1               5                   10

<210> SEQ ID NO 215
<211> LENGTH: 13
<212> TYPE: PRT
<213> ORGANISM: Unknown
<220> FEATURE:
<223> OTHER INFORMATION: Description of Unknown: Human,
      Xenopus laevis peptide

<400> SEQUENCE: 215

Lys Lys Gln Thr Leu Val Lys Arg Arg Gln Arg Lys Asp
1               5                   10

<210> SEQ ID NO 216
<211> LENGTH: 9
<212> TYPE: PRT
<213> ORGANISM: Unknown
<220> FEATURE:
<223> OTHER INFORMATION: Description of Unknown: Human,
      Xenopus laevis peptide

<400> SEQUENCE: 216

Glu Phe Thr Lys Arg Arg Arg Thr Leu
1               5

<210> SEQ ID NO 217
<211> LENGTH: 13
<212> TYPE: PRT
<213> ORGANISM: Unknown
<220> FEATURE:
<223> OTHER INFORMATION: Description of Unknown: Human,
      Xenopus laevis peptide

<400> SEQUENCE: 217

Asp Glu Ser Met Ile Lys Asp Arg Lys Asp Arg Leu Pro
1               5                   10

<210> SEQ ID NO 218
<211> LENGTH: 17
<212> TYPE: PRT
<213> ORGANISM: Unknown
<220> FEATURE:
<223> OTHER INFORMATION: Description of Unknown: Human,
      Xenopus laevis peptide

<400> SEQUENCE: 218

Gly Lys Lys Arg Arg Lys Leu Arg Arg Ala Arg Gly Arg Lys Arg Lys
1               5                   10                  15

Thr

```
<210> SEQ ID NO 219
<211> LENGTH: 18
<212> TYPE: PRT
<213> ORGANISM: Unknown
<220> FEATURE:
<223> OTHER INFORMATION: Description of Unknown: Involved
      in the preferential repair of
      active genes peptide

<400> SEQUENCE: 219
```

Pro Gln Lys Gln Glu Lys Lys Pro Arg Lys Ile Met Leu Asn Glu Ala
1               5                   10                  15

Ser Gly

```
<210> SEQ ID NO 220
<211> LENGTH: 25
<212> TYPE: PRT
<213> ORGANISM: Unknown
<220> FEATURE:
<223> OTHER INFORMATION: Description of Unknown: Involved
      in the preferential repair of
      active genes peptide

<400> SEQUENCE: 220
```

Pro Asn Lys Lys Ala Arg Val Leu Ser Lys Lys Glu Glu Arg Leu Lys
1               5                   10                  15

Lys His Ile Lys Lys Leu Gln Lys Arg
            20                  25

```
<210> SEQ ID NO 221
<211> LENGTH: 13
<212> TYPE: PRT
<213> ORGANISM: Unknown
<220> FEATURE:
<223> OTHER INFORMATION: Description of Unknown: Involved
      in the preferential repair of
      active genes peptide

<400> SEQUENCE: 221
```

Pro Leu Pro Lys Gly Gly Lys Arg Gln Lys Lys Val Pro
1               5                   10

```
<210> SEQ ID NO 222
<211> LENGTH: 36
<212> TYPE: PRT
<213> ORGANISM: Unknown
<220> FEATURE:
<223> OTHER INFORMATION: Description of Unknown: Involved
      in the preferential repair of
      active genes peptide

<400> SEQUENCE: 222
```

Asp Gly Asp Glu Asp Tyr Tyr Lys Gln Arg Leu Arg Arg Trp Asn Lys
1               5                   10                  15

Leu Arg Leu Gln Asp Lys Glu Lys Arg Leu Lys Leu Glu Asp Asp Ser
            20                  25                  30

Glu Glu Ser Asp
        35

```
<210> SEQ ID NO 223
<211> LENGTH: 30
<212> TYPE: PRT
<213> ORGANISM: Unknown
<220> FEATURE:
```

<223> OTHER INFORMATION: Description of Unknown: Involved
      in the preferential repair of
      active genes peptide
<220> FEATURE:
<221> NAME/KEY: MOD_RES
<222> LOCATION: (16)..(23)
<223> OTHER INFORMATION: Any amino acid

<400> SEQUENCE: 223

Asp Val Gln Thr Pro Lys Cys His Leu Lys Arg Arg Ile Gln Pro Xaa
1               5                   10                  15

Xaa Xaa Xaa Xaa Xaa Xaa Xaa Pro Lys Arg Lys Lys Phe Pro
            20                  25                  30

<210> SEQ ID NO 224
<211> LENGTH: 52
<212> TYPE: PRT
<213> ORGANISM: Unknown
<220> FEATURE:
<223> OTHER INFORMATION: Description of Unknown: Involved
      in the preferential repair of
      active genes peptide
<220> FEATURE:
<221> NAME/KEY: MOD_RES
<222> LOCATION: (29)..(43)
<223> OTHER INFORMATION: Any amino acid

<400> SEQUENCE: 224

Lys His Lys Ser Lys Thr Lys His His Ser Val Ala Glu Glu Thr
1               5                   10                  15

Leu Glu Lys His Leu Arg Pro Lys Gln Lys Pro Lys Xaa Xaa Xaa Xaa
            20                  25                  30

Xaa Xaa Xaa Xaa Xaa Xaa Xaa Xaa Xaa Xaa Xaa Pro His Leu Val Lys
        35                  40                  45

Lys Arg Arg Tyr
        50

<210> SEQ ID NO 225
<211> LENGTH: 13
<212> TYPE: PRT
<213> ORGANISM: Unknown
<220> FEATURE:
<223> OTHER INFORMATION: Description of Unknown: Involved
      in the preferential repair of
      active genes peptide

<400> SEQUENCE: 225

Pro Ala Gly Lys Lys Ser Arg Phe Gly Lys Lys Arg Asn
1               5                   10

<210> SEQ ID NO 226
<211> LENGTH: 22
<212> TYPE: PRT
<213> ORGANISM: Unknown
<220> FEATURE:
<223> OTHER INFORMATION: Description of Unknown: Zinc
      finger domain peptide

<400> SEQUENCE: 226

Pro Ala Ser Val Arg Ala Ser Ile Glu Arg Lys Arg Gln Arg Ala Leu
1               5                   10                  15

Met Leu Arg Gly Ala Arg
            20

<210> SEQ ID NO 227
<211> LENGTH: 18

-continued

```
<212> TYPE: PRT
<213> ORGANISM: Unknown
<220> FEATURE:
<223> OTHER INFORMATION: Description of Unknown: Zinc
      finger domain peptide

<400> SEQUENCE: 227

Pro Pro Leu Lys Phe Ile Val Lys Lys Asn Pro His His Ser Gln Trp
1               5                   10                  15

Gly Asp

<210> SEQ ID NO 228
<211> LENGTH: 16
<212> TYPE: PRT
<213> ORGANISM: Unknown
<220> FEATURE:
<223> OTHER INFORMATION: Description of Unknown: Zinc
      finger domain peptide

<400> SEQUENCE: 228

Asn Arg Glu Lys Met Lys Gln Lys Lys Phe Asp Lys Lys Val Lys Glu
1               5                   10                  15

<210> SEQ ID NO 229
<211> LENGTH: 10
<212> TYPE: PRT
<213> ORGANISM: Unknown
<220> FEATURE:
<223> OTHER INFORMATION: Description of Unknown: Hydrophilic
      peptide

<400> SEQUENCE: 229

Tyr Leu Arg Arg Ala Met Lys Arg Phe Asn
1               5                   10

<210> SEQ ID NO 230
<211> LENGTH: 28
<212> TYPE: PRT
<213> ORGANISM: Unknown
<220> FEATURE:
<223> OTHER INFORMATION: Description of Unknown: Hydrophilic
      peptide

<400> SEQUENCE: 230

Pro Ser Ala Lys Gly Lys Arg Asn Lys Gly Gly Arg Lys Lys Arg Ser
1               5                   10                  15

Lys Pro Ser Ser Ser Glu Glu Asp Glu Gly Pro Gly
            20                  25

<210> SEQ ID NO 231
<211> LENGTH: 10
<212> TYPE: PRT
<213> ORGANISM: Unknown
<220> FEATURE:
<223> OTHER INFORMATION: Description of Unknown: Hydrophilic
      peptide

<400> SEQUENCE: 231

Gln Arg Arg Pro His Gly Arg Glu Arg Arg
1               5                   10

<210> SEQ ID NO 232
<211> LENGTH: 11
<212> TYPE: PRT
<213> ORGANISM: Unknown
<220> FEATURE:
<223> OTHER INFORMATION: Description of Unknown: Hydrophilic
```

```
                                peptide

<400> SEQUENCE: 232

Arg Thr His Arg Gly Ser His Arg Lys Asp Pro
1               5                   10

<210> SEQ ID NO 233
<211> LENGTH: 17
<212> TYPE: PRT
<213> ORGANISM: Unknown
<220> FEATURE:
<223> OTHER INFORMATION: Description of Unknown: Hydrophilic
      peptide

<400> SEQUENCE: 233

Ser Ser Ser Ser Ser Ser Ser Lys Arg Gly Lys Lys Met Cys Ser Asp
1               5                   10                  15

Gly

<210> SEQ ID NO 234
<211> LENGTH: 10
<212> TYPE: PRT
<213> ORGANISM: Unknown
<220> FEATURE:
<223> OTHER INFORMATION: Description of Unknown: Hydrophilic
      peptide

<400> SEQUENCE: 234

Ala Leu Lys Arg His Leu Leu Lys Tyr Glu
1               5                   10

<210> SEQ ID NO 235
<211> LENGTH: 12
<212> TYPE: PRT
<213> ORGANISM: Unknown
<220> FEATURE:
<223> OTHER INFORMATION: Description of Unknown: Hydrophilic
      peptide

<400> SEQUENCE: 235

Ser Asn Arg Ala Arg Lys Ala Arg Leu Ala Glu Pro
1               5                   10

<210> SEQ ID NO 236
<211> LENGTH: 11
<212> TYPE: PRT
<213> ORGANISM: Unknown
<220> FEATURE:
<223> OTHER INFORMATION: Description of Unknown: Hydrophilic
      peptide

<400> SEQUENCE: 236

Pro Asn Leu His Arg Val Ala Arg Lys Leu Asp
1               5                   10

<210> SEQ ID NO 237
<211> LENGTH: 11
<212> TYPE: PRT
<213> ORGANISM: Unknown
<220> FEATURE:
<223> OTHER INFORMATION: Description of Unknown: Hydrophilic
      peptide

<400> SEQUENCE: 237

Glu Arg Lys Glu Lys Glu Lys Lys Glu Lys Arg
1               5                   10
```

```
<210> SEQ ID NO 238
<211> LENGTH: 10
<212> TYPE: PRT
<213> ORGANISM: Unknown
<220> FEATURE:
<223> OTHER INFORMATION: Description of Unknown: Hydrophilic
      peptide

<400> SEQUENCE: 238

Ile Arg Glu Arg Leu Lys Arg Arg Tyr Gly
1               5                   10

<210> SEQ ID NO 239
<211> LENGTH: 11
<212> TYPE: PRT
<213> ORGANISM: Unknown
<220> FEATURE:
<223> OTHER INFORMATION: Description of Unknown: Hydrophilic
      peptide

<400> SEQUENCE: 239

Gly Gly Pro Lys Lys Thr Lys Arg Glu Arg Lys
1               5                   10

<210> SEQ ID NO 240
<211> LENGTH: 16
<212> TYPE: PRT
<213> ORGANISM: Unknown
<220> FEATURE:
<223> OTHER INFORMATION: Description of Unknown: XPC gene
      product peptide

<400> SEQUENCE: 240

Lys Ser Lys Ala Lys Ser Lys Ala Arg Arg Glu Glu Glu Glu Glu Asp
1               5                   10                  15

<210> SEQ ID NO 241
<211> LENGTH: 6
<212> TYPE: PRT
<213> ORGANISM: Unknown
<220> FEATURE:
<223> OTHER INFORMATION: Description of Unknown: XPC gene
      product peptide

<400> SEQUENCE: 241

Gly Lys Arg Lys Arg Gly
1               5

<210> SEQ ID NO 242
<211> LENGTH: 13
<212> TYPE: PRT
<213> ORGANISM: Unknown
<220> FEATURE:
<223> OTHER INFORMATION: Description of Unknown: XPC gene
      product peptide

<400> SEQUENCE: 242

Gly Pro Ala Lys Lys Lys Val Ala Lys Val Thr Val Lys
1               5                   10

<210> SEQ ID NO 243
<211> LENGTH: 13
<212> TYPE: PRT
<213> ORGANISM: Unknown
<220> FEATURE:
<223> OTHER INFORMATION: Description of Unknown: XPC gene
      product peptide
```

```
<400> SEQUENCE: 243

Pro Ser Asp Leu Lys Lys Ala His His Leu Lys Arg Gly
1               5                   10

<210> SEQ ID NO 244
<211> LENGTH: 27
<212> TYPE: PRT
<213> ORGANISM: Unknown
<220> FEATURE:
<223> OTHER INFORMATION: Description of Unknown: Mismatch
      repair peptide

<400> SEQUENCE: 244

Glu Ile Asp Arg Arg Lys Lys Arg Pro Leu Glu Asn Asp Gly Pro Val
1               5                   10                  15

Lys Lys Lys Val Lys Lys Val Gln Gln Lys Glu
            20                  25

<210> SEQ ID NO 245
<211> LENGTH: 10
<212> TYPE: PRT
<213> ORGANISM: Unknown
<220> FEATURE:
<223> OTHER INFORMATION: Description of Unknown: Mismatch
      repair peptide

<400> SEQUENCE: 245

Lys Glu Asn Val Arg Asp Lys Lys Lys Gly
1               5                   10

<210> SEQ ID NO 246
<211> LENGTH: 11
<212> TYPE: PRT
<213> ORGANISM: Unknown
<220> FEATURE:
<223> OTHER INFORMATION: Description of Unknown: Mismatch
      repair peptide

<400> SEQUENCE: 246

Phe Gly Arg Arg Lys Leu Lys Lys Trp Val Thr
1               5                   10

<210> SEQ ID NO 247
<211> LENGTH: 12
<212> TYPE: PRT
<213> ORGANISM: Unknown
<220> FEATURE:
<223> OTHER INFORMATION: Description of Unknown: Mismatch
      repair peptide

<400> SEQUENCE: 247

Pro Leu Ile Lys Lys Arg Lys Asp Glu Ile Gln Gly
1               5                   10

<210> SEQ ID NO 248
<211> LENGTH: 21
<212> TYPE: PRT
<213> ORGANISM: Unknown
<220> FEATURE:
<223> OTHER INFORMATION: Description of Unknown: Mismatch
      repair peptide

<400> SEQUENCE: 248

Lys Glu Leu Glu Gly Leu Ile Asn Thr Lys Arg Lys Arg Leu Lys Tyr
1               5                   10                  15

Phe Ala Lys Leu Trp
```

<210> SEQ ID NO 249
<211> LENGTH: 11
<212> TYPE: PRT
<213> ORGANISM: Homo sapiens

<400> SEQUENCE: 249

Glu Lys His Glu Gly Lys His Gln Lys Leu Leu
1               5                   10

<210> SEQ ID NO 250
<211> LENGTH: 14
<212> TYPE: PRT
<213> ORGANISM: Saccharomyces cerevisiae

<400> SEQUENCE: 250

Pro Asp Ile Arg Arg Leu Thr Lys Lys Leu Asn Lys Arg Gly
1               5                   10

<210> SEQ ID NO 251
<211> LENGTH: 13
<212> TYPE: PRT
<213> ORGANISM: Saccharomyces cerevisiae

<400> SEQUENCE: 251

Asp Ala Lys Glu Leu Arg Lys His Lys Lys Tyr Ile Glu
1               5                   10

<210> SEQ ID NO 252
<211> LENGTH: 10
<212> TYPE: PRT
<213> ORGANISM: Saccharomyces cerevisiae

<400> SEQUENCE: 252

Val Lys Met Ala Lys Arg Lys Ala Asn Glu
1               5                   10

<210> SEQ ID NO 253
<211> LENGTH: 14
<212> TYPE: PRT
<213> ORGANISM: Unknown
<220> FEATURE:
<223> OTHER INFORMATION: Description of Unknown: Human,
      Schizosaccharomyces pombe peptide

<400> SEQUENCE: 253

Gly Glu Leu Ala Lys Arg Ser Glu Arg Arg Ala Glu Ala Glu
1               5                   10

<210> SEQ ID NO 254
<211> LENGTH: 18
<212> TYPE: PRT
<213> ORGANISM: Unknown
<220> FEATURE:
<223> OTHER INFORMATION: Description of Unknown: Human,
      Schizosaccharomyces pombe peptide

<400> SEQUENCE: 254

Lys Arg Lys Glu Pro Glu Pro Lys Gly Ser Thr Lys Lys Ala Lys
1               5                   10                  15

Thr Gly

<210> SEQ ID NO 255
<211> LENGTH: 7

```
<212> TYPE: PRT
<213> ORGANISM: Unknown
<220> FEATURE:
<223> OTHER INFORMATION: Description of Unknown: Human,
      Schizosaccharomyces pombe peptide

<400> SEQUENCE: 255

Gly Lys Phe Lys Arg Gly Lys
1               5

<210> SEQ ID NO 256
<211> LENGTH: 13
<212> TYPE: PRT
<213> ORGANISM: Unknown
<220> FEATURE:
<223> OTHER INFORMATION: Description of Unknown: RPA
      peptide

<400> SEQUENCE: 256

Pro Ser Gln Ala Glu Lys Lys Ser Arg Ala Arg Ala Gln
1               5                   10

<210> SEQ ID NO 257
<211> LENGTH: 10
<212> TYPE: PRT
<213> ORGANISM: Unknown
<220> FEATURE:
<223> OTHER INFORMATION: Description of Unknown: Altered
      in XPC cells peptide

<400> SEQUENCE: 257

Gly Ala Lys Lys Arg Lys Ile Asp Asp Ala
1               5                   10

<210> SEQ ID NO 258
<211> LENGTH: 8
<212> TYPE: PRT
<213> ORGANISM: Bos sp.

<400> SEQUENCE: 258

Pro Lys Lys Pro Arg Gly Lys Met
1               5

<210> SEQ ID NO 259
<211> LENGTH: 7
<212> TYPE: PRT
<213> ORGANISM: Bos sp.

<400> SEQUENCE: 259

Glu His Lys Lys Lys His Pro
1               5

<210> SEQ ID NO 260
<211> LENGTH: 9
<212> TYPE: PRT
<213> ORGANISM: Bos sp.

<400> SEQUENCE: 260

Glu Thr Lys Lys Lys Phe Lys Asp Pro
1               5

<210> SEQ ID NO 261
<211> LENGTH: 48
<212> TYPE: PRT
<213> ORGANISM: Bos sp.
<220> FEATURE:
<221> NAME/KEY: MOD_RES
```

```
<222> LOCATION: (8)..(48)
<223> OTHER INFORMATION: Glu or Asp

<400> SEQUENCE: 261

Glu Lys Ser Lys Lys Lys Lys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

<210> SEQ ID NO 262
<211> LENGTH: 13
<212> TYPE: PRT
<213> ORGANISM: Bos sp.

<400> SEQUENCE: 262

Glu Glu Glu Gly Gly Lys Lys Lys Lys Lys Phe Ala Lys
1               5                   10

<210> SEQ ID NO 263
<211> LENGTH: 26
<212> TYPE: PRT
<213> ORGANISM: Unknown
<220> FEATURE:
<223> OTHER INFORMATION: Description of Unknown: Structure-specific
      recognition 1 peptide

<400> SEQUENCE: 263

Arg Asp Glu Lys Lys Arg Lys Gln Leu Lys Lys Ala Lys Ala Lys Met
1               5                   10                  15

Ala Lys Asp Arg Lys Ser Arg Lys Lys Pro
            20                  25

<210> SEQ ID NO 264
<211> LENGTH: 22
<212> TYPE: PRT
<213> ORGANISM: Unknown
<220> FEATURE:
<223> OTHER INFORMATION: Description of Unknown: Structure-specific
      recognition 1 peptide

<400> SEQUENCE: 264

Gly Glu Ser Ser Lys Arg Asp Lys Ser Lys Lys Lys Lys Val Lys
1               5                   10                  15

Val Lys Met Glu Lys Lys
            20

<210> SEQ ID NO 265
<211> LENGTH: 19
<212> TYPE: PRT
<213> ORGANISM: Unknown
<220> FEATURE:
<223> OTHER INFORMATION: Description of Unknown: Structure-specific
      recognition 1 peptide

<400> SEQUENCE: 265

Gly Glu Asn Lys Ser Lys Lys Lys Arg Arg Arg Ser Glu Asp Ser Glu
1               5                   10                  15

Glu Glu Glu

<210> SEQ ID NO 266
<211> LENGTH: 8
<212> TYPE: PRT
```

<213> ORGANISM: Unknown
<220> FEATURE:
<223> OTHER INFORMATION: Description of Unknown: Redox factor
      1 from HeLa cells peptide

<400> SEQUENCE: 266

Met Pro Lys Arg Gly Lys Lys Gly
1               5

<210> SEQ ID NO 267
<211> LENGTH: 8
<212> TYPE: PRT
<213> ORGANISM: Unknown
<220> FEATURE:
<223> OTHER INFORMATION: Description of Unknown: Apurinic/
      apyrimidinic (AP)-endonuclease
      peptide

<400> SEQUENCE: 267

Met Pro Lys Arg Gly Lys Lys Gly
1               5

<210> SEQ ID NO 268
<211> LENGTH: 26
<212> TYPE: PRT
<213> ORGANISM: Drosophila melanogaster

<400> SEQUENCE: 268

Met Gly Pro Pro Lys Lys Ser Arg Lys Asp Arg Ser Gly Gly Asp Lys
1               5                   10                  15

Phe Gly Lys Lys Arg Arg Gly Gln Asp Glu
            20                  25

<210> SEQ ID NO 269
<211> LENGTH: 16
<212> TYPE: PRT
<213> ORGANISM: Drosophila melanogaster

<400> SEQUENCE: 269

Glu Met Ser Tyr Ser Arg Lys Arg Gln Arg Phe Leu Val Asn Gln Gly
1               5                   10                  15

<210> SEQ ID NO 270
<211> LENGTH: 21
<212> TYPE: PRT
<213> ORGANISM: Drosophila melanogaster

<400> SEQUENCE: 270

Tyr Tyr Glu His Arg Lys Lys Asn Ile Gly Ser Val His Pro Leu Phe
1               5                   10                  15

Lys Lys Phe Arg Gly
            20

<210> SEQ ID NO 271
<211> LENGTH: 9
<212> TYPE: PRT
<213> ORGANISM: Drosophila melanogaster

<400> SEQUENCE: 271

Ala Arg Gly Lys Lys Lys Gln Pro Lys
1               5

<210> SEQ ID NO 272
<211> LENGTH: 9
<212> TYPE: PRT

<213> ORGANISM: Drosophila melanogaster

<400> SEQUENCE: 272

Lys Pro Lys Gly Arg Ala Lys Lys Ala
1               5

<210> SEQ ID NO 273
<211> LENGTH: 11
<212> TYPE: PRT
<213> ORGANISM: Drosophila melanogaster

<400> SEQUENCE: 273

Gln Ala Lys Gly Arg Lys Lys Lys Glu Leu Pro
1               5                   10

<210> SEQ ID NO 274
<211> LENGTH: 10
<212> TYPE: PRT
<213> ORGANISM: Drosophila melanogaster

<400> SEQUENCE: 274

Glu Pro Pro Lys Gln Arg Ala Arg Lys Glu
1               5                   10

<210> SEQ ID NO 275
<211> LENGTH: 13
<212> TYPE: PRT
<213> ORGANISM: Drosophila melanogaster

<400> SEQUENCE: 275

Pro Pro Lys Ala Ala Ser Lys Arg Ala Lys Lys Gly Lys
1               5                   10

<210> SEQ ID NO 276
<211> LENGTH: 9
<212> TYPE: PRT
<213> ORGANISM: Drosophila melanogaster

<400> SEQUENCE: 276

Pro Lys Lys Arg Ala Lys Lys Thr Thr
1               5

<210> SEQ ID NO 277
<211> LENGTH: 13
<212> TYPE: PRT
<213> ORGANISM: Drosophila melanogaster

<400> SEQUENCE: 277

Glu Pro Ala Pro Gly Lys Lys Gln Lys Lys Ser Ala Asp
1               5                   10

<210> SEQ ID NO 278
<211> LENGTH: 20
<212> TYPE: PRT
<213> ORGANISM: Drosophila melanogaster

<400> SEQUENCE: 278

Glu Glu Glu Ala Lys Pro Ser Thr Glu Thr Lys Pro Ala Lys Gly Arg
1               5                   10                  15

Lys Lys Ala Pro
            20

<210> SEQ ID NO 279
<211> LENGTH: 9

```
<212> TYPE: PRT
<213> ORGANISM: Drosophila melanogaster

<400> SEQUENCE: 279

Lys Pro Ala Arg Gly Arg Lys Lys Ala
1               5

<210> SEQ ID NO 280
<211> LENGTH: 12
<212> TYPE: PRT
<213> ORGANISM: Drosophila melanogaster

<400> SEQUENCE: 280

Gly Ser Lys Thr Thr Lys Lys Ala Lys Lys Ala Glu
1               5                   10

<210> SEQ ID NO 281
<211> LENGTH: 12
<212> TYPE: PRT
<213> ORGANISM: Saccharomyces cerevisiae

<400> SEQUENCE: 281

Ile Glu Lys Arg Arg Lys Leu Tyr Ile Ser Gly Gly
1               5                   10

<210> SEQ ID NO 282
<211> LENGTH: 12
<212> TYPE: PRT
<213> ORGANISM: Saccharomyces cerevisiae

<400> SEQUENCE: 282

Asn Lys Lys Arg Gly Val Arg Gln Val Leu Leu Asn
1               5                   10

<210> SEQ ID NO 283
<211> LENGTH: 13
<212> TYPE: PRT
<213> ORGANISM: Saccharomyces cerevisiae

<400> SEQUENCE: 283

Lys Glu Gln Val Thr Thr Lys Arg Arg Arg Thr Arg Gly
1               5                   10

<210> SEQ ID NO 284
<211> LENGTH: 13
<212> TYPE: PRT
<213> ORGANISM: Saccharomyces cerevisiae

<400> SEQUENCE: 284

Asn Leu Arg Lys Lys Ile Lys Ser Phe Asn Lys Leu Gln
1               5                   10

<210> SEQ ID NO 285
<211> LENGTH: 12
<212> TYPE: PRT
<213> ORGANISM: Saccharomyces cerevisiae

<400> SEQUENCE: 285

Arg Gln Arg Lys Glu Arg Arg Gln Gly Lys Arg Glu
1               5                   10

<210> SEQ ID NO 286
<211> LENGTH: 16
<212> TYPE: PRT
<213> ORGANISM: Saccharomyces cerevisiae
```

```
<400> SEQUENCE: 286

Glu Asn Lys Phe Glu Lys Asp Leu Arg Lys Lys Leu Val Asn Asn Glu
1               5                   10                  15

<210> SEQ ID NO 287
<211> LENGTH: 15
<212> TYPE: PRT
<213> ORGANISM: Saccharomyces cerevisiae

<400> SEQUENCE: 287

Arg Asp Val Asn Lys Arg Lys Lys Gly Lys Gln Lys Arg Ile
1               5                   10                  15

<210> SEQ ID NO 288
<211> LENGTH: 15
<212> TYPE: PRT
<213> ORGANISM: Saccharomyces cerevisiae

<400> SEQUENCE: 288

Lys Arg Ile Ser Thr Ala Thr Gly Lys Leu Lys Lys Arg Lys Met
1               5                   10                  15

<210> SEQ ID NO 289
<211> LENGTH: 23
<212> TYPE: PRT
<213> ORGANISM: Saccharomyces cerevisiae

<400> SEQUENCE: 289

Gly Lys Asp Asp Tyr Gly Val Met Val Leu Ala Asp Arg Arg Phe Ser
1               5                   10                  15

Arg Lys Arg Ser Gln Leu Pro
            20

<210> SEQ ID NO 290
<211> LENGTH: 25
<212> TYPE: PRT
<213> ORGANISM: Saccharomyces cerevisiae

<400> SEQUENCE: 290

Pro Leu Ser Arg Arg Arg Val Arg Arg Lys Asn Gln Pro Leu Pro
1               5                   10                  15

Asp Ala Lys Lys Lys Phe Lys Thr Gly
            20                  25

<210> SEQ ID NO 291
<211> LENGTH: 15
<212> TYPE: PRT
<213> ORGANISM: Saccharomyces cerevisiae

<400> SEQUENCE: 291

Asn Glu Glu Arg Lys Arg Arg Lys Tyr Phe His Met Leu Tyr Leu
1               5                   10                  15

<210> SEQ ID NO 292
<211> LENGTH: 15
<212> TYPE: PRT
<213> ORGANISM: Saccharomyces cerevisiae

<400> SEQUENCE: 292

Glu Trp Ile Asn Ser Lys Arg Leu Ser Arg Lys Leu Ser Asn Leu
1               5                   10                  15
```

<210> SEQ ID NO 293
<211> LENGTH: 17
<212> TYPE: PRT
<213> ORGANISM: Saccharomyces cerevisiae

<400> SEQUENCE: 293

Glu Met Ser Ala Asn Asn Lys Arg Lys Phe Lys Thr Leu Lys Arg Ser
1               5                   10                  15
Asp

<210> SEQ ID NO 294
<211> LENGTH: 19
<212> TYPE: PRT
<213> ORGANISM: Saccharomyces cerevisiae

<400> SEQUENCE: 294

Trp Met Asn Ser Lys Val Arg Lys Arg Ile Thr Lys Asp Asp Phe
1               5                   10                  15
Gly Glu Lys

<210> SEQ ID NO 295
<211> LENGTH: 20
<212> TYPE: PRT
<213> ORGANISM: Saccharomyces cerevisiae

<400> SEQUENCE: 295

Arg Lys Val Ile Thr Ala Leu His His Arg Lys Arg Thr Lys Ile Asp
1               5                   10                  15
Asp Tyr Glu Asp
            20

<210> SEQ ID NO 296
<211> LENGTH: 17
<212> TYPE: PRT
<213> ORGANISM: Saccharomyces cerevisiae

<400> SEQUENCE: 296

Lys Thr Gly Ser Arg Cys Lys Lys Val Ile Lys Arg Thr Val Gly Arg
1               5                   10                  15
Pro

<210> SEQ ID NO 297
<211> LENGTH: 12
<212> TYPE: PRT
<213> ORGANISM: Saccharomyces cerevisiae

<400> SEQUENCE: 297

Phe His Pro Lys Arg Arg Arg Ile Tyr Gly Phe Arg
1               5                   10

<210> SEQ ID NO 298
<211> LENGTH: 10
<212> TYPE: PRT
<213> ORGANISM: Saccharomyces cerevisiae

<400> SEQUENCE: 298

Asp Ser Arg Gly Arg Lys Lys Ala Ser Met
1               5                   10

<210> SEQ ID NO 299
<211> LENGTH: 19
<212> TYPE: PRT
<213> ORGANISM: Saccharomyces cerevisiae

```
<400> SEQUENCE: 299

Asp Gly Glu Ser Leu Met Lys Arg Arg Arg Thr Glu Gly Gly Asn Lys
1               5                   10                  15

Arg Glu Lys

<210> SEQ ID NO 300
<211> LENGTH: 12
<212> TYPE: PRT
<213> ORGANISM: Saccharomyces cerevisiae

<400> SEQUENCE: 300

Asp Glu Asp Glu Arg Arg Lys Arg Arg Ile Glu Glu
1               5                   10

<210> SEQ ID NO 301
<211> LENGTH: 22
<212> TYPE: PRT
<213> ORGANISM: Saccharomyces cerevisiae

<400> SEQUENCE: 301

Met Ser Thr Pro Ala Arg Arg Arg Leu Met Arg Asp Phe Lys Arg Met
1               5                   10                  15

Lys Glu Asp Ala Pro Pro
            20

<210> SEQ ID NO 302
<211> LENGTH: 13
<212> TYPE: PRT
<213> ORGANISM: Saccharomyces cerevisiae

<400> SEQUENCE: 302

Gly Val Ala Lys Leu Arg Lys Glu Lys Ser Gly Ala Asp
1               5                   10

<210> SEQ ID NO 303
<211> LENGTH: 16
<212> TYPE: PRT
<213> ORGANISM: Saccharomyces cerevisiae

<400> SEQUENCE: 303

Asp Asp Tyr Asn Arg Lys Arg Pro Phe Arg Ser Thr Arg Pro Gly Lys
1               5                   10                  15

<210> SEQ ID NO 304
<211> LENGTH: 12
<212> TYPE: PRT
<213> ORGANISM: Saccharomyces cerevisiae

<400> SEQUENCE: 304

Glu Gly Lys Ala His Arg Arg Glu Lys Lys Tyr Glu
1               5                   10

<210> SEQ ID NO 305
<211> LENGTH: 15
<212> TYPE: PRT
<213> ORGANISM: Saccharomyces cerevisiae

<400> SEQUENCE: 305

Asn Arg Leu Arg Glu Lys Lys His Gly Lys Ala His Ile His His
1               5                   10                  15

<210> SEQ ID NO 306
```

```
<211> LENGTH: 14
<212> TYPE: PRT
<213> ORGANISM: Saccharomyces cerevisiae

<400> SEQUENCE: 306

Glu Arg Arg Lys Gln Leu Lys Lys Gln Gly Pro Lys Arg Pro
1               5                   10

<210> SEQ ID NO 307
<211> LENGTH: 17
<212> TYPE: PRT
<213> ORGANISM: Saccharomyces cerevisiae

<400> SEQUENCE: 307

Glu Thr Tyr Lys Lys Arg Ile Lys Glu Trp Glu Ser Cys Tyr Pro Asp
1               5                   10                  15

Glu

<210> SEQ ID NO 308
<211> LENGTH: 16
<212> TYPE: PRT
<213> ORGANISM: Saccharomyces cerevisiae

<400> SEQUENCE: 308

Leu Thr Cys Lys Lys Leu Lys Thr His Asn Arg Ile Ile Leu Ser Gly
1               5                   10                  15

<210> SEQ ID NO 309
<211> LENGTH: 36
<212> TYPE: PRT
<213> ORGANISM: Saccharomyces cerevisiae
<220> FEATURE:
<221> NAME/KEY: MOD_RES
<222> LOCATION: (20)..(28)
<223> OTHER INFORMATION: Any amino acid

<400> SEQUENCE: 309

Asn Ala Leu Arg Lys Ser Arg Lys Lys Ile Thr Lys Gln Tyr Glu Ile
1               5                   10                  15

Gly Thr Pro Xaa Xaa Xaa Xaa Xaa Xaa Xaa Xaa Xaa Gly Glu Ile Arg
            20                  25                  30

Lys Arg Asp Pro
        35

<210> SEQ ID NO 310
<211> LENGTH: 18
<212> TYPE: PRT
<213> ORGANISM: Saccharomyces cerevisiae

<400> SEQUENCE: 310

Lys Pro Thr Ser Lys Pro Lys Arg Val Arg Thr Ala Thr Lys Lys Lys
1               5                   10                  15

Ile Pro

<210> SEQ ID NO 311
<211> LENGTH: 15
<212> TYPE: PRT
<213> ORGANISM: Saccharomyces cerevisiae

<400> SEQUENCE: 311

Phe Tyr Lys Lys Arg Ser Pro Val Thr Arg Ser Lys Lys Ser Gly
1               5                   10                  15
```

-continued

```
<210> SEQ ID NO 312
<211> LENGTH: 10
<212> TYPE: PRT
<213> ORGANISM: Saccharomyces cerevisiae

<400> SEQUENCE: 312

Gly Phe Lys Lys Gly Lys Gly Cys Gln Arg
1               5                   10

<210> SEQ ID NO 313
<211> LENGTH: 10
<212> TYPE: PRT
<213> ORGANISM: Saccharomyces cerevisiae

<400> SEQUENCE: 313

Gly Phe Lys Lys Gly Lys Gly Cys Gln Arg
1               5                   10

<210> SEQ ID NO 314
<211> LENGTH: 45
<212> TYPE: PRT
<213> ORGANISM: Saccharomyces cerevisiae
<220> FEATURE:
<221> NAME/KEY: MOD_RES
<222> LOCATION: (21)..(28)
<223> OTHER INFORMATION: Any amino acid

<400> SEQUENCE: 314

Glu Arg Ala Lys Lys Ser Ala Val Thr Asp Ala Leu Lys Arg Ser Leu
1               5                   10                  15

Arg Gly Phe Gly Xaa Xaa Xaa Xaa Xaa Xaa Xaa Xaa Asp Lys Asp Phe
            20                  25                  30

Leu Ala Lys Ile Asp Lys Val Lys Phe Asp Pro Pro Asp
        35                  40                  45

<210> SEQ ID NO 315
<211> LENGTH: 11
<212> TYPE: PRT
<213> ORGANISM: Saccharomyces cerevisiae

<400> SEQUENCE: 315

Met Ala Arg Arg Arg Leu Pro Asp Arg Pro Pro
1               5                   10

<210> SEQ ID NO 316
<211> LENGTH: 10
<212> TYPE: PRT
<213> ORGANISM: Saccharomyces cerevisiae

<400> SEQUENCE: 316

Gly Gly Arg Ser Leu Arg Lys Arg Ser Ala
1               5                   10

<210> SEQ ID NO 317
<211> LENGTH: 8
<212> TYPE: PRT
<213> ORGANISM: Saccharomyces cerevisiae

<400> SEQUENCE: 317

Gln Leu Thr Lys Arg Arg Lys Asp
1               5

<210> SEQ ID NO 318
<211> LENGTH: 16
<212> TYPE: PRT
```

<213> ORGANISM: Saccharomyces cerevisiae

<400> SEQUENCE: 318

Asp Glu Thr Val Phe Val Lys Ser Lys Arg Val Lys Ala Ser Ser Ser
1               5                   10                  15

<210> SEQ ID NO 319
<211> LENGTH: 13
<212> TYPE: PRT
<213> ORGANISM: Saccharomyces cerevisiae

<400> SEQUENCE: 319

Gly Glu Asp Arg Lys Arg Glu Gly Arg Asn Leu Lys Arg
1               5                   10

<210> SEQ ID NO 320
<211> LENGTH: 16
<212> TYPE: PRT
<213> ORGANISM: Saccharomyces cerevisiae

<400> SEQUENCE: 320

Pro Ile Ser Arg Gln Ser Lys Lys Arg Lys Phe Asp Tyr Arg Val Pro
1               5                   10                  15

<210> SEQ ID NO 321
<211> LENGTH: 14
<212> TYPE: PRT
<213> ORGANISM: Saccharomyces cerevisiae

<400> SEQUENCE: 321

Gly Leu Lys Lys Pro Arg Lys Thr Lys Ser Ser Arg His
1               5                   10

<210> SEQ ID NO 322
<211> LENGTH: 13
<212> TYPE: PRT
<213> ORGANISM: Saccharomyces cerevisiae

<400> SEQUENCE: 322

Gly Arg Ile Leu Arg Ala Lys Arg Arg Asn Asp Glu Gly
1               5                   10

<210> SEQ ID NO 323
<211> LENGTH: 12
<212> TYPE: PRT
<213> ORGANISM: Saccharomyces cerevisiae

<400> SEQUENCE: 323

Gly Arg Gly Ser Asn Gly His Lys Arg Phe Lys Ser
1               5                   10

<210> SEQ ID NO 324
<211> LENGTH: 13
<212> TYPE: PRT
<213> ORGANISM: Saccharomyces cerevisiae

<400> SEQUENCE: 324

Thr Arg Arg His Leu Cys Lys Ile Lys Gly Leu Ser Glu
1               5                   10

<210> SEQ ID NO 325
<211> LENGTH: 29
<212> TYPE: PRT
<213> ORGANISM: Saccharomyces cerevisiae
<220> FEATURE:

```
<221> NAME/KEY: MOD_RES
<222> LOCATION: (10)..(21)
<223> OTHER INFORMATION: Any amino acid

<400> SEQUENCE: 325

Asp Gly Arg Lys Pro Ile Gly Gly His Xaa Xaa Xaa Xaa Xaa Xaa
1               5                   10                  15

Xaa Xaa Xaa Xaa Xaa Arg Lys Gly Arg Gly Asp Glu Arg
            20                  25

<210> SEQ ID NO 326
<211> LENGTH: 13
<212> TYPE: PRT
<213> ORGANISM: Saccharomyces cerevisiae

<400> SEQUENCE: 326

Glu Thr Glu Lys Arg Cys Lys Gln Lys Glu Gln Arg Tyr
1               5                   10

<210> SEQ ID NO 327
<211> LENGTH: 16
<212> TYPE: PRT
<213> ORGANISM: Saccharomyces cerevisiae

<400> SEQUENCE: 327

Met Asp Leu Arg Val Gly Arg Lys Phe Arg Ile Gly Arg Lys Ile Gly
1               5                   10                  15

<210> SEQ ID NO 328
<211> LENGTH: 28
<212> TYPE: PRT
<213> ORGANISM: Saccharomyces cerevisiae
<220> FEATURE:
<221> NAME/KEY: MOD_RES
<222> LOCATION: (5)..(12)
<223> OTHER INFORMATION: Any amino acid

<400> SEQUENCE: 328

Gly Arg Arg Gly Xaa Xaa Xaa Xaa Xaa Xaa Xaa Xaa Gly Leu Ser Lys
1               5                   10                  15

Lys Tyr Arg Asp Phe Asn Thr His Arg His Ile Pro
            20                  25

<210> SEQ ID NO 329
<211> LENGTH: 15
<212> TYPE: PRT
<213> ORGANISM: Saccharomyces cerevisiae

<400> SEQUENCE: 329

His Glu Leu Thr Lys Arg Ser Ser Arg Arg Val Glu Thr Glu Lys
1               5                   10                  15

<210> SEQ ID NO 330
<211> LENGTH: 14
<212> TYPE: PRT
<213> ORGANISM: Saccharomyces cerevisiae

<400> SEQUENCE: 330

Met Leu Ala Met Ala Arg Arg Lys Lys Lys Met Ser Ala Lys
1               5                   10

<210> SEQ ID NO 331
<211> LENGTH: 10
<212> TYPE: PRT
<213> ORGANISM: Saccharomyces cerevisiae
```

<400> SEQUENCE: 331

Glu His Tyr Lys Val Lys His Thr Glu Lys
1               5                   10

<210> SEQ ID NO 332
<211> LENGTH: 11
<212> TYPE: PRT
<213> ORGANISM: Saccharomyces cerevisiae

<400> SEQUENCE: 332

Leu His Pro Glu Lys Lys Arg Ser Ile Ser Glu
1               5                   10

<210> SEQ ID NO 333
<211> LENGTH: 18
<212> TYPE: PRT
<213> ORGANISM: Schizosaccharomyces pombe
<220> FEATURE:
<221> NAME/KEY: MOD_RES
<222> LOCATION: (6)..(10)
<223> OTHER INFORMATION: Any amino acid

<400> SEQUENCE: 333

Ser Ser Ile Asp Glu Xaa Xaa Xaa Xaa Xaa Ser Ile Lys Arg Lys Arg
1               5                   10                  15

Arg Ile

<210> SEQ ID NO 334
<211> LENGTH: 15
<212> TYPE: PRT
<213> ORGANISM: Schizosaccharomyces pombe

<400> SEQUENCE: 334

Gly Glu Leu Ala Lys Arg Val Ala Arg His Gln Lys Ala Arg Glu
1               5                   10                  15

<210> SEQ ID NO 335
<211> LENGTH: 9
<212> TYPE: PRT
<213> ORGANISM: Schizosaccharomyces pombe

<400> SEQUENCE: 335

Gly Ser Ala Lys Arg Lys Arg Asp Ser
1               5

<210> SEQ ID NO 336
<211> LENGTH: 9
<212> TYPE: PRT
<213> ORGANISM: Schizosaccharomyces pombe

<400> SEQUENCE: 336

Lys Gly Gly Glu Ser Lys Lys Lys Arg
1               5

<210> SEQ ID NO 337
<211> LENGTH: 15
<212> TYPE: PRT
<213> ORGANISM: Schizosaccharomyces pombe

<400> SEQUENCE: 337

Asp Lys Arg Tyr Gly Arg Ser Asp Lys Arg Thr Lys Leu Pro Lys
1               5                   10                  15

```
<210> SEQ ID NO 338
<211> LENGTH: 11
<212> TYPE: PRT
<213> ORGANISM: Schizosaccharomyces pombe

<400> SEQUENCE: 338

Pro Pro Ser Lys Arg Arg Arg Val Arg Gly Gly
1               5                   10

<210> SEQ ID NO 339
<211> LENGTH: 20
<212> TYPE: PRT
<213> ORGANISM: Schizosaccharomyces pombe

<400> SEQUENCE: 339

Asp Phe Lys Gln Ala Ile Leu Arg Lys Arg Lys Asn Glu Ser Pro Glu
1               5                   10                  15

Glu Val Glu Pro
            20

<210> SEQ ID NO 340
<211> LENGTH: 7
<212> TYPE: PRT
<213> ORGANISM: Schizosaccharomyces pombe

<400> SEQUENCE: 340

Asp Lys Lys Ala Lys Lys Gly
1               5

<210> SEQ ID NO 341
<211> LENGTH: 19
<212> TYPE: PRT
<213> ORGANISM: Schizosaccharomyces pombe

<400> SEQUENCE: 341

Asp Val Val Gln Phe Tyr Leu Lys Lys Tyr Thr Arg Ser Lys Arg
1               5                   10                  15

Asn Asp Gly

<210> SEQ ID NO 342
<211> LENGTH: 16
<212> TYPE: PRT
<213> ORGANISM: Schizosaccharomyces pombe

<400> SEQUENCE: 342

Pro Ser Pro Ala Leu Leu Lys Lys Thr Asn Lys Arg Arg Glu Leu Pro
1               5                   10                  15

<210> SEQ ID NO 343
<211> LENGTH: 16
<212> TYPE: PRT
<213> ORGANISM: Schizosaccharomyces pombe

<400> SEQUENCE: 343

Gly Leu Ala Lys Lys Tyr Arg Asp His Lys Thr His Leu His Ile Pro
1               5                   10                  15

<210> SEQ ID NO 344
<211> LENGTH: 16
<212> TYPE: PRT
<213> ORGANISM: Schizosaccharomyces pombe

<400> SEQUENCE: 344

Gly Leu Ala Lys Lys Tyr Arg Asp Phe Lys Thr His Val His Ile Pro
```

-continued

```
1               5                   10                  15
```

<210> SEQ ID NO 345
<211> LENGTH: 17
<212> TYPE: PRT
<213> ORGANISM: Homo sapiens

<400> SEQUENCE: 345

His Arg Arg Arg Gln Arg Thr Arg Lys Lys Lys Lys Lys Lys Lys
1               5                   10                  15

Arg

<210> SEQ ID NO 346
<211> LENGTH: 7
<212> TYPE: PRT
<213> ORGANISM: Homo sapiens

<400> SEQUENCE: 346

Leu Arg Arg Lys Ser Arg Pro
1               5

<210> SEQ ID NO 347
<211> LENGTH: 8
<212> TYPE: PRT
<213> ORGANISM: Homo sapiens

<400> SEQUENCE: 347

Ser Arg Arg Thr Lys Arg Arg Gln
1               5

<210> SEQ ID NO 348
<211> LENGTH: 8
<212> TYPE: PRT
<213> ORGANISM: Mus sp.

<400> SEQUENCE: 348

Gly Arg Lys Arg Lys Lys Arg Thr
1               5

<210> SEQ ID NO 349
<211> LENGTH: 8
<212> TYPE: PRT
<213> ORGANISM: Mus sp.

<400> SEQUENCE: 349

Gly Arg Arg Arg Lys Lys Arg Thr
1               5

<210> SEQ ID NO 350
<211> LENGTH: 7
<212> TYPE: PRT
<213> ORGANISM: Mus sp.

<400> SEQUENCE: 350

Ala Arg Lys Arg Lys Arg Thr
1               5

<210> SEQ ID NO 351
<211> LENGTH: 9
<212> TYPE: PRT
<213> ORGANISM: Mus sp.

<400> SEQUENCE: 351

Asn Arg Arg Gln Lys Gly Lys Arg Ser

```
1               5
```

```
<210> SEQ ID NO 352
<211> LENGTH: 8
<212> TYPE: PRT
<213> ORGANISM: Homo sapiens

<400> SEQUENCE: 352
```

```
Glu Cys Arg Arg Lys Lys Lys Glu
1               5
```

```
<210> SEQ ID NO 353
<211> LENGTH: 8
<212> TYPE: PRT
<213> ORGANISM: Homo sapiens

<400> SEQUENCE: 353
```

```
Glu Arg Lys Lys Arg Arg Arg Glu
1               5
```

```
<210> SEQ ID NO 354
<211> LENGTH: 11
<212> TYPE: PRT
<213> ORGANISM: Homo sapiens

<400> SEQUENCE: 354
```

```
Ala Lys Cys Arg Asn Lys Lys Glu Lys Thr
1               5                   10
```

```
<210> SEQ ID NO 355
<211> LENGTH: 7
<212> TYPE: PRT
<213> ORGANISM: Mus sp.

<400> SEQUENCE: 355
```

```
Ser Lys Lys Lys Ile Arg Leu
1               5
```

```
<210> SEQ ID NO 356
<211> LENGTH: 8
<212> TYPE: PRT
<213> ORGANISM: Mus sp.

<400> SEQUENCE: 356
```

```
Gln Lys Gly Asn Arg Lys Lys Met
1               5
```

```
<210> SEQ ID NO 357
<211> LENGTH: 8
<212> TYPE: PRT
<213> ORGANISM: Mus sp.

<400> SEQUENCE: 357
```

```
Val Lys Lys Val Lys Lys Lys Leu
1               5
```

```
<210> SEQ ID NO 358
<211> LENGTH: 6
<212> TYPE: PRT
<213> ORGANISM: Homo sapiens

<400> SEQUENCE: 358
```

```
Val Lys Arg Lys Lys Ile
1               5
```

<210> SEQ ID NO 359
<211> LENGTH: 9
<212> TYPE: PRT
<213> ORGANISM: Homo sapiens

<400> SEQUENCE: 359

Cys Arg Asn Arg Tyr Arg Lys Leu Glu
1               5

<210> SEQ ID NO 360
<211> LENGTH: 8
<212> TYPE: PRT
<213> ORGANISM: Homo sapiens

<400> SEQUENCE: 360

Ile Arg Lys Arg Arg Lys Met Lys
1               5

<210> SEQ ID NO 361
<211> LENGTH: 8
<212> TYPE: PRT
<213> ORGANISM: Homo sapiens

<400> SEQUENCE: 361

Pro Lys Lys Lys Arg Leu Arg Leu
1               5

<210> SEQ ID NO 362
<211> LENGTH: 11
<212> TYPE: PRT
<213> ORGANISM: Mus sp.

<400> SEQUENCE: 362

Gly Lys Lys Lys Lys Arg Lys Arg Glu Lys Leu
1               5                   10

<210> SEQ ID NO 363
<211> LENGTH: 11
<212> TYPE: PRT
<213> ORGANISM: Homo sapiens

<400> SEQUENCE: 363

Gly Lys Lys Lys Lys Arg Lys Arg Glu Lys Leu
1               5                   10

<210> SEQ ID NO 364
<211> LENGTH: 11
<212> TYPE: PRT
<213> ORGANISM: Homo sapiens

<400> SEQUENCE: 364

Gly Lys Lys Lys Arg Arg Ser Arg Glu Lys His
1               5                   10

<210> SEQ ID NO 365
<211> LENGTH: 8
<212> TYPE: PRT
<213> ORGANISM: Homo sapiens

<400> SEQUENCE: 365

Pro Lys Lys Cys Arg Ala Arg Phe
1               5

<210> SEQ ID NO 366

```
<211> LENGTH: 8
<212> TYPE: PRT
<213> ORGANISM: Xenopus laevis

<400> SEQUENCE: 366

Phe Lys Gln Arg Arg Ile Lys Leu
1               5

<210> SEQ ID NO 367
<211> LENGTH: 8
<212> TYPE: PRT
<213> ORGANISM: Xenopus laevis

<400> SEQUENCE: 367

Asn Arg Arg Arg Lys Lys Arg Thr
1               5

<210> SEQ ID NO 368
<211> LENGTH: 9
<212> TYPE: PRT
<213> ORGANISM: Xenopus laevis

<400> SEQUENCE: 368

Asn Arg Arg Gln Lys Glu Lys Arg Ile
1               5

<210> SEQ ID NO 369
<211> LENGTH: 11
<212> TYPE: PRT
<213> ORGANISM: Drosophila melanogaster

<400> SEQUENCE: 369

Asp Lys Arg Ser Arg Lys Arg Lys Arg Ser Lys
1               5                   10

<210> SEQ ID NO 370
<211> LENGTH: 9
<212> TYPE: PRT
<213> ORGANISM: Drosophila melanogaster

<400> SEQUENCE: 370

Arg Leu Arg Ile Asp Arg Lys Arg Asn
1               5

<210> SEQ ID NO 371
<211> LENGTH: 7
<212> TYPE: PRT
<213> ORGANISM: Drosophila melanogaster

<400> SEQUENCE: 371

Ala Lys Arg Ser Arg Arg Ser
1               5

<210> SEQ ID NO 372
<211> LENGTH: 15
<212> TYPE: PRT
<213> ORGANISM: Homo sapiens

<400> SEQUENCE: 372

Ile Arg Lys Arg Arg Lys Met Lys Ser Val Gly Asp Asp Glu Glu
1               5                   10                  15

<210> SEQ ID NO 373
<211> LENGTH: 11
<212> TYPE: PRT
```

<213> ORGANISM: Homo sapiens

<400> SEQUENCE: 373

Pro Pro Lys Lys Lys Arg Leu Arg Leu Ala Glu
1               5                   10

<210> SEQ ID NO 374
<211> LENGTH: 9
<212> TYPE: PRT
<213> ORGANISM: Homo sapiens

<400> SEQUENCE: 374

Cys Arg Asn Arg Tyr Arg Lys Leu Glu
1               5

<210> SEQ ID NO 375
<211> LENGTH: 7
<212> TYPE: PRT
<213> ORGANISM: Rattus sp.

<400> SEQUENCE: 375

Pro Arg Arg Lys Arg Arg Val
1               5

<210> SEQ ID NO 376
<211> LENGTH: 8
<212> TYPE: PRT
<213> ORGANISM: Rattus sp.

<400> SEQUENCE: 376

His Arg Tyr Lys Met Lys Arg Gln
1               5

<210> SEQ ID NO 377
<211> LENGTH: 8
<212> TYPE: PRT
<213> ORGANISM: Homo sapiens

<400> SEQUENCE: 377

Asp Gly Lys Arg Lys Arg Lys Asn
1               5

<210> SEQ ID NO 378
<211> LENGTH: 11
<212> TYPE: PRT
<213> ORGANISM: Homo sapiens

<400> SEQUENCE: 378

Asp Asp Ser Lys Arg Val Ala Lys Arg Lys Leu
1               5                   10

<210> SEQ ID NO 379
<211> LENGTH: 9
<212> TYPE: PRT
<213> ORGANISM: Homo sapiens

<400> SEQUENCE: 379

Asn Arg Glu Arg Arg Arg Lys Glu Glu
1               5

<210> SEQ ID NO 380
<211> LENGTH: 7
<212> TYPE: PRT
<213> ORGANISM: Homo sapiens

```
<400> SEQUENCE: 380

Trp Lys Gln Arg Arg Lys Phe
1               5

<210> SEQ ID NO 381
<211> LENGTH: 8
<212> TYPE: PRT
<213> ORGANISM: Drosophila melanogaster

<400> SEQUENCE: 381

Asn Arg Arg Lys Arg Lys Arg Ser
1               5

<210> SEQ ID NO 382
<211> LENGTH: 6
<212> TYPE: PRT
<213> ORGANISM: Drosophila melanogaster

<400> SEQUENCE: 382

Pro Lys Lys Lys Lys Leu
1               5

<210> SEQ ID NO 383
<211> LENGTH: 8
<212> TYPE: PRT
<213> ORGANISM: Caenorhabditis elegans

<400> SEQUENCE: 383

Ala Arg Arg Lys Arg Arg Arg Leu
1               5

<210> SEQ ID NO 384
<211> LENGTH: 8
<212> TYPE: PRT
<213> ORGANISM: Caenorhabditis elegans

<400> SEQUENCE: 384

Leu Lys Phe Lys Lys Val Arg Asp
1               5

<210> SEQ ID NO 385
<211> LENGTH: 7
<212> TYPE: PRT
<213> ORGANISM: Caenorhabditis elegans

<400> SEQUENCE: 385

Phe Lys Lys Phe Arg Lys Phe
1               5

<210> SEQ ID NO 386
<211> LENGTH: 7
<212> TYPE: PRT
<213> ORGANISM: Caenorhabditis elegans

<400> SEQUENCE: 386

Gly Lys Gln Lys Arg Arg Phe
1               5

<210> SEQ ID NO 387
<211> LENGTH: 13
<212> TYPE: PRT
<213> ORGANISM: Caenorhabditis elegans

<400> SEQUENCE: 387
```

Glu Arg Leu Lys Arg Asp Lys Glu Lys Arg Glu Lys Glu
1               5                   10

<210> SEQ ID NO 388
<211> LENGTH: 10
<212> TYPE: PRT
<213> ORGANISM: Caenorhabditis elegans

<400> SEQUENCE: 388

Thr Arg Gly Arg Pro Lys Lys Val Lys Glu
1               5                   10

<210> SEQ ID NO 389
<211> LENGTH: 11
<212> TYPE: PRT
<213> ORGANISM: Caenorhabditis elegans

<400> SEQUENCE: 389

Ser Lys Lys Arg Gly Arg Arg Lys Lys Thr
1               5                   10

<210> SEQ ID NO 390
<211> LENGTH: 9
<212> TYPE: PRT
<213> ORGANISM: Caenorhabditis elegans

<400> SEQUENCE: 390

Thr Arg Arg Gln Lys Arg Ala Lys Val
1               5

<210> SEQ ID NO 391
<211> LENGTH: 10
<212> TYPE: PRT
<213> ORGANISM: Caenorhabditis elegans

<400> SEQUENCE: 391

Ser Arg Lys Ser Lys Lys Arg Leu Arg Ala
1               5                   10

<210> SEQ ID NO 392
<211> LENGTH: 12
<212> TYPE: PRT
<213> ORGANISM: Drosophila melanogaster

<400> SEQUENCE: 392

Leu Lys Lys Ile Arg Arg Lys Ile Lys Asn Lys Ile
1               5                   10

<210> SEQ ID NO 393
<211> LENGTH: 8
<212> TYPE: PRT
<213> ORGANISM: Drosophila melanogaster

<400> SEQUENCE: 393

Glu Ser Arg Arg Lys Lys Lys Glu
1               5

<210> SEQ ID NO 394
<211> LENGTH: 8
<212> TYPE: PRT
<213> ORGANISM: Xenopus laevis

<400> SEQUENCE: 394

Asp Arg Asn Lys Lys Lys Lys Glu
1               5

```
<210> SEQ ID NO 395
<211> LENGTH: 6
<212> TYPE: PRT
<213> ORGANISM: Xenopus laevis

<400> SEQUENCE: 395

Ala Arg Arg Arg Arg Pro
1               5

<210> SEQ ID NO 396
<211> LENGTH: 6
<212> TYPE: PRT
<213> ORGANISM: Homo sapiens

<400> SEQUENCE: 396

Gly Arg Arg Arg Arg Ala
1               5

<210> SEQ ID NO 397
<211> LENGTH: 7
<212> TYPE: PRT
<213> ORGANISM: Homo sapiens

<400> SEQUENCE: 397

Asp Glu Lys Arg Arg Lys Val
1               5

<210> SEQ ID NO 398
<211> LENGTH: 7
<212> TYPE: PRT
<213> ORGANISM: Homo sapiens

<400> SEQUENCE: 398

Cys Arg Gln Lys Arg Lys Val
1               5

<210> SEQ ID NO 399
<211> LENGTH: 6
<212> TYPE: PRT
<213> ORGANISM: Mus sp.

<400> SEQUENCE: 399

Glu Arg Lys Arg Arg Asp
1               5

<210> SEQ ID NO 400
<211> LENGTH: 8
<212> TYPE: PRT
<213> ORGANISM: Mus sp.

<400> SEQUENCE: 400

Ser Arg Lys Lys Leu Arg Met Glu
1               5

<210> SEQ ID NO 401
<211> LENGTH: 9
<212> TYPE: PRT
<213> ORGANISM: Homo sapiens

<400> SEQUENCE: 401

Glu Glu Lys Arg Lys Arg Thr Tyr Glu
1               5
```

<210> SEQ ID NO 402
<211> LENGTH: 6
<212> TYPE: PRT
<213> ORGANISM: Homo sapiens

<400> SEQUENCE: 402

Gly Arg Arg Arg Arg Ala
1               5

<210> SEQ ID NO 403
<211> LENGTH: 7
<212> TYPE: PRT
<213> ORGANISM: Homo sapiens

<400> SEQUENCE: 403

Asp Glu Lys Arg Arg Lys Phe
1               5

<210> SEQ ID NO 404
<211> LENGTH: 9
<212> TYPE: PRT
<213> ORGANISM: Homo sapiens

<400> SEQUENCE: 404

Ser Arg Cys Arg Gln Lys Arg Lys Val
1               5

<210> SEQ ID NO 405
<211> LENGTH: 8
<212> TYPE: PRT
<213> ORGANISM: Homo sapiens

<400> SEQUENCE: 405

Ser Lys Lys Lys Lys Thr Lys Val
1               5

<210> SEQ ID NO 406
<211> LENGTH: 8
<212> TYPE: PRT
<213> ORGANISM: Homo sapiens

<400> SEQUENCE: 406

Asn Arg Pro Asp Lys Lys Lys Ile
1               5

<210> SEQ ID NO 407
<211> LENGTH: 6
<212> TYPE: PRT
<213> ORGANISM: Homo sapiens

<400> SEQUENCE: 407

Gln Arg Arg Lys Lys Pro
1               5

<210> SEQ ID NO 408
<211> LENGTH: 8
<212> TYPE: PRT
<213> ORGANISM: Homo sapiens

<400> SEQUENCE: 408

Gln Lys Lys Arg Arg Phe Lys Thr
1               5

<210> SEQ ID NO 409
<211> LENGTH: 6

```
<212> TYPE: PRT
<213> ORGANISM: Homo sapiens

<400> SEQUENCE: 409

Ser Arg Lys Arg Lys Met
1               5

<210> SEQ ID NO 410
<211> LENGTH: 10
<212> TYPE: PRT
<213> ORGANISM: Mus sp.

<400> SEQUENCE: 410

Glu Arg Lys Arg Leu Arg Asn Arg Leu Ala
1               5                   10

<210> SEQ ID NO 411
<211> LENGTH: 9
<212> TYPE: PRT
<213> ORGANISM: Mus sp.

<400> SEQUENCE: 411

Ala Thr Lys Cys Arg Lys Arg Lys Leu
1               5

<210> SEQ ID NO 412
<211> LENGTH: 15
<212> TYPE: PRT
<213> ORGANISM: Unknown
<220> FEATURE:
<223> OTHER INFORMATION: Description of Unknown: Max
      peptide
<220> FEATURE:
<221> NAME/KEY: MOD_RES
<222> LOCATION: (4)..(9)
<223> OTHER INFORMATION: Any amino acid

<400> SEQUENCE: 412

Asp Lys Arg Xaa Xaa Xaa Xaa Xaa Xaa Glu Arg Lys Arg Arg Asp
1               5                   10                  15

<210> SEQ ID NO 413
<211> LENGTH: 9
<212> TYPE: PRT
<213> ORGANISM: Unknown
<220> FEATURE:
<223> OTHER INFORMATION: Description of Unknown: Max
      peptide

<400> SEQUENCE: 413

Gln Ser Arg Lys Lys Leu Arg Met Glu
1               5

<210> SEQ ID NO 414
<211> LENGTH: 12
<212> TYPE: PRT
<213> ORGANISM: Gallus sp.

<400> SEQUENCE: 414

Asp Lys Glu Lys Lys Ile Lys Leu Glu Glu Asp Glu
1               5                   10

<210> SEQ ID NO 415
<211> LENGTH: 7
<212> TYPE: PRT
<213> ORGANISM: Gallus sp.
```

```
<400> SEQUENCE: 415

Ile Lys Lys Ala Lys Lys Val
1               5

<210> SEQ ID NO 416
<211> LENGTH: 6
<212> TYPE: PRT
<213> ORGANISM: Gallus sp.

<400> SEQUENCE: 416

Thr Arg Arg Lys Lys Asn
1               5

<210> SEQ ID NO 417
<211> LENGTH: 8
<212> TYPE: PRT
<213> ORGANISM: Xenopus borealis

<400> SEQUENCE: 417

Thr Arg Asp Asp Lys Arg Arg Ala
1               5

<210> SEQ ID NO 418
<211> LENGTH: 9
<212> TYPE: PRT
<213> ORGANISM: Xenopus borealis

<400> SEQUENCE: 418

Glu Val Glu Arg Arg Arg Arg Asp Lys
1               5

<210> SEQ ID NO 419
<211> LENGTH: 8
<212> TYPE: PRT
<213> ORGANISM: Homo sapiens

<400> SEQUENCE: 419

Thr Arg Asp Glu Lys Arg Arg Ala
1               5

<210> SEQ ID NO 420
<211> LENGTH: 9
<212> TYPE: PRT
<213> ORGANISM: Homo sapiens

<400> SEQUENCE: 420

Glu Val Glu Arg Arg Arg Arg Asp Lys
1               5

<210> SEQ ID NO 421
<211> LENGTH: 9
<212> TYPE: PRT
<213> ORGANISM: Unknown
<220> FEATURE:
<223> OTHER INFORMATION: Description of Unknown: YB-1
      peptide

<400> SEQUENCE: 421

Tyr Arg Arg Tyr Pro Arg Arg Arg Gly
1               5

<210> SEQ ID NO 422
<211> LENGTH: 10
<212> TYPE: PRT
<213> ORGANISM: Unknown
```

```
<220> FEATURE:
<223> OTHER INFORMATION: Description of Unknown: YB-1
      peptide

<400> SEQUENCE: 422

Gln Arg Arg Pro Tyr Arg Arg Arg Arg Phe
1               5                   10

<210> SEQ ID NO 423
<211> LENGTH: 8
<212> TYPE: PRT
<213> ORGANISM: Unknown
<220> FEATURE:
<223> OTHER INFORMATION: Description of Unknown: YB-1
      peptide

<400> SEQUENCE: 423

Tyr Arg Pro Arg Phe Arg Arg Gly
1               5

<210> SEQ ID NO 424
<211> LENGTH: 7
<212> TYPE: PRT
<213> ORGANISM: Unknown
<220> FEATURE:
<223> OTHER INFORMATION: Description of Unknown: YB-1
      peptide

<400> SEQUENCE: 424

Gln Arg Arg Tyr Arg Arg Asn
1               5

<210> SEQ ID NO 425
<211> LENGTH: 6
<212> TYPE: PRT
<213> ORGANISM: Unknown
<220> FEATURE:
<223> OTHER INFORMATION: Description of Unknown: YB-1
      peptide

<400> SEQUENCE: 425

Tyr Arg Arg Arg Arg Pro
1               5

<210> SEQ ID NO 426
<211> LENGTH: 8
<212> TYPE: PRT
<213> ORGANISM: Homo sapiens

<400> SEQUENCE: 426

Ala Lys Glu Arg Gln Lys Lys Asp
1               5

<210> SEQ ID NO 427
<211> LENGTH: 6
<212> TYPE: PRT
<213> ORGANISM: Homo sapiens

<400> SEQUENCE: 427

Glu Arg Arg Arg Arg Phe
1               5

<210> SEQ ID NO 428
<211> LENGTH: 8
<212> TYPE: PRT
<213> ORGANISM: Homo sapiens
```

```
<400> SEQUENCE: 428

Leu Lys Glu Arg Gln Lys Lys Asp
1               5

<210> SEQ ID NO 429
<211> LENGTH: 8
<212> TYPE: PRT
<213> ORGANISM: Homo sapiens

<400> SEQUENCE: 429

Ile Glu Arg Arg Arg Arg Phe Asn
1               5

<210> SEQ ID NO 430
<211> LENGTH: 10
<212> TYPE: PRT
<213> ORGANISM: Homo sapiens

<400> SEQUENCE: 430

Tyr Phe Arg Arg Arg Arg Leu Glu Lys Asp
1               5                   10

<210> SEQ ID NO 431
<211> LENGTH: 14
<212> TYPE: PRT
<213> ORGANISM: Homo sapiens

<400> SEQUENCE: 431

Lys Thr Val Ala Leu Lys Arg Arg Lys Ala Ser Ser Arg Leu
1               5                   10

<210> SEQ ID NO 432
<211> LENGTH: 9
<212> TYPE: PRT
<213> ORGANISM: Drosophila melanogaster

<400> SEQUENCE: 432

Leu Arg Arg Arg Gly Arg Gln Thr Tyr
1               5

<210> SEQ ID NO 433
<211> LENGTH: 9
<212> TYPE: PRT
<213> ORGANISM: Drosophila melanogaster

<400> SEQUENCE: 433

Leu Thr Arg Arg Arg Arg Ile Glu Met
1               5

<210> SEQ ID NO 434
<211> LENGTH: 11
<212> TYPE: PRT
<213> ORGANISM: Drosophila melanogaster

<400> SEQUENCE: 434

Gln Asn Arg Arg Met Lys Leu Lys Lys Glu Ile
1               5                   10

<210> SEQ ID NO 435
<211> LENGTH: 9
<212> TYPE: PRT
<213> ORGANISM: Caenorhabditis elegans

<400> SEQUENCE: 435
```

Ser Asn Arg Arg Arg Pro Asp His Arg
1               5

<210> SEQ ID NO 436
<211> LENGTH: 11
<212> TYPE: PRT
<213> ORGANISM: Caenorhabditis elegans

<400> SEQUENCE: 436

Val Tyr Arg Gly Arg Arg Val Arg Arg Glu
1               5                   10

<210> SEQ ID NO 437
<211> LENGTH: 21
<212> TYPE: PRT
<213> ORGANISM: Caenorhabditis elegans

<400> SEQUENCE: 437

Pro Pro Pro Pro Pro Pro Pro Ala Pro Pro Arg Arg Arg Arg Ser Ala
1               5                   10                  15

Asp Asn Lys Asp Asp
            20

<210> SEQ ID NO 438
<211> LENGTH: 8
<212> TYPE: PRT
<213> ORGANISM: Caenorhabditis elegans

<400> SEQUENCE: 438

Pro Lys Lys Pro Arg His Gln Phe
1               5

<210> SEQ ID NO 439
<211> LENGTH: 8
<212> TYPE: PRT
<213> ORGANISM: Saccharomyces cerevisiae

<400> SEQUENCE: 439

Glu Lys Arg Lys Lys Glu Arg Asn
1               5

<210> SEQ ID NO 440
<211> LENGTH: 10
<212> TYPE: PRT
<213> ORGANISM: Saccharomyces cerevisiae

<400> SEQUENCE: 440

Leu Leu Arg Arg Leu Lys Lys Glu Val Glu
1               5                   10

<210> SEQ ID NO 441
<211> LENGTH: 16
<212> TYPE: PRT
<213> ORGANISM: Saccharomyces cerevisiae

<400> SEQUENCE: 441

Glu Pro Leu Gly Arg Ile Arg Gln Lys Lys Arg Val Tyr Tyr Asp Asp
1               5                   10                  15

<210> SEQ ID NO 442
<211> LENGTH: 18
<212> TYPE: PRT
<213> ORGANISM: Saccharomyces cerevisiae

<400> SEQUENCE: 442

```
Glu Asp Ala Ile Lys Lys Arg Arg Glu Ala Arg Glu Arg Arg Leu
1               5                   10                  15

Arg Gln

<210> SEQ ID NO 443
<211> LENGTH: 19
<212> TYPE: PRT
<213> ORGANISM: Saccharomyces cerevisiae

<400> SEQUENCE: 443

Asp Lys Glu Thr Thr Ala Ser Arg Ser Lys Arg Ser Ser Arg Lys
1               5                   10                  15

Lys Arg Thr

<210> SEQ ID NO 444
<211> LENGTH: 9
<212> TYPE: PRT
<213> ORGANISM: Saccharomyces cerevisiae

<400> SEQUENCE: 444

Glu Ser Lys Lys Lys Pro Lys Leu
1               5

<210> SEQ ID NO 445
<211> LENGTH: 12
<212> TYPE: PRT
<213> ORGANISM: Saccharomyces cerevisiae

<400> SEQUENCE: 445

Lys Lys Thr Ala Ala Lys Lys Thr Lys Thr Lys Ser
1               5                   10

<210> SEQ ID NO 446
<211> LENGTH: 7
<212> TYPE: PRT
<213> ORGANISM: Homo sapiens

<400> SEQUENCE: 446

Gln Arg Lys Arg Gln Lys Leu
1               5

<210> SEQ ID NO 447
<211> LENGTH: 6
<212> TYPE: PRT
<213> ORGANISM: Homo sapiens

<400> SEQUENCE: 447

Lys Ala Lys Lys Gln Lys
1               5

<210> SEQ ID NO 448
<211> LENGTH: 7
<212> TYPE: PRT
<213> ORGANISM: Homo sapiens

<400> SEQUENCE: 448

Leu Arg Arg Lys Arg Gln Lys
1               5

<210> SEQ ID NO 449
<211> LENGTH: 11
<212> TYPE: PRT
<213> ORGANISM: Mus sp.
```

```
<400> SEQUENCE: 449

Arg Asp Ile Arg Arg Arg Gly Lys Asn Lys Val
1               5                   10

<210> SEQ ID NO 450
<211> LENGTH: 9
<212> TYPE: PRT
<213> ORGANISM: Mus sp.

<400> SEQUENCE: 450

Gln Asn Cys Arg Lys Arg Lys Leu Glu
1               5

<210> SEQ ID NO 451
<211> LENGTH: 7
<212> TYPE: PRT
<213> ORGANISM: Homo sapiens

<400> SEQUENCE: 451

Asp Lys Ile Arg Arg Lys Asn
1               5

<210> SEQ ID NO 452
<211> LENGTH: 8
<212> TYPE: PRT
<213> ORGANISM: Homo sapiens

<400> SEQUENCE: 452

Ala Arg Lys Thr Lys Lys Lys Ile
1               5

<210> SEQ ID NO 453
<211> LENGTH: 9
<212> TYPE: PRT
<213> ORGANISM: Unknown
<220> FEATURE:
<223> OTHER INFORMATION: Description of Unknown: Mouse and human
      GR (glucocorticoid receptor) peptide

<400> SEQUENCE: 453

Asp Lys Ile Arg Arg Lys Asn Cys Pro
1               5

<210> SEQ ID NO 454
<211> LENGTH: 13
<212> TYPE: PRT
<213> ORGANISM: Unknown
<220> FEATURE:
<223> OTHER INFORMATION: Description of Unknown: Mouse and human
      GR (glucocorticoid receptor) peptide

<400> SEQUENCE: 454

Glu Ala Arg Lys Thr Lys Lys Lys Ile Lys Gly Ile Gln
1               5                   10

<210> SEQ ID NO 455
<211> LENGTH: 8
<212> TYPE: PRT
<213> ORGANISM: Unknown
<220> FEATURE:
<223> OTHER INFORMATION: Description of Unknown: C/EBP (CCAAT/
      enhancer binding protein) peptide

<400> SEQUENCE: 455

Tyr Arg Val Arg Arg Glu Arg Asn
```

```
1               5

<210> SEQ ID NO 456
<211> LENGTH: 8
<212> TYPE: PRT
<213> ORGANISM: Unknown
<220> FEATURE:
<223> OTHER INFORMATION: Description of Unknown: C/EBP (CCAAT/
      enhancer binding protein) peptide

<400> SEQUENCE: 456

Val Arg Lys Ser Arg Asp Lys Ala
1               5

<210> SEQ ID NO 457
<211> LENGTH: 8
<212> TYPE: PRT
<213> ORGANISM: Unknown
<220> FEATURE:
<223> OTHER INFORMATION: Description of Unknown: C/EBP (CCAAT/
      enhancer binding protein) peptide

<400> SEQUENCE: 457

Asp Arg Leu Arg Lys Arg Val Glu
1               5

<210> SEQ ID NO 458
<211> LENGTH: 7
<212> TYPE: PRT
<213> ORGANISM: Homo sapiens

<400> SEQUENCE: 458

Asp Lys Ile Arg Arg Lys Asn
1               5

<210> SEQ ID NO 459
<211> LENGTH: 7
<212> TYPE: PRT
<213> ORGANISM: Homo sapiens

<400> SEQUENCE: 459

Ala Arg Lys Ser Lys Lys Leu
1               5

<210> SEQ ID NO 460
<211> LENGTH: 7
<212> TYPE: PRT
<213> ORGANISM: Homo sapiens

<400> SEQUENCE: 460

Asp Lys Ile Arg Arg Lys Asn
1               5

<210> SEQ ID NO 461
<211> LENGTH: 7
<212> TYPE: PRT
<213> ORGANISM: Homo sapiens

<400> SEQUENCE: 461

Gly Arg Lys Phe Lys Lys Phe
1               5

<210> SEQ ID NO 462
<211> LENGTH: 12
<212> TYPE: PRT
<213> ORGANISM: Unknown
```

```
<220> FEATURE:
<223> OTHER INFORMATION: Description of Unknown: Human and mouse
      peptide

<400> SEQUENCE: 462

Glu Glu Val Gln Arg Lys Arg Gln Lys Leu Met Pro
1               5                   10

<210> SEQ ID NO 463
<211> LENGTH: 10
<212> TYPE: PRT
<213> ORGANISM: Homo sapiens

<400> SEQUENCE: 463

Glu Glu Val Gln Arg Lys Arg Gln Lys Leu
1               5                   10

<210> SEQ ID NO 464
<211> LENGTH: 8
<212> TYPE: PRT
<213> ORGANISM: Homo sapiens

<400> SEQUENCE: 464

Gly Lys Thr Arg Thr Arg Lys Gln
1               5

<210> SEQ ID NO 465
<211> LENGTH: 7
<212> TYPE: PRT
<213> ORGANISM: Homo sapiens

<400> SEQUENCE: 465

Ala Arg Arg Lys Ser Arg Asp
1               5

<210> SEQ ID NO 466
<211> LENGTH: 9
<212> TYPE: PRT
<213> ORGANISM: Unknown
<220> FEATURE:
<223> OTHER INFORMATION: Description of Unknown: Rat, mouse,
      human peptide

<400> SEQUENCE: 466

Gln Arg Lys Glu Arg Lys Ser Lys Ser
1               5

<210> SEQ ID NO 467
<211> LENGTH: 9
<212> TYPE: PRT
<213> ORGANISM: Unknown
<220> FEATURE:
<223> OTHER INFORMATION: Description of Unknown: Rat, mouse,
      human peptide

<400> SEQUENCE: 467

Thr Lys Ser Lys Thr Lys Arg Lys Leu
1               5

<210> SEQ ID NO 468
<211> LENGTH: 7
<212> TYPE: PRT
<213> ORGANISM: Unknown
<220> FEATURE:
<223> OTHER INFORMATION: Description of Unknown: Ehrlich ascites
      S-II transcription factor peptide
```

```
<400> SEQUENCE: 468

Gly Lys Cys Lys Lys Lys Asn
1               5

<210> SEQ ID NO 469
<211> LENGTH: 9
<212> TYPE: PRT
<213> ORGANISM: Nicotiana sp.

<400> SEQUENCE: 469

Glu Arg Ser Lys Lys Arg Ser Arg Glu
1               5

<210> SEQ ID NO 470
<211> LENGTH: 11
<212> TYPE: PRT
<213> ORGANISM: Nicotiana sp.

<400> SEQUENCE: 470

Glu Arg Glu Leu Lys Arg Glu Lys Arg Lys Gln
1               5                   10

<210> SEQ ID NO 471
<211> LENGTH: 9
<212> TYPE: PRT
<213> ORGANISM: Nicotiana sp.

<400> SEQUENCE: 471

Ala Arg Arg Ser Arg Leu Arg Lys Gln
1               5

<210> SEQ ID NO 472
<211> LENGTH: 14
<212> TYPE: PRT
<213> ORGANISM: Drosophila sp.

<400> SEQUENCE: 472

Tyr Lys Leu Asp His Met Arg Arg Arg Ile Glu Thr Asp Glu
1               5                   10

<210> SEQ ID NO 473
<211> LENGTH: 7
<212> TYPE: PRT
<213> ORGANISM: Homo sapiens

<400> SEQUENCE: 473

Asp Lys Asn Arg Arg Lys Ser
1               5

<210> SEQ ID NO 474
<211> LENGTH: 7
<212> TYPE: PRT
<213> ORGANISM: Homo sapiens

<400> SEQUENCE: 474

Ile Arg Lys Asp Arg Arg Gly
1               5

<210> SEQ ID NO 475
<211> LENGTH: 7
<212> TYPE: PRT
<213> ORGANISM: Homo sapiens

<400> SEQUENCE: 475
```

Ile Lys Arg Ser Lys Lys Asn
1               5

<210> SEQ ID NO 476
<211> LENGTH: 8
<212> TYPE: PRT
<213> ORGANISM: Saccharomyces cerevisiae

<400> SEQUENCE: 476

Glu Gln Arg Arg His Arg Ile Glu
1               5

<210> SEQ ID NO 477
<211> LENGTH: 10
<212> TYPE: PRT
<213> ORGANISM: Saccharomyces cerevisiae

<400> SEQUENCE: 477

Thr Thr Arg Ala Glu Lys Lys Arg Leu Leu
1               5                   10

<210> SEQ ID NO 478
<211> LENGTH: 11
<212> TYPE: PRT
<213> ORGANISM: Saccharomyces cerevisiae

<400> SEQUENCE: 478

Ile Asp Lys Lys Arg Ser Lys Glu Ala Lys Glu
1               5                   10

<210> SEQ ID NO 479
<211> LENGTH: 13
<212> TYPE: PRT
<213> ORGANISM: Saccharomyces cerevisiae

<400> SEQUENCE: 479

Glu Ala Ala Leu Arg Arg Lys Ile Arg Thr Ile Ser Lys
1               5                   10

<210> SEQ ID NO 480
<211> LENGTH: 9
<212> TYPE: PRT
<213> ORGANISM: Mus sp.

<400> SEQUENCE: 480

Asn Lys Lys Met Arg Arg Asn Arg Phe
1               5

<210> SEQ ID NO 481
<211> LENGTH: 11
<212> TYPE: PRT
<213> ORGANISM: Mus sp.
<220> FEATURE:
<221> NAME/KEY: MOD_RES
<222> LOCATION: (5)..(8)
<223> OTHER INFORMATION: Any amino acid

<400> SEQUENCE: 481

Asn Arg Arg Lys Xaa Xaa Xaa Xaa Arg Gln Lys
1               5                   10

<210> SEQ ID NO 482
<211> LENGTH: 9
<212> TYPE: PRT
<213> ORGANISM: Mus sp.

<400> SEQUENCE: 482

Thr Lys Lys Gly Arg Arg Asn Arg Phe
1               5

<210> SEQ ID NO 483
<211> LENGTH: 11
<212> TYPE: PRT
<213> ORGANISM: Mus sp.
<220> FEATURE:
<221> NAME/KEY: MOD_RES
<222> LOCATION: (5)..(8)
<223> OTHER INFORMATION: Any amino acid

<400> SEQUENCE: 483

Asn Arg Arg Lys Xaa Xaa Xaa Xaa Arg His Lys
1               5                   10

<210> SEQ ID NO 484
<211> LENGTH: 10
<212> TYPE: PRT
<213> ORGANISM: Rattus sp.

<400> SEQUENCE: 484

Asn Lys Lys Met Arg Arg Asn Arg Phe Lys
1               5                   10

<210> SEQ ID NO 485
<211> LENGTH: 8
<212> TYPE: PRT
<213> ORGANISM: Mus sp.

<400> SEQUENCE: 485

Asn Lys Lys Met Arg Arg Asn Arg
1               5

<210> SEQ ID NO 486
<211> LENGTH: 9
<212> TYPE: PRT
<213> ORGANISM: Mus sp.

<400> SEQUENCE: 486

Thr Lys Lys Gly Arg Arg Asn Arg Phe
1               5

<210> SEQ ID NO 487
<211> LENGTH: 9
<212> TYPE: PRT
<213> ORGANISM: Homo sapiens

<400> SEQUENCE: 487

Asn Lys Lys Met Arg Arg Asn Arg Phe
1               5

<210> SEQ ID NO 488
<211> LENGTH: 9
<212> TYPE: PRT
<213> ORGANISM: Rattus sp.

<400> SEQUENCE: 488

Thr Lys Lys Gly Arg Arg Asn Arg Phe
1               5

<210> SEQ ID NO 489
<211> LENGTH: 8
<212> TYPE: PRT

```
<213> ORGANISM: Rattus sp.

<400> SEQUENCE: 489

Leu Arg Arg Gln Lys Arg Phe Lys
1               5

<210> SEQ ID NO 490
<211> LENGTH: 11
<212> TYPE: PRT
<213> ORGANISM: Rattus sp.

<400> SEQUENCE: 490

Gln Gln His His His Ser His His His His Gln
1               5                   10

<210> SEQ ID NO 491
<211> LENGTH: 8
<212> TYPE: PRT
<213> ORGANISM: Rattus sp.

<400> SEQUENCE: 491

Leu Arg Arg Gln Lys Arg Phe Lys
1               5

<210> SEQ ID NO 492
<211> LENGTH: 8
<212> TYPE: PRT
<213> ORGANISM: Rattus sp.

<400> SEQUENCE: 492

Leu Arg Arg Gln Lys Arg Phe Lys
1               5

<210> SEQ ID NO 493
<211> LENGTH: 8
<212> TYPE: PRT
<213> ORGANISM: Rattus sp.

<400> SEQUENCE: 493

Leu Lys Glu Lys Glu Arg Lys Ala
1               5

<210> SEQ ID NO 494
<211> LENGTH: 7
<212> TYPE: PRT
<213> ORGANISM: Rattus sp.

<400> SEQUENCE: 494

Met Lys Lys Ala Arg Lys Val
1               5

<210> SEQ ID NO 495
<211> LENGTH: 7
<212> TYPE: PRT
<213> ORGANISM: Rattus sp.

<400> SEQUENCE: 495

Pro Arg Arg Glu Arg Arg Tyr
1               5

<210> SEQ ID NO 496
<211> LENGTH: 9
<212> TYPE: PRT
<213> ORGANISM: Drosophila melanogaster
```

```
<400> SEQUENCE: 496

Asp Arg Arg Val Arg Lys Gly Lys Val
1               5

<210> SEQ ID NO 497
<211> LENGTH: 12
<212> TYPE: PRT
<213> ORGANISM: Mus sp.

<400> SEQUENCE: 497

Ser Lys His Gly Arg Arg Ala Arg Arg Leu Asp Pro
1               5                   10

<210> SEQ ID NO 498
<211> LENGTH: 7
<212> TYPE: PRT
<213> ORGANISM: Homo sapiens

<400> SEQUENCE: 498

Gly Arg Arg Thr Arg Arg Glu
1               5

<210> SEQ ID NO 499
<211> LENGTH: 12
<212> TYPE: PRT
<213> ORGANISM: Saccharomyces cerevisiae

<400> SEQUENCE: 499

Asp Glu Gln Lys Arg Ala Glu Lys Lys Ala Lys Glu
1               5                   10

<210> SEQ ID NO 500
<211> LENGTH: 10
<212> TYPE: PRT
<213> ORGANISM: Saccharomyces cerevisiae

<400> SEQUENCE: 500

Ile Arg Arg Ile His Lys Val Ile Arg Pro
1               5                   10

<210> SEQ ID NO 501
<211> LENGTH: 10
<212> TYPE: PRT
<213> ORGANISM: Saccharomyces cerevisiae

<400> SEQUENCE: 501

Leu Leu Arg Arg Leu Lys Lys Asp Val Glu
1               5                   10

<210> SEQ ID NO 502
<211> LENGTH: 8
<212> TYPE: PRT
<213> ORGANISM: Mus sp.

<400> SEQUENCE: 502

Ala Lys Ala Lys Ala Lys Lys Ala
1               5

<210> SEQ ID NO 503
<211> LENGTH: 8
<212> TYPE: PRT
<213> ORGANISM: Mus sp.

<400> SEQUENCE: 503
```

Tyr Lys Met Arg Arg Glu Arg Asn
1               5

<210> SEQ ID NO 504
<211> LENGTH: 8
<212> TYPE: PRT
<213> ORGANISM: Mus sp.

<400> SEQUENCE: 504

Val Arg Lys Ser Arg Asp Lys Ala
1               5

<210> SEQ ID NO 505
<211> LENGTH: 8
<212> TYPE: PRT
<213> ORGANISM: Rattus sp.

<400> SEQUENCE: 505

Ala Lys Ala Lys Ala Lys Lys Ala
1               5

<210> SEQ ID NO 506
<211> LENGTH: 8
<212> TYPE: PRT
<213> ORGANISM: Rattus sp.

<400> SEQUENCE: 506

Tyr Lys Met Arg Arg Glu Arg Asn
1               5

<210> SEQ ID NO 507
<211> LENGTH: 8
<212> TYPE: PRT
<213> ORGANISM: Rattus sp.

<400> SEQUENCE: 507

Val Arg Lys Ser Arg Asp Lys Ala
1               5

<210> SEQ ID NO 508
<211> LENGTH: 7
<212> TYPE: PRT
<213> ORGANISM: Unknown
<220> FEATURE:
<223> OTHER INFORMATION: Description of Unknown: Ig/EBP-1
      peptide

<400> SEQUENCE: 508

Tyr Arg Gln Arg Arg Glu Arg
1               5

<210> SEQ ID NO 509
<211> LENGTH: 11
<212> TYPE: PRT
<213> ORGANISM: Unknown
<220> FEATURE:
<223> OTHER INFORMATION: Description of Unknown: Ig/EBP-1
      peptide

<400> SEQUENCE: 509

Val Lys Lys Ser Arg Leu Lys Ser Lys Gln Lys
1               5                   10

<210> SEQ ID NO 510
<211> LENGTH: 13
<212> TYPE: PRT

```
<213> ORGANISM: Mus sp.

<400> SEQUENCE: 510

Glu Asp Pro Glu Lys Glu Lys Arg Ile Lys Glu Leu Glu
1               5                   10

<210> SEQ ID NO 511
<211> LENGTH: 5
<212> TYPE: PRT
<213> ORGANISM: Mus sp.

<400> SEQUENCE: 511

Met Arg Arg Lys Val
1               5

<210> SEQ ID NO 512
<211> LENGTH: 11
<212> TYPE: PRT
<213> ORGANISM: Drosophila melanogaster

<400> SEQUENCE: 512

Asp Tyr Tyr Lys Val Lys Arg Pro Lys Thr Asp
1               5                   10

<210> SEQ ID NO 513
<211> LENGTH: 9
<212> TYPE: PRT
<213> ORGANISM: Drosophila melanogaster

<400> SEQUENCE: 513

Gly Arg Ala Arg Gly Arg Arg His Gln
1               5

<210> SEQ ID NO 514
<211> LENGTH: 10
<212> TYPE: PRT
<213> ORGANISM: Drosophila melanogaster

<400> SEQUENCE: 514

Phe Arg Tyr Arg Lys Ile Lys Asp Ile Tyr
1               5                   10

<210> SEQ ID NO 515
<211> LENGTH: 8
<212> TYPE: PRT
<213> ORGANISM: Rattus sp.

<400> SEQUENCE: 515

Ala Lys Ala Lys Ala Lys Lys Ala
1               5

<210> SEQ ID NO 516
<211> LENGTH: 8
<212> TYPE: PRT
<213> ORGANISM: Mus sp.

<400> SEQUENCE: 516

Asp Lys Arg Gln Arg Asn Arg Cys
1               5

<210> SEQ ID NO 517
<211> LENGTH: 8
<212> TYPE: PRT
<213> ORGANISM: Gallus sp.
```

```
<400> SEQUENCE: 517

Asp Lys Arg Gln Arg Asn Arg Cys
1               5

<210> SEQ ID NO 518
<211> LENGTH: 8
<212> TYPE: PRT
<213> ORGANISM: Homo sapiens

<400> SEQUENCE: 518

Val Lys Ser Lys Ala Lys Lys Thr
1               5

<210> SEQ ID NO 519
<211> LENGTH: 8
<212> TYPE: PRT
<213> ORGANISM: Homo sapiens

<400> SEQUENCE: 519

Tyr Lys Ile Arg Arg Glu Arg Asn
1               5

<210> SEQ ID NO 520
<211> LENGTH: 8
<212> TYPE: PRT
<213> ORGANISM: Homo sapiens

<400> SEQUENCE: 520

Val Arg Lys Ser Arg Asp Lys Ala
1               5

<210> SEQ ID NO 521
<211> LENGTH: 8
<212> TYPE: PRT
<213> ORGANISM: Mus sp.

<400> SEQUENCE: 521

Gln Lys Lys Asn Arg Asn Lys Cys
1               5

<210> SEQ ID NO 522
<211> LENGTH: 11
<212> TYPE: PRT
<213> ORGANISM: Saccharomyces cerevisiae

<400> SEQUENCE: 522

Glu Gln Ile Arg Lys Leu Val Lys Lys His Gly
1               5                   10

<210> SEQ ID NO 523
<211> LENGTH: 9
<212> TYPE: PRT
<213> ORGANISM: Homo sapiens

<400> SEQUENCE: 523

Phe Arg Arg Ser Met Lys Arg Lys Ala
1               5

<210> SEQ ID NO 524
<211> LENGTH: 8
<212> TYPE: PRT
<213> ORGANISM: Mus sp.

<400> SEQUENCE: 524
```

Leu Lys Arg His Gln Arg Arg His
1               5

<210> SEQ ID NO 525
<211> LENGTH: 8
<212> TYPE: PRT
<213> ORGANISM: Homo sapiens

<400> SEQUENCE: 525

Leu Lys Arg His Gln Arg Arg His
1               5

<210> SEQ ID NO 526
<211> LENGTH: 10
<212> TYPE: PRT
<213> ORGANISM: Saccharomyces cerevisiae

<400> SEQUENCE: 526

Leu Lys Glu Ser Lys Arg Lys Tyr Asp Glu
1               5                   10

<210> SEQ ID NO 527
<211> LENGTH: 12
<212> TYPE: PRT
<213> ORGANISM: Homo sapiens

<400> SEQUENCE: 527

Glu Val Leu Lys Val Gln Lys Arg Arg Ile Tyr Asp
1               5                   10

<210> SEQ ID NO 528
<211> LENGTH: 7
<212> TYPE: PRT
<213> ORGANISM: Saccharomyces cerevisiae

<400> SEQUENCE: 528

Tyr Lys Ser Lys Lys Lys Ala
1               5

<210> SEQ ID NO 529
<211> LENGTH: 8
<212> TYPE: PRT
<213> ORGANISM: Saccharomyces cerevisiae

<400> SEQUENCE: 529

Thr Lys Lys Leu Pro Arg Lys Thr
1               5

<210> SEQ ID NO 530
<211> LENGTH: 12
<212> TYPE: PRT
<213> ORGANISM: Saccharomyces cerevisiae

<400> SEQUENCE: 530

Thr Arg Lys Lys Gly Gly Arg Arg Gly Arg Arg Leu
1               5                   10

<210> SEQ ID NO 531
<211> LENGTH: 11
<212> TYPE: PRT
<213> ORGANISM: Saccharomyces cerevisiae

<400> SEQUENCE: 531

Ala Arg Ala Thr Arg Arg Lys Arg Cys Lys Gly
1               5                   10

<210> SEQ ID NO 532
<211> LENGTH: 10
<212> TYPE: PRT
<213> ORGANISM: Saccharomyces cerevisiae

<400> SEQUENCE: 532

Gly Lys Gly Lys Tyr Arg Asn Arg Arg Trp
1               5                   10

<210> SEQ ID NO 533
<211> LENGTH: 15
<212> TYPE: PRT
<213> ORGANISM: Xenopus laevis

<400> SEQUENCE: 533

Gly Lys Gly Lys Met Arg Asn Arg Arg Ile Gln Arg Arg Gly
1               5                   10                  15

<210> SEQ ID NO 534
<211> LENGTH: 12
<212> TYPE: PRT
<213> ORGANISM: Xenopus laevis

<400> SEQUENCE: 534

Asn Lys Lys Val Lys Arg Arg Glu Leu Lys Lys Asn
1               5                   10

<210> SEQ ID NO 535
<211> LENGTH: 8
<212> TYPE: PRT
<213> ORGANISM: Xenopus laevis

<400> SEQUENCE: 535

Ala Lys Thr Ala Arg Arg Lys Ala
1               5

<210> SEQ ID NO 536
<211> LENGTH: 8
<212> TYPE: PRT
<213> ORGANISM: Xenopus laevis

<400> SEQUENCE: 536

Ile Lys Ala Lys Glu Lys Lys Pro
1               5

<210> SEQ ID NO 537
<211> LENGTH: 8
<212> TYPE: PRT
<213> ORGANISM: Xenopus laevis

<400> SEQUENCE: 537

Gly Lys Pro Lys Ala Lys Lys Pro
1               5

<210> SEQ ID NO 538
<211> LENGTH: 7
<212> TYPE: PRT
<213> ORGANISM: Xenopus laevis

<400> SEQUENCE: 538

Ala Lys Ala Lys Lys Arg Gln
1               5

```
<210> SEQ ID NO 539
<211> LENGTH: 6
<212> TYPE: PRT
<213> ORGANISM: Homo sapiens

<400> SEQUENCE: 539

Glu Arg Lys Arg Lys Ser
1               5

<210> SEQ ID NO 540
<211> LENGTH: 8
<212> TYPE: PRT
<213> ORGANISM: Homo sapiens

<400> SEQUENCE: 540

Gly Lys Arg Pro Arg Thr Lys Ala
1               5

<210> SEQ ID NO 541
<211> LENGTH: 6
<212> TYPE: PRT
<213> ORGANISM: Homo sapiens

<400> SEQUENCE: 541

His Lys Arg Arg Arg Ile
1               5

<210> SEQ ID NO 542
<211> LENGTH: 11
<212> TYPE: PRT
<213> ORGANISM: Homo sapiens

<400> SEQUENCE: 542

Leu Lys Lys Gln Arg Thr Lys Lys Asn Lys Glu
1               5                   10

<210> SEQ ID NO 543
<211> LENGTH: 9
<212> TYPE: PRT
<213> ORGANISM: Rattus sp.

<400> SEQUENCE: 543

Pro Lys Met Arg Arg Arg Thr Tyr Arg
1               5

<210> SEQ ID NO 544
<211> LENGTH: 11
<212> TYPE: PRT
<213> ORGANISM: Rattus sp.

<400> SEQUENCE: 544

Lys Lys Lys Ile Ser Gln Lys Lys Leu Lys Lys
1               5                   10

<210> SEQ ID NO 545
<211> LENGTH: 9
<212> TYPE: PRT
<213> ORGANISM: Podocoryne carnea

<400> SEQUENCE: 545

Tyr Met Arg Arg Arg Thr Tyr Arg Ala
1               5

<210> SEQ ID NO 546
<211> LENGTH: 10
```

```
<212> TYPE: PRT
<213> ORGANISM: Podocoryne carnea

<400> SEQUENCE: 546

Glu Val Lys Lys Val Ser Lys Lys Leu
1               5                   10

<210> SEQ ID NO 547
<211> LENGTH: 12
<212> TYPE: PRT
<213> ORGANISM: Unknown
<220> FEATURE:
<223> OTHER INFORMATION: Description of Unknown: Human, rat ribosomal
      S13 peptide

<400> SEQUENCE: 547

Glu Arg Asn Arg Lys Asp Lys Asp Ala Lys Phe Arg
1               5                   10

<210> SEQ ID NO 548
<211> LENGTH: 6
<212> TYPE: PRT
<213> ORGANISM: Saccharomyces cerevisiae

<400> SEQUENCE: 548

Glu Arg Lys Arg Lys Ser
1               5

<210> SEQ ID NO 549
<211> LENGTH: 8
<212> TYPE: PRT
<213> ORGANISM: Saccharomyces cerevisiae

<400> SEQUENCE: 549

Gln Arg Leu Gln Arg Lys Arg His
1               5

<210> SEQ ID NO 550
<211> LENGTH: 6
<212> TYPE: PRT
<213> ORGANISM: Saccharomyces cerevisiae

<400> SEQUENCE: 550

Ile Arg Lys Arg Arg Ala
1               5

<210> SEQ ID NO 551
<211> LENGTH: 51
<212> TYPE: PRT
<213> ORGANISM: Unknown
<220> FEATURE:
<223> OTHER INFORMATION: Description of Unknown: 35 kD subunit of U2
      small nuclear ribonucleoprotein auxiliary
      factor (U2AF) peptide

<400> SEQUENCE: 551

Gly Arg Arg Arg Lys Lys His Arg Ser Arg Ser Arg Ser Arg Glu Arg
1               5                   10                  15

Arg Ser Arg Ser Arg Asp Arg Gly Arg Gly Gly Gly Gly Gly Gly
            20                  25                  30

Gly Gly Gly Gly Gly Gly Arg Glu Asp Arg Arg Ser Arg Asp
        35                  40                  45

Arg Glu Arg
    50
```

```
<210> SEQ ID NO 552
<211> LENGTH: 7
<212> TYPE: PRT
<213> ORGANISM: Homo sapiens

<400> SEQUENCE: 552

Glu Phe Glu Asp Pro Arg Asp
1               5

<210> SEQ ID NO 553
<211> LENGTH: 8
<212> TYPE: PRT
<213> ORGANISM: Homo sapiens

<400> SEQUENCE: 553

Glu Thr Arg Glu Glu Arg Met Glu
1               5

<210> SEQ ID NO 554
<211> LENGTH: 9
<212> TYPE: PRT
<213> ORGANISM: Homo sapiens

<400> SEQUENCE: 554

Glu Ala Gly Asp Ala Pro Pro Asp Pro
1               5

<210> SEQ ID NO 555
<211> LENGTH: 11
<212> TYPE: PRT
<213> ORGANISM: Homo sapiens

<400> SEQUENCE: 555

Glu Glu Arg Met Glu Arg Lys Arg Arg Glu Lys
1               5                   10

<210> SEQ ID NO 556
<211> LENGTH: 78
<212> TYPE: PRT
<213> ORGANISM: Homo sapiens

<400> SEQUENCE: 556

His Arg Asp Arg Asp Arg Asp Arg Glu Arg Glu Arg Glu Ser Arg
1               5                   10                  15

Glu Arg Asp Lys Glu Arg Glu Arg Arg Ser Arg Ser Arg Asp Arg
                20                  25                  30

Arg Arg Arg Ser Arg Ser Arg Asp Lys Glu Glu Arg Arg Ser Arg
                35                  40                  45

Glu Arg Ser Lys Asp Lys Asp Arg Asp Arg Lys Arg Arg Ser Ser Arg
                50                  55                  60

Ser Arg Glu Arg Ala Arg Arg Glu Arg Glu Arg Lys Glu Glu
65                  70                  75

<210> SEQ ID NO 557
<211> LENGTH: 36
<212> TYPE: PRT
<213> ORGANISM: Homo sapiens

<400> SEQUENCE: 557

Arg Asp Arg Asp Arg Glu Arg Arg Ser His Arg Ser Glu Arg Glu
1               5                   10                  15

Arg Arg Arg Asp Arg Asp Arg Asp Arg Asp Arg Asp Arg Glu His Lys
```

```
                20                  25                  30

Arg Gly Glu Arg
        35

<210> SEQ ID NO 558
<211> LENGTH: 15
<212> TYPE: PRT
<213> ORGANISM: Saccharomyces cerevisiae

<400> SEQUENCE: 558

Gln Lys Arg Asn Asn Lys Lys Ser Lys Lys Arg Cys Ala Glu
1               5                   10                  15

<210> SEQ ID NO 559
<211> LENGTH: 8
<212> TYPE: PRT
<213> ORGANISM: Saccharomyces cerevisiae

<400> SEQUENCE: 559

Glu Lys Leu Arg Lys Leu Lys Ile
1               5

<210> SEQ ID NO 560
<211> LENGTH: 6
<212> TYPE: PRT
<213> ORGANISM: Saccharomyces cerevisiae

<400> SEQUENCE: 560

Asn Lys Arg Lys Arg Val
1               5

<210> SEQ ID NO 561
<211> LENGTH: 11
<212> TYPE: PRT
<213> ORGANISM: Saccharomyces cerevisiae

<400> SEQUENCE: 561

Ser Leu Lys Asn Arg Ser Asn Arg Lys Arg Glu
1               5                   10

<210> SEQ ID NO 562
<211> LENGTH: 9
<212> TYPE: PRT
<213> ORGANISM: Saccharomyces cerevisiae

<400> SEQUENCE: 562

Glu Pro Lys Arg Lys Arg Arg Leu Pro
1               5

<210> SEQ ID NO 563
<211> LENGTH: 8
<212> TYPE: PRT
<213> ORGANISM: Saccharomyces cerevisiae

<400> SEQUENCE: 563

Ala Arg Met Arg His Ser Lys Arg
1               5

<210> SEQ ID NO 564
<211> LENGTH: 14
<212> TYPE: PRT
<213> ORGANISM: Unknown
<220> FEATURE:
<223> OTHER INFORMATION: Description of Unknown: Chicken, Xenopus No. 38
      nucleolar (38 kD) peptide
```

```
<220> FEATURE:
<221> NAME/KEY: MOD_RES
<222> LOCATION: (6)..(8)
<223> OTHER INFORMATION: Any amino acid

<400> SEQUENCE: 564

Lys Ala Glu Lys Glu Xaa Xaa Xaa Lys Val Asp Asp Glu Glu
1               5                   10

<210> SEQ ID NO 565
<211> LENGTH: 15
<212> TYPE: PRT
<213> ORGANISM: Unknown
<220> FEATURE:
<223> OTHER INFORMATION: Description of Unknown: Chicken, Xenopus No. 38
      nucleolar (38 kD) peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid

<400> SEQUENCE: 565

Lys Xaa Xaa Xaa Lys Xaa Xaa Xaa Xaa Lys Xaa Xaa Xaa Xaa Arg
1               5                   10                  15

<210> SEQ ID NO 566
<211> LENGTH: 21
<212> TYPE: PRT
<213> ORGANISM: Unknown
<220> FEATURE:
<223> OTHER INFORMATION: Description of Unknown: Chicken, hamster
      nucleolin (92 kD) peptide
<220> FEATURE:
<221> NAME/KEY: MOD_RES
<222> LOCATION: (14)..(20)
<223> OTHER INFORMATION: Any amino acid

<400> SEQUENCE: 566

Lys Thr Glu Arg Glu Ala Glu Lys Ala Leu Glu Glu Lys Xaa Xaa Xaa
1               5                   10                  15

Xaa Xaa Xaa Xaa Arg
            20

<210> SEQ ID NO 567
<211> LENGTH: 32
<212> TYPE: PRT
<213> ORGANISM: Unknown
<220> FEATURE:
<223> OTHER INFORMATION: Description of Unknown: Chicken, hamster
      nucleolin (92 kD) peptide
<220> FEATURE:
<221> NAME/KEY: MOD_RES
<222> LOCATION: (2)..(6)
<223> OTHER INFORMATION: Any amino acid
<220> FEATURE:
<221> NAME/KEY: MOD_RES
<222> LOCATION: (8)..(14)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
```

```
<222> LOCATION: (21)..(23)
<223> OTHER INFORMATION: Any amino acid

<400> SEQUENCE: 567

Lys Xaa Xaa Xaa Xaa Lys Xaa Xaa Xaa Xaa Xaa Xaa Lys Xaa
1               5                   10                  15

Xaa Xaa Xaa Arg Xaa Xaa Xaa Glu Asp Thr Thr Glu Glu Thr Leu Arg
            20                  25                  30

<210> SEQ ID NO 568
<211> LENGTH: 50
<212> TYPE: PRT
<213> ORGANISM: Unknown
<220> FEATURE:
<223> OTHER INFORMATION: Description of Unknown: Chicken, hamster
      nucleolin (92 kD) peptide

<400> SEQUENCE: 568

Arg Gly Gly Arg Gly Gly Arg Gly Gly Arg Gly Gly Phe Gly Gly
1               5                   10                  15

Arg Gly Gly Gly Arg Gly Phe Gly Gly Arg Gly Gly Gly Phe Arg Gly
            20                  25                  30

Gly Arg Gly Gly Gly Gly Asp His Lys Pro Gln Gly Lys Lys Ile Lys
        35                  40                  45

Phe Glu
    50

<210> SEQ ID NO 569
<211> LENGTH: 10
<212> TYPE: PRT
<213> ORGANISM: Homo sapiens

<400> SEQUENCE: 569

Trp Tyr Lys His Phe Lys Lys Thr Lys Asp
1               5                   10

<210> SEQ ID NO 570
<211> LENGTH: 9
<212> TYPE: PRT
<213> ORGANISM: Saccharomyces cerevisiae

<400> SEQUENCE: 570

Gln Lys Lys Lys Gln Met Lys Ala Asp
1               5

<210> SEQ ID NO 571
<211> LENGTH: 30
<212> TYPE: PRT
<213> ORGANISM: Saccharomyces cerevisiae

<400> SEQUENCE: 571

Lys Lys Glu Lys Lys Glu Lys Lys Glu Lys Lys Glu Lys Lys Glu Lys
1               5                   10                  15

Lys Glu Lys Lys Glu Lys Lys Glu Lys Lys Glu Lys Lys Glu
            20                  25                  30

<210> SEQ ID NO 572
<211> LENGTH: 10
<212> TYPE: PRT
<213> ORGANISM: Saccharomyces cerevisiae

<400> SEQUENCE: 572

Lys Lys Glu Lys Lys Arg Lys Ser Glu Asp
```

```
1               5                  10

<210> SEQ ID NO 573
<211> LENGTH: 10
<212> TYPE: PRT
<213> ORGANISM: Saccharomyces cerevisiae

<400> SEQUENCE: 573

Glu Glu Lys Lys Ser Lys Lys Ser Lys Lys
1               5                  10

<210> SEQ ID NO 574
<211> LENGTH: 8
<212> TYPE: PRT
<213> ORGANISM: Saccharomyces cerevisiae

<400> SEQUENCE: 574

Thr Lys Lys Lys Ser Phe Lys Leu
1               5

<210> SEQ ID NO 575
<211> LENGTH: 19
<212> TYPE: PRT
<213> ORGANISM: Rattus sp.

<400> SEQUENCE: 575

Lys Ser Glu Arg Glu Arg Met Leu Arg Glu Ser Leu Lys Glu Glu Arg
1               5                  10                  15

Arg Arg Phe

<210> SEQ ID NO 576
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Pro Lys Lys Gly Ser Lys Lys Ala
1               5

<210> SEQ ID NO 577
<211> LENGTH: 12
<212> TYPE: PRT
<213> ORGANISM: Homo sapiens

<400> SEQUENCE: 577

Asp Gly Lys Lys Arg Lys Arg Ser Arg Lys Glu Ser
1               5                  10

<210> SEQ ID NO 578
<211> LENGTH: 11
<212> TYPE: PRT
<213> ORGANISM: Bos sp.

<400> SEQUENCE: 578

Gly Ala Lys Arg His Arg Lys Val Leu Arg Asp
1               5                  10

<210> SEQ ID NO 579
<211> LENGTH: 10
<212> TYPE: PRT
<213> ORGANISM: Bos sp.
```

```
<400> SEQUENCE: 579

Pro Ala Ile Arg Arg Leu Ala Arg Arg Gly
1               5                   10

<210> SEQ ID NO 580
<211> LENGTH: 7
<212> TYPE: PRT
<213> ORGANISM: Bos sp.

<400> SEQUENCE: 580

Glu His Ala Arg Arg Lys Thr
1               5

<210> SEQ ID NO 581
<211> LENGTH: 9
<212> TYPE: PRT
<213> ORGANISM: Bos sp.

<400> SEQUENCE: 581

Ala Arg Arg Ile Arg Gly Glu Arg Ala
1               5

<210> SEQ ID NO 582
<211> LENGTH: 9
<212> TYPE: PRT
<213> ORGANISM: Bos sp.

<400> SEQUENCE: 582

Gly Ser His His Lys Ala Lys Gly Lys
1               5

<210> SEQ ID NO 583
<211> LENGTH: 17
<212> TYPE: PRT
<213> ORGANISM: Psammechinus miliaris

<400> SEQUENCE: 583

Arg Gly Lys Ser Gly Lys Ala Arg Thr Lys Ala Lys Ser Arg Ser Ser
1               5                   10                  15

Arg

<210> SEQ ID NO 584
<211> LENGTH: 8
<212> TYPE: PRT
<213> ORGANISM: Bos sp.

<400> SEQUENCE: 584

Pro Lys Lys Gly Ser Lys Lys Ala
1               5

<210> SEQ ID NO 585
<211> LENGTH: 15
<212> TYPE: PRT
<213> ORGANISM: Bos sp.

<400> SEQUENCE: 585

Gln Lys Lys Asp Gly Lys Lys Arg Lys Arg Ser Arg Lys Glu Ser
1               5                   10                  15

<210> SEQ ID NO 586
<211> LENGTH: 13
<212> TYPE: PRT
<213> ORGANISM: Psammechinus miliaris
```

```
<400> SEQUENCE: 586

Gly Gly Lys Lys Arg His Arg Lys Arg Lys Gly Ser Tyr
1               5                   10

<210> SEQ ID NO 587
<211> LENGTH: 14
<212> TYPE: PRT
<213> ORGANISM: Unknown
<220> FEATURE:
<223> OTHER INFORMATION: Description of Unknown: Starfish H2B
      peptide

<400> SEQUENCE: 587

Pro Arg Thr Asp Lys Lys Arg Arg Arg Lys Arg Lys Glu Ser
1               5                   10

<210> SEQ ID NO 588
<211> LENGTH: 9
<212> TYPE: PRT
<213> ORGANISM: Unknown
<220> FEATURE:
<223> OTHER INFORMATION: Description of Unknown: Trout
      testis H1 (194 aa) peptide

<400> SEQUENCE: 588

Pro Ala Lys Ala Pro Lys Lys Lys Ala
1               5

<210> SEQ ID NO 589
<211> LENGTH: 9
<212> TYPE: PRT
<213> ORGANISM: Unknown
<220> FEATURE:
<223> OTHER INFORMATION: Description of Unknown: Trout
      testis H1 (194 aa) peptide

<400> SEQUENCE: 589

Glu Ala Lys Lys Pro Ala Lys Lys Ala
1               5

<210> SEQ ID NO 590
<211> LENGTH: 7
<212> TYPE: PRT
<213> ORGANISM: Unknown
<220> FEATURE:
<223> OTHER INFORMATION: Description of Unknown: Trout
      testis H1 (194 aa) peptide

<400> SEQUENCE: 590

Ala Lys Lys Pro Lys Lys Val
1               5

<210> SEQ ID NO 591
<211> LENGTH: 11
<212> TYPE: PRT
<213> ORGANISM: Unknown
<220> FEATURE:
<223> OTHER INFORMATION: Description of Unknown: Trout
      testis H1 (194 aa) peptide

<400> SEQUENCE: 591

Ala Lys Lys Ser Pro Lys Lys Ala Lys Lys Pro
1               5                   10

<210> SEQ ID NO 592
<211> LENGTH: 7
<212> TYPE: PRT
```

```
<213> ORGANISM: Unknown
<220> FEATURE:
<223> OTHER INFORMATION: Description of Unknown: Trout
      testis H1 (194 aa) peptide

<400> SEQUENCE: 592

Pro Lys Lys Val Lys Lys Pro
1               5

<210> SEQ ID NO 593
<211> LENGTH: 8
<212> TYPE: PRT
<213> ORGANISM: Parechinus angulosus

<400> SEQUENCE: 593

Pro Arg Arg Lys Ala Lys Arg Ala
1               5

<210> SEQ ID NO 594
<211> LENGTH: 7
<212> TYPE: PRT
<213> ORGANISM: Parechinus angulosus

<400> SEQUENCE: 594

Pro Lys Lys Ala Lys Lys Thr
1               5

<210> SEQ ID NO 595
<211> LENGTH: 8
<212> TYPE: PRT
<213> ORGANISM: Parechinus angulosus

<400> SEQUENCE: 595

Ala Lys Ala Lys Lys Ala Lys Ala
1               5

<210> SEQ ID NO 596
<211> LENGTH: 9
<212> TYPE: PRT
<213> ORGANISM: Parechinus angulosus

<400> SEQUENCE: 596

Ala Lys Lys Ala Arg Lys Ala Lys Ala
1               5

<210> SEQ ID NO 597
<211> LENGTH: 11
<212> TYPE: PRT
<213> ORGANISM: Parechinus angulosus

<400> SEQUENCE: 597

Ala Lys Lys Ala Lys Lys Pro Lys Lys Lys Ala
1               5                   10

<210> SEQ ID NO 598
<211> LENGTH: 10
<212> TYPE: PRT
<213> ORGANISM: Parechinus angulosus

<400> SEQUENCE: 598

Ala Lys Lys Ala Lys Lys Pro Ala Lys Lys
1               5                   10

<210> SEQ ID NO 599
<211> LENGTH: 8
```

```
<212> TYPE: PRT
<213> ORGANISM: Parechinus angulosus

<400> SEQUENCE: 599

Ser Pro Lys Lys Ala Lys Lys Pro
1               5

<210> SEQ ID NO 600
<211> LENGTH: 13
<212> TYPE: PRT
<213> ORGANISM: Parechinus angulosus

<400> SEQUENCE: 600

Ala Lys Lys Ser Pro Lys Lys Lys Ala Lys Arg Ser
1               5                   10

<210> SEQ ID NO 601
<211> LENGTH: 7
<212> TYPE: PRT
<213> ORGANISM: Parechinus angulosus

<400> SEQUENCE: 601

Pro Lys Lys Ala Lys Lys Ala
1               5

<210> SEQ ID NO 602
<211> LENGTH: 7
<212> TYPE: PRT
<213> ORGANISM: Parechinus angulosus

<400> SEQUENCE: 602

Ala Lys Lys Ala Lys Lys Ser
1               5

<210> SEQ ID NO 603
<211> LENGTH: 15
<212> TYPE: PRT
<213> ORGANISM: Parechinus angulosus

<400> SEQUENCE: 603

Pro Arg Lys Ala Gly Lys Arg Arg Ser Pro Lys Lys Ala Arg Lys
1               5                   10                  15

<210> SEQ ID NO 604
<211> LENGTH: 7
<212> TYPE: PRT
<213> ORGANISM: Unknown
<220> FEATURE:
<223> OTHER INFORMATION: Description of Unknown: Annelid sperm
      H1a (119 aa) peptide

<400> SEQUENCE: 604

Ala Arg Arg Arg Lys Thr Ala
1               5

<210> SEQ ID NO 605
<211> LENGTH: 8
<212> TYPE: PRT
<213> ORGANISM: Unknown
<220> FEATURE:
<223> OTHER INFORMATION: Description of Unknown: Annelid sperm
      H1a (119 aa) peptide

<400> SEQUENCE: 605

Ile Arg Lys Phe Ile Arg Lys Ala
1               5
```

<210> SEQ ID NO 606
<211> LENGTH: 6
<212> TYPE: PRT
<213> ORGANISM: Unknown
<220> FEATURE:
<223> OTHER INFORMATION: Description of Unknown: Annelid sperm
      H1a (119 aa) peptide

<400> SEQUENCE: 606

Pro Lys Lys Lys Lys Ala
1               5

<210> SEQ ID NO 607
<211> LENGTH: 12
<212> TYPE: PRT
<213> ORGANISM: Unknown
<220> FEATURE:
<223> OTHER INFORMATION: Description of Unknown: Annelid sperm
      H1a (119 aa) peptide

<400> SEQUENCE: 607

Ala Lys Lys Pro Lys Ala Lys Lys Val Lys Lys Pro
1               5                   10

<210> SEQ ID NO 608
<211> LENGTH: 17
<212> TYPE: PRT
<213> ORGANISM: Unknown
<220> FEATURE:
<223> OTHER INFORMATION: Description of Unknown: Annelid sperm
      H1a (119 aa) peptide

<400> SEQUENCE: 608

Ala Lys Lys Lys Thr Asn Arg Ala Arg Lys Pro Lys Thr Lys Lys Asn
1               5                   10                  15

Arg

<210> SEQ ID NO 609
<211> LENGTH: 7
<212> TYPE: PRT
<213> ORGANISM: Bos sp.

<400> SEQUENCE: 609

Pro Lys Arg Lys Val Ser Ser
1               5

<210> SEQ ID NO 610
<211> LENGTH: 11
<212> TYPE: PRT
<213> ORGANISM: Bos sp.

<400> SEQUENCE: 610

Glu Glu Pro Lys Arg Arg Ser Ala Arg Leu Ser
1               5                   10

<210> SEQ ID NO 611
<211> LENGTH: 10
<212> TYPE: PRT
<213> ORGANISM: Bos sp.

<400> SEQUENCE: 611

Pro Lys Arg Lys Ala Glu Gly Asp Ala Lys
1               5                   10

```
<210> SEQ ID NO 612
<211> LENGTH: 8
<212> TYPE: PRT
<213> ORGANISM: Bos sp.

<400> SEQUENCE: 612

Pro Lys Gly Lys Lys Gly Lys Ala
1               5

<210> SEQ ID NO 613
<211> LENGTH: 8
<212> TYPE: PRT
<213> ORGANISM: Bos sp.

<400> SEQUENCE: 613

Pro Lys Lys Pro Arg Gly Lys Met
1               5

<210> SEQ ID NO 614
<211> LENGTH: 7
<212> TYPE: PRT
<213> ORGANISM: Bos sp.

<400> SEQUENCE: 614

Glu His Lys Lys Lys His Pro
1               5

<210> SEQ ID NO 615
<211> LENGTH: 9
<212> TYPE: PRT
<213> ORGANISM: Bos sp.

<400> SEQUENCE: 615

Glu Thr Lys Lys Lys Phe Lys Asp Pro
1               5

<210> SEQ ID NO 616
<211> LENGTH: 48
<212> TYPE: PRT
<213> ORGANISM: Bos sp.
<220> FEATURE:
<221> NAME/KEY: MOD_RES
<222> LOCATION: (8)..(48)
<223> OTHER INFORMATION: Glu or Asp

<400> SEQUENCE: 616

Glu Lys Ser Lys Lys Lys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

<210> SEQ ID NO 617
<211> LENGTH: 13
<212> TYPE: PRT
<213> ORGANISM: Bos sp.

<400> SEQUENCE: 617

Glu Glu Glu Gly Gly Lys Lys Lys Lys Phe Ala Lys
1               5                   10

<210> SEQ ID NO 618
<211> LENGTH: 7
<212> TYPE: PRT
```

```
<213> ORGANISM: Bos sp.

<400> SEQUENCE: 618

Glu His Lys Lys Lys His Pro
1               5

<210> SEQ ID NO 619
<211> LENGTH: 12
<212> TYPE: PRT
<213> ORGANISM: Bos sp.

<400> SEQUENCE: 619

Pro Lys Gly Asp Lys Lys Gly Lys Lys Lys Asp Pro
1               5                   10

<210> SEQ ID NO 620
<211> LENGTH: 15
<212> TYPE: PRT
<213> ORGANISM: Bos sp.

<400> SEQUENCE: 620

Glu Glu Glu Glu Gly Gly Gly Lys Lys Lys Lys Phe Ala Lys
1               5                   10                  15

<210> SEQ ID NO 621
<211> LENGTH: 15
<212> TYPE: PRT
<213> ORGANISM: Unknown
<220> FEATURE:
<223> OTHER INFORMATION: Description of Unknown: Trout
      testis H6 (60 aa) peptide

<400> SEQUENCE: 621

Pro Lys Arg Lys Ser Ala Thr Lys Gly Asp Glu Pro Ala Arg Arg
1               5                   10                  15

<210> SEQ ID NO 622
<211> LENGTH: 11
<212> TYPE: PRT
<213> ORGANISM: Unknown
<220> FEATURE:
<223> OTHER INFORMATION: Description of Unknown: Trout
      testis H6 (60 aa) peptide

<400> SEQUENCE: 622

Lys Pro Lys Lys Ala Ala Ala Pro Lys Lys Ala
1               5                   10

<210> SEQ ID NO 623
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

His His His His His Ser Pro Ser Leu Leu Leu Leu Leu Leu Leu
1               5                   10                  15

Leu Leu Leu Leu Leu Leu Leu Leu
                20

<210> SEQ ID NO 624
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 624

His His His His His Ser Pro Ser Leu Ala Ile Leu Ala Ile Leu Ala
1               5                   10                  15

Ile Leu Ala Ile Leu Ala Ile
            20

<210> SEQ ID NO 625
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MOD_RES
<222> LOCATION: (1)..(6)
<223> OTHER INFORMATION: This region may encompass four to six residues

<400> SEQUENCE: 625

His His His His His His
1               5

<210> SEQ ID NO 626
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Pro Lys Thr Lys Arg Lys Val
1               5

<210> SEQ ID NO 627
<211> LENGTH: 35
<212> TYPE: PRT
<213> ORGANISM: Adenovirus
<220> FEATURE:
<221> NAME/KEY: MOD_RES
<222> LOCATION: (3)..(22)
<223> OTHER INFORMATION: Any amino acid and this region may encompass 7
      to 20 residues
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (30)..(33)
<223> OTHER INFORMATION: Any amino acid

<400> SEQUENCE: 627

Phe Val Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Met Xaa Ser Leu Xaa Tyr Met Xaa Xaa Xaa
            20                  25                  30

Xaa Met Phe
        35
```

```
<210> SEQ ID NO 628
<211> LENGTH: 6
<212> TYPE: PRT
<213> ORGANISM: Human immunodeficiency virus

<400> SEQUENCE: 628

Asn Arg Arg Arg Arg Trp
1               5

<210> SEQ ID NO 629
<211> LENGTH: 7
<212> TYPE: PRT
<213> ORGANISM: Human immunodeficiency virus

<400> SEQUENCE: 629

Trp Arg Glu Arg Gln Arg Gln
1               5

<210> SEQ ID NO 630
<211> LENGTH: 19
<212> TYPE: PRT
<213> ORGANISM: Saccharomyces cerevisiae

<400> SEQUENCE: 630

Ser Ser His His His His His His His His His His His His Gly
1               5                   10                  15

His Gly Gly

<210> SEQ ID NO 631
<211> LENGTH: 17
<212> TYPE: PRT
<213> ORGANISM: Unknown
<220> FEATURE:
<223> OTHER INFORMATION: Description of Unknown: Bipartite
      NLS peptide
<220> FEATURE:
<221> NAME/KEY: MOD_RES
<222> LOCATION: (4)..(14)
<223> OTHER INFORMATION: Any amino acid

<400> SEQUENCE: 631

Lys Asp Lys Xaa Xaa Xaa Xaa Xaa Xaa Xaa Xaa Xaa Xaa Xaa Arg Lys
1               5                   10                  15

Lys
```

ENCAPSULATION OF PLASMID DNA (LIPOGENES™) AND THERAPEUTIC AGENTS WITH NUCLEAR LOCALIZATION SIGNAL/FUSOGENIC PEPTIDE CONJUGATES INTO TARGETED LIPOSOME COMPLEXES

CROSS-REFERENCE TO RELATED APPLICATIONS

This application is a continuation of U.S. application Ser. No. 12/830,118, filed Jul. 2, 2010, now abandoned, which is a continuation of U.S. application Ser. No. 09/876,904, filed Jun. 8, 2001, now abandoned, which in turn claims priority under 35 U.S.C. §119(e) to U.S. Provisional Application No. 60/210,925, filed Jun. 9, 2000, the content of each of which is hereby incorporated by reference into the present disclosure.

SEQUENCE LISTING

The instant application contains a Sequence Listing which has been submitted in ASCII format via EFS-Web and is hereby incorporated by reference in its entirety. Said ASCII copy, created on Jan. 24, 2014, is named 062282-0202_SL.txt and is 126,633 bytes in size.

FIELD OF THE INVENTION

The present invention relates to the field of gene therapy and is specifically directed toward methods for producing peptide-lipid-polynucleotide complexes suitable for delivery of polynucleotides to a subject. The peptide-lipid-polynucleotide complexes so produced are useful in a subject for inhibiting the progression of neoplastic disease.

BACKGROUND OF THE INVENTION

Throughout this application various publications, patents and published patent specifications are referenced by author and date or by an identifying patent number. Full bibliographical citations for the publications are provided immediately preceding the claims. The disclosures of these publications, patents and published patent specifications are hereby incorporated by reference into the present disclosure to more fully describe the state of the art to which this invention pertains.

Gene therapy is a newly emerging field of biomedical research that holds great promise for the treatment of both acute and chronic diseases and has the potential to bring a revolutionary era to molecular medicine. However, despite numerous preclinical and clinical studies, routine use of gene therapy for the treatment of human disease has not yet been perfected. It remains an important unmet need of gene therapy to create gene delivery systems that effectively target specific cells of interest in a subject while controlling harmful side effects. Gene therapy is aimed at introducing therapeutically important genes into somatic cells of patients. Diseases already shown to be amenable to therapy with gene transfer in clinical trials include, cancer (melanoma, breast, lymphoma, head and neck, ovarian, colon, prostate, brain, chronic myelogenous leukemia, non-small cell lung, lung adenocarcinoma, colorectal, neuroblastoma, glioma, glioblastoma, astrocytoma, and others), AIDS, cystic fibrosis, adenosine deaminase deficiency, cardiovascular diseases (restenosis, familial hypercholesterolemia, peripheral artery disease), Gaucher disease, α1-antitrypsin deficiency, rheumatoid arthritis and others. Human diseases expected to be the object of clinical trials include hemophilia A and B, Parkinson's disease, ocular diseases, xeroderma pigmentosum, high blood pressure, obesity. ADA deficiency was the disease successfully treated by the first human "gene transfer" experiment conducted by Kenneth Culver in 1990. See, Culver, K. W. (1996) in: Gene Therapy: A Primer for Physicians, Second Ed., Mary Ann Liebert, Inc. Publ, New York, pp. 1-198.

The primary goals of gene therapy are to repair or replace mutated genes, regulate gene expression and signal transduction, manipulate the immune system, or target malignant and other cells for destruction. See, Anderson, W. F. (1992) Science 256:808-813; Lasic, D. (1997) in: Liposomes in Gene Delivery, CRC Press, pp. 1-295; Boulikas, T. (1998) Gene Ther. Mol. Biol. 1:1-172; Martin, F. and Boulikas, T. (1998) Gene Ther. Mol. Biol. 1:173-214; Ross, G. et al. (1996) Hum. Gene Ther. 7:1781-1790.

Human cancer presents a particular disease condition for which effective gene therapy methods would provide a particularly useful clinical benefit. Gene therapy concepts for treatment of such diseases include stimulation of immune responses as well as manipulation of a variety of alternative cellular functions that affect the malignant phenotype. Although many human tumors are non or weakly immunogenic, the immune system can be reinforced and instructed to eliminate cancer cells after transduction of a patient's cells ex vivo with the cytokine genes GM-CSF, IL-12, IL-2, IL-4, IL-7, IFN-γ, and TNF-α, followed by cell vaccination of the patient (e.g. intradermally) to potentiate T-lymphocyte-mediated antitumor effects (cancer immunotherapy). DNA vaccination with genes encoding tumor antigens and immunotherapy with synthetic tumor peptide vaccines are further developments that are currently being tested. The genes used for cancer gene therapy in human clinical trials include a number of tumor suppressor genes (p53, RB, BRCA1, E1A), antisense oncogenes (antisense c-fos, c-myc, K-ras), and suicide genes (HSV-tk, in combination with ganciclovir, cytosine deaminase in combination with 5-fluorocytosine). Other important genes that have been proposed for cancer gene therapy include bcl-2, MDR-1, p21, p16, bax, bcl-xs, E2F, IGF-I, VEGF, angiostatin, CFTR, LDL-R, TGF-β, and leptin. One major hurdle preventing successful implementation of these gene therapies is the difficulty of efficiently delivering an effective dose of polynucleotides to the site of the tumor. Thus, gene delivery systems with enhanced transfection capabilities would be highly advantageous.

A number of different vector technologies and gene delivery methods have been proposed and tested for delivering genes in vivo, including viral vectors and various nucleic acid encapsulation techniques. Alternative viral delivery vehicles for genes include murine retroviruses, recombinant adenoviral vectors, adeno-associated virus, HSV, EBV, HIV vectors, and baculovirus. Nonviral gene delivery methods use cationic or neutral liposomes, direct injection of plasmid DNA, and polymers. Various strategies to enhance efficiency of gene transfer have been tested such as fusogenic peptides in combination with liposomes or polymers to enhance the release of plasmid DNA from endosomes.

Each of the various gene delivery techniques has been found to possess different strengths and weaknesses. Recombinant retroviruses stably integrate into the chromosome but require host DNA synthesis to insert. Adenoviruses can infect non-dividing cells but cause immune reactions leading to the elimination of therapeutically transduced cells. Adeno-associated virus (AAV) is not pathogenic and does not elicit immune responses but new production strategies are required to obtain high AAV titers for preclinical and clinical studies. Wild-type AAVs integrate into chromosome 19, whereas recombinant AAVs are deprived of site-specific integration and may also persist episomally.

Herpes Simplex Virus (HSV) vectors can infect non-replicating cells, such as neuronal cells, and has a high payload capacity for foreign DNA but inflict cytotoxic effects. It seems that each delivery system will be developed independently of the others and that each will demonstrate strengths and weaknesses for certain applications. At present, retroviruses are most commonly used in human clinical trials, followed by adenoviruses, cationic liposomes and AAV.

As the challenges of perfecting gene therapy techniques have become apparent, a variety of additional delivery systems have been proposed to circumvent the difficulties observed with standard technologies. For example, cell-based gene delivery using polymer-encapsulated syngeneic or allogeneic cells implanted into a tissue of a patient can be used to secrete therapeutic proteins. This method is being tested in trials for amyotrophic lateral sclerosis using the ciliary neurotrophic factor gene, and may be extended to Factor VIII and IX for hemophilia, interleukin genes, dopamine-secreting cells to treat Parkinson's disease, nerve growth factor for Alzheimer's disease and other diseases. Other techniques under development include, vectors with the Cre-LoxP recombinase system to rid transfected cells of undesirable viral DNA sequences, use of tissue-specific promoters to express a gene in a particular cell type, or use of ligands recognizing cell surface molecules to direct gene vehicles to a particular cell type.

Additional methods that have been proposed for improving the efficacy of gene therapy technologies include designing p53 "gene bombs" that explode into tumor cells, exploiting the HIV-1 virus to engineer vectors for gene transfer, combining viruses with polymers or cationic lipids to improve gene transfer, the attachment of nuclear localization signal peptides to oligonucleotides to direct genes to nuclei, and the development of molecular switch systems allowing genes to be turned on or off at will. Nevertheless, because of the wide range of disease conditions for which gene therapies are required, and the complexities of developing treatments for such diseases, there remains a need for improved techniques for performing gene therapy. The present invention provides methods and compositions for addressing these issues.

DISCLOSURE OF THE INVENTION

A method is disclosed for encapsulating DNA and negatively charged drugs into liposomes having a different lipid composition between their inner and outer membrane bilayers. The liposomes are able to reach primary tumors and their metastases after intravenous injection to animals and humans. The method includes micelle formation between DNA with a mixture of cationic lipid and peptide molecules at molar ratios to nearly neutralization ratios in 10-90% ethanol; the cationic peptides specify nuclear localization and have a hydrophobic moiety endowed with membrane fusion to improve entrance across the cell membrane of the complex. These peptides insert with their cationic portion directed toward condensed DNA and their hydrophobic chain buried together with the hydrophobic chains of the lipids in the micelle membrane monolayer. The DNA/lipid/peptide micelles are converted into liposomes by mixing with pre-made liposomes or lipids followed by dilution in aqueous solutions and dialysis to remove the ethanol and allow liposome formation and extrusion through membranes to a diameter below 160 nm entrapping and encapsulating DNA with a very high yield. The encapsulated DNA has a high therapeutic efficacy in eradicating a variety of solid human tumors including, but not limited to, breast carcinoma and prostate carcinoma. A plasmid is constructed with DNA carrying anticancer genes including, but not limited to p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, TNF-α, HSV-tk (in combination with ganciclovir), E. coli cytosine deaminase (in combination with 5-fluorocytosine) and is combined with encapsulated cisplatin or with other similarly systemically delivered antineoplastic drugs to suppress cancer.

BRIEF DESCRIPTION OF THE DRAWINGS

FIG. 3A shows a SCID mouse with a large and small human breast tumor before and after staining with X-Gal to test the expression of the transferred gene. Both tumors turn dark blue. The intensity of the blue color is proportional to the expression of the beta-galactosidase gene. FIG. 3B shows that in the initial staining of the small tumor, the skin and the intestines at the injection area are the first organs to turn blue. FIG. 3C is a view of the back of the animal. The two tumors are clearly visible after removal of the skin (top). Dark staining of the small tumor and light blue staining of the large tumor is evident at an initial stage of staining (bottom). FIG. 3D is a view of the front side of the animal. The two tumors are clearly visible after removal of the skin. On the figure to the bottom the dark staining of both tumors is evident at a later stage during staining. FIG. 3E shows the front (top) and rear (bottom) higher magnification view of the dark staining of both tumors at a later stage during staining. Staining of the vascular system around the small tumor can also be seen (bottom).

BRIEF DESCRIPTION OF THE TABLES

Figure 1:
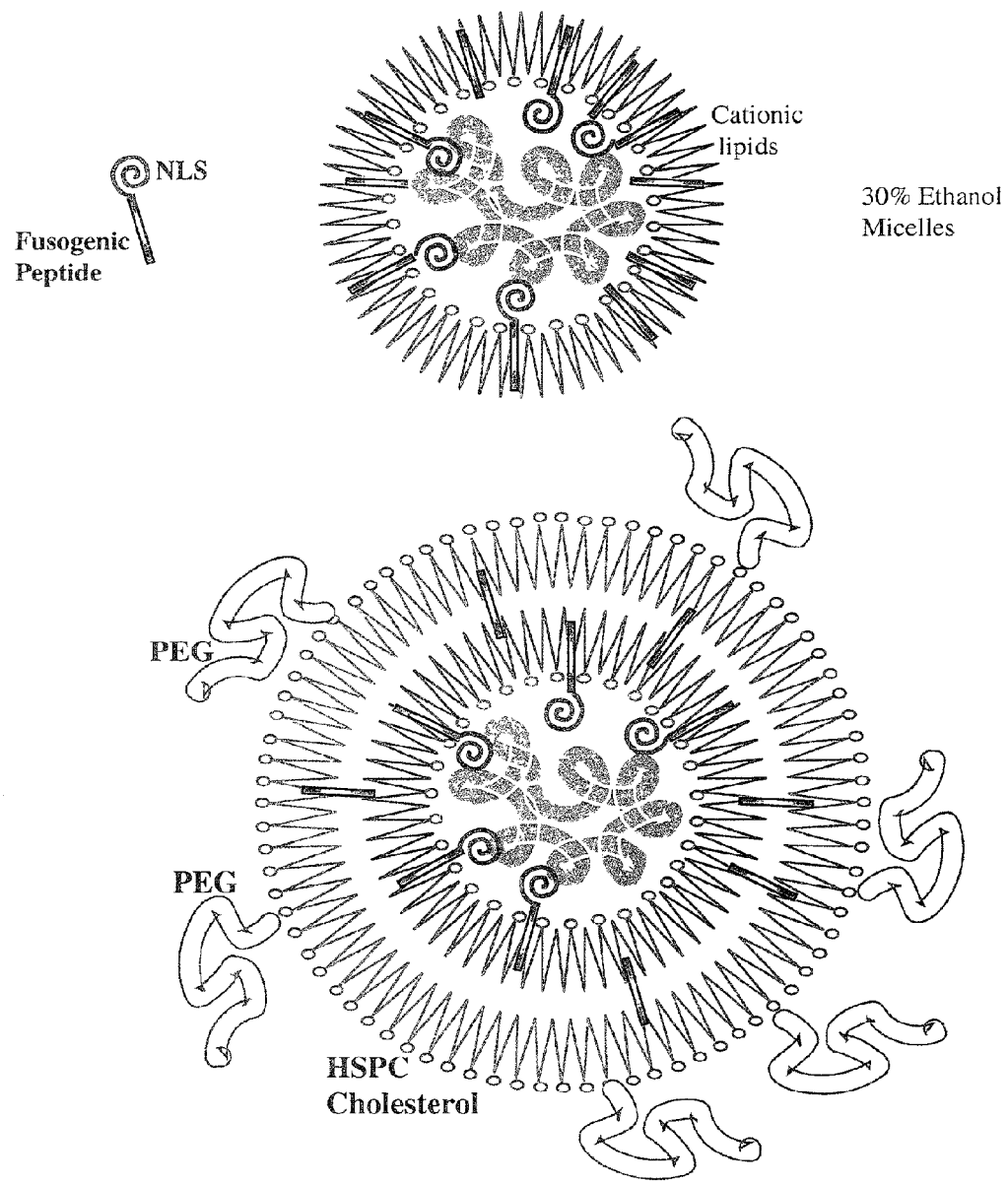
FIG. 1 illustrates the structure of the cancer targeted liposome complex.

Table 1 is a list of molecules able to form micelles.

Table 2 lists several fusogenic peptides and describes their properties, along with a reference.

Table 3 lists simple Nuclear Localization Signal (NLS) peptides.

Table 4 shows a list of "bipartite" or "split" NLS peptides.

Table 5 lists "nonpositive NLS" peptides lacking clusters of arginines/lysines.

Table 6 lists peptides with nucleolar localization signals (NoLS).

Table 7 lists peptides having karyophilic clusters on non-membrane protein kinases.

Table 8 lists peptide nuclear localization signals on DNA repair proteins.

Table 9 lists NLS peptides in transcription factors.

Table 10 lists NLS peptides in other nuclear proteins.

MODES FOR CARRYING OUT THE INVENTION

Definitions

The practice of the present invention will employ, unless otherwise indicated, conventional techniques of immunology, molecular biology, microbiology, cell biology and recombinant DNA. These methods are described in the following publications. See, e.g., Sambrook, et al. MOLECULAR CLONING: A LABORATORY MANUAL, $2^{nd}$ Edition (1989); CURRENT PROTOCOLS IN MOLECULAR BIOLOGY, F. M. Ausubel, et al. eds., (1987); the series METHODS IN ENZYMOLOGY (Academic Press, Inc.); PCR: A PRACTICAL APPROACH, M. MacPherson, et al., IRL Press at Oxford University Press (1991); PCR 2: A PRACTICAL APPROACH, MacPherson et al., eds. (1995); ANTIBODIES, A LABORATORY MANUAL, Harlow and Lane, eds. (1988); and ANIMAL CELL CULTURE, R. I. Freshney, ed. (1987).

As used in the specification and claims, the singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

A "gene" refers to a polynucleotide containing at least one open reading frame that is capable of encoding a particular polypeptide or protein after being transcribed and translated.

A "gene product" refers to the amino acid (e.g., peptide or polypeptide) generated when a gene is transcribed and translated.

The following abbreviations are used herein: DDAB: dimethyldioctadecyl ammonium bromide (same as N,N-distearyl-N,N-dimethylammonium bromide); DODAC: N,N-dioleyl-N,N-dimethylammonium chloride; DODAP: 1,2-dioleoyl-3-dimethylammonium propane; DMRIE: N-[1-(2,3-dimyristyloxy)propyl]-N,N-dimethyl-N-(2-hydroxyethyl) ammonium bromide; DMTAP: 1,2-dimyristoyl-3-trimethylammonium propane; DOGS: Dioctadecylamidoglycylspermine; DOTAP (same as DOTMA): N-(1-(2,3-dioleoyloxy)propyl)-N,N,N-trimethylammonium chloride; DOSPA: N-(1-(2,3-dioleyloxy)propyl)-N-(2-(sperminecarboxamido)ethyl)-N,N-dimethyl ammonium trifluoroacetate; DPTAP: 1,2-dipalmitoyl-3-trimethylammonium propane; DSTAP: 1,2-disteroyl-3-trimethylammonium propane; DOPE, 1,2-sn-dioleoylphoshatidylethanolamine; DC-Chol, 3β-(N—(N', N'-dimethylaminoethane)carbamoyl)cholesterol. See, Gao et al., Biochem. Biophys. Res. Comm. 179:280-285 (1991).

As used herein, the term "pharmaceutically acceptable anion" refers to anions of organic and inorganic acids that provide non-toxic salts in pharmaceutical preparations. Examples of such anions include the halides anions, chloride, bromide, and iodide, inorganic anions such as sulfate, phosphate, and nitrate, and organic anions. Organic anions may be derived from simple organic acids, such as acetic acid, propionic acid, glycolic acid, pyruvic acid, oxalic acid, malic acid, malonic acid, succinic acid, maleic, acid, fumaric acid, tartaric acid, citric acid, benzoic acid, cinnamic acid, mandelic acid, methane sulfonic acid, ethane sulfonic acid, p-toluenesulfonic acid, and the like. The preparation of pharmaceutically acceptable salts is described in Berge, et al., J. Pharm. Sci. 66:1-19 (1977), incorporated herein by reference.

Physiologically acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA: sugar alcohols such as mannitol or sorbitol; salt-forming counter ions such as sodium; and/or nonionic surfactants such as Tween, Pluronics or polyethylene glycol (PEG). PEG molecules also contain a fusogenic peptide with an attached Nuclear Localization Signal (NLS) covalently linked to the end of the PEG molecule.

The term "cationic lipid" refers to any of a number of lipid species that carry a net positive charge at physiological pH. Such lipids include, but are not limited to, DDAB, DMRIE, DODAC, DOGS, DOTAP, DOSPA and DC-Chol. Additionally, a number of commercial preparations of cationic lipids are available that can be used in the present invention. These include, for example, LIPOFECTIN (commercially available cationic liposomes comprising DOTMA and DOPE, from GIBCO/BRL, Grand Island, N.Y., USA); LIPOFECTAMINE (commercially available cationic liposomes comprising DOSPA and DOPE, from GIBCO/BRL); and TRANSFECTAM (commercially available cationic lipids comprising DOGS in ethanol from Promega Corp., Madison, Wis., USA).

This invention further provides a number of methods for producing micelles with entrapped therapeutic drugs. The method is particularly useful to produce micelles of drugs or compositions having a net overall negative charge, e.g., DNA, RNA or negatively charged small molecules. For example, the DNA can be comprised within a plasmid vector and encode for a therapeutic protein, e.g., wild-type p53, HSV-tk, p21, Bax, Bad, IL-2, IL-12, GM-CSF, angiostatin, endostatin and oncostatin. In one embodiment, the method requires combining an effective amount of the therapeutic agent with an effective amount of cationic lipids. Cationic lipids useful in the methods of this invention include, but are not limited to, DDAB, dimethyldioctadecyl ammonium bromide; DMRIE: N-[1-(2,3-dimyristyloxy)propyl]-N,N-dimethyl-N-(2-hydroxyethyl) ammonium bromide; DMTAP: 1,2-dimyristoyl-3-trimethylammonium propane; DOGS: Dioctadecylamidoglycylspermine; DOTAP (same as DOTMA): N-(1-(2,3-dioleoyloxy)propyl)-N,N,N-trimethylammonium chloride; DPTAP: 1,2-dipalmitoyl-3-trimethylammonium propane; DSTAP: 1,2-disteroyl-3-trimethylammonium propane.

In one aspect, a ratio of from about 30 to about 90% of phosphates contained within the negatively charged therapeutic agent are neutralized by positive charges on lipid molecules (negative charges are in excess) to form an electrostatic micelle complex in an effective concentration of ethanol. In one aspect, the ethanol solution is from about 20% to about 80% ethanol. In a further aspect, the ethanol concentration is about 30%. The ethanol/cationic lipid/therapeutic agent complex is then combined with an effective amount of a fusogenic-karyophilic peptide conjugate. In one aspect, an effective amount of the conjugate is a ratio range from about 0.0 to about 0.3 (positive charges on peptide to negative charges on phosphate groups) to neutralize the majority of the remaining negative charges on the phosphate groups of the therapeutic agents thereby leading to an almost complete neutralization of the complex. The optimal conditions give to the complex a slightly negative charge. However, when the positive charges on cationic lipids exceed the negative charges on the DNA, the excess of positive charges are neutralized by DPPG (dipalmitoyl phosphatidyl glycerol) and its derivatives, or by other anionic lipid molecules in the final micelle complex.

In an alternative embodiment, the above methods can be modified by addition of DNA condensing agents selected from spermine, spermidine, and magnesium or other divalent metal ions neutralizing a certain percentage (1-20%) of phosphate groups.

In a further embodiment, the cationic lipids are combined with an effective amount of fusogenic lipid DOPE at various molar ratios for example, in a molar ratio of from about 1:1 cationic lipid:DOPE. In an alternative embodiment, the cationic lipids are combined with an effective amount of a fusogenic/NLS peptide conjugate. Examples of fusogenic/NLS peptide conjugates include, but are not limited to (KAWLKAF)$_3$ (SEQ ID NO:1), GLFKAAAKLLKSL-WKLLLKA (SEQ ID NO:2), LLLKAFAKLLKSL-WKLLLKA (SEQ ID NO:3), as well as all derivatives of the prototype (Hydrophobic3-Karyophilic1-Hydrophobic2-Karyophilic1)$_{2-3}$ where Hydrophobic is any of the A, I, L, V, P, G, W, F and Karyophilic is any of the K, R, or H, containing a positively-charged residue every 3rd or 4th amino acid, which form alpha helices and direct a net positive charge to the same direction of the helix. Additional examples include but are not limited to GLFKAIAGFIKNGWKG-MIDGGGYC (SEQ ID NO:4) from influenza virus hemagglutinin HA-2; YGRKKRRQRRR (SEQ ID NO:5) from TAT of HIV; MSGTFGGILAGLIGLL(K/R/H)$_{1-6}$ (SEQ ID NO:6), derived from the N-terminal region of the S protein of duck hepatitis B virus, but with the addition of one to six positively-charged lysine, arginine or histidine residues, and combinations of these, able to interact directly with the phosphate groups of plasmid or oligonucleotide DNA, compensating for part of the positive charges provided by the cationic lipids. GAAIGLAWIPYFGPAA (SEQ ID NO:7) is derived from the fusogenic peptide of the Ebola virus transmembrane protein; residues 53-70 (C-terminal helix) of apolipoprotein (apo) AII peptide; the 23-residue fusogenic N-terminal peptide of HIV-1 transmembrane glycoprotein gp41; the 29-42-residue fragment from Alzheimer's β-amyloid peptide; the fusion peptide and N-terminal heptad repeat of Sendai virus; the 56-68 helical segment of lecithin cholesterol acyltransferase. Included within these embodiments are shorter versions of these peptides, that are known to induce fusion of unilamellar lipid vesicles or all that are similarly derivatized with the addition of one to six positively-charged lysine, arginine or histidine residues (K/R/H)$_{1-6}$ able to interact directly with the phosphate groups of plasmid or oligonucleotide DNA, compensating for part of the positive charges provided by the cationic lipids. The fusogenic peptides in the fusogenic/NLS conjugates represent hydrophobic amino acid stretches, and smaller fragments of these peptide sequences, that include all signal peptide sequences used in membrane or secreted proteins that insert into the endoplasmic reticulum. Alternatively, the conjugates represent transmembrane domains and smaller fragments of these peptide sequences.

In one aspect of the invention, the NLS peptide component in fusogenic/NLS peptide conjugates is derived from the fusogenic hydrophobic peptides. However, there is an addition of 5-6 amino acid karyophilic Nuclear Localization Signals (NLS) derived from a number of known NLS peptides, as well as from searches of the nuclear protein databases, for stretches of five or more karyophilic amino acid stretches in proteins containing at least four positively-charged amino aids flanked by a proline (P) or glycine (G). Examples of NLS peptides are shown in Tables 1-8. The NLS peptide component in fusogenic/NLS peptide conjugates are synthetic peptides containing the above said NLS, but further modified by additional K, R, H residues at the central part of the peptide or with P or G at the N- or C-terminus.

In a further aspect, the fusogenic/NLS peptide conjugates are derived from the said fusogenic hydrophobic peptides but with the addition of a stretch of H$_{4-6}$ (four to six histidine residues) in the place of NLS. Micelle formation takes place at pH 5-6 where histidyl residues are positively charged but lose their charge at the nearly neutral pH of the biological fluids, thus releasing the plasmid or oligonucleotide DNA from their electrostatic interaction.

The fusogenic peptide/NLS peptide conjugates are linked to each other with a short amino acid stretch representing an endogenous protease cleavage site.

In a preferred aspect of the invention, the structure of the preferred prototype fusogenic/NLS peptide conjugate used in this invention is: PKKRRGPSP(L/A/I)$_{12-20}$ (SEQ ID NO:8), where (L/A/I)$_{12-20}$ is a stretch of 12-20 hydrophobic amino acids containing A, L, I, Y, W, F and other hydrophobic amino acids.

The micelles made by the above methods are further provided by this invention by conversion into liposomes. An effective amount of liposomes (diameter from about 80 to about 160 nm), or of a lipid solution composed of cholesterol (from about 10% to about 50%), neutral phospholipid such as hydrogenated soy phosphatidylcholine (HSPC) (from about 40% to about 90%), and the derivatized vesicle-forming lipid PEG-DSPE (distearoylphosphatidyl ethanolamine) from about 1- to about 7 mole percent, is added to the micelle solution.

In a specific embodiment, the liposomes are composed of vesicle-forming lipids and between from about 1 to about 7 mole percent of distearoylphosphatidyl ethanolamine (DSPE) derivatized with a polyethyleneglycol. The composition of claim 20, wherein the polyethyleneglycol has a molecular weight is between about 1,000 to 5,000 daltons. Micelles are converted into liposomes with a concomitant decrease of the ethanol concentration which can be accomplished by removal of the ethanol by dialysis of the liposome complexes through permeable membranes or reduced to a diameter of 80-160 nm by extrusion through membranes.

Liposome encapsulated therapeutic agents produced by the above methods are further provided by this invention.

Also provided herein is a method for delivering a therapeutic agent such as plasmid DNA or oligonucleotides to a tissue cell in vivo by intravenous, or other type of injection of the micelles or liposomes. This method specifically targets a primary tumor and the metastases by the long circulating time of the micelle or liposome complex because of the exposure of PEG chains on its surface, its small size (80-160 nm) and the decrease in hydrostatic pressure in the solid tumor from the center to its periphery supporting a preferential extravasation through the tumor vasculature to the extracellular space in tumors. A method for delivering plasmid or oligonucleotide DNA across the cell membrane barrier of the tumors using the micelle or liposome complexes described herein is capable because of the presence of the fusogenic peptides in the complex. In particular, a method for delivering plasmid or oligonucleotide DNA to the liver, spleen and bone marrow after intravenous injection of the complexes is provided. Further provided is a method for delivering therapeutic genes to the liver, spleen and bone marrow of cancer and noncancer patients including but not limited to, factor VIII or IX for the therapy of hemophilias, multidrug resistance, cytokine genes for cancer immunotherapy, genes for the alleviation of pain, genes for the alleviation of diabetes and genes that can be introduced to liver, spleen and bone marrow tissue, to produce a secreted form of a therapeutic protein.

The disclosed therapies also provide methods for reducing tumor size by combining the encapsulated plasmid DNA carrying one or more anticancer genes selected from the group consisting of p53, RB, BRCA1, E1A, bcl-2, MDR-1, p21, p16, bax, bcl-xs, E2F, VEGF, angiostatin, oncostatin, endostatin, GM-CSF, IL-12, IL-2, IL-4, IL-7, IFN-γ, HSV-tk (in combination with ganciclovir), $E.\ coli$ cytosine deaminase (in combination with 5-fluorocytosine) with encapsulated antisense oligonucleotides (antisense c-fos, c-myc, K-ras), ribozymes or triplex-forming oligonucleotides directed against genes that control the cell cycle or signaling pathways. These methods can be modified by combining the encapsulated plasmid DNA carrying one or more anticancer genes of with encapsulated or free antineoplastic drugs, consisting of the group of adriamycin, angiostatin, azathioprine, bleomycin, busulfane, camptothecin, carboplatin, carmustine, chlorambucile, chlormethamine, chloroquinoxaline sulfonamide, cisplatin, cyclophosphamide, cycloplatam, cytarabine, dacarbazine, dactinomycin, daunorubicin, didox, doxorubicin, endostatin, enloplatin, estramustine, etoposide, extramustinephosphat, flucytosine, fluorodeoxyuridine, fluorouracil, gallium nitrate, hydroxyurea, idoxuridine, interferons, interleukins, leuprolide, lobaplatin, lomustine, mannomustine, mechlorethamine, mechlorethaminoxide, melphalan, mercaptopurine, methotrexate, mithramycin, mitobronitole, mitomycin, mycophenolic acid, nocodazole, oncostatin, oxaliplatin, paclitaxel, pentamustine, platinum-triamine complex, plicamycin, prednisolone, prednisone, procarbazine, protein kinase C inhibitors, puromycine, semustine, signal transduction inhibitors, spiroplatin, streptozotocine, stromelysin inhibitors, taxol, tegafur, telomerase inhibitors, teniposide, thalidomide, thiamiprine, thioguanine, thiotepa, tiamiprine, tretamine, triaziquone, trifosfamide, tyrosine kinase inhibitors, uramustine, vidarabine, vinblastine, vinca alcaloids, vincristine, vindesine, vorozole, zeniplatin, zeniplatin, and zinostatin.

The following examples are intended to illustrate, but not limit the invention.

Liposome Composition

Liposomes are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol and (DOPG), dicetylphosphate that are able to form vesicles. Preferred lipids for use in the present invention are cholesterol, hydrogenated soy phosphatidylcholine (HSPC) and, the derivatized vesicle-forming lipid PEG-DSPE.

Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs).

SUVs range in diameter from approximately 20 to 50 nm and consist of a single lipid bilayer surrounding an aqueous compartment. Unilamellar vesicles can also be prepared in sizes from about 50 nm to 600 nm in diameter. While unilamellar are single compartmental vesicles of fairly uniform size, MLVs vary greatly in size up to 10,000 nm, or thereabouts, are multi-compartmental in their structure and contain more than one bilayer. LUV liposomes are so named because of their large diameter that ranges from about 600 nm to 30,000 nm; they can contain more than one bilayer.

Liposomes may be prepared by a number of methods not all of which produce the three different types of liposomes. For example, ultrasonic dispersion by means of immersing a metal probe directly into a suspension of MLVs is a common way for preparing SUVs.

Preparing liposomes of the MLV class usually involves dissolving the lipids in an appropriate organic solvent and then removing the solvent under a gas or air stream. This leaves behind a thin film of dry lipid on the surface of the container. An aqueous solution is then introduced into the container with shaking, in order to free lipid material from the sides of the container. This process disperses the lipid, causing it to form into lipid aggregates or liposomes. Liposomes of the LUV variety may be made by slow hydration of a thin layer of lipid with distilled water or an aqueous solution of some sort. Alternatively, liposomes may be prepared by lyophilization. This process comprises drying a solution of lipids to a film under a stream of nitrogen. This film is then dissolved in a volatile solvent, frozen, and placed on a lyophilization apparatus to remove the solvent. To prepare a pharmaceutical formulation containing a drug, a solution of the drug is added to the lyophilized lipids, whereupon liposomes are formed.

Preparing Cationic Liposome/Cationic Peptide/Nucleic Acid Micelles

Cationic lipids, with the exception of sphingosine and some lipids in primitive life forms, do not occur in nature. The present invention uses single-chain amphiphiles which are chloride and bromide salts of the alkyltrimethylammonium surfactants including but not limited to C12 and C16 chains abbreviated DDAB (same as DODAB) or CTAB. The molecular geometry of these molecules determines the critical micelle concentration (ratio between free monomers in solution and molecules in micelles). Lipid exchange between the two states is a highly dynamic process; phospholipids have critical micelle concentration values below $10^{-8}$ M and are more stable in liposomes; however, single chain detergents, such as stearylamine, may emerge from the liposome membrane upon dilution or intravenous injection in milliseconds (Lasic, 1997).

Cationic lipids include, but are not limited to, DDAB: dimethyldioctadecyl ammonium bromide (same as N,N-distearyl-N,N-dimethylammonium bromide); DMRIE: N-[1-(2,3-dimyristyloxy)propyl]-N,N-dimethyl-N-(2-hydroxyethyl) ammonium bromide; DODAC: N,N-dioleyl-N,N-dimethylammonium chloride; DMTAP: 1,2-dimyristoyl-3-trimethylammonium propane; DODAP: 1,2-dioleoyl-3-dimethylammonium propane; DOGS: Dioctadecylamidoglycylspermine; DOTAP (same as DOTMA): N-(1-(2,3-dioleoyloxy)propyl)-N,N,N-trimethylammonium chloride; DOSPA: N-(1-(2,3-dioleyloxy)propyl)-N-(2-(sperminecarboxamido)ethyl)-N,N-dimethyl ammonium trifluoroacetate; DPTAP: 1,2-dipalmitoyl-3-trimethylammonium propane; DSTAP: 1,2-disteroyl-3-trimethylammonium propane; DC-Chol, 3β-(N—(N',N'-dimethylaminoethane)carbamoyl)cholesterol.

Lipid-based vectors used in gene transfer have been formulated in one of two ways. In one method, the nucleic acid is introduced into preformed liposomes made of mixtures of cationic lipids and neutral lipids. The complexes thus formed have undefined and complicated structures and the transfection efficiency is severely reduced by the presence of serum. Preformed liposomes are commercially available as LIPOFECTIN and LIPOFECTAMINE. The second method involves the formation of DNA complexes with mono- or poly-cationic lipids without the presence of a neutral lipid. These complexes are prepared in the presence of ethanol and are not stable in water. Additionally, these complexes are adversely affected by serum (see, Behr, Acc. Chem. Res. 26:274-78 (1993)). An example of a commercially available poly-cationic lipid is TRANSFECTAM. Other efforts to encapsulate DNA in lipid-based formulations have not overcome these problems (see, Szoka et al., Ann. Rev. Biophys. Bioeng. 9:467 (1980); and Deamer, U.S. Pat. No. 4,515,736).

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA. Particularly preferred nucleic acids are plasmids. Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, methylphosphonate, or O-alkyl phosphotriester linkages.

Encapsulating Cationic Liposome/Cationic Peptide/Nucleic Acid Micelles into Neutral Liposomes Cationic lipids used with fusogenic peptide/NLS conjugates to provide the inner layer of the particle can be any of a number of substances selected from the group of DDAB, DODAC, DMRIE, DMTAP, DOGS, DOTAP (DOTMA), DOSPA, DPTAP, DSTAP, DC-Chol. The cationic lipid is combined with DOPE. In one group of embodiments, the preferred cationic lipid is DDAB:DOPE 1:1.

Neutral lipids used herein to provide the outer layer of the particles can be any of a number of lipid species that exist either in an uncharged or neutral zwitterionic form at physiological pH. Such lipids are selected from a group consisting of diacylphosphatidylcholine, diacylphosphatidylethanolamine, ceramide, sphingomyelin, cephalin, and cerebrosides. In one group of embodiments, lipids containing saturated, mono-, or di-unsaturated fatty acids with carbon chain lengths in the range of C14 to C22 are preferred. In general, less saturated lipids are more easily sized, particularly when the liposomes must be sized below about 0.16 microns, for purposes of filter sterilization. Consideration of liposome size, rigidity and stability of the liposomes in the final preparation, its shelf life without leakage of the encapsulated DNA, and stability in the bloodstream generally guide the selection of neutral lipids for providing the outer coating of our gene vehicles. Lipids having a variety of acyl chain groups of varying chain length and degree of saturation are available or may be isolated or synthesized by well-known techniques. In another group of embodiments, lipids with carbon chain lengths in the range of C14 to C22 are used. Preferably, the neutral lipids used in the present invention are hydrogenated soy phosphatidylcholine (HSPC), cholesterol, and PEG-distearoylphosphatidyl ethanolamine (DSPE) or PEG-ceramide.

Methods for Preparing Liposomes

A variety of methods for preparing various liposome forms have been described in several issued patents, for example, U.S. Pat. Nos. 4,229,360; 4,224,179; 4,241,046; 4,737,323; 4,078,052; 4,235,871; 4,501,728; and 4,837,028, as well as in the articles Szoka et al., Ann. Rev. Biophys. Bioeng. 9:467 (1980) and Hope et al., Chem. Phys. Lip. 40:89 (1986). These methods do not produce all three different types of liposomes (MLVs, SUVs, LUVs). For example, ultrasonic dispersion by means of immersing a metal probe directly into a suspension of MLVs is a common way for preparing SUVs.

Preparing liposomes of the MLV class usually involves dissolving the lipids in an appropriate organic solvent and then removing the solvent under a gas or air stream. This leaves behind a thin film of dry lipid on the surface of the container. An aqueous solution is then introduced into the container with shaking, in order to free lipid material from the sides of the container. This process disperses the lipid, causing it to form into lipid aggregates or liposomes. Liposomes of the LUV variety may be made by slow hydration of a thin layer of lipid with distilled water or an aqueous solution of some sort. Alternatively, liposomes may be prepared by lyophilization. This process comprises drying a solution of lipids to a film under a stream of nitrogen. The film is then dissolved in a volatile solvent, frozen, and placed on a lyophilization apparatus to remove the solvent. To prepare a pharmaceutical formulation containing a drug, a solution of the drug is added to the lyophilized lipids, whereupon liposomes are formed.

Following liposome preparation, the liposomes may be sized to achieve a desired size range and relatively narrow distribution of liposome sizes. Preferably, the preformed liposomes are sized to a mean diameter of about 80 to 160 nm (the upper size limit for filter sterilization before in vivo administration). Several techniques are available for sizing liposomes to a desired size. Sonicating a liposome suspension either by bath or probe sonication produces a progressive size reduction down to small unilamellar vesicles less than about 0.05 microns (50 nm) in size. Extrusion of liposome through a small-pore polycarbonate is our preferred method for reducing liposome sizes to a relatively well-defined size distribution. The liposomes may be extruded through successively smaller-pore membranes, to achieve a gradual reduction in liposome size.

One way used to coat DNA with lipid is by controlled detergent depletion from a cationic lipid/DNA/detergent complex. This method can give complexes with stability in plasma. Hofland et al. (1996), have prepared such complexes by dialysis of a mixture of DOSPA/DOPE/DNA/octylglucoside.

Pharmaceutical compositions comprising the cationic liposome/nucleic acid complexes of the invention are prepared according to standard techniques and further comprise a pharmaceutically acceptable carrier. Generally, normal saline will be employed as the pharmaceutically acceptable carrier.

For in vivo administration, the pharmaceutical compositions are preferably administered parenterally, i.e., intravenously, intraperitoneally, subcutaneously, intrathecally, injection to the spinal cord, intramuscularly, intraarticularly, portal vein injection, or intratumorally. More preferably, the pharmaceutical compositions are administered intravenously or intratumorally by a bolus injection. In other methods, the pharmaceutical preparations may be contacted with the target tissue by direct application of the preparation to the tissue. The application may be made by topical "open" or "closed" procedures. The term "topical" means the direct application of the pharmaceutical preparation to a tissue exposed to the environment, such as the skin, to any surface of the body, nasopharynx, external auditory canal, ocular administration and administration to the surface of any body cavities, inhalation to the lung, genital mucosa and the like.

"Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue.

"Closed" procedures are invasive procedures in which the internal target tissues are not directly visualized, but accessed via insertion of instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

EXAMPLES

Materials and Methods

DDAB, DOPE (dioleoylphosphatidylethanolamine) and most other lipids used here were purchased from Avanti Polar Lipids; PEG-DSPE was from Syngena.

Engineering of Plasmid pLF

The pGL3-C (Promega) was cut with XbaI and blunt-end ligated using the Klenow fragment of E. coli DNA polymerase. It was then cut with HindIII and the 1689-bp fragment, carrying the luciferase gene, was gel-purified. The pGFP-N1 plasmid (Clontech) was cut with SmaI and HindIII and the 4.7 kb fragment, isolated from an agarose gel, was ligated with the luciferase fragment. JM109 E. coli cells were transformed and 20 colonies were selected; about half of them showed the presence of inserts; 8 clones with inserts were cut with BamHI and XhoI to further confirm the presence of the luciferase gene; seven of them were positive.

Radiolabeled plasmid pLF was generated by culturing Escherichia coli in $^3$H-thymidine-5'-triphosphate or $^{32}$P inorganic phosphate (5 mCi) (Dupont/NEN, Boston, Mass.) and purified using standard techniques as described above.

DLS Measurements

A Coulter N4M light scattering instrument was used, at a 90° angle, set at a run time of 200 sec, using 4 to 25 microsec sample time. The scan of the particle size distribution was obtained in 1 ml sample volume using plastic cuvettes, at 20° C. and at 0.01 poise viscosity.

In one aspect, this invention provides a method for entrapping DNA into lipids that enhances the content of plasmid per volume unit, and reduces the toxicity of the cationic lipids used to trap plasmid or oligonucleotide DNA. The DNA becomes hidden in the inner membrane bilayer of the final complex. Furthermore, the gene transfer complex is endowed with long circulation time in body fluids and extravasates preferentially into solid tumors and their metastatic foci and nodules. The extravasation occurs through their vasculature at most sites of the human or animal body after intravenous injection of the gene-carrying vehicles. This occurs because of their small size (100-160 nm), their content in neutral to slightly negatively-charged lipids in their outer membrane bilayers, and their coating with PEG. These gene delivery vehicles are able to cross the cell membrane barrier after they reach the extracellular tumor space because of the presence of fusogenic peptides conjugated with karyophilic peptides. The vehicles assume a certain predefined orientation in the lipid membrane with their positive ends directed toward DNA and their hydrophobic tail buried inside the hydrophobic lipid bilayer. The labile NLS-fusogenic peptide linkage is cleaved after endocytosis and the remaining NLS peptide bound to plasmid DNA aids its nuclear uptake. This occurs especially when non-dividing cells are targeted, such as liver, spleen or bone marrow cells that represent the major sites for extravasation and concentration of these vehicles other than solid tumors.

Organic Solvent

A suitable solvent for preparing a micelle from the desired lipid components is ethanol, methanol, or other aliphatic alcohols such as propanol, isopropanol, butanol, tert-butanol, iso-butanol, pentanol and hexanol. Mixtures of two or more solvents may be used in the practice of the invention. It is also to be understood that any solvent that is miscible with an ethanol solution, even in small amounts, can be used to improve micelle formation and its subsequent conversion into liposomes, including chloroform, dichloromethane, di ethyl-ether, cyclohexane, cyclopentane, benzene, and toluene.

Cationic Lipids

In a further embodiment, the liposome encapsulated DNA described herein further comprises an effective amount of cationic lipids. Cationic lipids have been widely used for gene transfer; a number of clinical trials (34 out of 220 total RAC-approved protocols as of December, 1997) use cationic lipids. Although many cell culture studies have been documented, systemic delivery of genes with cationic lipids in vivo has been very limited. All clinical protocols use subcutaneous, intradermal, intratumoral, and intracranial injection as well as intranasal, intrapleural, or aerosol administration but not I.V. delivery, because of the toxicity of the cationic lipids and DOPE (see, Martin and Boulikas, 1998). Liposomes formulated from DOPE and cationic lipids based on diacyltrimethylammonium propane (dioleoyl-, dimyristoyl-, dipalmitoyl-, disteroyl-trimethylammonium propane or DOTAP, DMTAP, DPTAP, DSTAP, respectively) or DDAB were highly toxic when incubated in vitro with phagocytic cells (macrophages and U937 cells), but not towards non-phagocytic T lymphocytes. The rank order of toxicity was DOPE/DDAB>DOPE/DOTAP>DOPE/DMTAP>DOPE/DPTAP>DOPE/DSTAP; and the toxicity was determined from the effect of the cationic liposomes on the synthesis of nitric oxide (NO) and TNF-α produced by activated macrophages (Filion and Phillips, 1997).

Another aspect to be considered before I.V. injection is undertaken, is that negatively charged serum proteins can interact and cause inactivation of cationic liposomes (Yang and Huang, 1997). Condensing agents used for plasmid delivery including polylysine, transferrin-polylysine, a fifth-generation poly(amidoamine) (PAMAM) dendrimer, poly(ethyleneimine), and several cationic lipids (DOTAP, DC-Chol/DOPE, DOGS/DOPE, and DOTMA/DOPE), were found to activate the complement system to varying extents. Strong complement activation was seen with long-chain polylysines, the dendrimer, poly(ethyleneimine), and DOGS. Modifying the surface of preformed DNA complexes with polyethyleneglycol (Plank et al., 1996) considerably reduced complement activation.

Cationic lipids increase the transfection efficiency by destabilizing the biological membranes, including plasma, endosomal, and lysosomal membranes. Incubation of isolated lysosomes with low concentrations of DOTAP caused a striking increase in free activity of β-galactosidase, and even a release of the enzyme into the medium. This demonstrates that the lysosomal membrane is deeply destabilized by the lipid. The mechanism of destabilization was thought to involve an interaction between cationic liposomes and anionic lipids of the lysosomal membrane, thus allowing a fusion between the lipid bilayers. The process was less pronounced at pH 5 than at pH 7.4, and anionic amphipathic lipids were able to prevent partially this membrane destabilization (Wattiaux et al., 1997).

In contrast to DOTAP and DMRIE that were 100% charged at pH 7.4, DC-CHOL was only about 50% charged as monitored by a pH-sensitive fluorophore. This difference decreases the charge on the external surfaces of the liposomes, and was proposed to promote an easier dissociation of bilayers containing DC-CHOL from the plasmid DNA, and an increase in release of the DNA-lipid complex into the cytosol from the endosomes (Zuidam and Barenholz, 1997).

Although cationic lipids have been used widely for the delivery of genes, very few studies have used systemic I.V. injection of cationic liposome-plasmid complexes. This is because of the toxicity of the lipid component in animal models, not humans. Administration by I.V. injection of two types of cationic lipids of similar structure, DOTMA and DOTAP, shows that the transfection efficiency is determined mainly by the structure of the cationic lipid and the ratio of cationic lipid to DNA; the luciferase and GFP gene expression in different organs was transient, with a peak level between 4 and 24 hr, dropping to less than 1% of the peak level by day 4 (Song et al., 1997).

A number of different organs in vivo can be targeted after liposomal delivery of genes or oligonucleotides. Intravenous injection of cationic liposome-plasmid complexes by tail vein in mice, targeted mainly the lung and to a smaller extent the liver, spleen, heart, kidney and other organs (Zhu et al., 1993). Intraperitoneal injection of a plasmid-liposome complex expressing antisense K-ras RNA in nude mice inoculated i.p. with AsPC-1 pancreatic cancer cells harboring K-ras point mutations and PCR analysis indicated that the injected DNA was delivered to various organs except brain (Aoki et al., 1995).

A number of factors for DOTAP:cholesterol/DNA complex preparation including the DNA:liposome ratio, mild sonication, heating, and extrusion were found to be crucial for improved systemic delivery; maximal gene expression was obtained when a homogeneous population of DNA:liposome complexes between 200 to 450 nm in size were used. Cryoelectron microscopy showed that the DNA was condensed on the interior of invaginated liposomes between two lipid bilayers in these formulations, a factor that was thought to be responsible for the high transfection efficiency in vivo and for the broad tissue distribution (Templeton et al., 1997).

Steps to improve liposome-mediated gene delivery to somatic cells include, persistence of the plasmid in blood circulation, port of entry and transport across the cell membrane, release from endosomal compartments into the cytoplasm, nuclear import by docking through the pore complexes of the nuclear envelope, expression driven by the appropriate promoter/enhancer control elements, and persistence of the plasmid in the nucleus for long periods (Boulikas, 1998a).

Plasmid Condensation with Spermine

In a further embodiment, the liposome encapsulated DNA described herein is condensed with spermine and/or spermidine. DNA can be presented to cells in culture as a complex with polycations such as polylysine, or basic proteins such as protamine, total histones or specific histone fractions, protamine (Boulikas and Martin, 1997). The interaction of plasmid DNA with protamine sulfate, followed by the addition of DOTAP cationic liposomes, offered a better protection of plasmid DNA against enzymatic digestion. The method gave consistently higher gene expression in mice via tail vein injection as compared with DOTAP/DNA complexes. 50 µg of luciferase-plasmid per mouse gave 20 ng luciferase protein per mg extracted tissue protein in the lung, that was detected as early as 1 h after injection, peaked at 6 h and declined thereafter. Intraportal injection of protamine/DOTAP/DNA led to about a 100-fold decrease in gene expression in the lung as compared with I.V. injection. Endothelial cells were the primary locus of lacZ transgene expression (Li and Huang, 1997). Protamine sulfate enhanced plasmid delivery into several different types of cells in vitro, using the monovalent cationic liposomal formulations (DC-Chol and lipofectin). This effect was less pronounced with the multivalent cationic liposome formulation, lipofectamine (Sorgi et al., 1997).

Spermine is found to enhance the transfection efficiency of DNA-cationic liposome complexes in cell culture and in animal studies. This biogenic polyamine at high concentrations caused liposome fusion most likely promoted by the simultaneous interaction of one molecule of spermine (four positively charged amino groups) with the polar head groups of two or more molecules of lipids. At low concentrations (0.03-0.1 mM) it promoted anchorage of the liposome-DNA complex to the surface of cells and enhanced significantly transfection efficiency (Boulikas, unpublished).

The polycations polybrene, protamine, DEAE-dextran, and poly-L-lysine significantly increased the efficiency of adenovirus-mediated gene transfer in cell culture. This was thought to act by neutralizing the negative charges presented by membrane glycoproteins that reduce the efficiency of adenovirus-mediated gene transfer (Arcasoy et al., 1997).

Oligonucleotide Transfer

In a further embodiment, the liposome encapsulates oligonucleotide DNA. Encapsulation of oligonucleotides into liposomes increased their therapeutic index, prevented degradation in cultured cells, and in human serum and reduced toxicity to cells (Thierry and Dritschilo, 1992; Capaccioli et al., 1993; Lewis et al., 1996). However, most studies have been performed in cell culture, and very few in animals in vivo. There are still an important number of improvements needed before these approaches can move into clinical studies.

Zelphati and Szoka (1997), have found that complexes of fluorescently labeled oligonucleotides with DOTAP liposomes, entered the cell using an endocytic pathway mainly involving uncoated vesicles. Oligonucleotides were redistributed from punctate cytoplasmic regions into the nucleus. This process was independent of acidification of the endosomal vesicles. The nuclear uptake of oligonucleotides depended on several factors, such as charge of the particle, where positively charged complexes were required for enhanced nuclear uptake. DOTAP increased over 100 fold the antisense activity of a specific anti-luciferase oligonucleotide. Physicochemical studies of oligonucleotide-liposome complexes of different cationic lipid compositions indicated that either phosphatidylethanolamine or negative charges on other lipids in the cell membrane are required for efficient fusion with cationic liposome-oligonucleotide complexes to promote entry to the cell (Jaaskelainen et al., 1994).

Similar results were reported by Lappalainen et al. (1997). Digoxigenin-labeled oligodeoxynucleotides (ODNs) complexed with the polycationic DOSPA and the monocationic DDAB (with DOPE as a helper lipid) were taken up by CaSki cells in culture by endocytosis. The nuclear membrane was found to pose a barrier against nuclear import of ODNs that accumulated in the perinuclear area. Although DOSPA/DOPE liposomes could deliver ODNs into the cytosol, they were unable to mediate nuclear import of ODNs. On the contrary, oligonucleotide-DDAB/DOPE complexes with a net positive charge were released from vesicles into the cytoplasm. It was determined that DDAB/DOPE mediated nuclear import of the oligonucleotides.

DOPE-heme (ferric protoporphyrin IX) conjugates, inserted in cationic lipid particles with DOTAP, protected oligoribonucleotides from degradation in human serum and increased oligoribonucleotide uptake into 2.2.15 human hepatoma cells. The enhancing effect of heme was evident only at a net negative charge in the particles (Takle et al., 1997). Uptake of liposomes labeled with $^{111}$In and composed of DC-Chol and DOPE was primarily by liver, with some accumulation in spleen and skin and very little in the lung after I.V. tail injection. Preincubation of cationic liposomes with phosphorothioate oligonucleotide induced a dramatic, yet transient, accumulation of the lipid in lung that gradually redistributed to liver. The mechanism of lung uptake involved entrapment of large aggregates of oligonucleotides within pulmonary capillaries at 15 min post-injection via embolism. Labeled oligonucleotide was localized primarily to phagocytic vacuoles of Kupffer cells at 24 h post-injection. Nuclear uptake of oligonucleotides in vivo was not observed (Litzinger et al., 1996).

Polyethylene Glycol (PEG)-Coated Liposomes

In a further embodiment, the liposome encapsulated DNA described herein, further comprise coating of the final complex in step 2 (FIG. 1) with PEG. It is often desirable to conjugate a lipid to a polymer that confers extended half-life, such as polyethylene glycol (PEG). Derivatized lipids that are employed, include PEG-modified DSPE or PEG-ceramide.

Addition of PEG components prevents complex aggregation, increases circulation lifetime of particles (liposomes, proteins, other complexes, drugs) and increases the delivery of lipid-nucleic acid complexes to the target tissues. See, Maxfield et al., Polymer 16:505-509 (1975); Bailey, F. E. et al., in: Nonionic Surfactants, Schick, M. J., ed., pp. 794-821 (1967); Abuchowski, A. et al., J Biol. Chem. 252:3582-3586 (1977); Abuchowski, A. et al., Cancer Biochem. Biophys. 7:175-186 (1984); Katre, N. V. et al., Proc. Natl. Acad. Sci. USA 84:1487-1491 (1987); Goodson, R. et al. Bio Technology 8:343-346 (1990).

Conjugation to PEG is reported to have reduced immunogenicity and toxicity. See, Abuchowski et al., J. Biol. Chem. 252:3578-3581 (1977). The extent of enhancement of blood circulation time of liposomes, by coating with PEG is described in U.S. Pat. No. 5,013,556. Typically, the concentration of the PEG-modified phospholipids, or PEG-ceramide in the complex will be about 1-7%. In a particularly preferred embodiment, the PEG-modified lipid is a PEG-DSPE.

Coating the surface of liposomes with inert materials designed to camouflage the liposome from the body's host defense systems was shown to increase remarkably the plasma longevity of liposomes. The biological paradigm for this "surface modified" sub-branch was the erythrocyte, a cell that is coated with a dense layer of carbohydrate groups, and that manages to evade immune system detection and to circulate for several months (before being removed by the same type of cell responsible for removing liposomes).

The first breakthrough came in 1987 when a glycolipid (the brain tissue-derived ganglioside GM 1), was identified that, when incorporated within the lipid matrix, allowed liposomes to circulate for many hours in the blood stream (Allen and Chonn, 1987). A second glycolipid, phosphatidylinositol, was also found to impart long plasma residence times to liposomes and, since it was extracted from soybeans, not brain tissue, was believed to be a more pharmaceutically acceptable excipient (Gabizon et al., 1989).

A major advance in the surface-modified sub-branch was the development of polymer-coated liposomes (Allen et al. 1991). Polyethylene glycol (PEG) modification had been used for many years to prolong the half-lives of biological proteins (such as enzymes and growth factors) and to reduce their immunogenicity (e.g. Beauchamp et al., 1983). It was reported in the early 1990s that PEG-coated liposomes circulated for remarkably long times after intravenous administration. Half-lives on the order of 24 h were seen in mice and rats, and over 30 hours in dogs. The term "stealth" was applied to these liposomes because of their ability of evade interception by the immune system. The PEG hydrophilic polymers form dense "conformational clouds" to prevent other macromolecules from interaction with the surface, even at low concentrations of the protecting polymer (Gabizon and Papahadjopoulos, 1988; Papahadjopoulos et al., 1991; reviewed by Torchilin, 1998). The increased hydrophilicity of the liposomes after their coating with the amphipathic PEG5000 leads to a reduction in nonspecific uptake by the reticuloendothelial system.

Whereas the half-life of antimyosin immunoliposomes was 40 min, by coating with PEG, they increased their half-life to 1000 min after intravenous injection to rabbits (Torchilin et al., 1992).

Micelles, Surfactants and Small Unilamellar Vesicles

In a further embodiment, the liposome encapsulated DNA described herein, further comprise an initial step of micelle formation between cationic lipids and condensed plasmid or oligonucleotide DNA in ethanol solutions. Micelles are small amphiphilic colloidal particles formed by certain kinds of lipid molecules, detergents or surfactants under defined conditions of concentration, solvent and temperature. They are composed of a single lipid layer. Micelles can have their hydrophilic head groups assembled exposing their hydrophobic tails to the solvent (for example in 30-60% aqueous ethanol solution) or can reverse their structures exposing their polar heads toward the solvent such as by lowering the concentration of the ethanol to below 10% (reverse micelles). Micelle systems are in thermodynamic equilibrium with the solvent molecules and environment. This results in constant phase changes, especially upon contact with biological materials, such as upon introduction to cell culture, injection to animals, dilution, contact with proteins or other macromolecules. These changes result in rapid micelle disassembly or flocculation. This is in contrast to the much higher stability of liposome bilayers.

Single-chain surfactants are able to form micelles (see Table 1, below). These include the anionic (sodium dodecyl sulfate, cholate or oleate) or cationic (cetyl-trimethylammonium bromide, CTAB) surfactants. CTAB, CTAC, and DOIC micelles yielded larger solubility gaps (lower concentration of colloidally suspended DNA) than corresponding SUV particles containing neutral lipid and CTAB (1:1) (Lasic, 1997).

lipid molecules electrostatically attached to the DNA. These cationic lipid molecules exert their toxicity by interfering with the nucleosome and domain structure of the chromatin causing local destabilization. This disturbance or aberrant chromatin reorganization could be exerted at the level of the nuclear matrix where plasmid DNA is attached for transcription, autonomous replication, or integration via recombination.

Surfactants have found wide application in formulations such as emulsions (including microemulsions) and liposomes. The most common way of classifying and ranking the properties of the many different types of surfactants, both natural and synthetic, is by the use of the hydrophile/lipophile balance (HLB). The use of surfactants in drug products, formulations and in emulsions has been reviewed (Rieger, in: Pharmaceutical Dosage Forms, Marcel Dekker, Inc., New York, 1988, p. 285).

Nonionic surfactants find wide application in pharmaceutical and cosmetic products and are usable over a wide range of pH values. In general, their HLB values range from 2 to about 18, depending on their structure. Nonionic surfactants include, nonionic esters such as ethylene glycol esters, propylene glycol esters, glyceryl esters, polyglyceryl esters, sor-

TABLE 1

Molecules able to form micelles

| Molecule | Reference |
| --- | --- |
| CTAB, CTAC, DOIC | Lasic, 1997 |
| Detergent/phospholipid micelles | Lusa et al., 1998 |
| Dodecyl betaine (amphoteric surfactant) | de la Maza et al., 1998 |
| Dodecylphosphocholine cholate | Lasic, 1997 |
| Glycine-conjugated bile salt (anionic steroid detergent-like molecule) | Leonard and Cohen, 1998 |
| Lipid-dodecyl maltoside micelles | Lambert et al., 1998 |
| mixed micelles (Triton X-100 & phosphatidylcholine) | Lopez et al., 1998 |
| Octylglucoside (non-ionic straight chain detergent) | Leonard and Cohen, 1998 |
| Oleate | Lasic, 1997 |
| PEG-dialkylphosphatidic acid (dihexadecylphosphatidyl (DHP)-PEG2000) | Tirosh et al., 1998 |
| Phosphatidylcholine (neutral zwitterionic) | Schroeder et al., 1990 |
| Polyethyleneglycol (MW 5000)-distearoyl phosphatidyl ethanolamine (PEG-DSPE) | Weissig et al., 1998 |
| sodium dodecyl sulfate (anionic straight chain detergent) | Leonard and Cohen, 1998 |
| Sodium taurofusidate (conjugated fungal bile salt analog) | Leonard and Cohen, 1998 |
| Taurine-conjugated bile salts (anionic steroid detergent-like molecule) | Leonard and Cohen, 1998 |
| Triton X-100 surfactant | Lasic, 1997 |

There is a critical detergent/phospholipid ratio at which lamellar-to-micellar transition occurs. For example, the vesicle-micelle transition was observed for dodecyl maltoside with large unilamellar liposomes. A striking feature of the solubilization process by dodecyl maltoside was the discovery of a new phase, consisting of a very viscous "gel-like" structure composed of long filamentous thread-like micelles, over 1 to 2 microns in length.

A long circulating complex needs to be slightly anionic. Therefore the liposomes used for the conversion of the micelles into liposomes contain bipolar lipids (PC, PE) and 1-30% negatively charged lipids (DPPG). The cationic lipids which are toxic, are hidden in the inner liposome membrane bilayer. Those reaching the solid tumor will exert their toxic effects causing apoptosis. Apoptosis will be caused by the delivery of the toxic drug or anti-neoplastic gene or oligonucleotide to the cancer cell but also by the nuclear localization of the cationic lipids (along with plasmid DNA) to the nucleus. Indeed, a number of studies suggest that plasmid DNA is imported to nuclei; its translocation docks cationic bitan esters, sucrose esters, and ethoxylated esters. Nonionic alkanolamides and ethers, such as fatty alcohol ethoxylates, propoxylated alcohols, and ethoxylated/propoxylated, block polymers are also included in this class. The polyoxyethylene surfactants are the most popular members of the nonionic surfactant class.

Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

Cationic surfactants include quaternary ammonium salts and ethoxylated amines. The quaternary ammonium salts are the most used members of this class. If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Classical micelles may not be effective as gene transfer vehicles, but important intermediates in the formation of liposome complexes encapsulating drugs or nucleic acids. The stability of single chain surfactants-DNA-colloidal systems is lower than SUV particles containing neutral lipid and CTAB (1:1). However, second generation micelles are able to target tumors in vivo. Weissig and co-workers (1998) used the soybean trypsin inhibitor (STI) as a model protein to target tumors. STI was modified with a hydrophobic residue of N-glutaryl-phosphatidyl-ethanolamine (NGPE) and incorporated into both polyethyleneglycol (MW 5000)-distearoyl phosphatidyl ethanolamine (PEG-DSPE) micelles (<20 nm) and PEG-DSPE-modified long-circulating liposomes (ca. 100 nm). As determined from the protein label by using $^{111}$In attached to soybean trypsin inhibitor via protein-attached diethylene triamine pentaacetic acid, DTPA, PEG-lipid micelles accumulated better than the same protein anchored in long-circulating PEG-liposomes in subcutaneously established Lewis lung carcinoma in mice after tail vein injection.

Loading a liposomal dispersion with an amphiphilic drug may cause a phase transformation into a micellar solution. The transition from high ratios of phospholipid to drug (from 2:1 to 1:1 downwards) were accompanied by the conversion of liposomal dispersions of milky-white appearance (particle size 200 nm) to nearly transparent micelles (particle size below 25 nm). See, Schutze and Muller-Goymann (1998).

Fusogenic Peptides

In a further embodiment, the liposome encapsulated DNA described herein further comprises an effective amount of a fusogenic peptide. Fusogenic peptides belong to a class of helical amphipathic peptides characterized by a hydrophobicity gradient along the long helical axis. This hydrophobicity gradient causes the tilted insertion of the peptides in membranes, thus destabilizing the lipid core and, thereby, enhancing membrane fusion (Decout et al., 1999).

Hemagglutinin (HA) is a homotrimeric surface glycoprotein of the influenza virus. In infection, it induces membrane fusion between viral and endosomal membranes at low pH. Each monomer consists of the receptor-binding HA1 domain and the membrane-interacting HA2 domain. The $NH_2$-terminal region of the HA2 domain (amino acids 1 to 127), the so-called "fusion peptide," inserts into the target membrane and plays a crucial role in triggering fusion between the viral and endosomal membranes. Based on the substitution of eight amino acids in region 5-14 with cysteines and spin-labeling electron paramagnetic resonance, it was concluded that the peptide forms an alpha-helix tilted approximately 25 degrees from the horizontal plane of the membrane with a maximum depth of 15 Å from the phosphate group (Macosko et al., 1997). Use of fusogenic peptides from influenza virus hemagglutinin HA-2 enhanced greatly the efficiency of transferrin-polylysine-DNA complex uptake by cells. The peptide was linked to polylysine and the complex was delivered by the transferrin receptor-mediated endocytosis (reviewed by Boulikas, 1998a). This peptide has the sequence: GLFEAIAGFI ENGWEGMIDG GGYC (SEQ ID NO:9) and is able to induce the release of the fluorescent dye calcein from liposomes prepared with egg yolk phosphatidylcholine, which was higher at acidic pH. This peptide was also able to increase up to 10-fold the anti-HIV potency of antisense oligonucleotides, at a concentration of 0.1-1 mM, using CEM-SS lymphocytes in culture. This peptide changes conformation at the slightly more acidic environment of the endosome, destabilizing and breaking the endosomal membrane (reviewed by Boulikas, 1998a).

The presence of negatively charged lipids in the membrane is important for the manifestation of the fusogenic properties of some peptides, but not of others. Whereas the fusogenic action of a peptide, representing a putative fusion domain of fertilin, a sperm surface protein involved in sperm-egg fusion, was dependent upon the presence of negatively charged lipids, that of the HIV2 peptide was not (Martin and Ruysschaert, 1997).

For example, to analyze the two domains on the fusogenic peptides of influenza virus hemagglutinin HA, HA-chimeras were designed in which the cytoplasmic tail and/or transmembrane domain of HA was replaced with the corresponding domains of the fusogenic glycoprotein F of Sendai virus. Constructs of HA were made in which the cytoplasmic tail was replaced by peptides of human neurofibromin type 1 (NF1) (residues 1441 to 1518) or c-Raf-1, (residues 51 to 131) and were expressed in CV-1 cells by using the vaccinia virus-T7 polymerase transient-expression system. Membrane fusion between CV-1 cells and bound human erythrocytes (RBCs) mediated by parental or chimeric HA proteins showed that, after the pH was lowered, a flow of the aqueous fluorophore calcein from preloaded RBCs into the cytoplasm of the protein-expressing CV-1 cells took place. This indicated that membrane fusion involves both leaflets of the lipid bilayers and leads to formation of an aqueous fusion pore (Schroth-Diaz et al., 1998).

A remarkable discovery was that the TAT protein of HIV is able to cross cell membranes (Green and Loewenstein, 1998) and that a 36-amino acid domain of TAT, when chemically cross-linked to heterologous proteins, conferred the ability to transduce into cells. The 11-amino acid fusogenic peptide of TAT (YGRKKRRQRRR (SEQ ID NO:10)) is a nucleolar localization signal (see Boulikas, 1998b).

Another protein of HIV, the glycoprotein gp41, contains fusogenic peptides. Linear peptides derived from the membrane proximal region of the gp41 ectodomain have potential applications as anti-HIV agents and inhibit infectivity by adopting a helical conformation (Judice et al., 1997). The 23 amino acid residue, N-terminal peptide of HIV-1 gp41 has the capacity to destabilize negatively charged large unilamellar vesicles. In the absence of cations, the main structure was a pore-forming alpha-helix, whereas in the presence of $Ca^{2+}$ the conformation switched to a fusogenic, predominantly extended beta-type structure. The fusion activity of HIV(ala) (bearing the R22→A substitution) was reduced by 70%, whereas fusogenicity was completely abolished when a second substitution (V2→E) was included, arguing that it is not an alpha-helical but an extended structure adopted by the HIV-1 fusion peptide that actively destabilizes cholesterol-containing, electrically neutral membranes (Pereira et al., 1997).

The prion protein (PrP) is a glycoprotein of unknown function normally found at the surface of neurons and of glial cells. It is involved in diseases such as bovine spongiform encephalopathy, and Creutzfeldt-Jakob disease in humans, where PrP is converted into an altered form (termed PrPSc). According to computer modeling calculations, the 120 to 133 and 118 to 135 domains of PrP are tilted lipid-associating peptides inserting in a oblique way into a lipid bilayer and able to interact with liposomes to induce leakage of encapsulated calcein (Pillot et al., 1997b).

The C-terminal fragments of the Alzheimer amyloid peptide (amino acids 29-40 and 29-42) have properties related to those of the fusion peptides of viral proteins inducing fusion of liposomes in vitro. These properties could mediate a direct interaction of the amyloid peptide with cell membranes and account for part of the cytotoxicity of the amyloid peptide. In view of the epidemiologic and biochemical linkages between the pathology of Alzheimer's disease and apolipoprotein E (apoE) polymorphism, examination of the potential interaction between the three common apoE isoforms and the C-terminal fragments of the amyloid peptide showed that only apoE2 and apoE3, not apoE4, are potent inhibitors of the amyloid peptide fusogenic and aggregational properties. The protective effect of apoE against the formation of amyloid aggregates was thought to be mediated by the formation of stable apoE/amyloid peptide complexes (Pillot et al., 1997a; Lins et al., 1999).

The fusogenic properties of an amphipathic net-negative peptide (WAE 11), consisting of 11 amino acid residues were strongly promoted when the peptide was anchored to a liposomal membrane. The fusion activity of the peptide appeared to be independent of pH and membrane merging, and the target membranes required a positive charge that was provided by incorporating lysine-coupled phosphatidylethanolamine (PE-K). Whereas the coupled peptide could cause vesicle aggregation via nonspecific electrostatic interaction with PE-K, the free peptide failed to induce aggregation of PE-K vesicles (Pecheur et al., 1997).

A number of studies suggest that stabilization of an alpha-helical secondary structure of the peptide after insertion in lipid bilayers in membranes of cells or liposomes is responsible for the membrane fusion properties of peptides. $Zn^{2+}$, enhances the fusogenic activity of peptides because it stabilizes the alpha-helical structure. For example, the HEXXH (SEQ ID NO:11) domain of the salivary antimicrobial peptide, located in the C-terminal functional domain of histatin-5, a recognized zinc-binding motif is in a helicoidal conformation (Martin et al., 1999; Melino et al., 1999; Curtain et al., 1999).

Fusion peptides have been formulated with DNA plasmids to create peptide-based gene delivery systems. A combination of the YKAKnWK (SEQ ID NO:12) peptide, used to condense plasmids into 40 to 200 nm nanoparticles, with the GLFEALLELLESLWELLLEA (SEQ ID NO:13) amphipathic peptide, that is a pH-sensitive lytic agent designed to facilitate release of the plasmid from endosomes enhanced expression systems containing the beta-galactosidase reporter gene (Duguid et al., 1998). See Table 2, below.

TABLE 2

Fusogenic peptides

| Fusogenic peptide | Source Protein | Properties | Reference |
|---|---|---|---|
| GLFEAIAGFIENGWEG MIDGGGYC (SEQ ID NO: 9) | Influenza virus hemagglutinin HA-2 | Endowed with membrane fusion properties | Bongartz et al., 1994 |
| YGRKKRRQRRR (SEQ ID NO: 5) | TAT of HIV | Endowed with membrane fusion properties | Green and Loewensiein, 1988 |
| 23-residue fusogenic N-terminal peptide | HIV-1 trans-membrane glycoprotein gp41 | Was able to insert as an alpha-helix into neutral phospholipid bilayers | Curtain et al., 1999 |
| 70 residue peptide (SV-117) | Fusion peptide and N-terminal heptad repeat of Sendai virus | Induced lipid mixing of egg phosphatidylcholine-phosphatidyiglycerol (PC/PG) large unilamellar vesicles (LUVs) | Ghosh and Shai, 1999 |
| 23 hydrophobic amino acids in the amino-terminal region | S protein of hepatitis B virus (HBV) | A high degree of similarity with known fusogenic peptides from other viruses. | Rodriguez-Crespo et al, 1994 |
| MSGTFGGILAGLIGLL (SEQ ID NO: 6) | N-terminal region of the S protein of duck hepatitis B Virus (DHBV) | Was inserted into the hydrophobic core of the lipid bilayer and induced leakage of internal aqueous contents from both neutral and negatively charged liposomes | Rodriguez-Crespo et al, 1999 |
| MSPSSLLGLLAGLQVV (SEQ ID NO: 14) | S protein of woodchuck hepatitis B virus (WHV) | Was inserted into the hydrophobic core of the lipid bilayer and induced leakage of internal aqueous contents from both neutral and negatively charged liposomes | Rodriguez-Crespo et al., 1999 |
| N-terminus of Nef | Nef protein of human immuno-deficiency type 1 (HIV-1) | Membrane-perturbing and fusogenic activities in artificial membranes; causes cell killing in E. coli and yeast | Macreadie et al., 1997 |
| Amino-terminal sequence F1 polypeptide | F1 polypeptide of measles virus (MV) | Can be used as a carrier system for CTL epitopes | Partidos et al., 1996 |

TABLE 2-continued

Fusogenic peptides

| Fusogenic peptide | Source Protein | Properties | Reference |
|---|---|---|---|
| 19-27 amino acid segment | Glycoprotein gp51 of bovine leukemia virus | Adopts an amphiphilic structure and plays a key role in the fusion events induced by bovine leukemia virus | Voneche et al., 1992 |
| 120 to 133 and 118 to 135 domains | Prion protein | Tilted lipid-associating peptide; interact with liposomes to induce leakage of encapsulated calcein | Pillot et al, 1997b |
| 29-42-residue fragment | Alzheimer's beta-amyloid peptide | Endowed with capacities resembling those of the tilted fragment of viral fusion proteins | Lins et al., 1999 |
| Non-aggregated amyloid beta-peptide (1-40) | Alzheimer's beta-amyloid peptide | Induces apoptotic neuronal cell death | Pillot et al., 1999 |
| LCAT 56-68 helical segment | Lecithin cholesterol acyltransferase (LCAT) | Forms stable beta-sheets in lipids | Peelman et al., 1999; Decout et al., 1999 |
| Peptide sequence B18 | Membrane-associated sea urchin sperm protein binding | Triggers fusion between lipid vesicles; a histidine-rich motif for binding zinc is required for the fusogenic function | Ulrich et al., 1999 |
| 53-70 (C-terminal helix) | Apolipoprotein (apo) AII | Induces fusion of unilamellar lipid vesicles and displaces apo AI from HDL and r-HDL | Lambert et al., 1998 |
| Residues 90-111 | PH-30 alpha (a protein functioning in sperm-egg fusion) | Membrane-fusogenic activity to acidic phospholipid bilayers | Niidome et al., 1997 |
| Casein signal peptides | Alpha s2- and beta-casein | Interact with dimyristoylphosphatidyl-glycerol and -choline liposomes; show both lytic and fusogenic activities | Creuzenet et al., 1997 |
| Pardaxin | Amphipathic polypeptide, purified from the gland secretion of the Red Sea Moses sole flatfish Pardachirus marmoratus | Forms voltage-gated, cation-selective pores; mediated the aggregation of liposomes composed of phosphatidylserine but not of phosphatidylcholine | Lelkes and Lazarovici, 1988 |
| Histatin-5 | Salivary antimicrobial peptide | Aggregates and fuses negatively charged small unilamellar vesicles in the presence of Zn2/ | Melino et al., 1999 |
| Gramicidin (linear hydrophobic polypeptide) | Antibiotic | Induces aggregation and fusion of vesicles | Massari and Colonna, 1986; Tournois et al., 1990 |

TABLE 2-continued

Fusogenic peptides

| Fusogenic peptide | Source Protein | Properties | Reference |
|---|---|---|---|
| Amphipathic negatively charged peptide consisting of 11 residues (WAE) | Synthetic | Forms an alpha-helix inserted and anchored into the membrane (favored at 37° C.) oriented almost parallel to the lipid acyl chains; promotes fusion of large unilamellar liposomes (LUV) | Martin et al., 1999 |
| A polymer of polylysine (average 190) partially substituted with histidyl residues | Synthetic | Histidyl residues become cationic upon protonation of the imidazole groups at pH below 6.0.; disrupt endosomal membranes | Midoux and Monsigny, 1999 |
| GLFEALLELLESLWELL LEA (SEQ ID NO: 4) | Synthetic | Amphipathic peptide; a pH-sensitive lytic agent to facilitate release of the plasmid from endosomes | Duguid et al., 1998 |
| (LKKL)$_4$ (SEQ ID NO: 15) | Synthetic | Amphiphilic fusogenic peptide, able to interact with four molecules of DMPC | Gupta and Kothekar, 1997 |
| Ac-(Leu-Ala-Arg-Leu)$_3$-NHCH$_3$ (SEQ ID NO: 16) | Synthetic; basic amphipathic peptides | Caused a leakage of contents from small unilamellar vesicles composed of egg yolk phosphatidylcholine and egg yolk phosphatidic acid (3:1) | Suenaga et al., 1989; Lee et al., 1992 |
| Amphiphilic anionic peptides E5 and E5L | Synthetic | Can mimic the fusogenic activity of influenza hemagglutinin (HA) | Murata et al., 1991 |
| 30-amino acid peptide with the major repeat unit Glu-Ala-Leu-Ala (GALA)$_7$ (SEQ ID NO: 17) | Synthetic; designed to mimic the behavior of the fusogenic sequences of viral fusion proteins | Becomes an amphipathic alpha-helix as the pH is lowered to 5.0; fusion of phosphatidylcholine small unilamellar vesicles induced by GALA requires a peptide length greater than 16 amino acids | Parente et al., 1988 |
| Poly Glu-Aib-Leu-Aib (SEQ ID NO: 18) Aib represents 2-aminoisobutyric acid | Synthetic | Amphiphilic structure upon the formation of alpha-helix; caused fusion of EYPC liposomes and dipalmitoylphosphatidyl-choline liposomes more strongly with decreasing pH | Kono et al., 1993 |

Fusogenic Lipids

DOPE is a fusogenic lipid; elastase cleavage of N-methoxy-succinyl-Ala-Ala-Pro-Val-DOPE (SEQ ID NO:19) converted this derivative to DOPE (overall positive charge) to deliver an encapsulated fluorescent probe, calcein, into the cell cytoplasm (Pak et al., 1999). An oligodeoxynucleic sequence of 30 bases complementary to a region of beta-endorphin mRNA elicited a concentration-dependent inhibition of beta-endorphin production in cell culture after it was encapsulated within small unilamellar vesicles (50 nm) containing dipalmitoyl-DL-alpha-phosphatidyl-L-serine endowed with fusogenic properties (Fresta et al., 1998).

Nuclear Localization Signals (NLS)

In a further embodiment, the liposome encapsulated plasmid or oligonucleotide DNA described herein further comprise an effective amount of nuclear localization signal (NLS) peptides. Trafficking of nuclear proteins from the site of their synthesis in the cytoplasm to the sites of function in the nucleus through pore complexes is mediated by NLSs on proteins to be imported into nuclei (Tables 3-10, below). Protein translocation from the cytoplasm to the nucleoplasm involves: (i) the formation of a complex of karyopherin α with NLS-protein; (ii) subsequent binding of karyopherin β; (iii) binding of the complex to FXFG peptide repeats on nucleoporins; (iv) docking of Ran-GDP to nucleoporin and to karyopherin heterodimer by p10; (v) a number of association-dissociation reactions on nucleoporins that dock the import substrate toward the nucleoplasmic side with a concomitant GDP-GTP exchange reaction transforming Ran-GDP into Ran-GTP and catalyzed by karyopherin α; and (vi) dissociation from karyopherin and release of the karyopherin α/NLS-protein by Ran-GTP to the nucleoplasm.

Karyophilic and acidic clusters were found in most non-membrane serine/threonine protein kinases whose primary structure has been examined (Table 6). These karyophilic clusters might mediate the anchoring of the kinase molecules to transporter proteins for their regulated nuclear import and might constitute the nuclear localization signals. In contrast to protein transcription factors that are exclusively nuclear possessing strong karyophilic peptides composed of at least four arginines, (R), and lysines, (K), within an hexapeptide flanked by proline and glycine helix-breakers, protein kinases often contain one histidine and three K+R residues (Boulikas, 1996). This was proposed to specify a weak NLS structure resulting in the nuclear import of a fraction of the total cytoplasmic kinase molecules, as well as in their weak retention in the different ionic strength nuclear environment. Putative NLS peptides in protein kinases may also contain hydrophobic or bulky aromatic amino acids proposed to further diminish their capacity to act as strong NLS.

Most mammalian proteins that participate in DNA repair pathways seem to possess strong karyophilic clusters containing at least four R+K over a stretch of six amino acids (Table 7).

Rules to Predict Nuclear Localization of an Unknown Protein

Several simple rules have been proposed for the prediction of the nuclear localization of a protein of an unknown function from its amino acid sequence:

(i) An NLS is defined as four arginines (R) plus lysines (K) within an hexapeptide; the presence of one or more histidines (H) in the tetrad of the karyophilic hexapeptide, often found in protein kinases that have a cytoplasmic and a nuclear function, may specify a weak NLS whose function might be regulated by phosphorylation or may specify proteins that function in both the cytoplasm and the nucleus (Boulikas, 1996);

(ii) The K/R clusters are flanked by the α-helix breakers G and P thus placing the NLS at a helix-turn-helix or end of a α-helix. Negatively-charged amino acids (D, E) are often found at the flank of the NLS and on some occasions may interrupt the positively-charged NLS cluster;

(iii) Bulky amino acids (W, F, Y) are not present within the NLS hexapeptide;

(iv) NLS signals may not be flanked by long stretches of hydrophobic amino acids (e.g. five); a mixture of charged and hydrophobic amino acids serves as a mitochondrial targeting signal;

(v) The higher the number of NLSs, the more readily a molecule is imported to the nucleus (Dworetzky et al., 1988). Even small proteins, for example histones (10-22 kDa), need to be actively imported to increase their import rates compared with the slow rate of diffusion of small molecules through pores;

(vi) Signal peptides are stronger determinants than NLSs for protein trafficking. Signal peptides direct proteins to the lumen of the endoplasmic reticulum for their secretion or insertion into cellular membranes (presence of transmembrane domains) (Boulikas, 1994);

(vii) Signals for the mitochondrial import of proteins (a mixture of hydrophobic and karyophilic amino acids) may antagonize nuclear import signals and proteins possessing both type of signals may be translocated to both mitochondria and nuclei;

(viii) Strong association of a protein with large cytoplasmic structures (membrane proteins, intermediate filaments) make such proteins unavailable for import even though they posses NLS-like peptides (Boulikas, 1994);

(ix). Transcription factors and other nuclear proteins posses a great different number of putative NLS stretches. Of the sixteen possible forms of putative NLS structures the most abundant types are the θθxθθ, θθθxθ, θθθθ, and θθxθxθ, where θ is R or K, together accounting for about 70% of all karyophilic clusters on transcription factors (Boulikas, 1994);

(x) A small number of nuclear proteins seem to be void of a typical karyophilic NLS. Either non karyophilic peptides function for their nuclear import, as such molecules possess bipartite NLSs, or these NLS-less proteins depend absolutely for import on their strong complexation in the cytoplasm with a nuclear protein partner able to be imported (Boulikas, 1994). This mechanism may ensure a certain stoichiometric ratio of the two molecules in the nucleus, and might be of physiological significance; and (xi) A number of proteins may be imported via other mechanisms not dependent on classical NLS.

A number of processes have been found to be regulated by nuclear import including nuclear translocation of the transcription factors NF-κB, rNFIL-6, ISGF3, SRF, c-Fos, GR as well as human cyclins A and B1, casein kinase II, cAMP-dependent protein kinase II, protein kinase C, ERK1 and ERK2. Failure of cells to import specific proteins into nuclei can lead to carcinogenesis. For example, BRCA1 is mainly localized in the cytoplasm in breast and ovarian cancer cells, whereas in normal cells the protein is nuclear. mRNA is exported through the same route as a complex with nuclear proteins possessing nuclear export signals (NES). The majority of proteins with NES are RNA-binding proteins that bind to and escort RNAs to the cytoplasm. However, other proteins with NES function in the export of proteins; CRM1, that binds to the NES sequence on other proteins and interacts with the nuclear pore complex, is an essential mediator of the NES-dependent nuclear export of proteins in eukaryotic cells. Nuclear localization and export signals (NLS and NES) are found on a number of important molecules, including p53, v-Rel, the transcription factor NF-ATc, the c-Abl nonreceptor tyrosine kinase, and the fragile X syndrome mental retardation gene product. The deregulation of their normal import/export trafficking has important implications for human disease. Both nuclear import and export processes can be manipulated by conjugation of proteins with NLS or NES peptides. During gene therapy, the foreign DNA needs to enter nuclei for its transcription. A pathway is proposed involving the complexation of plasmids and oligonucleotides with nascent nuclear proteins possessing NLSs as a prerequisite for their nuclear import. Covalent linkage of NLS peptides to oligonucleotides and plasmids or formation of complexes of plasmids with proteins possessing multiple NLS peptides was proposed (Boulikas, 1998b) to increase their import rates and the efficiency of gene expression. Cancer cells were predicted to import more efficiently foreign DNA into nuclei, compared with terminally differentiated cells because of their increased rates of proliferation and protein import.

Antineoplastic Drugs

In a further embodiment, the liposome encapsulated plasmid or oligonucleotide DNA described herein, further comprises its use for reducing tumor size or restricting its growth with combination with encapsulated or free antineoplastic agents. Antineoplastic agents preferably are: (i) alkylating agents having the bis-(2-chloroethyl)-amine group such as chlormethine, chlorambucile, melphalan, uramustine, mannomustine, extramustinephosphat, mechlorethaminoxide, cyclophosphamide, ifosfamide, or trifosfamide; (ii) alkylating agents having a substituted aziridine group, for example tretamine, thiotepa, triaziquone, or mitomycine; (iii) alkylating agents of the methanesulfonic ester type such as busulfane; (iv) alkylating N-alkyl-N-nitrosourea derivatives, for example carmustine, lomustine, semustine, or streptozotocine; (v) alkylating agents of the mitobronitole, dacarbazine, or procarbazine type; (vi) complexing agents such as cisplatin; (vii) antimetabolites of the folic acid type, for example methotrexate; (viii) purine derivatives such as mercaptopurine, thioguanine, azathioprine, tiamiprine, vidarabine, or puromycine and purine nucleoside phosphorylase inhibitors; (ix) pyrimidine derivatives, for example fluorouracil, floxuridine, tegafur, cytarabine, idoxuridine, flucytosine; (x) antibiotics such as dactinomycin, daunorubicin, doxorubicin, mithramycin, bleomycin or etoposide; (xi) vinca alkaloids; (xii) inhibitors of proteins overexpressed in cancer cells such as telomerase inhibitors, glutathione inhibitors, proteasome inhibitors; (xiii) modulators or inhibitors of signal transduction pathways such as phosphatase inhibitors, protein kinase C inhibitors, casein kinase inhibitors, insulin-like growth factor-1 receptor inhibitor, ras inhibitors, ras-GAP inhibitor, protein tyrosine phosphatase inhibitors; (xiv) tumor angiogenesis inhibitors such as angiostatin, oncostatin, endostatin, thalidomide; (xv) modulators of the immune response and cytokines such as interferons, interleukins, TNF-alpha; (xvi) modulators of the extracellular matrix such as matrix metalloproteinase inhibitors, stromelysin inhibitors, plasminogen activator inhibitor; (xvii) hormone modulators for hormone-dependent cancers (breast cancer, prostate cancer) such as antiandrogen, estrogens; (xviii) apoptosis regulators; (xix) bFGF inhibitor; (xx) multiple drug resistance gene inhibitor; (xxi) monoclonal antibodies or antibody fragments against antigenes overexpressed in cancer cells (anti-Her2/neu for breast cancer); (xxii) anticancer genes whose expression will cause apoptosis, arrest the cell cycle, induce an immune response against cancer cells, inhibit tumor angiogenesis i.e. formation of blood vessels, tumor suppressor genes (p53, RB, BRCA1, E1A, bcl-2, MDR-1, p21, p16, bax, bcl-xs, E2F, IGF-I VEGF, angiostatin, oncostatin, endostatin, GM-CSF, IL-12, IL-2, IL-4, IL-7, IFN-γ, and TNF-α); and (xxiii) antisense oligonucleotides (antisense c-fos, c-myc, K-ras). Optionally these drugs are administered in combination with chlormethamine, prednisolone, prednisone, or procarbazine or combined with radiation therapy. Future new anticancer drugs added to the arsenal are expected to be ribozymes, triplex-forming oligonucleotides, gene inactivating oligonucleotides, a number of new genes directed against genes that control the cell proliferation or signaling pathways, and compounds that block signal transduction.

Anti-cancer drugs include: acivicin, aclarubicin, acodazole hydrochloride, acronine, adozelesin, adriamycin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interferon alfa-2a, interferon α-2b, interferon α-n1, interferon α-n3, interferon β-i a, interferon γ-i b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, prednisone, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, taxol, tecogalan sodium, tegafur, teloxantrone hydrochloride, temoporfin, teniposide, teroxirone, testolactone, thiamiprine, thioguanine, thiotepa, tiazofurin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vaprcotide, verteporfin, vinblastine sulfate, vincristine sulfate, vindesine, vindesine sulfate, vinepidine sulfate, vinglycinate sulfate, vinleurosine sulfate, vinorelbine tartrate, vinzolidine sulfate, vinzolidine sulfate, vorozole, zeniplatin, zinostatin, zorubicin hydrochloride.

Other anti-cancer drugs include: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, anti androgen, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-aminotriazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dioxamycin, diphenyl spiromustine, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium gallium nitrate texaphyrin, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-, irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukinc, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, velaresol, veramine, verdins, verteporfin, vinorelbine, vinxaltine, vitaxin, vorozole, zanoterone, zeniplatin, zilascorb, zinostatin stimalamer.

pH-Sensitive Peptide-DNA Complexes

In a further embodiment of the invention, the genes in plasmid DNA are brought in interaction with fusogenic peptide/NLS conjugates. In a further embodiment the NLS moiety is a stretch of histidyl residues able to assume a net positive charge at a pH of about 5 to 6 and to show a reduction or loose completely this charge at pH above 7. The electrostatic interaction of these positively-charged peptides with the negatively-charged plasmid DNA molecules, established at pH 5-6 is weakened at physiological pH (pH-sensitive peptide-DNA complexes).

The first step of the present invention involves complex formation between the plasmid or oligonucleotide DNA with the histidyl/fusogenic peptide conjugate and lipid components in 10-90% ethanol at pH 5.0 to 6.0. The conditions must be where the histidyl residues have a net positive charge and can establish electrostatic interactions with plasmids, oligonucleotides or negatively-charged drugs. At the same time, the presence of the positively-charged lipid molecules promotes formation of micelles. At the second step, micelles are converted into liposomes by dilution with water and mixing with pre-made liposomes or lipids at pH 5-6. This is followed by dialysis against pH 7 and extrusion through membranes, entrapping and encapsulating plasmids or oligonucleotides to with a very high yield.

Whereas the composition of peptides and cationic lipids in the first step provides the lipids of the internal bilayer, the type of liposomes or lipids added at step 2 provide the external coating of the final liposome formulation (FIG. 1). Examples for the formulations of peptides include: HHHHHSPSL$_{16}$ (SEQ ID NO:623), and HHHHHSPS(LAI)$_5$ (SEQ ID NO:624).

These are added at a 1:0.5:0.5 molar ratio (negative charge on DNA:cationic liposome: histidine peptide). The peptide inserts in an alpha-helical conformation inside the lipid bilayer and not only carries out DNA condensation but also endows membrane fusion properties to the complex to improve entrance across the cell membrane. The type of hydrophobic amino acids (for example, content in aromatic amino acids), in the peptide chain is very important as is the length of the peptide chain in ensuring integrity and rigidity of the complexes. Coating the outer surface of the complexes with polyethyleneglycol, hyaluronic acids and other polymers conjugated to lipids gives the particles long circulation properties in body fluids and the ability to target solid tumors and their metastases after intravenous injection, and also the ability to cross the tumor cell membrane.

Protease-Sensitive Linkages in Peptides Between the NLS and Fusogenic Moieties

Conversion of Micelles into Liposomes

An important issue of the present invention is the conversion of micelles formed between the DNA and the cationic lipids, in the presence of ethanol, into liposomes. This is done by the direct addition of the micelle complex into an aqueous solution of preformed liposomes. The liposomes have an average size of 80-160 nm or vice versa, leading to a solution of a final ethanol concentration below 10%. A formulation suitable for pharmaceutical use and for injection into humans and animals will require that the liposomes are of neutral composition (such as cholesterol, PE, PC) coated with PEG.

However, another important aspect is the research application of the present invention, such as for transfection of cells in culture. The composition of the aqueous solution of liposomes is any type of liposomes containing cationic lipids and suitable therefore for transfection of cells in culture such as DDAB:DOPE 1:1. These liposomes are pre-formed and downsized by sonication or extrusion through membranes to a diameter of 80-160 nm. The ethanolic micelle preparations are then added to the aqueous solution of liposomes with a concomitant dilution of the ethanol solution to below 10%. This step will result in further condensation of DNA or interaction of the negatively-charged phosphate groups on DNA with positively charged groups on lipids. Care must be taken so as only part of the negative charges on DNA are neutralized by lipids in the micelle. The remaining charge neutralization of the DNA is to be provided by the cationic component of the preformed liposomes in the second step.

Regulatory DNA and Nuclear Matrix-Attached DNA

In a further embodiment of the present invention, the genes in plasmid DNA are driven by regulatory DNA sequences isolated from nuclear matrix-attached DNA using shotgun selection approaches.

The compact structural organization of chromatin and the proper spatial orientation of individual chromosomes within a cell are partially provided by the nuclear matrix. The nuclear matrix is composed of DNA, RNA and proteins and serves as the site of DNA replication, gene transcription, DNA repair, and chromosomal attachment in the nucleus. Diverse sets of DNA sequences have been found associated with nuclear matrices and is referred to as matrix attachment regions or MARs. The MARs serve many functions, acting as activators of gene transcription, silencers of gene expression, insulators of transcriptional activity, nuclear retention signals and origins of DNA replication. Current studies indicate that different subsets of MARs are found in different tissue types and may assist in regulating the specific functions of cells. The presence of this complex assortment of structural and regulatory molecules in the matrix, as well as the in situ localization of DNA replication and transcription complexes to the matrix strongly suggest that the nuclear matrix plays a fundamental, unique role in nuclear processes. The structuring of genomes into domains has a functional significance. The inclusion of specific MAR elements within gene transfer vectors could have utility in many experimental and gene therapy applications. Many gene therapy applications require specific expression of one or more genes in targeted cell types for prolonged time periods. MARs within vectors could enhance transcription of the introduced transgene, prolong the retention of that sequence within the nucleus or insulate expression of that transgene from the expression of a cotransduced gene (reviewed by Boulikas, 1995; Bode et al, 1996).

Various biochemical procedures have been used to identify regulatory regions within genes. Traditionally, identification and selection of regulatory DNA sequences depend on tedious procedures such as transcription factor footprinting in vitro or in vivo, or subcloning of smaller fragments from larger genomic DNA sequences upstream of reporter genes. These methods have been used primarily to identify regions proximal to the 5' end of genes. However, in many instances, regulatory regions are found at considerable distances from the proximal 5' end of the gene, and confer cell type- or developmental stage-specificity. For example, studies from the groups of Grosveld and Engel (Lakshmanan et al., 1999) have shown that over 625 kb of genomic sequences surrounding the GATA-3 locus are required for the correct developmental expression of the gene in transgenic mice. Extensive DNA stretches at distances 5-20 kb upstream of the gene were found to be responsible for the central nervous system-specificity of expression. The region between 20 to 130 kb upstream of the gene harbored regulatory regions for urogenital-specific expression of GATA-3, whereas sequences 90-180 kb downstream of the gene conferred endocardial-specific expression.

The presently disclosed method has the potential of rapidly identifying regulatory control regions. In cells, chromatin loops are formed and different attachment regions are used in different cell types or stages of development to modulate the expression of a gene. The presently disclosed method for isolating regulatory regions based on their attachment to the nuclear matrix can identify regulatory regions irrespective of their distance from the gene. Although the human genome project is expected to be almost complete by the year 2000, information on the location and nature of the vast majority of the estimated 500,000 regulatory regions will not be available.

Example 1

Plasmid DNA condenses with various agents, as well as various formulations of cationic liposomes. The condensation affects the level of expression of the reporter beta-galactosidase gene after transfection of K562 human erythroleukemia cell cultures. Liposome compositions are shown in the Table below and in FIG. 2. All lipids were from Avanti Polar Lipids (700 Industrial Park Drive, Alabaster, Ala. 35007). The optimal ratio of lipid to DNA was 7 nmoles total lipid/µg DNA. The transfection reagent (10 µg DNA mixed with 70 nmoles total lipid) was transferred to a small culture flask followed by the addition of 10 ml K562 cell culture (about 2 million cells total); mixing of cells with the transfection reagent was at 5-10 min after mixing DNA with liposomes. Cells were assayed for beta-galactosidase activity several times at 1-30 days post-transfection. The transfected cells were maintained in cell culture as normal cell cultures.

Best results were obtained when the cells used for transfection were at low number, not near confluence. In all experiments the transfection material was added directly in the presence of serum and antibiotics without removal of the transfection reagent or washings of the cells. This simplifies the transfection procedure and is suitable for lymphoid and other type of cell cultures that do not attach to the dish, but grow in suspension. All DNA condensing agents were purchased from Sigma. They were suspended at 0.1 mg/ml in water. Plasmid pCMVβ was purchased from Clontech and was purified using the Anaconda kit of Althea Technologies (San Diego, Calif.). PolyK is polylysine, mw 9,400. PolyR is polyarginine. PolyH is polyhistidine.

Figure 2:
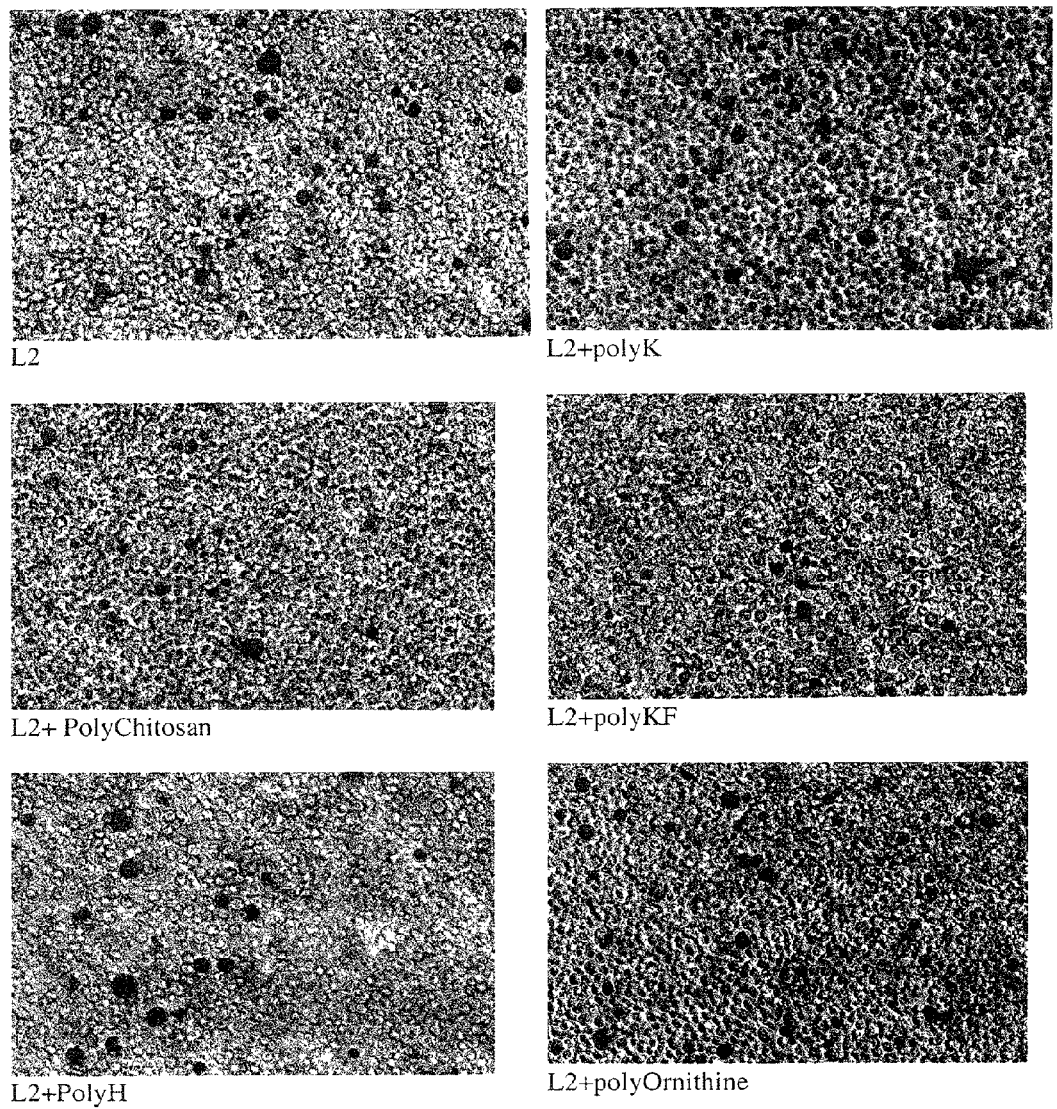
FIG. 2 illustrates the results of plasmid DNA condensation with various agents as well as various formulation of cationic liposomes in affecting the level of expression of the reporter beta-galactosidase gene after transfection of K562 human erythroleukemia cell cultures.

To 100 µl plasmid solution (10 µg total plasmid DNA) 20 µl or 500 of polyK, polyR, polyH, were added; the volume was adjusted to 250 µl with water followed by addition of about 70 µl liposomes (7 nmoles/µg DNA). After incubation for 10 min to 1 h at 20° C. the transfection mixture was brought in contact with the cell culture. The best DNA condensing reagent was polyhistidine compared with the popular polylysine. The best cationic lipid was DC-cholesterol (DC-CHOL: 3β[N—(N', N'-dimethylaminoethane)carbamoyl]cholesterol). SFV is Semliki Forest virus expressing beta-galactosidase. The results are shown in FIG. 2.

| Liposome | Molecular weight | Composition | Preparation |
|---|---|---|---|
| L2 | DDAB mw 631<br>DOPE mw 744 | DDAB 4.2 µmoles/ml<br>DOPE 4.2 µmoles/ml | 15 mg DDAB +<br>0.88 ml 20 mg/ml DOPE |
| L3 | DOGS-NTA mw 1015.4 | DOGS-NTA 1 µmole/ml<br>DOPE 1 µmole/ml | 5 mg DOGS<br>0.185 ml DOPE |
| L4 | DC-Chol (mw 537)<br>DOPE (mw 744) | DC-Chol 1 µmole/ml<br>DOPE 1 µmole/ml | 0.106 ml DC-Chol (25 mg/ml) +<br>0.185 ml DOPE (20 mg/ml) |
| L5 | DOTAP (mw 698)<br>DOPE (mw 744) | DOTAP 1.4 µmoles/ml<br>DOPE 1.3 µmole/ml | 0.5 ml 10 mg/ml DOTAP +<br>0.25 ml DOPE (20 mg/ml) |
| L6 | DODAP (mw 648) | DODAP 1.54 µmoles/ml<br>DOPE 1.3 µmole/ml | 0.5 ml 10 mg/ml<br>DODAP = 5 mg = 7.72 µmoles +<br>0.25 ml DOPE (20 mg/ml) |

Example 2

Targeting Genes to Tumors Using Gene Vehicles (Lipogenes)

As shown in FIG. 3, tumor targeting in SCID (severe combined immunodeficient) mice were implanted subcutaneously, at two sites, with human MCF-7 breast cancer cells. The cells were allowed to develop into large, measurable solid tumors at about 30 days post-inoculation. Mice were injected intraperitoneally with 0.2 mg plasmid pCMVβ DNA (size of the plasmid is ~4 kb) per animal carrying the bacterial beta-galactosidase reporter gene. Plasmid DNA (200 µg, 2.0 mg/ml, 0.1 ml) was incubated for 5 min with 200 µl neutral liposomes of the composition 40% cholesterol, 20% dioleoylphosphatidylethanolamine(DOPE), 12% palmitoyloleoylphosphatidylcholine (POPC), 10% hydrogenated soy phosphatidylcholine (HSPC), 10% distearoylphosphatidylethanolamine (DSPE), 5% sphingomyelin (SM), and 3% derivatized vesicle-forming lipid M-PEG-DSPE.

At this stage, weak complexation of plasmid DNA with neutral (zwitterionic) liposomes takes place. This ensures homogeneous distribution of plasmid DNA to liposomes at the subsequent step of addition of cationic liposomes. After complexation of plasmid DNA with zwitterionic liposomes, 50 µl of cationic liposomes (DC-Chol 1 µmole/ml:DOPE 1.4 µmole/ml) were added and incubated at room temperature for 10 min. At this stage, a mixed liposome population is present and, most likely, formation of a type of liposome-DNA complexes containing lipids from the zwitterionic and cationic lipids takes place. The material was injected (0.35 ml total volume) to the intraperitoneal cavity of the animal. At 5 days post-injection the animal was sacrificed, the skin was removed and the carcass was incubated into X-gal staining solution for about 30 min at 37° C. The animal was incubated in fixative in X-gal staining for about 30 min (addition of 100 µl concentrated glutaraldehyde to 30 ml X-gal staining solution) and the incubation in staining solution continued. Photos were taken in a time course during the incubation period revealing the preferred organs where beta-galactosidase expression took place.

Figure 3A:
FIGS. 3A-3E illustrate tumor targeting in SCID mice.
Figure 3A:
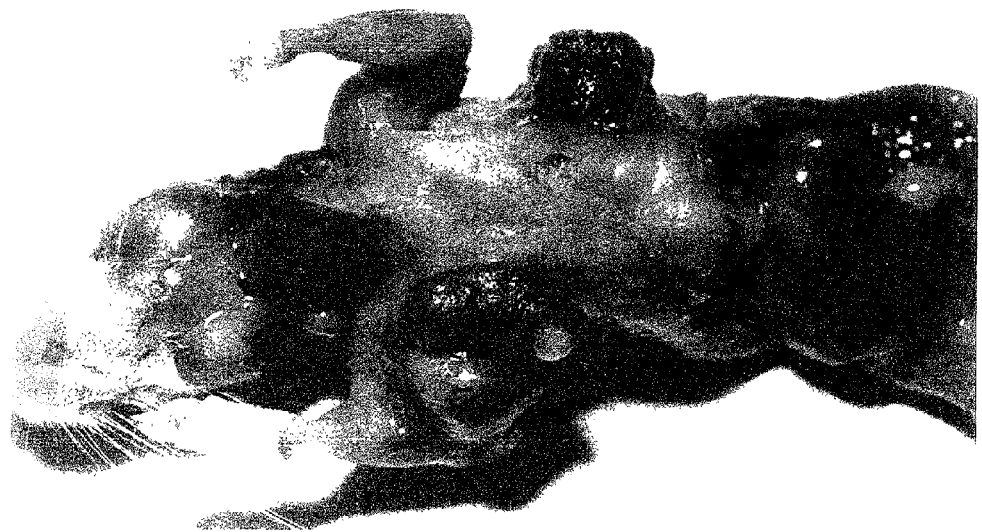
Figure 3B:
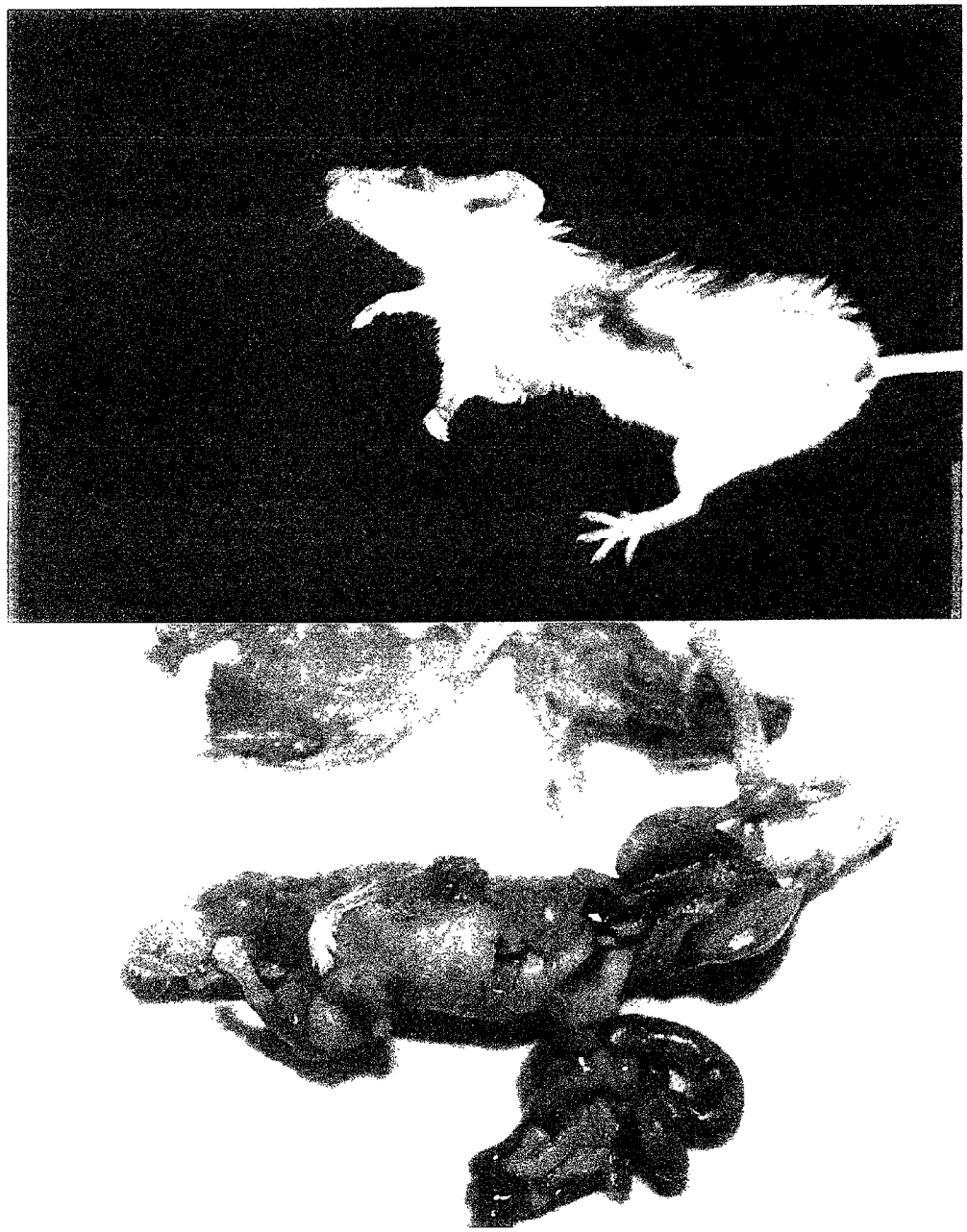
Figure 3C:
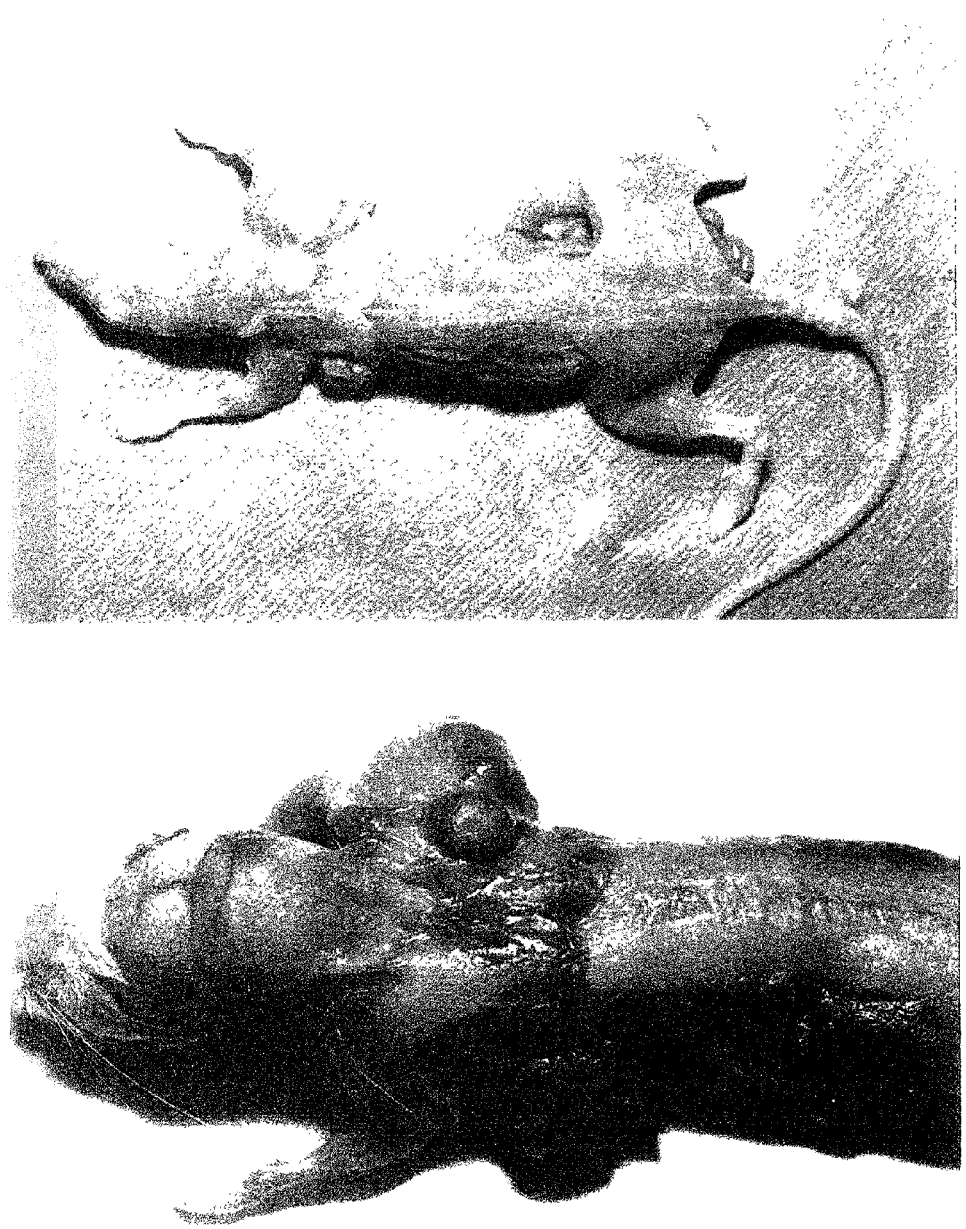
Figure 3D:
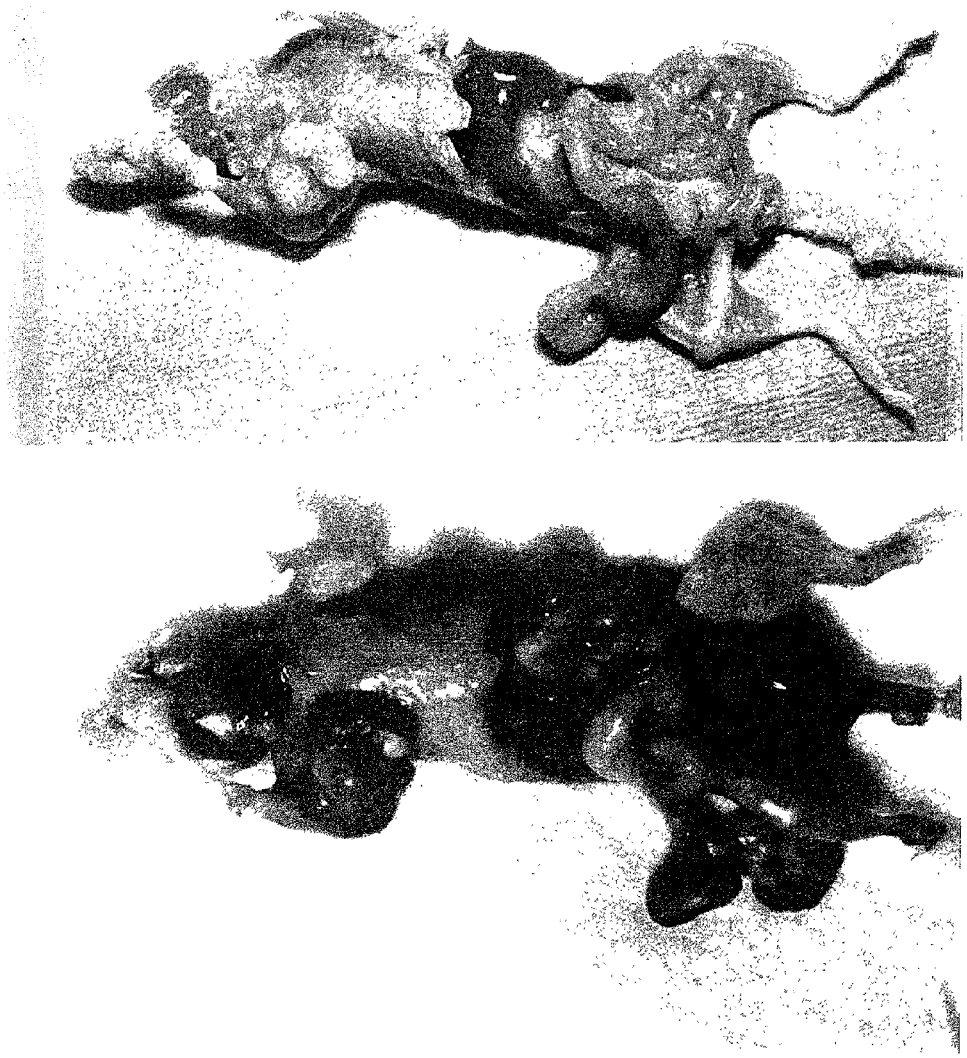
Figure 3E:
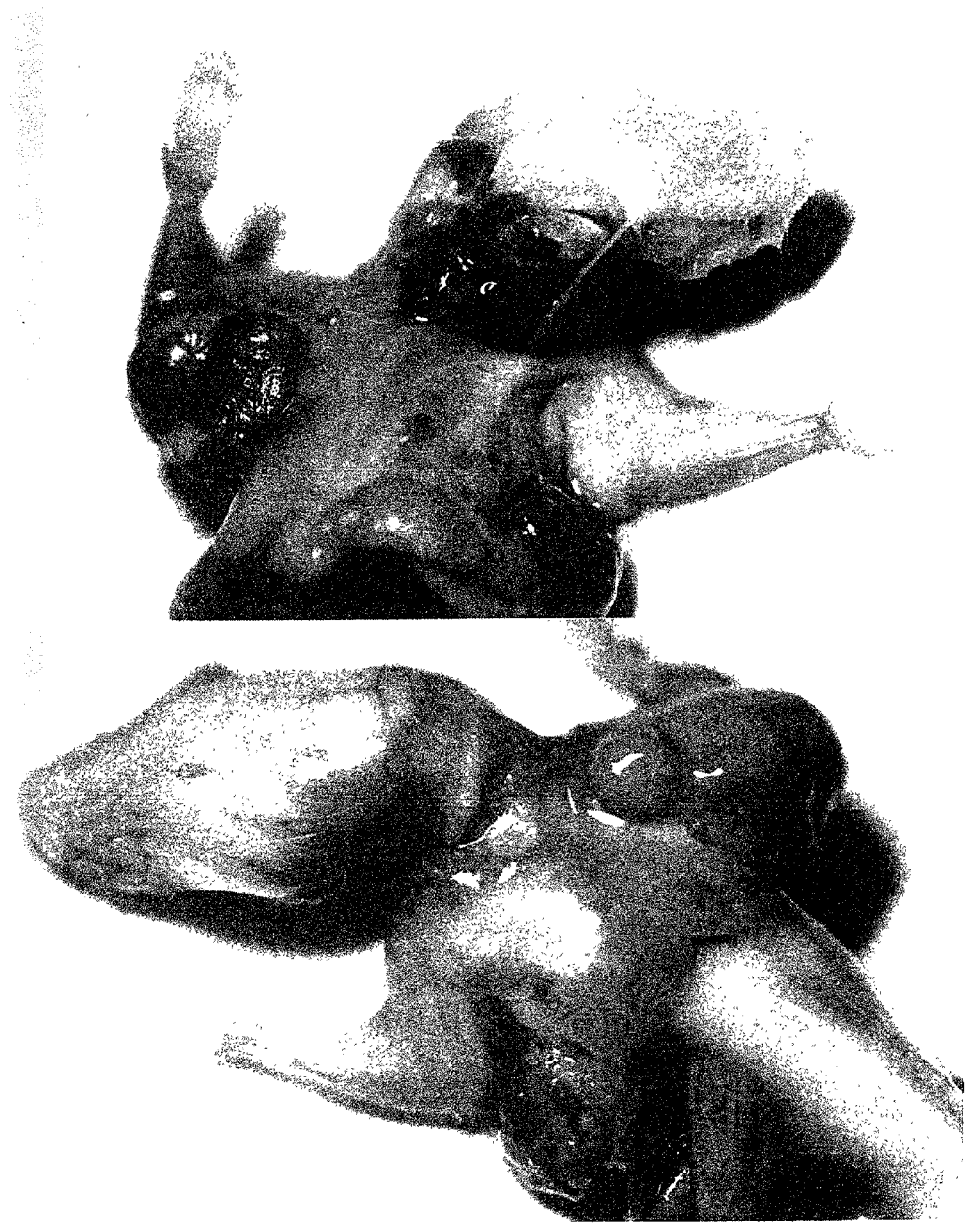

Because of the tumor vasculature targeting shown in FIG. 3E, the data imply that transfer of the genes of angiostatin, endostatin, or oncostatin to the tumors (whose gene products restrict vascular growth and inhibit blood supply to the tumor) is expected to be a rational approach for cancer treatment. Also, a combination therapy using anticancer lipogenes with encapsulated drugs into tumor targeting liposomes appears as a rational cancer therapy.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

TABLE 3

Simple NLS

```
Signal oligopeptide  Protein and features

PKKKRKV              Wild-type SV40 large T protein
(SEQ ID NO: 20)      A point mutation converting lysine-128 (double underlined) to
                     threonine results in the retention of large T in the cytoplasm.
                     Transfer of this peptide to the N-terminus of β-galactosidase
                     or pyruvate kinase
                     at the gene level and microinjection of plasmids into Vero cells
                     showed nuclear location of chimeric proteins.

PKKKRMV              SV40 large T with a K→M change. Site-directed mutagenesis only
(SEQ ID NO: 21)      slightly impaired nuclear import of large T.

PKKKRKVEDP           Synthetic NLS peptide from SV40 large T antigen crosslinked to BSA
(SEQ ID NO: 22)      or IgG mediated their nuclear localization after microinjection in
                     Xenopus oocytes. The PKKGSKKA from Xenopus H2B was
                     ineffective and PKTKRKV was less effective.

CGYGPKKKRKVGG        Synthetic peptide from SV40 large T antigen conjugated to various
(SEQ ID NO: 23)      proteins and microinjected into the cytoplasm of TC-7 cells.
                     Specified nuclear localization up to protein sizes of 465 kD
                     (ferritin). IgM of 970 kD and with an estimated radius of 25-40
                     nm was retained in the cytoplasm.
```

TABLE 3-continued

Simple NLS

| Signal oligopeptide | Protein and features |
|---|---|
| CYDDEA<u>T</u>AD<u>S</u>QH<u>S</u>TPPKKK RKVEDPK̲DFESELLS (SEQ ID NO: 24) | SV40 large T protein long NLS. The long NLS but not the short NLS, was able to localize the bulky IgM (970 kD) into the nucleus. Mutagenesis at the four possible sites of phosphorylation (double underlined) impaired nuclear import. |
| CGGPKKKRKVG (SEQ ID NO: 25) | SV40 large T protein. This synthetic peptide crosslinked to chicken serum albumin and microinjected into HeLa cells caused nuclear localization. |
| PKKKIKV (SEQ ID NO: 26) | A mutated (R→I) version of SV40 large T NLS. Effective NLS. |
| MKx$_{11}$<u>CRLKKLK</u>CSEKPKC AKCLKx$_5$Rx$_3$KTKR (SEQ ID NO: 27) 74 N-terminal amino acid | Yeast GAL4 (99 kD). Fusions of the GAL4 gene portion encoding the 74 N-terminal amino acid with E. coli β-galactosidase introduced into yeast cells specify nuclear localization. |
| MKx$_{11}$<u>CRLKKLK</u>CSEKPKC A (SEQ ID NO: 28) 29 N-terminal amino acid | Yeast GAL4. Acted as an efficient nuclear localization sequence when fused to invertase but not to β-galactosidase introduced by transformation into yeast cells. |
| PKKARED (SEQ ID NO: 29) VSRKRPR (SEQ ID NO: 30) | Polyoma large T protein. Identified by fusion with pyruvate kinase cDNA and microinjection of Vero African green monkey cells. Mutually independent NLS. Can exert cooperative effects. |
| CGYGVSRKRPRPG (SEQ ID NO: 31) | Polyoma virus large T protein. This synthetic peptide crosslinked to chicken serum albumin and microinjected into HeLa cells caused nuclear localization. |
| APTKRKGS (SEQ ID NO: 32) | SV40 VP1 capsid polypeptide (46 kD). NLS (N terminus) determined by infection of monkey kidney cells with a fusion construct containing the 5' terminal portion of SV40 VP1 gene and the complete cDNA sequence of poliovirus capsid VP1 replacing the VP1 gene of SV40. |
| AP<u>K</u>RKSGVSKC (1-11) (SEQ ID NO: 33) | Polyoma virus major capsid protein VP1 (11 N-terminal amino acid). Yeast expression vectors coding for 17 N-terminal amino acid of VP1 fused to β-galactosidase gave a protein that was transported to the nucleus in yeast cells. Subtractive constructs of VP1 lacking $A^1$ to $C^{11}$ were cytoplasmic. This, FITC-labeled, synthetic peptide crosslinked to BSA or IgG, caused nuclear import after microinjection into 3T6 cells. Replacement of $K^3$ with T did not. |
| PNKKKRK (SEQ ID NO: 34) (amino acid position 317-323) | SV40 VP2 capsid protein (39 kD). The 3' end of the SV40 VP2-VP3 genes containing this peptide when fused to poliovirus VP1 capsid protein at the gene level resulted in nuclear import of the hybrid VP1 in simian cells infected with the hybrid SV40. |
| EEDGPQKKKRRL (307-318) (SEQ ID NO: 35) | Polyoma virus capsid protein VP2. A construct having truncated VP2 lacking the 307-318 peptide transfected into COS-7 cells showed cytoplasmic retention of VP2. The 307-318 peptide crosslinked to BSA or IgG specified nuclear import following their microinjection into NIH 3T6 cells. |
| GKKRSKA (SEQ ID NO: 36) | Yeast histone H2B. This peptide specified nuclear import when fused to β-galactosidase. |
| KRPRP (SEQ ID NO: 37) | Adenovirus E1a. This pentapeptide, when linked to the C-terminus of E. coli galactokinase, was sufficient to direct its nuclear accumulation after microinjection in Vero monkey cells. |
| CGGLSSKRPRP (SEQ ID NO: 38) | Adenovirus type 2/5 E1a. This synthetic peptide crosslinked to chicken bovine albumin and microinjected into HeLa cells caused nuclear localization. |

TABLE 3-continued

Simple NLS

| Signal oligopeptide | Protein and features |
|---|---|
| LV<u>RKKRK</u>TE$_3$SP (NLS1) (SEQ ID NO: 39) LKDKDAKKSKQE (NLS2) (SEQ ID NO: 40) | Xenopus N1 (590 amino acid). Abundant in X. laevis oocytes, forming complexes with histones H3, H4 via two acidic domains each containing 21 and 9 (D + E), respectively. The NLS1 is required but not sufficient for nuclear accumulation of protein N1. NLS 1 and 2 are contiguous at the C-terminus. |
| GNKAKRQRST (SEQ ID NO: 41) | v-Rel or p59$^{v-rel}$ the transforming protein, product of the v-rel oncogene of the avian reticuloendotheliosis retrovirus strain T (Rev-T). v-Rel NLS added to the normally cytoplasmic β-galactosidase directed that protein to the nucleus. |
| PFLDRLRRDQK (SEQ ID NO: 42) PKQKRKMAR (SEQ ID NO: 43) | NS1 protein of influenza A virus, that accumulates in nuclei of virus-infected cells. Determined to be an NLS by deletion mutagenesis of NS1 in recombinant SV40. The 1st NLS is conserved among all NS1 proteins of influenza A viruses. |
| SVTKKRKLE (SEQ ID NO: 44) | Human lamin A. Dimerization of lamin A was proposed to give a complex with two NLSs that was transported more efficiently. |
| SASKRRRLE (SEQ ID NO: 45) | Xenopus lamin A. NLS inferred from its similarity to human lamin A NLS. |
| TKGKRKRID (SEQ ID NO: 46) | Xenopus lamin L$_I$. NLS inferred from its sequence similarity to human lamin A NLS. |
| CVRTTKGKRKRIDV (SEQ ID NO: 47) | Xenopus lamin L$_I$. This synthetic peptide crosslinked to chicken bovine albumin and microinjected into HeLa cells caused nuclear localization. |
| ACIDKRVKLD (SEQ ID NO: 48) | Human c-myc oncoprotein. This synthetic peptide crosslinked to chicken bovine albumin and microinjected into HeLa cells caused nuclear localization. |
| ACIDKRVKLD (SEQ ID NO: 49) (M1, fully potent NLS) RQRRNELKRSP (SEQ ID NO: 50) (M2, medium potency NLS) | Human c-myc oncoprotein. Conjugation of the M1 peptide to human serum albumin and microinjection of Vero cells gives complete nuclear accumulation. M2 gave slower and only partial nuclear localization. |
| SALIKKKKKMAP (SEQ ID NO: 51) | Murine c-abl (IV) gene product. The p160$^{gag/v-abl}$ has a cytoplasmic and plasma membrane localization, whereas the mouse type IV c-abl protein is largely nuclear. |
| PPKKRMRRRIE (SEQ ID NO: 52) PKKKKKRP (SEQ ID NO: 53) | Adenovirus 5 DBP (DNA-binding protein) found in nuclei of infected cells and involved in virus replication and early and late gene expression. Both NLS are needed, and disruption of either site impaired nuclear localization of the 529 amino acid protein. |
| YRKCLQAGMNLEARKTKK KIKGIQQATA (497-524 amino acid) (SEQ ID NO: 54) | Rat GR, glucocorticoid receptor (795 amino acid) NLS1 determined by fusion with β-galactosidase (116 kD). NLS1 is 100% conserved between human, mouse and rat GR. Whereas the 407-615 amino acid fragment of GR specifies nuclear location, the 407-740 amino acid fragment was cytoplasmic in the absence of hormone, indicating that sequence 615-740 may inhibit the nuclear location activity. A second (NLS2) is localized in an extensive 256 amino acid C-terminal domain. NLS 2 requires hormone binding for activity. |
| <u>RKDRRGGRML</u><u>KHKRQ</u>RDD GEGRGEVGSAGDMRAMIN O ACIDNLWPSPLMI<u>KRSKK</u> (amino acid 256-303) (SEQ ID NO: 55) | Human ER (estrogen receptor, 595 amino acid) NLS. NLS is between the hormone-binding and DNA-binding regions; ER, in contrast with GR, lacks a second NLS. Can direct a fusion product with β-galactosidase to the nucleus. |
| RKFKKFNK (SEQ ID NO: 56) | Rabbit PG (progesterone receptor). 100% homology in humans; F→L change in chickens. When this sequence was deleted, the receptor became cytoplasmic but could be shifted into the nucleus by addition of hormone; in this case the hormone mediated the dimerization of a mutant PG with a wild type PG molecule. |

TABLE 3-continued

Simple NLS

| Signal oligopeptide | Protein and features |
|---|---|
| GKRKNKPK (SEQ ID NO: 57) | Chicken Ets1 core NLS. Within a 77 amino acid C-terminal segment 90% homologous to Ets2. When deleted by deletion mutagenesis at the gene level the mutant Ets1 became cytoplasmic. |
| PLLKKIKQ (SEQ ID NO: 58) | c-myb gene product; directs puruvate kinase to the nucleus. |
| PPQKKIKS (SEQ ID NO: 59) | N-myc gene product; directs puruvate kinase to the nucleus. |
| PQPKKKP (SEQ ID NO: 60) | p53; directs puruvate kinase to the nucleus. |
| SKRVAKRKL (SEQ ID NO: 61) | c-erb-A gene product; directs puruvate kinase to the nucleus. |
| CGGLSSKRPRP (SEQ ID NO: 62) | Adenovirus type2/5 E1a. This synthetic peptide conjugated with a bifunctional crosslinker to chicken serum albumin (CSA) and microinjected into HeLa cells directed CSA to the nucleus. |
| MTGSKTRKHRGSGA (SEQ ID NO: 63) MTGSKHRKHPGSGA (SEQ ID NO: 64) | Yeast ribosomal protein L29. Double-stranded oligonucleotides encoding the 7 amino acid peptides (underlined) and inserted at the N-terminus of the β-galactosidase gene resulted in nuclear import. |
| RHRKHP (SEQ ID NO: 65) KRRKHP (SEQ ID NO: 66) KYRKHP (SEQ ID NO: 67) KHRRHP (SEQ ID NO: 68) KHKKHP (SEQ ID NO: 69) RHLKHP (SEQ ID NO: 70) KHRKYP (SEQ ID NO: 71) KHRQHP (SEQ ID NO: 72) | Mutated peptides derived from yeast L29 ribosomal protein NLS, found to be efficient NLS. The last two are less effective NLS, resulting in both nuclear and cytoplasmic location of β-galactosidase fusion protein. |
| PETTVVRRRGRSPRRRTPSP RRRRSPRRRRSQS (SEQ ID NO: 73) (One sequence, C-terminus) | Double NLS of hepatitis B virus core antigen. The two underlined arginine clusters represent distinct and independent NLS. Mutagenesis showed that the antigen fails to accumulate in the nucleus only when both NLS are simultaneously deleted or mutated. |
| ASKSRKRKL (SEQ ID NO: 74) | Viral Jun, a transcription factor of the AP-1 complex. Accumulates in nuclei most rapidly during G2 and slowly during G1 and S. The cell cycle dependence of viral but not of cellular Jun is due to a C→S mutation in NLS of viral Jun. This NLS conjugated to rabbit IgG can mediate cell cycle-dependent translocation. |
| GGLCSARLHRHALLAT (SEQ ID NO: 75) | Human T-cell leukemia virus Tax trans-activator protein. The most basic region within the 48 N-terminal segment. Missense mutations in this domain result in its cytoplasmic retention. |
| DTREKKKFLKRRLLRLDE (604-620) (SEQ ID NO: 76) | Mouse nuclear Mx1 protein (72 kD), Induced by interferons (among 20 other proteins). Selectively inhibits influenza virus mRNA synthesis in the nucleus and virus multiplication. The cytoplasmic Mx2 has R→S and R→E changes in this region. |

TABLE 3-continued

Simple NLS

| Signal oligopeptide | Protein and features |
|---|---|
| CGYGPKKKRKV (SV40 large T) (SEQ ID NO: 77) CGYGDRNKKKKE (human retinoic acid receptor) (SEQ ID NO: 78) CGYGARKTKKKIK (human glucocorticoid receptor) (SEQ ID NO: 79) CGYGIRKDRRGGR (human estrogen receptor) (SEQ ID NO: 80) CGYGARKLKKLGN (human androgen receptor) (SEQ ID NO: 81) | Synthetic peptides crosslinked to bovine serum albumin (BSA) and introduced into MCF 7 or HeLa S3 cells with viral co-internalization method using adenovirus serotype 3B induced nuclear import of BSA. |
| RKRQRALMLRQAR 30-42 (SEQ ID NO: 82) | Human XPAC (xeroderma pigmentosum group A complementing protein) involved in DNA excision repair. By site-directed mutagenesis and immunofluorescence. NLS is encoded by exon 1 which is not essential for DNA repair function. |
| EYLSRKGKLEL (SEQ ID NO: 83) (at the N-terminus) | T-DNA-linked VirD2 endonuclease of the Agrobacterium tumefaciens tumor-inducing ($T_i$) plasmid. A fusion protein with β-galactosidase is targeted to the nucleus. The T-plasmid integrates into plant nuclear DNA; VirD2 produces a site-specific nick for T integration. VirD2 also contains a bipartite NLS at its C-terminus (see Table 2). |
| KKSKKKRC (SEQ ID NO: 84) (95-102) | Putative core NLS of yeast TRM1 (63 kD) that encodes the tRNA modification enzyme $N^2$, $N^2$-dimethylguanosine-specific tRNA methyltransferase. Localizes at the nuclear periphery. The 70-213 amino acid segment of TRM1 causes nuclear localization of β-galactosidase fusion protein in yeast cells. Site-directed mutagenesis of the 95-102 peptide resulted in its cytoplasmic retention. TRM1 is both nuclear and mitochondrial. The 1-48 amino acid segment specifies mitochondrial import. |
| PQSRKKLR (SEQ ID NO: 85) | Max protein; specifically interacts with c-Myc protein. Fusion of 126-151 segment of Max to chicken pyruvate kinase (PK) gene, including this putative NLS, followed by transfection of COS-1 cells and indirect immunofluorescence with anti-PK showed nuclear targeting. |
| QPQRYGGGRGRRW (SEQ ID NO: 86) | Gag protein of human foamy retrovirus; a mutant that completely lacks this box exhibits very little nuclear localization; binds DNA and RNA in vitro. |

TABLE 4

"Bipartite" or "split" NLS

| Signal Oligopeptide | Protein and features |
|---|---|
| C-terminus | Xenopus nucleoplasmin. Deletion analysis demonstrated the presence of a signal responsible for nuclear location. |
| TKKAGQAKKK (SEQ ID NO: 87) | Xenopus nucleoplasmin |
| TKKAGQAKKKKLD (SEQ ID NO: 88) | Xenopus nucleoplasmin. Whereas these 17 amino acids had NLS activity, shorter versions of the 17 amino acid sequences were unable to locate pyruvate kinase to the nucleus. |

TABLE 4-continued

"Bipartite" or "split" NLS

| Signal Oligopeptide | Protein and features |
|---|---|
| TKKAGQAKKK(KLD)<br>(SEQ ID NO: 89) | *Xenopus* nucleoplasmin. This 14 amino acid segment was identified as a minimal nuclear location sequence but was unable to locate puruvate kinase to the nucleus; three more amino acids at either end (shown in parenthesis) were needed. |
| CGQAKKKKLD<br>(SEQ ID NO: 90) | *Xenopus* nucleoplasmin-derived synthetic peptide; crosslinked to chicken serum albumin and micro-injected to HeLa cells specified nuclear localization. This suggests that nucleoplasmin may possess a simple NLS. |
| KRPAMINO ACID<br>TKKAGQAKKKK<br>(SEQ ID NO: 91) | *Xenopus* nucleoplasmin bipartite NLS. Two clusters of basic amino acids (underlined) separated by 10 amino acid are half NLS components. |
| HRKYEAPRHx$_6$PRKR<br>(SEQ ID NO: 92) | Yeast L3 ribosomal protein (387 amino acid) N-terminal 21 amino acid. Possible bipartite NLS. (Ribosomal proteins are transported to the nucleus to assemble with nascent rRNA). Fusion genes with β-galactosidase were used to transform yeast cells followed by fluorescence staining with b-gal antibody. The 373 amino acid of L3 fused to β-gal failed to localize to the nucleus, unless a 8 amino acid bridge containing a proline was inserted between L3 and β-gal. |
| NKKKRKLSRGSSQKTKGTSASAK<br>ARHKRRNRSSRS<br>(one sequence)<br>(SEQ ID NO: 93) | SV40 Vp3 structural protein. (35 amino acid C-terminus). By DEAE-dextran-mediated transfection of TC7 cells with mutated constructs. |
| RVTIRTVRVRRPPKGKHRK<br>(SEQ ID NO: 94) | Simian sarcoma virus v-sis gene product (p28$^{sis}$). The cellular counterpart c-sis gene encodes a precursor of the PDGF B-chain (platelet-derived growth factor). The NLS is 100% conserved between v-sis gene product and PDGF. This protein is normally transported across the ER; introduction of a charged amino acid within the hydrophobic signal peptide results in a mutant protein that is translocated into the nucleus. Puruvate kinase-NLS fusion product is transported less efficiently than cytoplasmic v-sis mutant proteins to the nucleus. |
| KRKIEEPEPEPKKAK<br>(SEQ ID NO: 95) | Putative bipartite NLS of *Xenopus laevis* protein factor xnf7. Inferred by similarity to the bipartite NLS of nucleoplasmin. During oocyte maturation xnf7 is cytoplasmic until mid-blastulagastrula stage due to high phosphorylation. Partial dephosphorylation results in nuclear accumulation. |
| KKYENVVIKRSPRKRGRPRKD<br>(SEQ ID NO: 96) | Yeast SWI5 gene product, a transcription factor. Underlined basic amino acid show similarity to bipartite NLS of *Xenopus* nucleoplasmin. The SWI5 gene is transcribed during S, G2 and M phases, during which the SWI5 protein remains cytoplasmic due to phosphorylation by CDC28-dependent histone H1 kinase at three serine residues two near and one (double underlined) in the NLS. Translocated at the end of anaphase/G1 due to dephosphorylation of NLS. NLS confers cell cycle-regulated nuclear import of SWI5-β-galactosidase fusion protein. |
| MKRKRNS 735-741<br>(SEQ ID NO: 97)<br>GIESIDNVMGMIGILPDMTPSTE<br>MSMRGVRISKMGVDETSSAEKIV<br>449-495<br>(SEQ ID NO: 98) | Bipartite NLS of influenza virus polymerase basic protein 2 (PB2). Mutational analysis of PB2 and transfection of BHK cells showed that both regions are involved in nuclear import. Deletion of 449-495 region gives perinuclear localization to the cytoplasmic side. |

TABLE 4-continued

"Bipartite" or "split" NLS

| Signal Oligopeptide | Protein and features |
| --- | --- |
| AHRARRLH<br>(SEQ ID NO: 99)<br>6-13 (BSI)<br>PPRRRVRQQPP<br>(SEQ ID NO: 100)<br>23-33 (BSII)<br>PARARRRRAP<br>(SEQ ID NO: 101)<br>39-48 (BSIII) | "Tripartite" or "doubly bipartite" NLS of adenovirus DNA polymerase (AdPoI). BSI and II functioned interdependently as an NLS for the nuclear targeting of AdPoI, for which BSIII was dispensable. BSII-III was more efficient NLS than BSI-II. |
| KRKx$_{11}$KKKSKK 207-226<br>(SEQ ID NO: 102) | Human poly(ADP-ribose) polymerase (116 kD). The linear distance between the two basic clusters is not crucial for NLS activity in this bipartite NLS. Lysine 222 (double underlined) is an essential NLS component. DNA binding and poly(ADP-ribosyl)ating active site are independent of NLS. |
| GRKRAFHGDDPFGEGPPDKKGD<br>(SEQ ID NO: 103) | Herpes simplex virus ICP8 protein (infected-cell protein). This C-terminal portion of ICP8 introduced into pyruvate kinase (PK) caused nuclear targeting in transfected Vero cells. Inclusion of additional ICP8 regions to PK led to inhibition of nuclear localization. |
| KRPREDDDGEPSERKRARDDR<br>(SEQ ID NO: 104) | Bipartite NLS of VirD2 endonuclease of rhizogenes strains of Agrobacterium tumefaciens. Within the C-terminal 34 amino acid. Each region (underlined) independently directs "β-glucuronidase to the nucleus, but both motifs are necessary for maximum efficiency. VirD2 is tightly bound to the 5' end of the single stranded DNA transfer intermediate T-strand transferred from Agrobacterium to the plant cell genome. |

TABLE 5

"Nonpositive NLS" lacking clusters of arginines/lysines

| Signal oligopeptide | Protein and features |
| --- | --- |
| QLVWMACNSAMIN<br>Q<br>ACIDFEDLRVLSFIRGTKVS<br>PRG 327-356<br>(SEQ ID NO: 105) | Influenza virus nucleoprotein (NP). The underlined region (327-345) when fused to chimpanzee a$_1$-globin at the cDNA level and microinjected into *Xenopus oocytes* specifies nuclear localization. |
| MNKIPIKDLLNPQ<br>(NLS1 at N-terminus) (SEQ ID<br>NO: 106)<br>VRILESWFAKNIEN<br>PYLDT (NLS2 at amino acid<br>141-159, part of the<br>homeodomain)<br>(SEQ ID NO: 107) | Yeast MAT a2 repressor protein, containing a homeodomain. The two NLS are distinct, each capable of targeting β-galactosidase to the nucleus. However, deletion of NLS2 results in a2 accumulation at the pores. NLS1 and 2 may act at different steps in a localization pathway. Part of the homeodomain mediates nuclear localization in addition to DNA binding. The core pentapeptide containing proline and two other hydrophobic amino acids flanked by lysines or arginines (underlined) was suggested as one type of NLS core. |
| Rx7Kx$_{15}$KIPRx$_3$HFY<br>EERLSWYSDNED (SEQ ID<br>NO: 108)<br>152-206 (C-terminal<br>segment) | *Drosophila* HP1 (206 amino acids) that binds to heterochromatin and is involved in gene silencing. NLS identified by β-galactosidase/HP1 fusion proteins introduced by P-element mediated transformation into *Drosophila* embryos. |
| FV$_{x7\_20}$MxSLxYMx$_4$MF | Adenovirus type 5 E1A internal, developmentally-regulated NLS. This NLS functions in *Xenopus oocytes* but not in somatic cells. This NLS can be utilized up to the early neurula stage. |

TABLE 6

Nucleolar localization signals (NoLS)

| Signal oligopeptide | Protein and features |
|---|---|
| MPKTRRRPRRSQRKRPPTP (SEQ ID NO: 109) | Nucleolus localization signal in amino terminus of human p27$^{X-III}$ protein (also called Rex) of T cell leukemia virus type I (HTLV-I). When this peptide is fused to N-terminus of β-galactosidase, directs it to the nucleolus. Deletion of residues 2-8 (underlined), 12-18 (double-underline) or substitution of the central RR (dotted-underlined) with TT abolish nucleolar localization. Other amino acids between positions 20-80 increase nucleolar localization efficiency. |
| RLPVRRRRRRVP (SEQ ID NO: 110) | Adenovirus pTP1 and pTP2 (preterminal proteins, 80 kD) between amino acid residues 362-373. The 140 kD DNA polymerase of adenovirus when it has lost its own NLS can enter the nucleus via its interaction with pTP. The staining was nuclear and nucleolar with some perinuclear staining as well. The NLS fused to the N-terminus of E. coli β-galactosidase was functional in nuclear targeting. |
| GRKKRRQRRRP (SEQ ID NO: 111) RKKRRQRRR(AHQ) Nucleolar localization signal (SEQ ID NO: 112) | HIV (human immunodeficiency virus) Tat protein; localizes pyruvate kinase to the nucleolus. Tat is constitutively nucleolar. Tat positive trans-activator protein of HIV-1 (human immunodeficiency virus type 1). The 3 amino acids shown in parenthesis are essential for the localization of the β-galactosidase to the nucleolus. The 9 amino acid basic region is able to localize β-gal to the nucleus but not to the nucleolus. |
| KRVKLDQRRRP (SEQ ID NO: 113) | Artificial sequence from c-Myc and HIV Tat NLSs that effectively localizes pyruvate kinase to the nucleolus. |
| FKRKHKKDISQNKRAVRR (SEQ ID NO: 114) | Human HSP70 (heat shock protein of 70 kD); localizes pyruvate kinase to the nucleus and nucleolus. HSP70 is physiologically cytoplasmic but with heat-shock HSP70 redistributes to the nucleoli, suggesting that the nucleolar targeting sequence is cryptic at physiological temperature and is revealed under heat-shock. |
| RQARRNRRRRWRERQR (35-50) (SEQ ID NO: 115) | HIV-1 Rev protein (116 amino acid, nucleolar). Mutations in either of the two regions of arginine clusters severely impair nuclear localization. β-galactosidase fused to R$_4$W was targeted to the nucleus, and fused to the entire 35-50 region, was targeted to the nucleolus. |
| RQARRNRRRRWRERQRQ (35-51) (SEQ ID NO: 116) | HIV-1 Rev protein. A fusion of this Rev peptide with β-galactosidase became nuclear but not nucleolar. The 1-59 amino acid segment of Rev fused to β-galactosidase localized entirely within the nucleolus. Whereas the NRRRRW (bold) is responsible for nuclear targeting, the RR and WRERQRQ (double underlined) specify nucleolar localization. Rev may function to export HIV structural mRNAs from the nucleus to the cytoplasm. |

TABLE 7

Karyophilic clusters on non-membrane protein kinases

| Karyophilic peptides | Non-membrane protein kinase | Species | Features |
|---|---|---|---|
| 73 FVVHKRCHE (SEQ ID NO: 117) 96 DDPRSKHKFKIH (SEQ ID NO: 118) 577 TKHPGKRLG (SEQ ID NO: 119) | Protein kinase C (673 aa) | Bovine, human β type | Known to translocate to the nucleus following treatment of cells with mitogens. |
| 71 FVVHRRCHEF (SEQ ID NO: 120) 95 DDPRNKHKFRLH (SEQ ID NO: 121) 591 TKHPAKRLG (SEQ ID NO: 122) | Protein kinase C (697 aa) | bovine, human γ type | |
| 72 FVVHKRCHE (SEQ ID NO: 123) 96 DDPRSKHKFKIH (SEQ ID NO: 124) 577 TKHPGKRLG (SEQ ID NO: 125) | Protein kinase C (673 aa) | rabbit type α and β | |

TABLE 7-continued

Karyophilic clusters on non-membrane protein kinases

| Karyophilic peptides | Non-membrane protein kinase | Species | Features |
|---|---|---|---|
| 71 FVVHRRCHE (SEQ ID NO: 126) 95 DDPRNKHKFRLH (SEQ ID NO: 127) 594 TKHPGKRLG (SEQ ID NO: 128) | PKC-I (701 aa) | rat brain | |
| 22 GENKMKSRLRKG (not conserved) (SEQ ID NO: 129) 80SYVVHKRCHEYVT (conserved) (SEQ ID NO: 130) 211PDDKDQSKKKTR TIK (not conserved) (SEQ ID NO: 131) 614PPFKPKIKHRKMC P (not conserved) (SEQ ID NO: 132) | Protein kinase C (639 aa, 75 kDa) | Drosophila | 14 exons, 20 kb; 3 transcripts in adult flies; not expressed in 0-3 h Drosophila embryos; the VVHKRCHE (SEQ ID NO: 133) motif (or VVHRRCHE (SEQ ID NO: 134)) is conserved among all PKC known. |
| 148 KKVLQDKRFK NRELQIMRKLD (SEQ ID NO: 135) | Glycogen synthase kinase 3 GSK-3α (483 aa) GSK-3β (420 aa) | rat brain | Phosphorylates glycogen synthase, c-Jun, c-Myb; two isoforms encoded by discrete genes; highly expressed in brain; both α and β forms are cytosolic but also associated with the plasma membrane consistent with their role in signal transduction from the cell surface. |
| LQDRRFKNRELQ (SEQ ID NO: 136) | Zw3 zeste-white 3 | Drosophila | Product of the segment polarity gene zw3; the protein encoded has 34% homology to cdc2; mutations in zw3 give embryos that lack most of the ventral denticles, differentiated structures derived from the most anterior region of each segment. |
| 289ECLKKFNARRKL KGAIL (SEQ ID NO: 137) | $Ca^{2+}$/calmodulin-dependent protein kinase II (CaM kinase II) β subunit (542 aa, 60.3 kDa) | rat brain | Composed of nine 50 kDa α-subunits and three 60 kDa β-subunits; both are catalytic; calmodulin- and ATP-binding domains; highly expressed in forebrain neurons, concentrated in postsynaptic densities; acts as a $Ca^{2+}$-triggered switch and could be involved in long-lasting changes in synapses. |
| 290LKKFNARRKL KGAILTTM (SEQ ID NO: 138) 450EETRVWHRRDGK (SEQ ID NO: 139) | CaM kinase II (478 aa, 54 kDa) α-subunit | rat brain | This particular isoform is exclusively expressed in the brain; high enzyme levels in specific brain areas; might be involved in short- and long-term responses to transient stimuli. |
| 185 GFAKRVKGRT WTLCG (SEQ ID NO: 140) | CADPK catalytic subunit (349 aa, 40.6 kDa) | bovine (cardiac muscle) | By Edman degradation of protein fragments; mediates the action of and is activated by cAMP; consists of two regulatory (R) and two catalytic (C) subunits; cAMP releases the C subunit from the inactive $R_2C_2$ cADPK; two cDNAs were cloned encoding two isoforms of the catalytic subunit of cADPK in mouse. |
| 186 GFAKRVKGRTW TLCG (SEQ ID NO: 141) | CADPK (catalytic subunit) (350 aa) | bovine | cDNA was isolated by screening a bovine pituitary cDNA library; 93% sequence similarity to known bovine cADPK; represents the second gene for the catalytic subunit of cADPK. |

TABLE 7-continued

Karyophilic clusters on non-membrane protein kinases

| Karyophilic peptides | Non-membrane protein kinase | Species | Features |
| --- | --- | --- | --- |
| 29 EEEIQELKRKLH KCQSVLP (SEQ ID NO: 142) 389 KILKKRHIVDTR (SEQ ID NO: 143) | CGDPK (SEQ ID NO: 144) (670 aa, 76.3 kDa) | bovine lung | By protein sequencing; composed of two identical subunits activated in an allosteric manner by binding of cGMP and not by dissociation of catalytic subunit as in cADPK; sequence similar to cADPK. |
| 117 KTLKKHTIVK (SEQ ID NO: 145) | TPK3 (398 aa) cADPK | S. cerevisiae | cAMP-DPK is a tetrameric protein with two catalytic and two regulatory subunits; cAMP activates the kinase by dissociating the catalytic subunits from the tetramer; all three TPK 1, 2, 3 are catalytic subunits. |
| $16S_2H_{13}GHG_2$ 166 EYCHRHKIVHRD LKP (SEQ ID NO: 146) 495 PLVTKKSKTRWH FG (SEQ ID NO: 147) | SNF1 (633 aa, 72 kDa) | S. cerevisiae | Ser/Thr kinase; autophosphorylated; plays a central role is carbon catabolite repression in yeast required for expression of glucose-repressible genes; region 60-250 shows high sequence similarity to cAMP-dependent protein kinase (cADPK). |
| 70 PVKKKKIKREIK (SEQ ID NO: 148) 269 DILQRHSRKRW ERF (SEQ ID NO: 149) 146 PKSSRHHHTDG (SEQ ID NO: 150) 142 PKSSRHHHTDG (SEQ ID NO: 151) | Casein kinase II (α-subunit, catalytic) (336 aa) CKII (β-subunit, regulatory) (215 aa) CKII (β-subunit, regulatory) (209 aa, 24.2 kDa) | Drosophila melanogaster Drosophila melanogaster bovine (lung) | CKII is composed of α and β subunits in a $α_2β_2$ 130-150 kDa protein; the α-subunit is the catalytic and the β is autophosphorylated. |
| 108 PKQRHRKSLG (SEQ ID NO: 152) 129 GSMCKVKLAK HRYTNE (SEQ ID NO: 153) 506 DRKHAKIRNQ (SEQ ID NO: 154) 638 GNIFRKLSQRR KKTIEQ (SEQ ID NO: 155) 773 PPLNVAKGRKL HP (SEQ ID NO: 156) | KIN1 (1064 aa, 117 kDa) | S. cerevisiae | 30% aa similarity to bovine cADPK and 27% (KIN1) or 25% (KIN2) aa similarity to v-Src within the kinase domain; the catalytic domains of KIN1 and KIN2 are near the N-terminus and are structural mosaics with features characteristic of both Tyr and Ser/Thr kinases. |
| 87 ELRQFHRRSLG (SEQ ID NO: 157) 111 GKVKLVKHRQ TKE (SEQ ID NO: 158) 217 GSLKEHHARKF ARG (SEQ ID NO: 159) 807 LSVPKGRKLHP (SEQ ID NO: 160) | KIN2 (1152 aa, 126 kDa) | S. cerevisiae | |
| 60 FLRRGIKKKLTLD (SEQ ID NO: 161) 472 PSKDDKFRHWC RKIKSKIKEDKRIKRE (SEQ ID NO: 162) | STE7 (515 aa) | S. cerevisiae | Implicated in the control of the three cell types in yeast: (a, α, and a/α) of which a and α cells are haploid and are specialized for mating whereas a/α cells are diploid and are specialized for meiosis and sporulation; with the exception of the mating type locus, MAT, all cells contain the same DNA sequences. STE7 gene produces insensitivity to cell-division arrest induced by the yeast mating hormone, α-factor. |
| 722 QRRVKKLPSTTL (SEQ ID NO: 163) | S6KIIα (733aa) | Xenopus | |

TABLE 7-continued

Karyophilic clusters on non-membrane protein kinases

| Karyophilic peptides | Non-membrane protein kinase | Species | Features |
|---|---|---|---|
| QRRVKKLPSITL (SEQ ID NO: 164) | S6KII β | Xenopus | |
| 742 QRRVKKLPSTTL (SEQ ID NO: 165) | S6KII (752 aa) | Chicken | |
| 713QRRVRKLPSTTL (SEQ ID NO: 166) | S6KII (724 aa) | Mouse | |
| 16GVVYKGRHKTTG (SEQ ID NO: 167) 120 FCHSRRVLHRDLKP (SEQ ID NO: 168) | CDC2Hs (297 aa) $p34$cdc2 | Human | Isolated by expressing a human cDNA library in S. pombe and selecting for clones that complement a mutation in the cdc2 yeast gene; the human CDC2 gene can complement both the inviability of a null allele of S. cerevisiae CDC28 and cdc2 mutants of S. pombe; CDC2 mRNA appears after that of CDK2. |
| GVVYKARHKLSGR (SEQ ID NO: 169) | cdc2 (297 aa) | S. pombe | High homology to S. cerevisiae CDC28. |
| 119HSHRVLHRDLKP (SEQ ID NO: 170) | CDK2 (cell division kinase 2) (298 aa) | Human | The human CDK2 protein has 65% sequence identity to human $p34$cdc2 and 89% sequence identity to Xenopus Eg1 kinase; human CDK2 was able to complement the inviability of a null allele of S. cerevisiae CDC28 but not cdc2 mutants in S. pombe. CDK2 mRNA appears in late G1/early S. |
| 109 FCHSHRVLHRDLKP (SEQ ID NO: 171) | Eg1 (297 aa) | Xenopus | Cdk2-related |
| 125 GIAYCHSHRILHRDLKP (SEQ ID NO: 172) | CDC28 (298 a) | S. cerevisiae | The homolog of S. pombe Cdc2 |
| 119 HSHRVIHRDLKP (SEQ ID NO: 173) | cdk3 (305 aa) | Human | |
| 56 KELKHKNIVR (SEQ ID NO: 174) | PSSALRE (291 aa) (SEQ ID NO: 175) | Human | cdc2-related kinase. |
| 1 MDRMKKIKRQ (N-terminus) (SEQ ID NO: 176) 141 DKPLSRRLRRV (SEQ ID NO: 177) | PCTAIRE-1 (496 aa) | Human | cdc2-related kinase. |
| 1 MKKFKRR (SEQ ID NO: 178) 129 RNRIHRRIS (SEQ ID NO: 179) 172 SRRSRRAS (SEQ ID NO: 180) 304 HRRKVLHR (SEQ ID NO: 181) 512 GHGKNRRQSMLF (SEQ ID NO: 182) | PCTAIRE-2 (523 aa) | Human | cdc2 related kinase. |
| 163 HTRKILHR (SEQ ID NO: 183) 369 PGRGKNRRQSIF (SEQ ID NO: 184) | PCTAIRE-3 (380 aa) | Human | cdc2 related kinase. |
| 69 EVFRRKRRLH (SEQ ID NO: 185) 302 DKPTRKTLRKSRKHH (SEQ ID NO: 186) | KKIALRE (358 aa) (SEQ ID NO: 187) | Human | cdc2-related kinase. |

TABLE 7-continued

Karyophilic clusters on non-membrane protein kinases

| Karyophilic peptides | Non-membrane protein kinase | Species | Features |
|---|---|---|---|
| 1 MVKRHKNT (SEQ ID NO: 188)<br>87 DGELFHYIRKHGP (SEQ ID NO: 189)<br>114 DAVAHCHRFRFR HRD (SEQ ID NO: 190)<br>295 KKSSSKKVVRRL QQRDD (SEQ ID NO: 191) | mim1$^+$ gene product (new inducer of mitosis); protein kinase (370 aa) | S. pombe | |
| 194 PAQKLRKKNNFD (SEQ ID NO: 192)<br>388 KQHRPRKNTNFT PLPP (SEQ ID NO: 193)<br>592 KYAVKKLKVKF SGP (SEQ ID NO: 194) | Wee1$^+$ gene product (877 aa) | S. pombe | The Wee1$^+$ gene functions as a dose-dependent inhibitor that delays the initiation of mitosis until the yeast cell has attained a certain size; Wee1 has a protein kinase consensus probably regulating cdc2 kinase. |
| 266 PNETRRIKRAN RAG (SEQ ID NO: 195) | CDC7 (497 aa) | S. cerevisiae | Required for mitotic but not meiotic DNA replication presumably to phosphorylate specific replication protein factors; implicated in DNA repair and meiotic recombination; some homology with CDC28 and oncogene protein kinases but differs in a large region within the phosphorylation receptor domain. |
| 48 YDHVRKTRVAIKK (SEQ ID NO: 196) | ERK1 (MAP kinase) (367 aa; 42 kDa) | Rat | Known to translocate to the nucleus following their activation by phosphorylation at T-190, and Y-192 (T-183, Y-185 in ERK2). |
| 59 ILKHFKHE (SEQ ID NO: 197) | FUS3 (353 aa) | S. cerevisiae | MAP-(ERK1)-related. |
| 252 QIKSKRAKEY (SEQ ID NO: 198) | KSS1 (368 aa) | S. cerevisiae | MAP-(ERK1)-related. |
| ELVKHLVKHGSN (SEQ ID NO: 199)<br>GKAKKIRSQLL (SEQ ID NO: 200) | SWI6 (803 aa, 90 kDa) | S. cerevisiae | Activator of CACGA-box with sequence similarity to cdc10; required at START of cell cycle. |
| EQRLKRHRIDVSDED (SEQ ID NO: 201)<br>SNIKSKCRRVV (SEQ ID NO: 202) | cdc10 | S. pombe | |
| 37 PPKRIRTD (suggested by the authors) (SEQ ID NO: 203)<br>492 KLARKQKRP (SEQ ID NO: 204) | CTD kinase (528 aa) 58 kDa subunit (catalytic) | S. cerevisiae | Consists of 3 subunits of 58, 38, and 32 kDa; disruption of the 58 kDa gene gives cells that lack CTD kinase, grow slowly, are cold sensitive, but have different phosphorylated forms of RNA pol II. |
| 29 GVSSVVRRCIHKP (SEQ ID NO: 205) | Phosphorylase kinase (catalytic subunit) (386 aa) | Rabbit (skeletal muscle) | |
| 489 KKYMARRKW QKTGHAV (SEQ ID NO: 206) | Myosin light chain kinase (MLCK) (669 aa) | Chicken gizzard | $Ca^{2+}$/calmodulin-activated; phosphorylated by cADPK; first described as responsible for the phosphorylation of a specific class of myosin light chains; required for initiation of contraction in smooth muscle. |

TABLE 7-continued

Karyophilic clusters on non-membrane protein kinases

| Karyophilic peptides | Non-membrane protein kinase | Species | Features |
|---|---|---|---|
| 314 PWLNNLAEKAK RCNRRLKSQ (SEQ ID NO: 207) 334 ILLKKYLMKRR WKKNFIAVS (SEQ ID NO: 208) | Myosin light chain kinase (partial 368 carboxy-terminal aa sequence) | Rabbit (skeletal muscle) | By protein sequencing. |
| 28 GVSSVVRRCIHKP (SEQ ID NO: 209) | Phosphorylase kinase (PhK) (catalytic γ subunit) (389 aa) | Mouse (muscle) | Glycogenolytic regulatory enzyme; undergoes complex regulation; composed of 16 subunits containing equimolar ratios of α, β, γ and δ subunits; high levels in skeletal muscle; isoforms in cardiac muscle and liver; cDNA probe does not hybridize to X chromosome in mice and is thus distinct from the mutant recessive PhK deficiency that results in glycogen storage disease. |

TABLE 8

Nuclear localization signals on DNA repair proteins

| Putative NLS | Gene product | Equivalent protein in other species | Features |
|---|---|---|---|
| HIGHER EUKARYOTES | | | |
| None (N-terminus) MDPGKDKEGvpqpsgppaRKKF (bipartite NLS) (SEQ ID NO: 210) | ERCC1 | RAD10 | 297 aa; DBD; interacts strongly with ERCC4 (XPF) to form an excision endonuclease; unless the KDKx$_{11}$RKK is a bipartite NLS it may depend upon its binding with ERCC4 for its nuclear import. |
| None 681DKRFARGDKRGKLPR (near the C-terminus)(four positive, one negative over a heptapeptide stretch) (SEQ ID NO: 211) | ERCC2 (XPD) | RAD3 (S. cer) | 760 aa; DNA helicase component of TFIIH, essential for cell viability; contains one nucleotide-binding, one DNA-binding, and seven domains characteristic of helicases; 52% identity with S. cer RAD3 at the amino acid level. |
| 8 DRDKKKSRKRHYEDEE (SEQ ID NO: 212) 522 YVAIKTKKRILLYTM (SEQ ID NO: 213) (weak NLS if at all, hydrophobic environment) 769 PSKHVHPLFKRFRK (SEQ ID NO: 214) | ERCC3 (XPB) | SSL2 (S cer) Haywire(Dros) | 782 aa; helicase, component of TFIIH essential for cell viability; helix-turn-helix, DNA-BD, and helicase domains |
| 84 KKQTLVKRRQRKD (SEQ ID NO: 215) 210 EFTKRRRTL (SEQ ID NO: 216) 390 DESMIKDRKDRLP (SEQ ID NO: 217) 1170 GKKRRKLRRARGRK RKT (SEQ ID NO: 218) | ERCC5 (XPG) | RAD2; Rad13 | 1186 aa in human, 1196 in X. laevis; 3' incision endonuclease; involved in homologous recombination; strongly nuclear |

TABLE 8-continued

Nuclear localization signals on DNA repair proteins

| Putative NLS | Gene product | Equivalent protein in other species | Features |
|---|---|---|---|
| 253 PQKQEKKPRKIMLNEASG (SEQ ID NO: 219)<br>314 PNKKARVLSKKEERLKK HIKKLQKR(SEQ ID NO: 220)<br>406 PLPKGGKRQKKVP (SEQ ID NO: 221)<br>455 DGDEDYYKQRLRRWNK LRLQDKEKRLKLEDDSEESD (SEQ ID NO: 222)<br>1028 DVQTPKCHLKRRIQP $X_8$PKRKKFP(SEQ ID NO: 223)<br>1180 KHKSKTKHHSVAEEETL EKHLRPKQKPK$X_{15}$PHLVKK RRY(SEQ ID NO: 224)<br>1324 PAGKKSRFGKKRN (SEQ ID NO: 225) | ERCC6 CS-B | RAD26 | 1493 aa; involved in the preferential repair of active genes; nonessential for cell viability |
| 21 PASVRASIERKRQRALM LRGAR(SEQ ID NO: 226)<br>160 PPLKFIVKKNPHHSQW GD (weak)(SEQ ID NO: 227)<br>210 NREKMKQKKFDKKVKE (weak because of F) (SEQ ID NO: 228) | XPA | RAD14 | 273 aa; zinc finger domain; involved in lesion recognition |
| 72 YLRRAMKRFN (weak) (SEQ ID NO: 229)<br>262 PSAKGKRNKGGRKKRSK PSSSEEDEGPG(SEQ ID NO: 230)<br>297 QRRPHGRERR (weak) (SEQ ID NO: 231)<br>368 RTHRGSHRKDP (weak) (SEQ ID NO: 232)<br>384 SSSSSSSKRGKKMCSDG (SEQ ID NO: 233)<br>531 ALKRHLLKYE (weak) (SEQ ID NO: 234)<br>594 SNRARKARLAEP (SEQ ID NO: 235)<br>660 PNLHRVARKLD (weak) (SEQ ID NO: 236)<br>716 ERKEKEKKEKR (SEQ ID NO: 237)<br>740 IRERLKRRYG (SEQ ID NO: 238)<br>801 GGPKKTKRERK (SEQ ID NO: 239) | XPC | RAD4 (23% identity, 44% similarity) | 823 aas, 92.9 kDa; very hydrophilic protein; might be involved in lesion recognition since XPC cells (40% of all XP cases) can repair active parts of the genome whereas inactive and the nontranscribed strand of active genes are not repaired |
| 20 KSKAKSKARREEEEED (SEQ ID NO: 240)<br>54 GKRKRG(SEQ ID NO: 241)<br>69 GPAKKKVAKVTVK (SEQ ID NO: 242)<br>103 PSDLKKAHHLKRG (SEQ ID NO: 243) | XPC | | 940 aa; the first 117 aa are lacking in the Legerski and Peterson, (1992) XPC sequence (see above); the following 823 aa are identical. |
| 82 EIDRRKKRPLENDGPVKK KVKKVQQKE(SEQ ID NO: 244)<br>375 KENVRDKKKG (SEQ ID NO: 245)<br>571 FGRRLKKWVT (SEQ ID NO: 246)<br>710 PLIKKRKDEIQG (SEQ ID NO: 247)<br>1091 KELEGLINTKRKRLKYF AKLW (SEQ ID NO: 248) | Rep-3 (mouse) Duc-1 (HeLa) | Swi4 (S pom) | 1137 aa; mismatch repair protein; Rep-3 is in the immediate 5' flanking region of DHFR gene (89 bp) but transcribed from the opposite strand; a bidirectional promoter is used for both transcripts. |
| 422 EKHEGKHQKLL(weak) (SEQ ID NO: 249) | hMSH2 | MSH2 (S cer) | human mismatch repair protein; homologous to S. cerevisiae MSH2; associated with the hereditary nonpolyposis colon cancer gene on chromosome 2p16. |

TABLE 8-continued

Nuclear localization signals on DNA repair proteins

| Putative NLS | Gene product | Equivalent protein in other species | Features |
|---|---|---|---|
| 397 PDIRRLTKKLNKRG (SEQ ID NO: 250) 547 DAKELRKHKKYIE (SEQ ID NO: 251) 869 VKMAKRKANE (SEQ ID NO: 252) | MSH2 (S cer) | | |
| 95 GELAKRSERRAEAE (SEQ ID NO: 253) 354 KRKEPEPKGSTKKKAK TG(SEQ ID NO: 254) 394 GKFKRGK (SEQ ID NO: 255) | Human Rad2 | Rad2 (S. pom) | 400 aa; required for fidelity of chromosome separation at mitosis; limited similarity to RAD2 (ssDNA nuclease), rad13, and XPG (ERCC5). |
| None | mouse RAD51 | | 339 aa; recombination-repair protein; 83% homology to S cerevisiae RAD51 and 55% homology to E. coli RecA. |
| None | HHR23B/ p58 | RAD23 | Subunit of XPC (125 kDa) |
| None | HHR23A | RAD23 | Subunit of XPC (125 kDa) |
| 32 PSQAEKKSRARAQ (SEQ ID NO: 256) | RPA (34 kDa subunit) | | RPA (70, 34, and 14 kDa subunits) might stabilize the helicase-melted DNA around the lesion; antibodies against RPA 32 kDa subunit inhibit DNA replication. |
| GAKKRKIDDA (SEQ ID NO: 257) | ATPase Q1 | RecQ (E. coli) | 649 aa; altered in XPC cells; undetermined role in repair |
| PKKPRGKM (SEQ ID NO: 258) EHKKKHP (SEQ ID NO: 259) ETKKKFKDP (SEQ ID NO: 260) EKSKKKK(E/D)$_{41}$ (SEQ ID NO: 261) E$_3$G$_2$KKKKKFAK (SEQ ID NO: 262) | HMG-1 | | Calf thymus HMG 1 (259 aa); involved in the recognition of cisplatin lesions |
| 512 RDEKKRKQLKKAKAK MAKDRKSRKKP (SEQ ID NO: 263) 619 GESSKRDKSKKKKVKV KMEKK (SEQ ID NO: 264) 674 GENKSKKKRRRSEDSEE EE(SEQ ID NO: 265) | SSRP1 | ABF (S cer) | 709 aa, 81 kDa, structure-specific recognition protein 1; involved in recognition of cisplatin-induced lesions; also involved in Ig gene recombination; one HMG-box, similarity to SRY, MTFII, LEF-1, TCF-1a, and ABF2. |
| 1 MPKRGKKG(SEQ ID NO: 266) | Ref-1 (HAP1) | | Redox factor 1 from HeLa cells; 37 kDa, 318 aa; apurinic/apyrimidinic (AP) endonuclease for DNA repair but also of redox activity stimulating Jun/Fos DNA binding. |
| 1 MPKRGKKG (SEQ ID NO: 267) | HAP1 (bovine) | ExoIII (E. coli) ExoA (S. pneumoniae) | 323 aa; apurinic/apyrimidinic (AP)-endonuclease |
| | | DROSOPHILA | |
| 1 MGPPKKSRKDRSGGDKF GKKRRGQDE (SEQ ID NO: 268) EMSYSRKRQRFLVNQG (weak)(SEQ ID NO: 269) YYEHRKKNIGSVHPLFK KFRG(bipartite)(SEQ ID NO: 270) | Haywire | ERCC3 (XPB) SSL2 (S cer) | helicase with 66% identity to human ERCC3; flies expressing marginal levels of Haywire display motor defects and reduced life span |
| 77 ARGKKKQPK (SEQ ID NO: 271) 98 KPKGRAKKA (SEQ ID NO: 272) 157 QAKGRKKKELP (SEQ ID NO: 273) 179 EPPKQRARKE (SEQ ID NO: 274) 241 PPKAASKRAKKGK (SEQ ID NO: 275) | Rrp1 | HAP1 | Recombination repair protein 1); 679 aa; the 252 aa C-terminal domain is homologous to AP-endonucleases, whereas the 1-426 aa domain is highly charged, carries all of the putative NLSs. |

TABLE 8-continued

Nuclear localization signals on DNA repair proteins

| Putative NLS | Gene product | Equivalent protein in other species | Features |
|---|---|---|---|
| 282 PKKRAKKTT (SEQ ID NO: 276) | | | |
| 317 EPAPGKKQKKSAD (SEQ ID NO: 277) | | | |
| 336 EEEAKPSTETKPAKGRKKAP (SEQ ID NO: 278) | | | |
| 372 KPARGRKKA (SEQ ID NO: 279) | | | |
| 394 GSKTTKKAKKAE (SEQ ID NO: 280) | | | |

S. CEREVISIAE

| Putative NLS | Gene product | Equivalent protein in other species | Features |
|---|---|---|---|
| 200 IEKRRKLYISGG (SEQ ID NO: 281) | RAD1 | ERCC4 (XPF) Rad16 | 1100 aa; 30% sequence identity to Rad16; RAD1 interacts strongly with RAD10 |
| 515 NKKRGVRQVLLN (SEQ ID NO: 282) | | | |
| 565 KEQVTTKRRRTRG (conserved in Rad16)(SEQ ID NO: 283) | | | |
| 1024 NLRKKIKSENKLQ (SEQ ID NO: 284) | | | |
| 89 RQRKERRQGKRE (SEQ ID NO: 285) | RAD2 | XPGC Rad13 | 1031 aa, 117.8 kDa; ssDNA endonuclease; rad mutants are defective in incision |
| 907 ENKFEKDLRKKLVNNE (SEQ ID NO: 286) | | | |
| 984 RDVNKRKKKGKQKRI (SEQ ID NO: 287) | | | |
| 1017 KRISTATGKLKKRKM (SEQ ID NO: 288) | | | |
| 672 GKDDYGVMVLADRRF SRKRSQLP (contains the bulky F)(SEQ ID NO: 289) | RAD3 (*S. cer*) | ERCC2 or XPD; Rad15 or Rhp3 | 778 aa, 89,779 Da; 30% sequence identity to rad16; ATP-dependent DNA helicase; single-stranded DNA-dependent ATPase. |
| 26 PLSRRRRVRRKNQPLPDAKKKFKTG (SEQ ID NO: 290) | RAD4 | XPC | 754 aa; mutations in RAD4 that that inactivate the excision repair function of RAD4 result in truncated proteins missing the C-terminal one-third of RAD4. |
| 134 NEERKRRKYFHMLYL (SEQ ID NO: 291) | | | |
| 160 EWINSKRLSRKLSNL (weak) (SEQ ID NO: 292) | | | |
| 254 EMSANNKRKFKTLKRSD weak (SEQ ID NO: 293) | | | |
| 382 WMNSKVRKRRITKDDFGEK (SEQ ID NO: 294) | | | |
| 403 RKVITALHHRKRTKIDDYED (SEQ ID NO: 295) | | | |
| 504 KTGSRCKKVIKRTVGRP (SEQ ID NO: 296) | | | |
| 150 FHPKRRRIYGFR (SEQ ID NO: 297) | RAD5 | | 1169 aa; helicase involved in postreplication-repair (RAD6 epistasis group); binds DNA with the seven helicase motifs and with zinc fingers; increases the instability of poly (GT) repeats in the yeast genome. |
| 215 DSRGRKKASM (SEQ ID NO: 298) | | | |
| 297 DGESLMKRRRTEGGNKREK (SEQ ID NO: 299) | | | |
| 1152 DEDERRKRRIEE (SEQ ID NO: 300) | | | |
| 1 MSTPARRRLMRDFKRMKEDAPP (SEQ ID NO: 301) | RAD6 | | RAD6 mediates the ubiquitination of H2A and H2B histones |
| 15 GVAKLRKEKSGAD (SEQ ID NO: 302) | RAD10 | ERCC1 | 210 aa; forms an endonuclease with RAD1; the basic and tyrosine-rich central domain was suggested to bind DNA by ionic interactions and tyrosine intercalation. |
| 76 DDYNKRPFRSTRPGK (SEQ ID NO: 303) | | | |

TABLE 8-continued

Nuclear localization signals on DNA repair proteins

| Putative NLS | Gene product | Equivalent protein in other species | Features |
|---|---|---|---|
| 172 EGKAHRREKKYE (SEQ ID NO: 304) 200 NRLREKKHGKAHIHH (SEQ ID NO: 305) | RAD14 | XPAC | 247 aa, 29.3 kDa; two zinc fingers; involved in lesion recognition; 27% sequence identity and 54% sequence similarity (if conserved residues are grouped together) to human XPA; deletion of RAD14 gene generates high UV sensitivity. |
| 345 ERRKQLKKQGPKRP (SEQ ID NO: 306) 479 ETYKKRIKEWESCYPDE (SEQ ID NO: 307) | Ixr1 (S. cer) | | 591 aa; two consecutive HMG boxes; involved in recognition of 1,2-intrastrand d(GpG) and d(ApG) cisplatin crosslinks. |
| None | RAD23 | HHR23 | |
| 483 LTCKKLKTHNRIILSG weak (SEQ ID NO: 308) 934 NALRKSRKKITKQYEIGT PX$_9$GEIRKRDP (SEQ ID NO: 309) | RAD26 (yeast ERCC6) | ERCC6 CS-B (hum) | 1075 aa; disruption of the RAD26 gene gives viable yeast cells unable to preferentially repair the actively transcribed strands; surprisingly, in contrast to human CS-B cells, disruption of the RAD26 in yeast does not cause sensitivity to UV, Cisplatin, or X-rays. |
| 634 KPTSKPKRVRTATKKKIP (SEQ ID NO: 310) 408 FYKKRSPVTRSKKSG (SEQ ID NO: 311) | MRE11 | Rad32 (S pom) | meiotic recombination protein; functions in the same pathway with RAD51 |
| none; 361 GFKKGKGCQR (SEQ ID NO: 312) | RAD51 | RecA (E. coli) | 402 aa; essential for repair of DSBs and recombination; associates strongly with RAD52; self associates; neither RAD51 nor RAD52 possess a typical simple NLS. |
| none; 328 GFKKGKGCQR (SEQ ID NO: 313) | RAD51 (K. lactis) | | 364 aa |
| none; 155 ERAKKSAVTDALKRSLR GFGX$_8$DKDFLAKIDKVKFDP PD(tripartite) (SEQ ID NO: 314) | RAD52 | Rad22 | 504 aa; rad52 mutants are defective in ionizing radiation, mitotic recombination, mating-type switching, and repair of DSDs. |
| 1 MARRRLPDRPP (SEQ ID NO: 315) 65 GGRSLRKRSA (SEQ ID NO: 316) 99 QLTKRRKD (SEQ ID NO: 317) | RAD54 | | 898 aa; recombination-repair protein; ATP-binding motif; helicase domains; in the same subfamily of helicases with MOT1 and SNF2. |
| 269 DETVFVKSKRVKASSS (extremely weak if at all NLS) (SEQ ID NO: 318) 317 GEDRKREGRNLKR (SEQ ID NO: 319) | RAD55 | | Similarity to RecA, and lower similarity to RAD51, RAD57, and DMC1 |
| 371 PISRQSKKRKFDYRVP (SEQ ID NO: 320) | RAD57 | | 460 aa; nucleotide-binding domain; limited similarity to RAD51 |
| 62 GLKKPRKKTKSSRH (SEQ ID NO: 321) 688 GRILRAKRRNDEG (SEQ ID NO: 322) 784 GRGSNGHKRFKS (weak) (SEQ ID NO: 323) | SSL2 | ERCC3 (XPB) | 843 aa; putative helicase that seems to function in repair but also in the removal of secondary structures in the 5' untranslated region of mRNA to allow ribosome binding and scanning. |

TABLE 8-continued

Nuclear localization signals on DNA repair proteins

| Putative NLS | Gene product | Equivalent protein in other species | Features |
|---|---|---|---|
| 50 TRRHLCKIKGLSE (weak) (SEQ ID NO: 324) 277 DGRKPIGGHX₁₂RKGRG DER (bipartite)(SEQ ID NO: 325) | DMC1 | RecA | 334 aa; yeast homolog of RecA, meiosis-specific; dmc1 mutants are defective in reciprocal recombination and accumulate DSBs |
| 11 ETEKRCKQKEQRY (SEQ ID NO: 326) | PMS1 | | 904 aa, 103 kDa; mismatch-repair protein; MutL (*Salmonella*) and HexB (*Streptococcus*) homolog |
| None 1 MDLRVGRKFRIGRKIG (SEQ ID NO: 327) 139 GRRGX₈GLSKKYRDFNT HRHIP (Bipartite weak NLS) (SEQ ID NO: 328) | HRR25 | Hhp1, Hhp1 (*S pom*) CKI (mamm | Mutations in HRR25 Ser/Thr protein kinase cause defects in DNA repair and retardation in cell cycling |
| 96 HELTKRSSRRVETEK (SEQ ID NO: 329) | YKL510 | | 383 aa; structure-specific endonuclease; two domains of about 100 aa with sequence similarity to N- and C-terminal regions of RAD2. |
| 200 MLAMARRKKKMSAK (SEQ ID NO: 330) 617 EHYKVKHTEK (weak NLS)(SEQ ID NO: 331) 670 LHPEKKRSISE (weak NLS) (SEQ ID NO: 332) | MOT1 | | Modifier of transcription 1; 1867 aa; DNA helicase of *S. cerevisiae* required for viability; increases gene expression of several., but not all, pheromone-responsive genes in the absence of STE12; the 1257 to 1825 aa domain (568 aa residues) has homology to SNF2 and RAD54 |
| S. POMBE | | | |
| 60 SSIDEx₅SIKRKRRI (SEQ ID NO: 333) | Swi4 | Duc-1 Rep-3 | 113 kDa; KCII sites are upstream of NLS like in SV40 large T; the homologous prokaryotic MutS and HexA lack NLS |
| 96 GELAKRVARHQKARE (weak NLS)(SEQ ID NO: 334) 362 GSAKRKRDS (SEQ ID NO: 335) 372 KGGESKKKR (SEQ ID NO: 336) | Rad2 | | 380 aa |
| None | Rad9 | — | 427 aa; no homology to other DNA repair proteins; rad9 fission yeast mutants are sensitive to both UV and ionizing radiation; may be involved in recombination-repair. |
| None 681 DKRYGRSDKRTKLPK (SEQ ID NO: 337) | Rhp3 or rad15 | ERCC2 RAD3 | 772 aa; DNA helicase; 65% identity to RAD3 and 55% identity to ERCC2; essential for viability |
| 464 PPSKRRRVRGG (SEQ ID NO: 338) | Rad16 | RAD1 | Function in repair of UV damage for both cyclobutane dimer and (6-4) photoproduct lesions; Rad16 interacts with Swi10. |
| 431 DFKQAILRKRKNESPE EVEP (SEQ ID NO: 339) | Rad21 | | 628 aa, 67.8 kDa, acidic protein; a single base substitution in mutant rad21-45, changing an Ile into a Thr, is responsible for the low efficiency in repair of DSBs after g-radiation although capable of arresting at G2. |

TABLE 8-continued

Nuclear localization signals on DNA repair proteins

| Putative NLS | Gene product | Equivalent protein in other species | Features |
|---|---|---|---|
| 490 DKKAKKG (SEQ ID NO: 340) | Rad22 | RAD52 | 496 aa; functions in recombination-repair and mating-type switching. |
| 394 DVVQFYLKKKYTRSKRN DG (weak because of Y) (SEQ ID NO: 341) 575 PSPALLKKTNKRRELP (SEQ ID NO: 342) | Rad32 | MRE11 (*S cer*) | 648 aa; meiotic recombination protein; rad32 mutants are sensitive to g- and UV radiation; functions in the same pathway with Rhp51 (RAD51). |
|  | Rad51 |  | recombination-repair |
| GLAKKYRDHKTHLHIP (weak NLS because of Y and H) (SEQ ID NO: 343) | Hhp1 | CKI (mamm) HRR25 (*S cer*) | Ser/Thr protein kinase; mutation in this gene causes repair defects |
| None GLAKKYRD$^F$PKTHVHIP (H in Hhp1 is replaced by F in Hhp2) (SEQ ID NO: 344) | Hhp2 | CKI (mamm) HRR25 (*S cer*) | Ser/Thr protein kinase; mutation in this gene causes repair defects |

TABLE 9

NLS in Transcription factors

| NLS and Flanks | Protein factor and features |
|---|---|
| highly basic | |
| HR$_4$QRTRK$_7$R (SEQ ID NO: 345) | Human GCF (GC-factor) |
| LRRKSRP (SEQ ID NO: 346) | |
| SRRTKRRQ (SEQ ID NO: 347) | |
| GRKRKKRT (SEQ ID NO: 348) | Oct-6 protein transcription factor from mouse cells |
| GRRRKKRT (SEQ ID NO: 349) | Mouse Oct-2 protein transcription factors (Oct-2.1 for Oct-2.6 isoforms) |
| ARKRKRT (SEQ ID NO: 350) | Oct-3 from mouse P19 embryonal carcinoma cells |
| NRRQKGKRS (SEQ ID NO: 351) | |
| ECRRKKKE (SEQ ID NO: 352) | Human ATF-1. In basic region/leucine zipper. |
| ERKKRRRE (SEQ ID NO: 353) | Human ATF-3 (in basic region that binds DNA) |
| AKCRNKKKEKT (SEQ ID NO: 354) | |
| SKKKIRL (SEQ ID NO: 355) | Mouse Pu.1 (Friend erythroleukemia cells). Related to ets oncogene |
| QKGNRKKM (SEQ ID NO: 356) | |
| VKKVKKKL (SEQ ID NO: 357) | |
| VKRKKI (SEQ ID NO: 358) | Human PRDII-BF1 that binds to IFN-β gene promoter. (The largest DNA-binding protein known, of 298 kD). |
| CRNRYRKLE (SEQ ID NO: 359) | |
| IRKRRKMK (SEQ ID NO: 360) | |
| PKKKRLRL (SEQ ID NO: 361) | |
| GKKKKRKREKL (within the HMG-box) (SEQ ID NO: 362) | Murine LEF-1 (397 aa). Lymphoid-specific with an HMG1-like box. NLS is identical to that of human TCF-1α. |
| GKKKKRKREKL (within the HMG-box) (SEQ ID NO: 363) | Human TCF-1α (399 aa) (T cell-specific transcription factor that activates the T cell receptor Cα). Contains an HMG box. NLS core is identical to that of murine LEF-1. |
| GKKKRRSREKH (within the HMG-box) (SEQ ID NO: 364) | Human TCF-1 (uniquely T cell-specific). HMG box containing. |
| PKKCRARF (SEQ ID NO: 365) | |
| FKQRRIKL (SEQ ID NO: 366) | *Xenopus laevis* Oct-1 (within POU-domain) |
| NRRRKKRT (SEQ ID NO: 367) | |
| NRRQKEKRI (SEQ ID NO: 368) | |
| DKRSRKRKRSK (SEQ ID NO: 369) | *Drosophila* Suvar (3) 7 gene product involved in position-effect variegation (932 aas). Five widely spaced zinc-fingers could help condensation of the chromatin fiber. |
| RLRIDRKRN (SEQ ID NO: 370) | |
| AKRSRRS (SEQ ID NO: 371) | |

TABLE 9-continued

NLS in Transcription factors

| NLS and Flanks | Protein factor and features |
| --- | --- |
| IRKRRKMKSVGD$_2$E$_2$ (SEQ ID NO: 372) (not suggested as NLS by the authors; between the 1st and 2nd zinc finger) PPKKKRLRLAE (suggested as NLS by the authors; just before 2nd zinc finger) (SEQ ID NO: 373) CRNRYRKLE (within 1st zinc finger) (SEQ ID NO: 374) | Human MBP-1 (class I MHC enhancer binding protein 1) mw 200 kD. Induced by phorbol esters and mitogens in Jurkat T cells. |
| PRRKRRV (SEQ ID NO: 375) HRYKMKRQ (SEQ ID NO: 376) DGKRKRKN (SEQ ID NO: 377) DDSKRVAKRKL (SEQ ID NO: 378) NRERRRKEE (SEQ ID NO: 379) WKQRRKF (SEQ ID NO: 380) NRRKRKRS (SEQ ID NO: 381) PKKKKL (SEQ ID NO: 382) ARRKRRRL (SEQ ID NO: 383) LKFKKVRD (SEQ ID NO: 384) FKKFRKF (SEQ ID NO: 385) GKQKRRF (SEQ ID NO: 386) ERLKRDKEKREKE (SEQ ID NO: 387) TRGRPKKVKE (SEQ ID NO: 388) SKKRGRRRKKT (SEQ ID NO: 389) TRRQKRAKV (SEQ ID NO: 390) SRKSKKRLRA (SEQ ID NO: 391) | rat TTF-1 (thyroid nuclear factor that binds to the promoter of thyroid-specific genes). An homeodomain protein. Human thyroid hormone receptor α (c-erbA-1 gene). Belongs to the family of cytoplasmic proteins that are receptors of hydrophobic ligands such as steroids, vitD, retinoic acid, thyroid hormones. The ligand binding may expose the NLS for nuclear import of the receptor-ligand complex. Drosophila gcl (germ cell-less) gene product (569 aa, 65 kD), located in nuclei, required for germ line formation. C. elegans Sdc-3 protein (sex-determining protein) (2,150 aas). A zinc finger protein. |
| LKKIRRKIKNKI (SEQ ID NO: 392) ESRRKKKE (SEQ ID NO: 393) Group 0000 | Drosophila BBF-2 (related to CREB/ATF) |
| DRNKKKKE (SEQ ID NO: 394) ARRRRP (SEQ ID NO: 395) | Xenopus RAR (retinoic acid receptor) |
| GRRRRA (SEQ ID NO: 396) DEKRRKV (SEQ ID NO: 397) CRQKRKV (SEQ ID NO: 398) | Human ATF-2 (the 2nd and 3rd NLS are in basic region that binds DNA) |
| ERKRRD (SEQ ID NO: 399) SRKKLRME (SEQ ID NO: 400) | Myn (murine homolog of Max). Forms a specific DNA-binding complex with c-Myc oncoprotein through a helix-loop-helix/leucine zipper. |
| EEKRKRTYE (SEQ ID NO: 401) | human NFκB p65 (550 aa). Not binding DNA; complexed with p50 that binds DNA. NFκB p50 also contains a NLS (Table 3b). |
| GRRRRA (SEQ ID NO: 402) DEKRRKF (SEQ ID NO: 403) SRCRQKRKV (SEQ ID NO: 404) | Human HB16, a cAMP response element-binding protein |
| SKKKKTKV (SEQ ID NO: 405) NRPDKKKI (SEQ ID NO: 406) QRRKKP (SEQ ID NO: 407) QKKRRFKT (SEQ ID NO: 408) | Human TFIIE-β (general transcription initiation protein factor; forms tetramer α$_2$β$_2$ with TFIIE-α) |
| SRKRKM (SEQ ID NO: 409) | Human kup transcriptional activator (433 aas). Two distantly spaced zinc fingers. Expressed in hematopoietic cells and testis. |
| ERKRLRNRLA (SEQ ID NO: 410) ATKCRKRKL (SEQ ID NO: 411) (19 aa stretch) | Mouse Jun-B homologue to avian sarcoma virus 17 oncogene v-jun product. One region is similar to yeast GCN4 and to Fos. |
| DKRx$_6$ERKRRD (N-terminus) (SEQ ID NO: 412) QSRKKLRME (C-terminus) (SEQ ID NO: 413) | Max (specifically associates with c-Myc, N-Myc, L-Myc). The Max-Myc complex binds to DNA; neither Max nor Myc alone exhibit appreciable DNA binding. |
| DKEKKIKLEEDE (within an acidic region) (SEQ ID NO: 414) IKKAKKV (SEQ ID NO: 415) TRRKKN (SEQ ID NO: 416) | Chicken VBP (vitellogenin gene-binding protein). Leucine zipper. Related to rat DBP. |

TABLE 9-continued

NLS in Transcription factors

| NLS and Flanks | Protein factor and features |
| --- | --- |
| TRDDKRRA (SEQ ID NO: 417)<br>EVERRRRDK (SEQ ID NO: 418) | *Xenopus borealis* B1 factor. Closely related to the mammalian USF. Binds to CACGTG in TFIIIA promoter to developmentally regulate its expression. |
| TRDEKRRA (SEQ ID NO: 419)<br>EVERRRRDK (SEQ ID NO: 420) | Human USF (upstream stimulatory factor) activating the major late adenovirus promoter |
| YRRYPRRRG (SEQ ID NO: 421)<br>QRRPYRRRRF (SEQ ID NO: 422)<br>YRPRFRRG (SEQ ID NO: 423)<br>QRRYRRN (SEQ ID NO: 424)<br>YRRRRP (SEQ ID NO: 425) | YB-1, a protein that binds to the MHC class II Y box. YB-1 is a negative regulator. |
| AKERQKKD (SEQ ID NO: 426)<br>ERRRRF (SEQ ID NO: 427) | Human TFEB Binds to IgH enhancer. |
| LKERQKKD (SEQ ID NO: 428)<br>IERRRRFN (SEQ ID NO: 429)<br>YFRRRRLEKD (SEQ ID NO: 430) | Human TFE3 (536 aa). Binds to µE3 enhancer of IgH genes. |
| KTVALKRRKASSRL (SEQ ID NO: 431) | Human Dr1 (176 aa, 19 kD). Interacts with TBP (TATA-binding protein) thus inhibiting association of TFIIA and/or TFIIB with TBP. TBP-Dr1 association is affected by Dr1 phosphorylation to repress activated and basal transcription. |
| 1 LRRRGRQTY (SEQ ID NO: 432)<br>27 LTRRRRIEM (SEQ ID NO: 433)<br>51 QNRRMKLKKEI (SEQ ID NO: 434) | *Drosophila* ultrabithorax protein (from the conserved 61 amino acid homeodomain segment only). Conserved in the antenappedia homeodomain protein. |
| SNRRRPDHR (SEQ ID NO: 435)<br>VYRGRRRVRRE (SEQ ID NO: 436)<br>$P_7AP_2RRRRSADNKD_2$ (SEQ ID NO: 437)<br>PKKPRHQF (SEQ ID NO: 438) | *C. elegans* sex-determining Tra-1 protein. Zinc finger. Peaks in the second larval stage. |
| EKRKKERN (SEQ ID NO: 439)<br>LLRRLKKEVE (SEQ ID NO: 440)<br>EPLGRIRQKKRVY$_2$D$_2$ (SEQ ID NO: 441)<br>(EDAIKKRREARERRRLRQ) (SEQ ID NO: 442)<br>DKETTASRSKRRSSRKKRT (SEQ ID NO: 443)<br>ESKKKKPKL (SEQ ID NO: 444)<br>KKTAAKKTKTKS (SEQ ID NO: 445) | Yeast NPS1 transcription protein factor (1359 aa) involved in cell growth control at G2 phase. Has a catalytic domain of protein kinases. |
| QRKRQKL (SEQ ID NO: 446)<br>KAKKQK (SEQ ID NO: 447)<br>LRRKRQK (SEQ ID NO: 448) | Human 243 transcriptional activator (968 aas), induced by mitogens in T cells. N-terminal half is homologous to oncoprotein Rel and *Drosophila* Dorsal protein involved in development. The C-terminal half contains repeats found in proteins involved in cell-cycle control of yeast and tissue differentiation in *Drosophila*. |
| RDIRRRGKNKV (SEQ ID NO: 449)<br>QNCRKRKLE (SEQ ID NO: 450)<br>Group θθθxθθ | Mouse NF-E2 (45 kD), an erythroid transcription factor from mouse erythroleukemia (MEL) cells. Involved in globin gene regulation. Binds to AP-1-like sites. Homology to Jun B, GCN4, Fos, ATF1 and CREB in basic region/leucine zipper (see FIG. 2). |
| DKIRRKN (SEQ ID NO: 451)<br>ARKTKKKI (SEQ ID NO: 452) | Human glucocorticoid receptor |
| 473 DKIRRKNCP (SEQ ID NO: 453)<br>EARKTKKKIKGIQ (SEQ ID NO: 454)<br>Group θθθxθ | Mouse and human GR (glucocorticoid recptor) |
| YRVRRERN (SEQ ID NO: 455)<br>VRKSRDKA (SEQ ID NO: 456)<br>DRLRKRVE (SEQ ID NO: 457) | C/EBP (CCAAT/enhancer binding protein). Functions in liver-specific gene expression. |
| DKIRRKN (SEQ ID NO: 458)<br>ARKSKKL (SEQ ID NO: 459) | Human mineralocorticoid receptor |
| DKIRRKN (SEQ ID NO: 460)<br>GRKFKKF (SEQ ID NO: 461) | Human PR (progesterone receptor) |

TABLE 9-continued

NLS in Transcription factors

| NLS and Flanks | Protein factor and features |
|---|---|
| EEVQRKRQKLMP (SEQ ID NO: 462) | Human and mouse NFκB 105 kD precursor of p50 (968 aas) (first R is at 361 position). |
| EEVQRKRQKL (SEQ ID NO: 463) | Human NF-κB p50 (DNA-binding subunit). Identical to protein KBF1, homologous to rel oncogene product. NF-κB p65 also contains a NLS (Table 3a). |
| GKTRTRKQ (SEQ ID NO: 464) ARRKSRD (SEQ ID NO: 465) | Human TEF-1 (SV40 transcriptional enhancer factor 1). 426 aa. |
| QRKERKSKS (SEQ ID NO: 466) TKSKTKRKL (SEQ ID NO: 467) | Rat, mouse, human IRF-1 (interferon regulatory factor-1). Induced in lymphoma T cells by the pituitary peptide hormone prolactin. Regulates the growth-inhibitory interferon genes. |
| GKCKKKN (SEQ ID NO: 468) | Ehrlich ascites S-II transcription factor. A general factor that acts at the elongation step. |
| ERSKKRSRE (SEQ ID NO: 469) ERELKREKRKQ (SEQ ID NO: 470) ARRSRLRKQ (SEQ ID NO: 471) | Tobacco TAF-1 transcriptional activator |
| YKLDHMRRRIETDE (SEQ ID NO: 472) | Drosophila TFIIEα (433 aa), a general transcription factor for RNA polymerase II. Composed of subunits α and β. |
| DKNRRKS (SEQ ID NO: 473) IRKDRRG (SEQ ID NO: 474) IKRSKKN (SEQ ID NO: 475) | Human ER (estrogen receptor); 595 aa. |
| EQRRHRIE (SEQ ID NO: 476) TTRAEKKRLL (SEQ ID NO: 477) IDKKRSKEAKE (SEQ ID NO: 478) | Yeast ADA2 (434 aa), a potential transcriptional adaptor required for the function of certain acidic activation domains. |
| EAALRRKIRTISK (SEQ ID NO: 479) | Yeast GCN5 gene product (439 aa), required for the function of GCN4 transcriptional activator and for the activity of the HAP2-3-4 complex. |

Group θθxθθ

| | |
|---|---|
| NKKMRRNRF (SEQ ID NO: 480) NRRKx4RQK (SEQ ID NO: 481) | Mouse LFB3 |
| TKKGRRNRF (SEQ ID NO: 482) NRRKx4RHK (SEQ ID NO: 483) | Mouse LFB1 |
| NKKMRRNRFK (SEQ ID NO: 484) | rat vHNF1-A |
| NKKMRRNR (SEQ ID NO: 485) | murine HNF-1β |
| TKKGRRNRF (SEQ ID NO: 486) | mouse HNF-1 |
| NKKMRRNRF (SEQ ID NO: 487) | human vHNF1 |
| TKKGRRNRF (SEQ ID NO: 488) | rat liver HNF1 |
| LRRQKRFK (SEQ ID NO: 489) QQH3SH4Q (SEQ ID NO: 490) | rat HNF-3β |
| LRRQKRFK (SEQ ID NO: 491) | rat HNF-3γ |
| LRRQKRFK (SEQ ID NO: 492) | rat HNF-3α |
| LKEKERKA (SEQ ID NO: 493) MKKARKV (SEQ ID NO: 494) | rat DBP a protein factor that binds to the D site of the albumin gene promoter |
| PRRERRY (SEQ ID NO: 495) | rat AT-BP1. Highly acidic domain. Two zinc fingers. Binds to the B-domain of α1-antitrypsin gene promoter and to the NF-κB site in the MHC gene enhancer. |
| DRRVRKGKV (SEQ ID NO: 496) | A 19 kD Drosophila melanogaster nonhistone associated with heterochromatin. |
| SKHGRRARRLDP (SEQ ID NO: 497) | murine EBF (early B-cell factor) of 591 aa. Regulates the pre-B and B lymphocyte-specific mb-1 gene. Expressed in pre-B and B-cell lines but not in plasmocytomas, T-cell and nonlymphoid cell lines. |
| GRRTRRE (SEQ ID NO: 498) | human Sp1 |
| DEQKRAEKKAKE (SEQ ID NO: 499) IRRIHKVIRP (SEQ ID NO: 500) LLRRLKKDVE (SEQ ID NO: 501) | yeast SNF2, a transcriptional regulator of many genes. |

Group θxθθxθ

| | |
|---|---|
| AKAKAKKA (SEQ ID NO: 502) YKMRRERN (SEQ ID NO: 503) VRKSRDKA (SEQ ID NO: 504) | mouse AGP/EBP (87% similarity to C/EBP), ubiquitously expressed |

TABLE 9-continued

NLS in Transcription factors

| NLS and Flanks | Protein factor and features |
| --- | --- |
| AKAKAKKA (SEQ ID NO: 505)<br>YKMRRERN (SEQ ID NO: 506)<br>VRKSRDKA (SEQ ID NO: 507) | rat LAP, a 32-kD liver-enriched transcriptional activator, also present in lung, with 71% sequence similarity to C/EBP. Leucine zipper. Accumulates to maximal levels around birth. |
| YRQRRER (SEQ ID NO: 508)<br>VKKSRLKSKQK (SEQ ID NO: 509) | Ig/EBP-1 (immunoglobulin gene enhancer-binding protein). Forms heterodimers with C/EBP. |
| EDPEKEKRIKELE (SEQ ID NO: 510)<br>MRRKV (SEQ ID NO: 511)<br>DYYKVKRPKTD (SEQ ID NO: 512)<br>GRARGRRHQ (SEQ ID NO: 513)<br>FRYRKIKDIY (SEQ ID NO: 514)<br>Group θxθxθθ | mouse c-Myb<br><br>*Drosophila* eyes absent protein (760 aa), a nuclear protein that functions in early development to prevent programmed cell death and to allow the event that generate the eye to proceed. Mutations cause programmed cell death of eye progenitor cells. |
| AKAKAKKA (SEQ ID NO: 515)<br>DKRQRNRC (SEQ ID NO: 516)<br>FkrtirkD<br>FkrtirkD<br>DKRQRNRC (SEQ ID NO: 517)<br>VKSKAKKT (SEQ ID NO: 518)<br>YKIRRERN (SEQ ID NO: 519)<br>VRKSRDKA (SEQ ID NO: 520) | rat IL-6DBP interacting with interleukin-6 responsive elements. Has a leucine zipper domain.<br>mouse H-2RIIBP (MHC class I genes H-2 region II binding protein). Member of the nuclear hormone receptor superfamily.<br>chicken RXR, related to RAR (retinoic acid receptor), a nuclear protein factor from the thyroid/steroid hormone receptor family<br>human NF-IL6 (345 aa). Specifically binds to IL1-responsive element in the IL-6 gene. Leucine zipper. Homology to C/EBP. |
| QKKNRNKC (SEQ ID NO: 521)<br>Group θθθxxθθ | mouse PPAR (peroxisome proliferator activated receptor) |
| EQIRKLVKKHG (SEQ ID NO: 522)<br>FRRSMKRKA (SEQ ID NO: 523)<br>Group θθxxθθ | yeast RAP1<br>It binds regulatory sites at yeast mating type silencers.<br>human vitamin D receptor (427 aa) |
| LKRHQRRH (SEQ ID NO: 524)<br><br>LKRHQRRH (SEQ ID NO: 525)<br>Group θθθxxθ | mouse WT1 (the murine homolog of human Wilms' tumor predisposition gene WT1)<br>human WT33 (Wilms' tumor predisposition) |
| LKESKRKYDE (SEQ ID NO: 526)<br>EVLKVQKRRIYD (SEQ ID NO: 527) | yeast SWI3 99 kD, highly acidic protein. Global transcription activator.<br>human RBAP-1 (retinoblastoma-associated protein 1) factor (412 aa). A protein that binds to the pocket (functional domain) of the retinoblastoma (RB) protein involved in suppression of cell growth (tumor suppressor). The transcription factor E2F, implicated in cell growth, binds to the same pocket of RB. |

TABLE 10

NLS in other nuclear proteins

| Putative NLS | Protein |
| --- | --- |
| YKSKKKA (SEQ ID NO: 528)<br>TKKLPRKT (SEQ ID NO: 529) | Yeast L3 |
| TRKKGGRRGRRL (SEQ ID NO: 530) C-terminus | Yeast 59 ribosomal protein |
| ARATRRKRCKG (SEQ ID NO: 531) | Yeast L16 ribosomal protein |
| GKGKYRNRRW (SEQ ID NO: 532) | yeast L2 ribosomal protein (homologous to *Xenopus* L1). Encoded by intronless genes. |
| GKGKMRNRRRIQRRG (SEQ ID NO: 533)<br>NKKVKRRELKKN (SEQ ID NO: 534)<br>AKTARRKA (SEQ ID NO: 535)<br>IKAKEKKP (SEQ ID NO: 536)<br>GKPKAKKP (SEQ ID NO: 537)<br>AKAKKRQ (SEQ ID NO: 538) | *Xenopus laevis* L1 ribosomal protein (homologous to yeast L2) Encoded by intronless genes. |

TABLE 10-continued

NLS in other nuclear proteins

| Putative NLS | Protein |
| --- | --- |
| ERKRKS (SEQ ID NO: 539)<br>GKRPRTKA (SEQ ID NO: 540)<br>HKRRRI (SEQ ID NO: 541)<br>LKKQRTKKNKE (SEQ ID NO: 542)<br>PKMRRRTYR (SEQ ID NO: 543)<br>KKKISQKKLKK (SEQ ID NO: 544)<br>YMRRRTYRA (SEQ ID NO: 545)<br>EVKKVSKKKL (SEQ ID NO: 546) | human S6 ribosomal protein (homologous to yeast S10)<br><br>Rat L17 ribosomal protein (184 aas)<br><br>Podocoryne carnea (hydrozoan, Coelenteratum) L17 ribosomal protein (184 aas) highly homologous to rat L17. |
| ERNRKDKDAKFR (SEQ ID NO: 547) | human, rat ribosomal S13 protein |
| ERKRKS (SEQ ID NO: 548)<br>QRLQRKRH (SEQ ID NO: 549)<br>IRKRRA (SEQ ID NO: 550) | yeast S10 ribosomal protein (homologous to human S6) |
| GRRRKKHRSRSRSRERRSRSRDRGRG$_{12}$GRER DRRRSRDRER (SEQ ID NO: 551) | 35 kD subunit of U2 small nuclear ribonucleoprotein auxiliary factor (U2AF), an essential mammalian splicing factor. U2AF$^{35}$ interacts with the 65 kD subunit (U2AF$^{65}$). Both proteins are concentrated in a small number of subnuclear organelles, the coiled bodies. |
| EFEDPRD (SEQ ID NO: 552)<br>ETREERME (SEQ ID NO: 553)<br>EAGDAPPDP (SEQ ID NO: 554)<br>EERMERKRREK (SEQ ID NO: 555)<br>HRDRDRDRERERRESRERDKERERRRSRSRD RRRRSRSRDKEERRRSRERSKDKDRDRKRRS SRSRERARRERERKEE (SEQ ID NO: 556)<br>RDRDRERRRSHRSERERRRDRDRDRDREH KRGER (SEQ ID NO: 557) | human UsnRNP-associated 70 k protein (437 aas) that is phosphorylated at Arg/Ser-rich domains; involved in splicing |
| QKRNNKKSKKKRCAE (SEQ ID NO: 558)<br>EKLRKLKI (near C-terminus) (SEQ ID NO: 559) | yeast TRM1 enzyme for the N$^2$,N$^2$-dimethylguanosine modification of both mitochondrial and cytoplasmic tRNAs. TRM1 is both nuclear and mitochondrial. The first motif is within a region (70-213 aa segment) known to cause nuclear localization of β-galactosidase. |
| NKRKRV (SEQ ID NO: 560)<br>SLKNRSNRKRE (SEQ ID NO: 561)<br>EPKRKRRLP (SEQ ID NO: 562)<br>ARMRHSKR (C-terminus) (SEQ ID NO: 563) | Yeast nucleoporin NUP1 (1076 aa, 113 kD); an integral component of the pore complex. Involved in both binding and translocation steps of nuclear import. |
| KAEKEx$_3$KVD$_2$E$_2$ (SEQ ID NO: 564)<br>Kx$_3$Kx$_5$Kx$_3$R (SEQ ID NO: 565) | Chicken, *Xenopus* No 38 nucleolar (38 kD); involved in intranuclear packaging of preribosomal particles. Shuttles between nucleus and cytoplasm. |
| KTEREAEKALEEKx$_7$R (SEQ ID NO: 566)<br>Kx$_5$Kx$_7$Kx$_4$RX3EDTTEETLR (SEQ ID NO: 567)<br>RG$_2$RG$_2$RG$_3$RG$_2$FG$_2$RG$_3$RGFG$_2$RG$_3$FRG$_2$RG$_4$ DHKPQGKKIKFE (SEQ ID NO: 568) (C-terminus) | Chicken, hamster nucleolin (92 kD). Binds preribosomal RNA. Shuttles between nucleus and cytoplasm. |
| WYKHFKKTKD (SEQ ID NO: 569) | human SATB1 (763 aa) which binds selectively to AT-rich MARs with mixed A, T, C on one strand excluding G. Binds to minor groove with little contact with bases. |
| QKKKQMKAD (SEQ ID NO: 570)<br>(KKEKKE)$_5$ (SEQ ID NO: 571)<br>KKEKKRKSED (SEQ ID NO: 572)<br>EEKKSKKSKK (SEQ ID NO: 573) | yeast CBF5p, a centromere-binding protein (55 kDa, 483 aa). The KKE repeat at its C-terminus occurs in microtubule-binding domains; yeast cells containing only three copies of the KKE repeat of CBF5p delay at G$_2$/M; depletion of CBE5p arrests cells at G$_1$/S. |
| TKKKSFKL (SEQ ID NO: 574)<br>KSERERMLRESLKEERRRF (SEQ ID NO: 575) | yeast CCE1, a cruciform cutting endonuclease<br>rat nucleoporin 155 or Nup155 (1390 aas, 155 kDa), a protein of the nuclear pore complex; contains 46 consensus sites for various kinases; associated with both the nucleoplasmic and the cytoplasmic region of pores. |
| PKKGSKKA (SEQ ID NO: 576)<br>DGKKRKRSRKES (SEQ ID NO: 577) | human H2B variant differentially expressed during the cell cycle |
| GAKRHRKVLRD (SEQ ID NO: 578) 14-24<br>PAIRRLARRG (SEQ ID NO: 579) 32-41<br>EHARRKT (SEQ ID NO: 580) 74-80 | Calf thymus histone H4 (102 aa) |
| ARRIRGERA 127-135 (SEQ ID NO: 581) | Calf thymus H3 (135 aa) |
| GSHHKAKGK 121-129 (SEQ ID NO: 582) | Calf thymus H2A (129 aa) |

TABLE 10-continued

NLS in other nuclear proteins

| Putative NLS | Protein |
| --- | --- |
| RGKSGKARTKAKSRSSR 3-19 (SEQ ID NO: 583) | Sea urchin *Psammechinus miliaris* H2A (123 aa) |
| PKKGSKKA 10-17 (SEQ ID NO: 584) | Calf thymus H2B |
| QKKDGKKRKRSRKES 22-36 (SEQ ID NO: 585) | (125 aa) |
| GGKKRHRKRKGSY 22-34 (SEQ ID NO: 586) | Sea urchin *Psammechinus miliaris* H2B (122 aa) |
| PRTDKKRRRKRKES 19-32 (SEQ ID NO: 587) | Starfish H2B (121 aa) |
| PAKAPKKKA 12-20 (SEQ ID NO: 588) | Trout testis H1 |
| EAKKPAKKA 104-112 (SEQ ID NO: 589) | (194 aa) |
| AKKPKKV 128-134 (SEQ ID NO: 590) | |
| AKKSPKKAKKP 142-152 (SEQ ID NO: 591) | |
| PKKVKKP 183-189 (SEQ ID NO: 592) | |
| PRRKAKRA 30-37 (SEQ ID NO: 593) | Sea urchin *Parechinus angulosus* sperm H1 (248 aa) |
| PKKAKKT 119-125 (SEQ ID NO: 594) | |
| AKAKKAKA 129-136 (SEQ ID NO: 595) | |
| AKKARKAKA 139-147 (SEQ ID NO: 596) | |
| AKKAKKPKKKA 171-181 (SEQ ID NO: 597) | |
| AKKAKKPAKK 182-191 (SEQ ID NO: 598) | |
| SPKKAKKP 192-199 (SEQ ID NO: 599) | |
| AKKSPKKKAKRS 200-212 (SEQ ID NO: 600) | |
| PKKAKKA 213-219 (SEQ ID NO: 601) | |
| AKKAKKS 227-233 (SEQ ID NO: 602) | |
| PRKAGKRRSPKKARK 234-248 (SEQ ID NO: 603) | |
| ARRRKTA 1-7 (SEQ ID NO: 604) | Annelid sperm H1a |
| IRKFIRKA 55-61 (SEQ ID NO: 605) | (119 aa) |
| PKKKKA 83-88 (SEQ ID NO: 606) | |
| AKKPKAKKVKKP 89-100 (SEQ ID NO: 607) | |
| AKKKTNRARKPKTKKNR 104-120 (SEQ ID NO: 608) | |
| PKRKVSS 1-7 (SEQ ID NO: 609) | Calf thymus HMG14 |
| EEPKRRSARLS 14-24 (SEQ ID NO: 610) | (100 aa) |
| PKRKAEGDAK 1-10 (SEQ ID NO: 611) | Calf thymus HMG17 |
| PKGKKGKA 52-59 (SEQ ID NO: 612) | (89 aa; 9,247 D) |
| PKKPRGKM (SEQ ID NO: 613) | Calf thymus HMG 1 |
| EHKKKHP (SEQ ID NO: 614) | (259 aa) |
| ETKKKFKDP (SEQ ID NO: 615) | |
| EKSKKKK(E/D)$_{41}$ (SEQ ID NO: 616) | |
| E$_3$G$_2$KKKKKFAK (SEQ ID NO: 617) | |
| EHKKKHP (SEQ ID NO: 618) | Calf thymus HMG 2 |
| PKGDKKGKKKDP (SEQ ID NO: 619) | (256 aa) |
| E$_4$G$_3$KKKKKFAK (SEQ ID NO: 620) | |
| PKRRSATKGDEPARR 1-15 (SEQ ID NO: 621) | Trout testis H6 (60 aa) |
| KPKKAAAPKKA 30-34 (SEQ ID NO: 622) | |

References

U.S. Patent Documents

U.S. Pat. No. 4,394,448 July, 1983 Szoka, Jr. et al.
U.S. Pat. No. 4,598,051 July, 1986 Papahadjopoulos et al.
U.S. Pat. No. 5,013,556 May, 1991 Woodle et al.

Journal Articles

Allen, T. M. and Chonn, A. (1987) "Large unilamellar liposomes with low uptake into the reticuloendothelial system" *FEBS Lett.* 223:42-46.

Allen, T. M. et al. (1991) "Liposomes containing synthetic lipid derivatives of polyethylene glycol show prolonged circulation half-lives in vivo" *Biochim. Biophys. Acta* 1066:29-36.

Anderson, W. F. (1992) "Human gene therapy" *Science* 256:808-813.

Aoki, K. et al. (1995) "Liposome-mediated in vivo gene transfer of antisense K-ras construct inhibits pancreatic tumor dissemination in the murine peritoneal cavity" *Cancer Res.* 55:3810-3816.

Arcasoy, S. M. et al. (1997) "Polycations increase the efficiency of adenovirus-mediated gene transfer to epithelial and endothelial cells in vitro" *Gene Ther.* 4:32-38.

Beauchamp, C. O. et al. (1983) "A new procedure for the synthesis of polyethylene glycol-protein adducts; effects on function, receptor recognition, and clearance of superoxide dismutase, lactoferrin, and alpha 2-macroglobulin" *Anal. Biochem.* 131:25-33.

Bongartz, J.-P. et al. (1994) "Improved biological activity of antisense oligonucleotides conjugated to a fusogenic peptide" *Nucl. Acids Res.* 22:4681-4688.

Boulikas, T. (1993) "Nuclear localization signals (NLS)" *Crit. Rev. Eukar. Gene Expression* 3:193-227.

Boulikas, T. (1994) "Putative nuclear localization signals (NLS) in protein transcription factors" *J. Cell. Biochem.* 55:32-58.

Boulikas, T. (1996a) "Cancer gene therapy and immunotherapy" *Intl. J. Oncol.* 9:941-954.

Boulikas, T. (1996b) "Gene therapy to human diseases: ex vivo and in vivo studies" *Intl. J. Oncol.* 9:1239-1251.

Boulikas, T. (1996c) "Liposome DNA delivery and uptake by cells" *Oncol. Rep.* 3:989-995.

Boulikas, T. (1996d) "Nuclear import of protein kinases and cyclins" *J. Cell. Biochem.* 60:61-82.

Boulikas, T. (1997a) "Gene therapy of prostate cancer: p53, suicidal genes, and other targets" *Anticancer Res.* 17:1471-1506.

Boulikas, T. (1997b) "Nuclear import of DNA repair proteins" *Anticancer Res.* 17:843-864.

Boulikas, T. (1997c) "Nuclear localization signal peptides for the import of plasmid DNA in gene therapy" *Int. J. Oncol.* 10:301-309.

Boulikas, T. (1998a) "Status of gene therapy in 1997: Molecular mechanisms, disease targets, and clinical applications" *Gene Ther. Mol. Biol.* 1:1-172.

Boulikas, T. (1998b) "Nucleocytoplasmic trafficking: implications for the nuclear import of plasmid DNA during gene therapy" *Gene Ther. Mol. Biol.* 1:713-740.

Boulikas, T. and Martin, F. (1997) "Histones, protamine, and polylysine but not poly(E:K) enhance transfection efficiency" *Int. J. Oncol.* 10:317-322.

Capaccioli, S. et al. (1993) "Cationic lipids improve antisense oligonucleotide uptake and prevent degradation in cultured cells and in human serum" *Biochem. Biophys. Res. Comm.* 197:818-825.

Creuzenet, C. et al. (1997) "Interaction of alpha s2- and beta-casein signal peptides with DMPC and DMPG liposomes" *Peptides* 18:463-472.

Culver, K. W. (1996) in: Gene Therapy: A primer for physicians, Second Edition. Mary Ann Liebert, Inc. Publications, NY, pp. 1-198.

Curtain, C. et al. (1999) "The interactions of the N-terminal fusogenic peptide of HIV-1 gp41 with neutral phospholipids" *Eur. Biophys. J.* 28:427-436.

de la Maza, A. et al. (1998) "Solubilization of phosphatidylcholine liposomes by the amphoteric surfactant dodecyl betaine" *Chem. Phys. Lipids* 94:71-79.

Decout, A. et al. (1999) "Contribution of the hydrophobicity gradient to the secondary structure and activity of fusogenic peptides" *Mol. Membr. Biol.* 16:237-246.

Duguid, J. G. et al. (1998) "A physicochemical approach for predicting the effectiveness of peptide-based gene delivery systems for use in plasmid-based gene therapy" *Biophys. J.* 74:2802-2814.

Filion, M. C. and Phillips, N. C. (1997) "Toxicity and immunomodulatory activity of liposomal vectors formulated with cationic lipids toward immune effector cells" *Biochim. Biophys. Acta* 1329:345-356.

Fresta, M. et al. (1998) "Liposomal delivery of a 30-mer antisense oligodeoxynucleotide to inhibit proopiomelanocortin expression" *J. Pharm. Sci.* 87:616-625.

Gabizon, A. and Papahadjopoulos, D. (1988) "Liposome formulations with prolonged circulation time in blood and enhanced uptake by tumors" *Proc. Natl. Acad. Sci. USA* 85:6949-6953.

Gabizon, A. et al. (1989) "Pharmacokinetics and tissue localization of doxorubicin encapsulated in stable liposomes with long circulation times" *J. Natl. Cancer Inst.* 81:1484-1488.

Ghosh, J. K. and Shai, Y. (1999) "Direct Evidence that the N-Terminal Heptad Repeat of Sendai Virus Fusion Protein Participates in Membrane Fusion" *J. Mol. Biol.* 292:531-546.

Green, M. and Loewenstein, P. M. (1988) "Autonomous functional domains of chemically synthesized human immunodeficiency virus tat transactivator protein" *Cell* 55:1179-1188.

Gupta, D. and Kothekar, V. (1997) "500 picosecond molecular dynamics simulation of amphiphilic polypeptide Ac(LKKL)4 NHEt with 1,2 di-mysristoyl-sn-glycero-3-phosphorylcholine (DMPC) molecules" *Indian J. Biochem. Biophys.* 34:501-511.

Hofland, H. E. J. et al. (1996) "Formation of stable cationic lipid/DNA complexes for gene transfer" *Proc. Natl. Acad. Sci. USA* 93:7305-7309.

Jaaskelainen, I. et al. (1994) "Oligonucleotide-cationic liposome interactions. A physicochemical study" *Biochim. Biophys. Acta* 1195:115-123.

Judice, J. K. et al. (1997) "Inhibition of HIV type 1 infectivity by constrained alpha-helical peptides: implications for the viral fusion mechanism" *Proc. Natl. Acad. Sci. USA* 94:13426-13430.

Kono, K. et al. (1993) "Fusion activity of an amphiphilic polypeptide having acidic amino acid residues: generation of fusion activity by alpha-helix formation and charge neutralization" *Biochim. Biophys. Acta* 1164:81-90.

Lambert, G. et al. (1998) "The C-terminal helix of human apolipoprotein AII promotes the fusion of unilamellar liposomes and displaces apolipoprotein AI from high-density lipoproteins" *Eur. J. Biochem.* 253:328-338.

Lambert, O. et al. (1998) "A new "gel-like" phase in dodecyl maltoside-lipid mixtures: implications in solubilization and reconstitution studies" *Biophys. J.* 74:918-930.

Lappalainen, K. et al. (1997) "Intracellular distribution of oligonucleotides delivered by cationic liposomes: light and electron microscopic study" *Histochem. Cytochem.* 45:265-274.

Lasic, D. (1997) in: Liposomes in Gene Delivery, CRC Press, pp. 1-295.

Lee, S. et al. (1992) "Effect of amphipathic peptides with different alpha-helical contents on liposome-fusion" *Biochim. Biophys. Acta* 1103:157-162.

Lelkes, P. I. and Lazarovici, P. (1988) "Pardaxin induces aggregation but not fusion of phosphatidylserine vesicles" *FEBS Lett.* 230:131-136.

Leonard, A. N. and Cohen, D. E. (1998) "Submicellar bile salts stimulate phosphatidylcholine transfer activity of sterol carrier protein 2" *J. Lipid Res.* 39:1981-1988.

Lewis, J. G. et al. (1996) "A serum-resistant cytofectin for cellular delivery of antisense oligodeoxynucleotides and plasmid DNA" *Proc. Natl. Acad. Sci. USA* 93:3176-3181.

Li, S. and Huang, L. (1997) "In vivo gene transfer via intravenous administration of cationic lipid-protamine-DNA (LPD) complexes" *Gene Ther.* 4:891-900.

Lins, L. et al. (1999) "Molecular determinants of the interaction between the C-terminal domain of Alzheimer's beta-amyloid peptide and apolipoprotein E alpha-helices" *J. Neurochem.* 73:758-769.

Litzinger, D. C. et al. (1996) "Fate of cationic liposomes and their complex with oligonucleotide in vivo" *Biochim. Biophys. Acta* 1281:139-149.

Lopez, O. et al. (1998) "Direct formation of mixed micelles in the solubilization of phospholipid liposomes by Triton X-100" *FEBS Lett.* 426:314-318.

Lusa, S. et al. (1998) "Direct observation of lipoprotein cholesterol ester degradation in lysosomes" *Biochem. J.* 332:451-457.

Macosko, J. C. et al. (1997) "The membrane topology of the fusion peptide region of influenza hemagglutinin determined by spin-labeling EPR" *J. Mol. Biol.* 267:1139-1148.

Macreadie, I. G. et al. (1997) "Cytotoxicity resulting from addition of HIV-1 Nef N-terminal peptides to yeast and bacterial cells" *Biochem. Biophys. Res. Commun.* 232:707-711.

Martin, F. and Boulikas, T. (1998) "The challenge of liposomes in gene therapy" *Gene Ther. Mol. Biol.* 1:173-214.

Martin, I. et al. (1999) "Membrane fusion induced by a short fusogenic peptide is assessed by its insertion and orientation into target bilayers" *Biochemistry* 38:9337-9347.

Martin, I. and Ruysschaert, J. M. (1997) "Comparison of lipid vesicle fusion induced by the putative fusion peptide of fertilin (a protein active in sperm-egg fusion) and the NH2-terminal domain of the HIV2 gp41" *FEBS Lett.* 405:351-355.

Massari, S. and Colonna, R. (1986) "Gramicidin induced aggregation and size increase of phosphatidylcholine vesicles" *Chem. Phys. Lipids* 39:203-220.

Melino, S. et al. (1999) "Zn(2+) ions selectively induce antimicrobial salivary peptide histatin-5 to fuse negatively charged vesicles. Identification and characterization of a zinc-binding motif present in the functional domain" *Biochemistry* 38:9626-9633.

Midoux, P. and Monsigny, M. (1999) "Efficient gene transfer by histidylated polylysine/pDNA complexes" *Bioconjug. Chem.* 10:406-411.

Murata, M. et al. (1991) "Modification of the N-terminus of membrane fusion-active peptides blocks the fusion activity" *Biochem. Biophys. Res. Commun.* 179:1050-1055.

Niidome, T. et al. (1997) "Membrane interaction of synthetic peptides related to the putative fusogenic region of PH-30 alpha, a protein in sperm-egg fusion" *J. Peptide Res.* 49:563-569.

Pak, C. C. et al. (1999) "Elastase activated liposomal delivery to nucleated cells" *Biochim. Biophys. Acta* 1419:111-126.

Papahadjopoulos, D. et al. (1991) "Sterically stabilized liposomes: Improvements in pharmacokinetics and antitumor therapeutic efficacy" *Proc. Natl. Acad. Sci. USA* 88:11460-11464.

Parente, R. A. et al. (1988) "pH-dependent fusion of phosphatidylcholine small vesicles. Induction by a synthetic amphipathic peptide" *J. Biol. Chem.* 263:4724-4730.

Partidos, C. D. et al. (1996) "Priming of measles virus-specific CTL responses after immunization with a CTL epitope linked to a fusogenic peptide" *Virology* 215:107-110.

Pecheur, E. I. et al. (1997) "Membrane anchorage brings about fusogenic properties in a short synthetic peptide" *Biochemistry* 36:3773-3781.

Peelman, F. et al. (1999) "Characterization of functional residues in the interfacial recognition domain of lecithin cholesterol acyltransferase (LCAT)" *Protein Eng.* 12:71-78.

Pereira, F. B. et al. (1997) "Permeabilization and fusion of uncharged lipid vesicles induced by the HIV-1 fusion peptide adopting an extended conformation: dose and sequence effects" *Biophys. J.* 73:1977-1986.

Pillot, T. et al. (1999) "The nonfibrillar amyloid beta-peptide induces apoptotic neuronal cell death: involvement of its C-terminal fusogenic domain" *J. Neurochem.* 73:1626-1634.

Pillot, T. et al. (1997) "Specific modulation of the fusogenic properties of the Alzheimer beta-amyloid peptide by apolipoprotein E isoforms" *Eur. J. Biochem.* 243:650-659.

Pillot, T. et al. (1997) "The 118-135 peptide of the human prion protein forms amyloid fibrils and induces liposome fusion" *J. Mol. Biol.* 274:381-393.

Plank, C. et al. (1996) "Activation of the complement system by synthetic DNA complexes: a potential barrier for intravenous gene delivery" *Hum. Gene Ther.* 7:1437-1446.

Rodriguez-Crespo, I. et al. (1994) "Prediction of a putative fusion peptide in the S protein of hepatitis B virus" *J. Gen. Virol.* 75:637-639.

Rodriguez-Crespo, I. et al. (1999) "Fusogenic activity of hepadnavirus peptides corresponding to sequences downstream of the putative cleavage site" *Virology* 261:133-142.

Ross, G. et al. (1996) "Gene therapy in the United States: a five-year status report" *Hum. Gene Ther.* 7:1781-1790.

Schroeder, F. et al. (1990) "Intermembrane cholesterol transfer: role of sterol carrier proteins and phosphatidylserine" *Lipids* 25:669-674.

Schroth-Diez, B. et al. (1998) "Fusion activity of transmembrane and cytoplasmic domain chimeras of the influenza virus glycoprotein hemagglutinin" *J. Virol.* 72:133-141.

Schutze, W. and Muller-Goymann, C. C. (1998) "Phase transformation of a liposomal dispersion into a micellar solution induced by drug-loading" *Pharm. Res.* 15:538-543.

Song, Y. K. et al. (1997) "Characterization of cationic liposome-mediated gene transfer in vivo by intravenous administration" *Hum. Gene Ther.* 8:1585-1594.

Sorgi, F. L. et al. (1997) "Protamine sulfate enhances lipid-mediated gene transfer" *Gene Ther.* 4:961-968.

Suenaga, M. et al. (1989) "Basic amphipathic helical peptides induce destabilization and fusion of acidic and neutral liposomes" *Biochim. Biophys. Acta* 981:143-150.

Takle, G. B. et al. (1997) "Delivery of oligoribonucleotides to human hepatoma cells using cationic lipid particles conjugated to ferric protoporphyrin IX (heme)" *Antisense Nucleic Acid Drug Dev.* 7:177-185.

Templeton, N. S. et al. (1997) "Improved DNA: liposome complexes for increased systemic delivery and gene expression" *Nature Biotechnol.* 15:647-652.

Thierry, A. R. and Dritschilo, A. (1992) "Intracellular availability of unmodified, phosphorothioated and liposomally encapsulated oligodeoxynucleotides for antisense activity" *Nucl. Acids Res.* 20:5691-5698.

Tirosh, O. et al. (1998) "Hydration of polyethylene glycol-grafted liposomes" *Biophys. J.* 74:1371-1379.

Torchilin, V. P. (1998) "Polymer-coated long-circulating microparticulate pharmaceuticals" *J. Microencapsul.* 15:1-19.

Torchilin, V. P. et al. (1992) "Targeted accumulation of polyethylene glycol-coated immunoliposomes in infarcted rabbit myocardium" *FASEB J.* 6:2716-2719.

Tournois, H. et al. (1990) "Gramicidin A induced fusion of large unilamellar dioleoylphosphatidylcholine vesicles and its relation to the induction of type II nonbilayer structures" *Biochemistry* 29:8297-8307.

Ulrich, A. S. et al. (1999) "Ultrastructural characterization of peptide-induced membrane fusion and peptide self-assembly in the lipid bilayer" *Biophys. J.* 77:829-841.

Voneche, V. et al. (1992) "The 19-27 amino acid segment of gp51 adopts an amphiphilic structure and plays a key role in the fusion events induced by bovine leukemia virus" *J. Biol. Chem.* 267:15193-15197.

Wattiaux, R. et al. (1997) "Cationic lipids destabilize lysosomal membrane in vitro" *FEBS Lett.* 417:199-202.

Weissig, V. et al. (1998) "Accumulation of protein-loaded long-circulating micelles and liposomes in subcutaneous Lewis lung carcinoma in mice" Pharm. Res. 15:1552-1556.

Zelphati, O. and Szoka, Jr., F. C. (1997) "Intracellular distribution and mechanism of delivery of oligonucleotides mediated by cationic lipids" *Pharm. Res.* 13:1367-1372.

Zuidam, N. J. and Barenholz, Y. (1997) "Electrostatic parameters of cationic liposomes commonly used for gene delivery as determined by 4-heptadecyl-7-hydroxycoumarin-" *Biochim. Biophys. Acta* 1329:211-222.

What is claimed is:

1. A method for producing micelles with negatively charged entrapped therapeutic agents, comprising:
   a) combining an effective amount of a negatively charged therapeutic agent with a buffer solution containing about 20% to about 80% ethanol and an effective amount of a cationic lipid in a ratio where about 30% to about 90% the negatively charged atoms on the therapeutic agents are neutralized by positive charges on the cationic lipids to form an electrostatic micelle complex; and
   b) combining the electrostatic micelle complex of step a) with an effective amount of a fusogenic-karyophilic peptide conjugate in a ratio wherein the negatively charged therapeutic agents are almost completely neutralized by a majority of the cationic lipids and fusogenic-karyophilic peptide conjugates, thereby producing micelles with entrapped therapeutic agents.

2. The method of claim 1, further comprising combining an effective amount of an anionic lipid in step b) when the total of the positive charges contributed by the cationic lipids exceed the total of negative charges contributed by the therapeutic agents.

3. The method of claim 1, further comprising combining an effective amount of a DNA condensing agent selected from the group consisting of spermine, spermidine, polylysine, polyarginine, polyhistidine, polyornithine and magnesium or a divalent metal ion.

4. A method for producing liposome encapsulated micelles with negatively charged polynucleotides, comprising:
   a) combining an effective amount of a negatively charged polynucleotide with a buffer solution containing about 20% to about 80% ethanol and an effective amount of a cationic lipid in a ratio where about 30% to about 90% the negatively charged atoms on the negatively charged polynucleotides are neutralized by positive charges on the cationic lipids to form an electrostatic micelle complex; and
   b) combining the electrostatic micelle complex of step a) with an effective amount of a fusogenic-karyophilic peptide conjugate and an effective amount of an encapsulating lipid solution in a ratio wherein the negatively charged polynucleotides are almost completely neutralized by a majority of the cationic lipids and fusogenic-karyophilic peptide conjugates and liposomes, thereby producing said liposome encapsulated micelles.

5. The method of claim 4, wherein the encapsulating lipid solution comprises a liposome.

6. The method of claim 5, wherein the liposome comprises vesicle-forming lipids and between about 1 to about 7 mole percent of distearoylphosphatidyl ethanolamine (DSPE) derivatized with an effective amount of polyethyleneglycol.

7. The method of claim 4, wherein at least one lipid in step a or step b is chosen from the group consisting of: cholesterol, phosphatidycholine (PC), phosphatidyethanolamine (PE), phosphatidylinositol (PI), sphingomyelin (SM), dioleoylphosphatidylethanolamine (DOPE), hydrogenated soy phosphatidylcholine (HSPC), lecithin, phosphatidylethanolamine, lysolecithin, lysophosphatidylethanolamine phosphatidylserine, phosphatidylinositol, sphingomyelin, cephalin, cardiolipin, phosphatidic acid, cerebrosides, distearoylphosphatidylethanolamine (DSPE), dioleoylphophatidycholine (DOPC), dipalmitoylphosphatidylcholine (DPPC), palmitoyloleoylphosphatidylcholine (POPC), palmitoyloleoylphophatidylethanolamine (POPE), dioleoylphophatidylethanolamine-4-(N-maleimido-methyl) cyclohexane-1-carboxylate (DOPE-mal), stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, dipalmitoylphosphatidylglycerol (DPPG), dioleoylphosphatidylglycerol and (DOPG), and PEG-DSPE.

8. A micelle with an entrapped therapeutic agent produced by the method comprising
   a) combining an effective amount of a negatively charged therapeutic agent with a buffer solution containing about 20% to about 80% ethanol and an effective amount of a cationic lipid in a ratio where about 30% to about 90% the negatively charged atoms on the therapeutic agents are neutralized by positive charges on the cationic lipids to form an electrostatic micelle complex; and
   b) combining the electrostatic micelle complex of step a) with an effective amount of a fusogenic-karyophilic peptide conjugate in a ratio wherein the negatively charged therapeutic agents are almost completely neutralized by a majority of the cationic lipids and fusogenic-karyophilic peptide conjugates, thereby producing micelles with entrapped therapeutic agents.

9. The micelle of claim 8, wherein the method further comprises combining an effective amount of an anionic lipid in step b) when the total of the positive charges contributed by the cationic lipids exceed the total of negative charges contributed by the therapeutic agents.

10. The micelle of claim 9, wherein the method further comprises combining an effective amount of a DNA condensing agent selected from the group consisting of spermine, spermidine, polylysine, polyarginine, polyhistidine, polyornithine and magnesium or a divalent metal ion.

11. A liposome encapsulated therapeutic agent produced by a method comprising:
   a) combining an effective amount of a negatively charged therapeutic agent with a buffer solution containing about 20% to about 80% ethanol and an effective amount of a cationic lipid in a ratio where about 30% to about 90% the negatively charged atoms on the therapeutic agents are neutralized by positive charges on the cationic lipids to form an electrostatic micelle complex; and
   b) combining the electrostatic micelle complex of step a) with an effective amount of a fusogenic-karyophilic peptide conjugate and an effective amount of an encapsulating lipid solution in a ratio wherein the negatively charged therapeutic agents are almost completely neutralized by a majority of the cationic lipids and fusogenic-karyophilic peptide conjugates and liposomes, thereby producing said liposome encapsulated micelles.

* * * * *